(12) United States Patent
Hausch et al.

(10) Patent No.: US 11,834,463 B2
(45) Date of Patent: Dec. 5, 2023

(54) HIGH AFFINITY MACROCYCLIC FKB51-INHIBITORS FOR TREATMENT OF PSYCHIATRIC DISORDERS

(71) Applicants: TECHNISCHE UNIVERSITÄT DARMSTADT, Darmstadt (DE); MAX-PLANCK-GESELLSCHAFT ZUR FÖRDERUNG DER WISSENSCHAFTEN E.V., Munich (DE)

(72) Inventors: Felix Hausch, Reinheim (DE); Andreas Voll, Darmstadt (DE); Michael Bauder, Darmstadt (DE)

(73) Assignees: Technische Universität Darmstadt, Darmstadt (DE); Max-Planck-Gesellschaft zur Förderung der Wissenschaften E.V., Munich (DE)

( * ) Notice: Subject to any disclaimer, the term of this patent is extended or adjusted under 35 U.S.C. 154(b) by 0 days.

(21) Appl. No.: 18/019,369

(22) PCT Filed: Aug. 27, 2021

(86) PCT No.: PCT/EP2021/073784
§ 371 (c)(1),
(2) Date: Feb. 2, 2023

(87) PCT Pub. No.: WO2022/049005
PCT Pub. Date: Mar. 10, 2022

(65) Prior Publication Data
US 2023/0212185 A1    Jul. 6, 2023

(30) Foreign Application Priority Data

Sep. 4, 2020    (EP) .................... 20194718

(51) Int. Cl.
*A61K 31/435* (2006.01)
*C07D 498/04* (2006.01)
*A61K 45/06* (2006.01)

(52) U.S. Cl.
CPC ............ *C07D 498/04* (2013.01); *A61K 45/06* (2013.01)

(58) Field of Classification Search
CPC .................................................. A61K 31/435
USPC .......................................................... 514/293
See application file for complete search history.

(56) References Cited

FOREIGN PATENT DOCUMENTS

| WO | 2014015993 A1 | 1/2014 |
| WO | 2015039758 A1 | 3/2015 |
| WO | 2015110271 A1 | 7/2015 |

OTHER PUBLICATIONS

Feng, Structure-Affinity Relationship Analysis of Selective FKBP51 Ligands, Journal of Medicinal Chemistry, 2015, pp. 7796-7806, vol. 58, ACS Publications.

*Primary Examiner* — Raymond J Henley, III
(74) *Attorney, Agent, or Firm* — Hudak, Shunk & Farine Co. LPA

(57) ABSTRACT

High affinity macrocyclic FKB51-Inhibitors (HAM-FKB51-Inhibitors), which enable the selective inhibition of FK506-binding proteins (FKBPs). The molecules are useful for the treatment of psychiatric disorders, metabolic disorders, pain diseases, and cancers.

10 Claims, 3 Drawing Sheets

HIGH AFFINITY MACROCYCLIC FKB51-INHIBITORS FOR TREATMENT OF PSYCHIATRIC DISORDERS

FIELD OF THE INVENTION

The present invention relates to High Affinity Macrocyclic FKB51-inhibitors (HAM-FKB51-Inhibitors), which enable the selective inhibition of FK506-binding proteins (FKBPs). The molecules of the present invention are useful for the treatment of psychiatric disorders, metabolic disorders, pain diseases, and cancers.

BACKGROUND OF THE INVENTION

FK506-binding proteins (FKBPs) are part of the immunophillin family and best known for their immunosuppressive activity as complexes with the natural products FK506 and rapamycin. In addition, FKBPs are prominently expressed in the central nervous system and non-immunosuppressive FKBP ligands have repeatedly displayed neuroprotective and neurotrophic effects.

Among the human FKBPs, FKBP51 has gained particular interest as a regulator of stress-coping behaviour and as a risk factor for stress-related psychiatric disorders, as a risk factor promoting chronic pain states, and a regulator of metabolic processes, thus suggesting FKBP51 inhibition as a potential therapeutic approach for indications related to these biological systems. However, the development of potent drug-like inhibitors for FKBPs in general, and for FKBP51 in particular, is challenging owing to the shallow FK506 binding site.

In the past, inhibitors of FKBPs have been described. For example bicyclic aza-amides derivatives and stereoisomeric forms, as described in WO/2014/015993. Said bicyclic aza-amides derivatives have been identified as specific inhibitors of FKBPs, including FKBP51, are useful for the treatment of psychiatric disorders and neurodegenerative diseases, disorders and conditions, for treating vision disorders and/or improving vision; for treating memory impairment and/or enhancing memory performance and for treating alopecia and promoting hair growth.

WO2015/110271 describes Diazabicyclo-[4.3.1]-decane derivatives as potent inhibitors of FKBP-function, with very potent binding to certain members of FKBP-family, such as FKBP51, for example.

However, the inhibitors known in the prior art still show sub-optimal physicochemical and pharmacokinetic characteristics, which need to be improved. Moreover, at the same time any modification of the FKBP-inhibitors bears the risk of a reduction of selectivity and/or affinity to the target molecule, which needs to be avoided.

Therefore, it is the object of the present invention to provide compounds and/or pharmaceutically acceptable salts thereof, which selectively bind to a defined FKBP-member, such as FKBP 51, inhibit the function of said FKBP-member, and at the same time show improved physicochemical and pharmacokinetic characteristics.

The high affinity macrocyclic FKB51-Inhibitors (HAM-FKB51-Inhibitors) presented herein are the first description of molecules, which enable the selective inhibition of FKPB51 with a macrocyclic scaffold, which is known to allow for improved physicochemical and pharmacokinetic characteristics (such as for example higher stability, slower metabolism, improved dose-response relationship, higher plasma stability and improved plasma-half-time).

SUMMARY OF THE INVENTION

The FK506-binding protein (FKBP) family of immunophilins consists of proteins with a variety of protein-protein interaction domains and versatile cellular functions. This highly conserved protein family binds to immunosuppressive drugs, such as FK506 and rapamycin. This protein family displays peptidyl propyl isomerase (PPlase) activity.

The immunosuppressant drugs FK506 and rapamycin are well known as potent T-cell specific immunosuppressants, and are effective against autoimmunity, transplant or graft rejection, inflammation, allergic responses, other autoimmune or immune-mediated diseases, and infectious diseases.

FK506 and rapamycin apart from binding to FKBPs also interact and inhibit calcineurin (CaN) and mTOR respectively thereby mediating their immunosuppressive action.

The high molecular weight multidomain homologs FKBP51 and FKBP52 act as co chaperons for the heat shock protein (Hsp90) and modulate the signal transduction of the glucocorticoid receptor by participating in the Heat shock protein 90 (Hsp90)-steroid receptor complex.

FKBP51 has emerged as a key player in human stress biology and plays an important role in depression, obesity, glucose homeostasis, chronic pain states and certain cancers. Human genetic studies have clearly validated FKBP51 as a risk factor for mood disorders like depression. Characterization of FKBP51-deficient mice revealed that FKBP51 plays a prominent role in the feedback control of the hypothalamus-pituitary-adrenal axis, a key stress response system in mammals. Furthermore, FKBP51$^{-/-}$ mice had an improved sleep profile and enhanced glucose tolerance, were resistant to diet-induced obesity, and were protected from experimentally induced forms of chronic pain. Importantly, no potentially adverse effects were observed in FKBP51$^{-/-}$-mice so far, suggesting FKBP51 as a novel and safe drug target for depression, obesity or chronic pain.

The immunosuppressive compounds, like FK506, disclosed in the prior art suppress the immune system, by definition, and also exhibit other toxic side effects. Accordingly, there is a need for non-immunosuppressant, small molecule compounds, and compositions and methods for use of such compounds, that are useful in treating psychiatric, metabolic, oncologic, pain-related or neurodegenerative diseases, disorders and conditions.

Further studies led to α-ketoamide analogs of FK506 devoid of immunosuppressive activity. So far there has been only few investigations on the activity of monocyclic, pipecolate or proline-based compounds concerning FKBP51 based on the α-ketoamide motif.

Also, the main physiological role of FKBP51 is believed to be the inhibition of glucocorticoid receptor signalling, especially in stressful situations. However, the FKBP51-GR interplay (glucocorticoid receptor interplay) has been difficult to assess pharmacologically, largely due to lack of appropriate chemical probes. The most selective and most wide used compound to study FKBP51 are compounds from the SAFit class such as SAFit2. These compounds block the FK506-binding site on FKBP51, but do not affect other functional domains such as the HSP90-binding domain (TPR domain).

However, the inhibitors known in the prior art still show sub-optimal physicochemical and pharmacokinetic characteristics, which need to be improved.

The high affinity macrocyclic FKB51-Inhibitors (HAM-FKB51-Inhibitors) presented herein are the first description of molecules, which enable the selective inhibition of FKPB51 with a macrocyclic scaffold, which is known to allow for improved physicochemical and pharmacokinetic characteristics (such as for example higher stability, slower metabolism, improved dose-response relationship, higher plasma stability and improved plasma-half-time).

Thus, in one aspect the invention relates to a compound with the general structure of formula I:

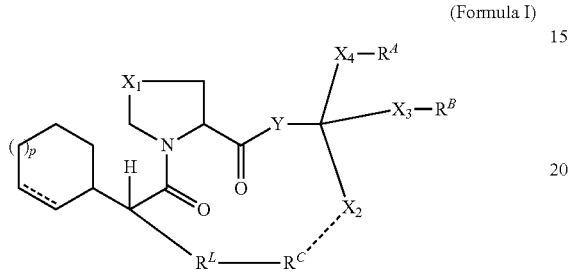

(Formula I)

wherein $X_1$ represents —$CH_2$—, —$CH_2CH_2$—, —CH=CH—, —$CH_2$—S—, or —S—$CH_2$—;

Y represents —NH—, or —O—;

p is an integer of 0 or 1;

⇌ represents a C=C bond or a C—C bond;

⋯ represents a bond between $R^C$ and $X_2$;

$R^L$ represents:

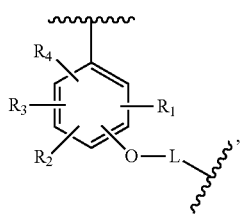

or —$NR^{Me}$—C(=O)-L-, —$NR^{Me}$-L-, or L;

$R^c$ represents: —O-L, or

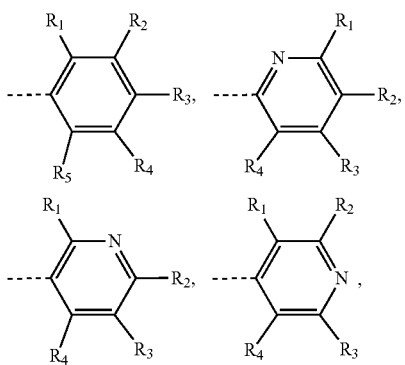

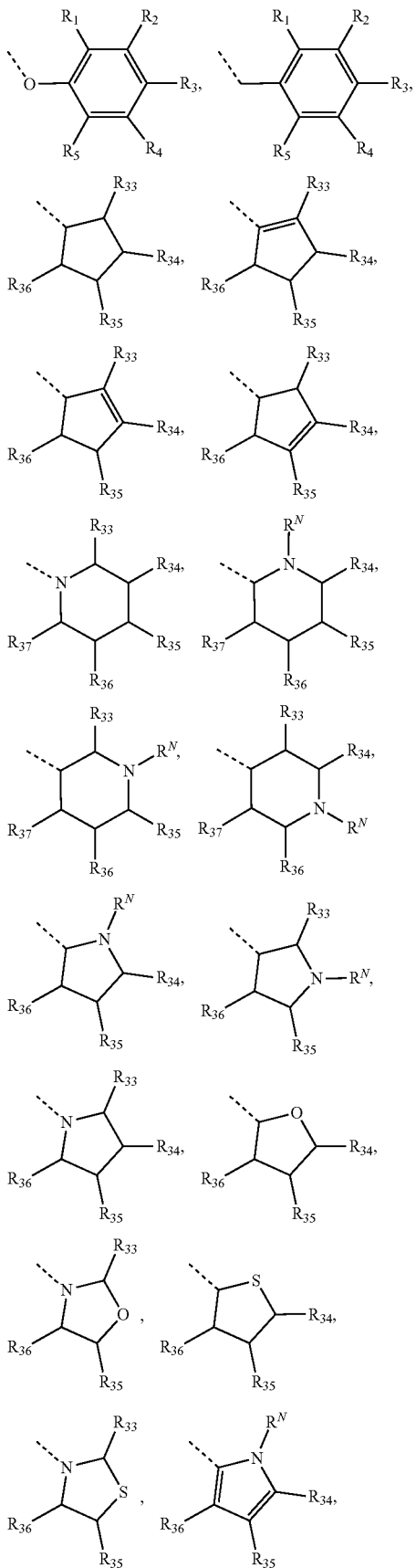

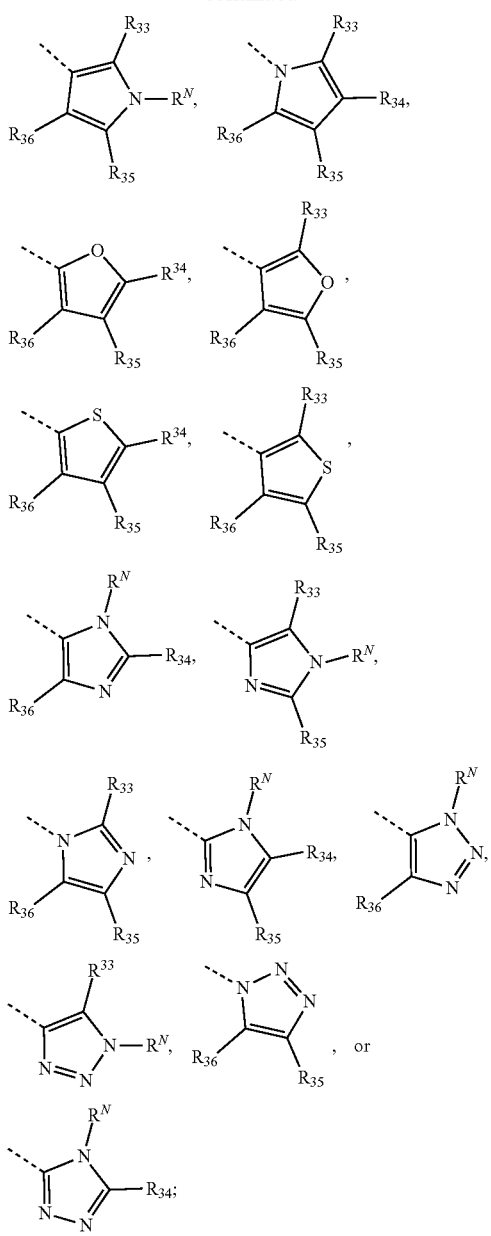
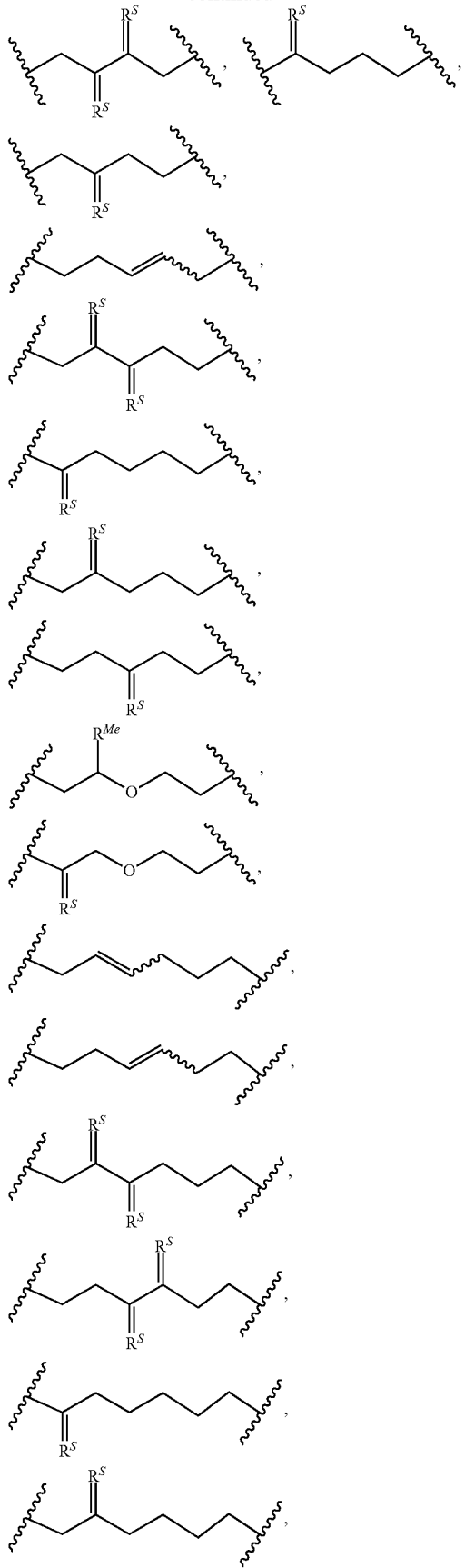
wherein in each of the substructures $R^c$ one of the substituents $R^1$, $R^2$, $R^3$, $R^4$, $R^5$, $R^{33}$, $R^{34}$, $R^{35}$, $R^{36}R^{37}$ or $R^N$ is replaced by L, —O-L, —C(=O)NR$^{Me}$-L, or —NR$^{Me}$-L;
L represents: X5 or
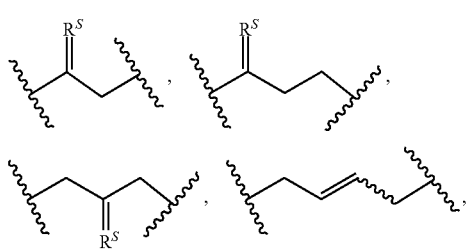

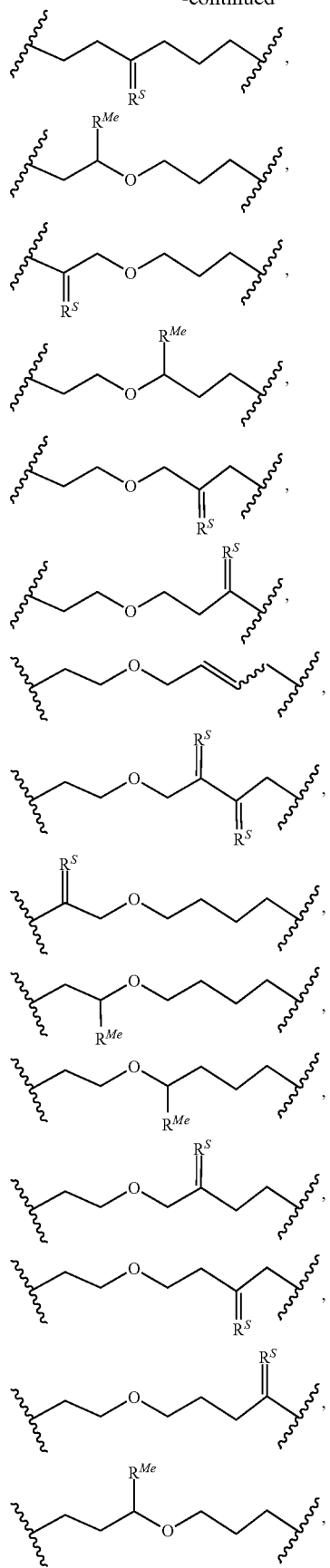
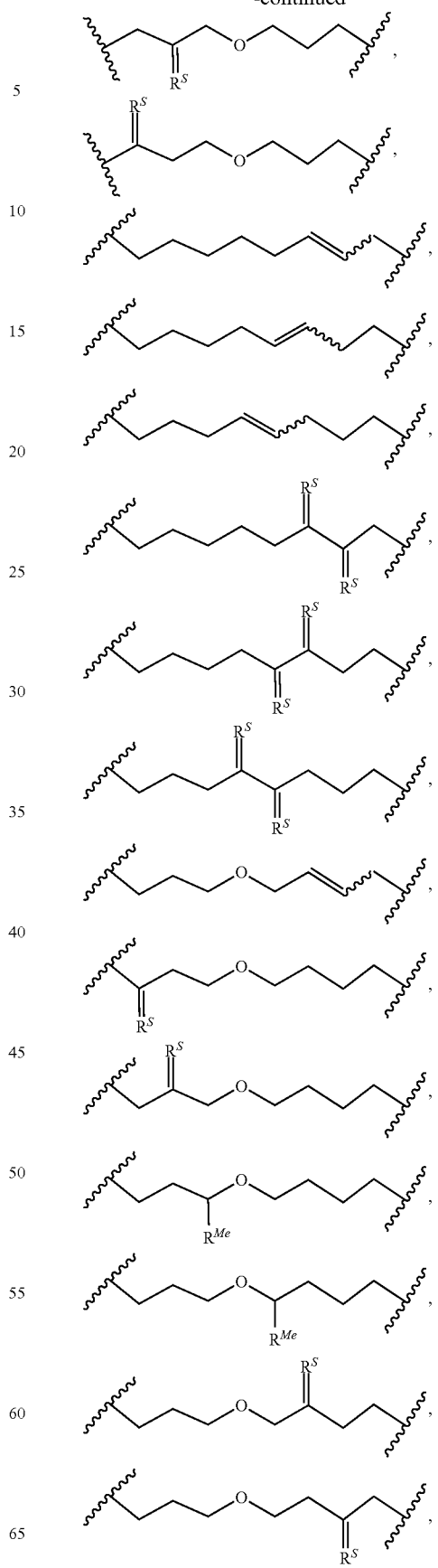

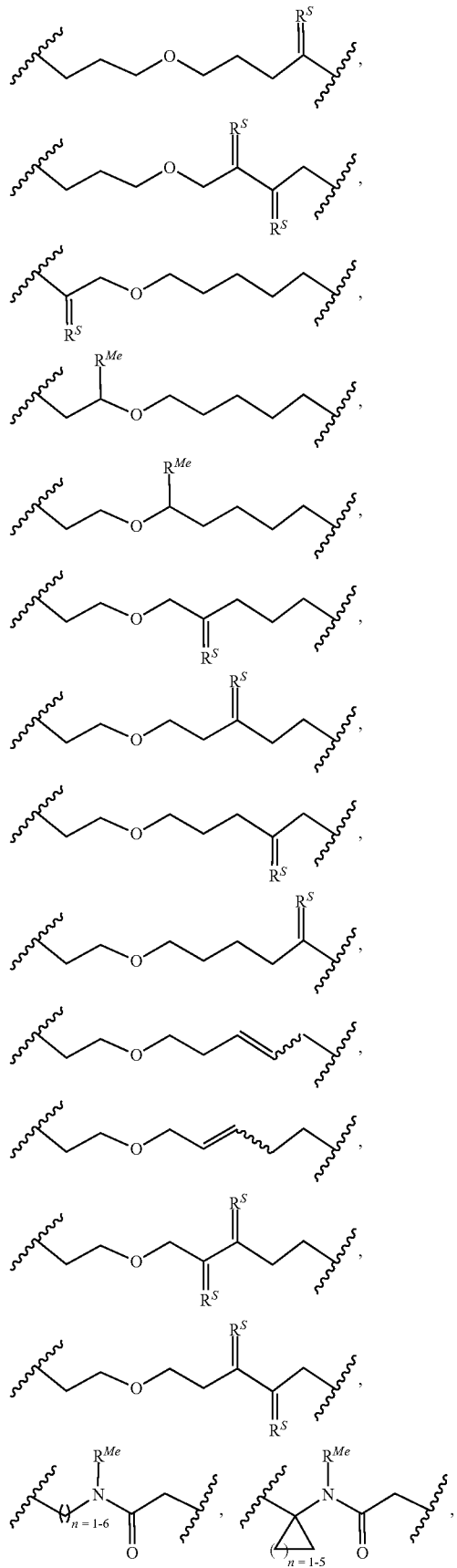
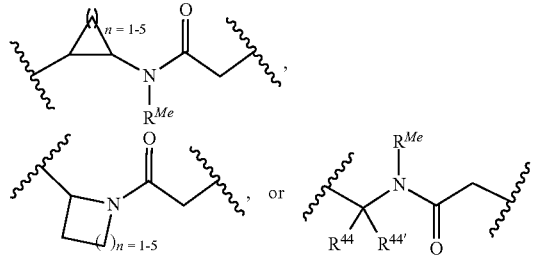
wherein L is connected to $R^C$ and $R^L$ as follows: $R^C$-L-$R^L$ or $R^L$-L-$R^c$;
$R^{Me}$ represents H or Me;
===$R^S$ represent independently of each other —H, -Me, —OH or =O;
$R^A$ represents R28, or:
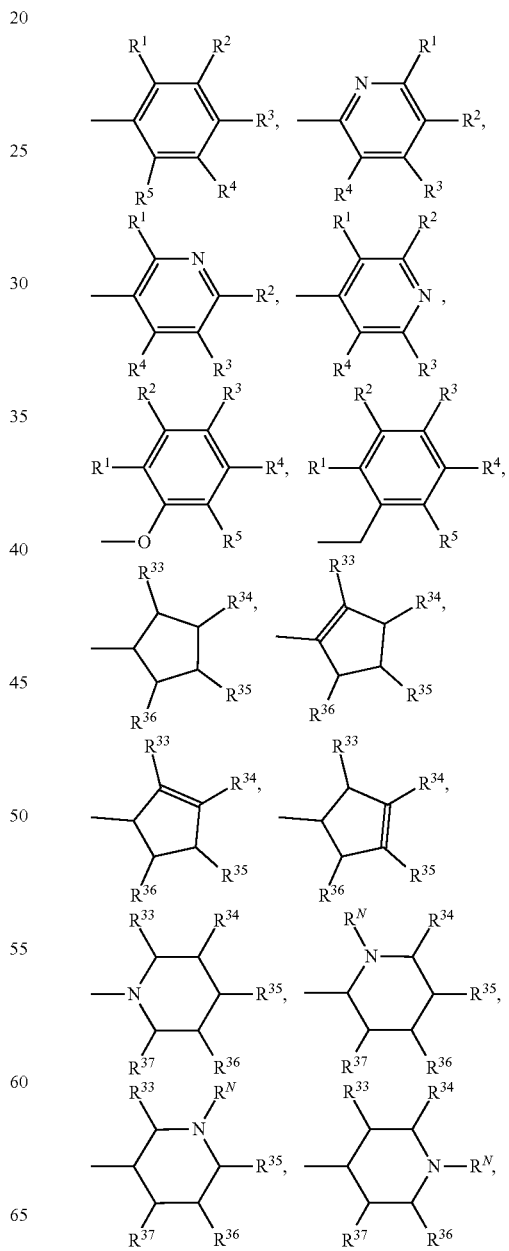

-continued
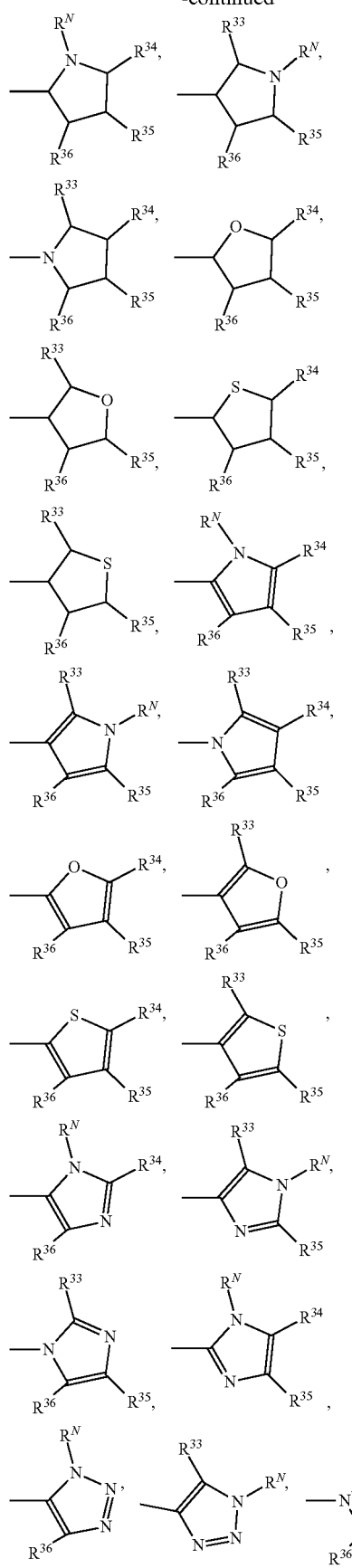
-continued
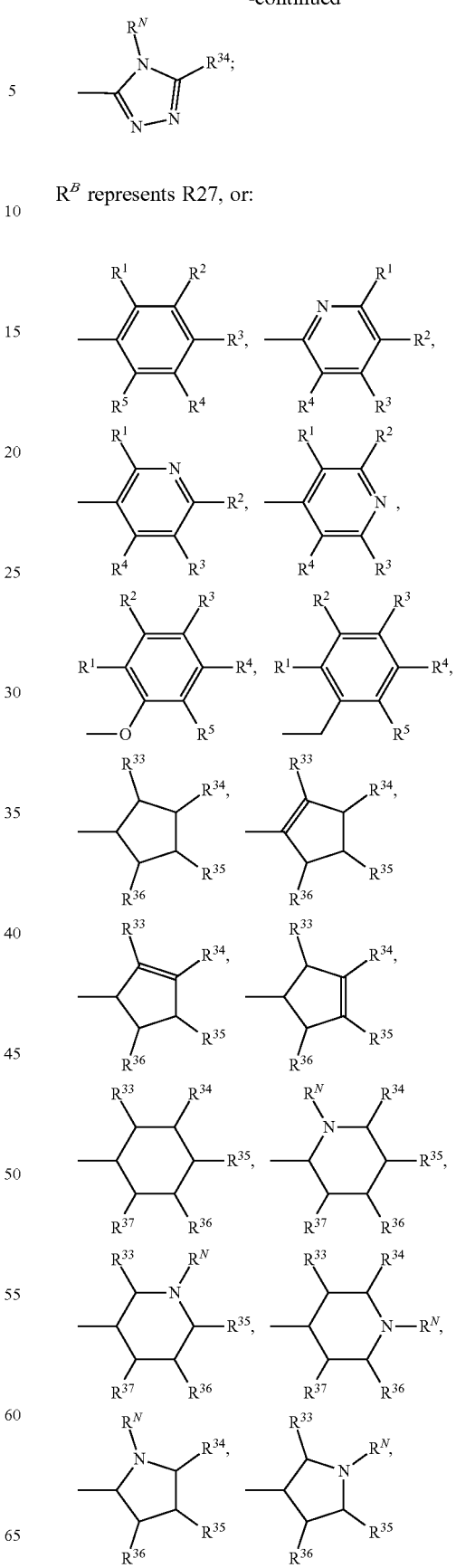
$R^B$ represents R27, or:

-continued

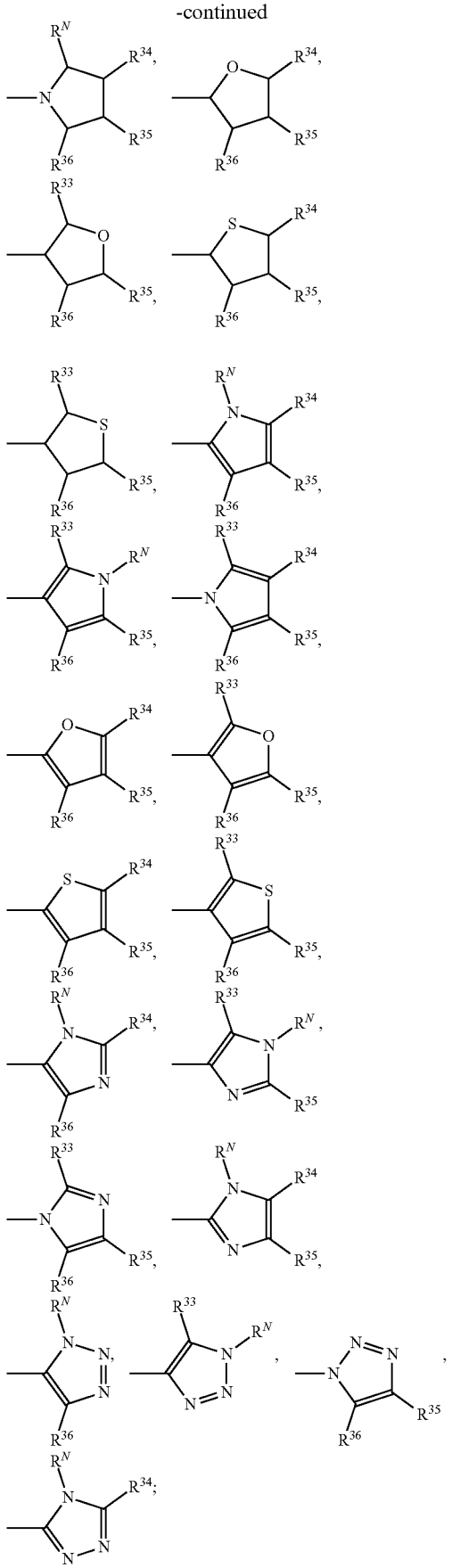

$R^1$-$R^{22}$, $R^{18'}$-$R^{22'}$, $R^{26}$-$R^{43}$, represent independently of each other —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OCH$_2$—COOH, —OPh, —OCH$_2$-Ph, —OCPh$_3$, —CH$_2$—OH, —C$_2$H$_4$—OH, —C$_3$H$_6$—OH, —CH(OH)—CH$_2$—OH, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—×O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —P(O)(OH)$_2$, —P(O)(OCH$_3$)$_2$, —P(O)(OC$_2$H$_5$)$_2$, —P(O)(OCH(CH$_3$)$_2$)$_2$, —C(OH)[P(O)(OH)$_2$]$_2$, —Si(CH$_3$)$_2$(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CH$_2$—CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —SO$_2$NH$_2$, —SO$_2$NHCH$_3$, —SO$_2$NHC$_2$H$_5$, —SO$_2$NHC$_3$H$_7$, —SO$_2$NH-cyclo-C$_3$H$_5$, —SO$_2$NHCH(CH$_3$)$_2$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N(cyclo-C$_3$H$_5$)$_2$, —SO$_2$N[CH(CH$_3$)$_2$]$_2$, —SO$_2$N[C(CH$_3$)$_3$]$_2$, —O—S(=O)CH$_3$, —O—S(=O)C$_2$H$_5$, —O—S(=O)C$_3$H$_7$, —O—S(=O)-cyclo-C$_3$H$_5$, —O—S(=O)CH(CH$_3$)$_2$, —O—S(=O)C(CH$_3$)$_3$, —S(=O)(=NH)CH$_3$, —S(=O)(=NH)C$_2$H$_5$, —S(=O)(=NH)C$_3$H$_7$, —S(=O)(=NH)-cyclo-C$_3$H$_5$, —S(=O)(=NH)CH(CH$_3$)$_2$, —S(=O)(=NH)C(CH$_3$)$_3$, —NH—SO$_2$—CH$_3$, —NH—SO$_2$—C$_2$H$_5$, —NH—SO$_2$—C$_3$H$_7$, —NH—SO$_2$-cyclo-C$_3$H$_5$, —NH—SO$_2$—CH(CH$_3$)$_2$, —NH—SO$_2$—C(CH$_3$)$_3$, —O—SO$_2$—CH$_3$, —O—SO$_2$—C$_2$H$_5$, —O—SO$_2$—C$_3$H$_7$, —O—SO$_2$-cyclo-C$_3$H$_5$, —O—SO$_2$—CH(CH$_3$)$_2$, —O—SO$_2$—C(CH$_3$)$_3$, —OCF$_3$, —CH$_2$—OCF$_3$, —C$_2$H$_4$—OCF$_3$, —C$_3$H$_6$—OCF$_3$, —OC$_2$F$_5$, —CH$_2$—OC$_2$F$_5$, —C$_2$H$_4$—OC$_2$F$_5$, —C$_3$H$_6$—OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CS—N(C$_3$H$_7$)$_2$, —NH—CO—NHC$_3$H$_7$, —NH—CO—N(C$_3$H$_7$)$_2$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—NH-cyclo-C$_3$H$_5$, —NH—CO—N(cyclo-C$_3$H$_5$)$_2$, —NH—CO—N[CH(CH$_3$)$_2$]$_2$, —NH—CS—N(C$_2$H$_5$)$_2$, —NH—CO—N[C(CH$_3$)$_3$]$_2$, —NH—CS—NH$_2$, —NH—CS—NHCH$_3$, —NH—CS—N(CH$_3$)$_2$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —O—CO—NH-cyclo-C$_3$H$_5$, —NH—C(=NH)—NH-cyclo-C$_3$H$_5$, —NH—C(=NH)—NH[CH(CH$_3$)$_2$]—O—CO—NH[CH(CH$_3$)$_2$], —NH—C(=NH)—NH[C(CH$_3$)$_3$],
—NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —O—CO—NHC$_3$H$_7$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$,
—O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_5$H$_9$, -cyclo-C$_6$H$_{11}$, —CH$_2$-cyclo-C$_6$H$_{11}$, —CH$_2$—CH$_2$-cyclo-C$_6$H$_{11}$, -cyclo-C$_7$H$_{13}$, -cyclo-C$_8$H$_{15}$, -Ph, —CH$_2$-Ph, —CH$_2$—CH$_2$-Ph, —CH=CH-Ph, —CPh$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH$_2$—CH$_3$, —CH$_2$—CH=CH—CH$_3$, —CH$_2$—CH$_2$—CH=CH—CH$_3$, —CH$_2$—CH=CH—C$_2$H$_5$, —CH$_2$—CH=CH—CH$_2$, —CH=CH—CH$_2$—CH$_3$, —CH=CH—CH$_2$—CH=CH$_2$, —C(CH$_3$)=CH—

CH=CH$_2$, —CH=C(CH$_3$)—CH=CH$_2$, —CH=CH—C(CH$_3$)=CH$_2$,
—C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$,
—C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —C$_2$H$_4$—CH=C(CH$_3$)$_2$, —CH(CH$_3$)—C$_2$H$_4$—CH=CH$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)—C$_2$H$_5$, —CH=CH—CH(CH$_3$)—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH=CH—C$_2$H$_4$—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —C(CH$_3$)$_2$—CH=C(CH$_3$)$_2$, —C(CH$_3$)$_2$—CH=CH—CH$_3$, —CH=CH—CH$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$,
—CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —C$_3$H$_6$—C≡C—CH$_3$, —CH$_2$—CH=CH—CH=CH—CH$_3$, —CH=CH—CH$_2$—CH=CH—C$_2$H$_5$, —CH$_2$—CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH=CH—CH=CH$_2$, —CH=CH—CH=CH—CH$_2$—CH$_3$, —CH=CH—CH=C(CH$_3$)—CH$_3$, —CH=CH—C(CH$_3$)=CH—CH$_3$, —CH=C(CH$_3$)—CH=CH—CH$_3$, —C(CH$_3$)=CH—CH=CH—CH$_3$, —CH=CH—CH=CH—CH=CH$_2$, —CH$_2$—CH(CH$_3$)—C≡C—CH$_3$, —CH=C(CH$_3$)—CH=CH$_2$, —CH=CH—C(CH$_3$)=CH$_2$, —CH(CH$_3$)—CH=CH—CH=CH$_2$, —CH(CH$_3$)—C≡CH, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_8$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C≡C—CH$_3$,

—CH(CH₃)—CH₂—C≡C—CH₃,    —CH(CH₃)—C≡C—C₂H₅,    —CH₂—C≡C—CH(CH₃)₂, —C≡C—CH(CH₃)—C₂H₅,    —C≡C—CH₂—CH(CH₃)₂, —CH(C₂H₅)—C≡C—CH₃, —C(CH₃)₂—C≡C—CH₃, —CH(C₂H₅)—CH₂—C≡CH,    —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃,    —CH(C≡CH)₂,    —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃,    —C≡C—C≡C—C₂H₅, —C(C≡CH)₂—CH₃, —C≡C—CH(CH₃)—C≡CH, —CH(CH₃)—C≡C—C≡CH,    —CH(C≡CH)—CH₂—C≡CH, —CH(C≡CH)—C≡C—CH₃,

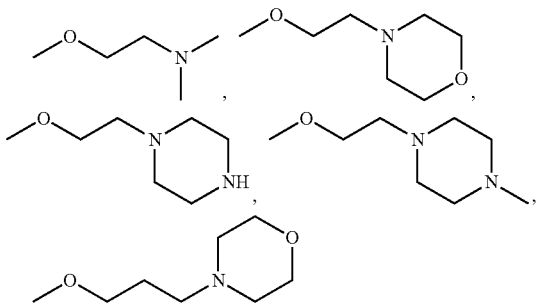

or
R¹⁸ and R¹⁸' or R¹⁹ and R¹⁹' or R²⁰ and R²⁰' or R²¹ and R²¹' or R²² and R²²' or can form together
=O,

or =CR²³'R²⁴', wherein R²³' and R²⁴' represent of each other —H, —CH₃, —C₂H₅, —CF₃, —CH₂CF₃, —C₂F₅;
R²³-R²⁵ or R⁴⁵ represent independently of each other —H, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂,    —CH₂—OC(CH₃)₃, —C₂H₄—OC(CH₃)₃, —C₃H₆—OC(CH₃)₃, —CH₂—OC₄H₉,    —C₂H₄—OC₄H₉,    —C₃H₆—OC₄H₉, —CH₂—OPh,    —C₂H₄—OPh,    —C₃H₆—OPh, —CH₂—OCH₂-Ph, —C₂H₄—OCH₂-Ph, —C₃H₆—OCH₂-Ph, —CH₂F, —CHF₂, —CF₃, —CH₂Cl, —CH₂Br, —CH₂I,
—CH₂—CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂—CH₂-Ph, —CH=CH-Ph, —CPh₃, —CH₃,
—C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂,    —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂,    —C₂H₄—CH(CH₃)—C₂H₅, —CH(CH₃)—C₄H₉,    —CH₂—CH(CH₃)—C₃H₇, —CH(CH₃)—CH₂—CH(CH₃)₂,    —CH(CH₃)—CH(CH₃)—C₂H₅,    —CH₂—CH(CH₃)—CH(CH₃)₂, —CH₂—C(CH₃)₂—C₂H₅,
—C(CH₃)₂—C₃H₇, —C(CH₃)₂—CH(CH₃)₂, —C₂H₄—C(CH₃)₃,    —CH(CH₃)—C(CH₃)₃,    —CH=CH₂, —CH₂—CH=CH₂, —C(CH₃)=CH₂,
—CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂,    —C(CH₃)=CH—CH₃, —CH=CH—CH₂—CH₃, —C₃H₆—CH=CH₂,
—C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂,    —CH=CH—C(CH₃)=CH₂, —C₂H₄—C(CH₃)=CH₂,    —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃,    —CH=CH—CH(CH₃)₂, —CH=C(CH₃)—C₂H₅,    —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃) =CH₂, —C₄H₈—CH=CH₂, —C₃H₆—CH=CH—CH₃,    —C₂H₄—CH=CH—C₂H₅,    —CH₂—CH=CH—C₃H₇, —CH=CH—C₄H₉,
—C₃H₆—C(CH₃)=CH₂,    —C₂H₄—CH(CH₃)—CH=CH₂,    —CH₂—CH(CH₃)—CH₂—CH=CH₂, —C₂H₄—CH=C(CH₃)₂,    —CH(CH₃)—C₂H₄—CH=CH₂, —C₂H₄—C(CH₃)=CH—CH₃, —CH₂—CH(CH₃)—CH=CH—CH₃,    —CH(CH₃)—CH₂—CH=CH—CH₃,    —CH₂—CH=CH—CH(CH₃)₂, —CH₂—CH=C(CH₃)—C₂H₅,    —CH₂—C(CH₃) =CH—C₂H₅,    —CH(CH₃)—CH=CH—C₂H₅, —CH=CH—CH₂—CH(CH₃)₂,    —CH=CH—CH(CH₃)—C₂H₅,    —CH=C(CH₃)—C₃H₇, —C(CH₃) =CH—C₃H₇,    —CH₂—CH(CH₃)—C(CH₃)=CH₂, —C[C(CH₃)₃]=CH₂,    —CH(CH₃)—CH₂—C(CH₃) =CH₂,    —CH(CH₃)—CH(CH₃)—CH=CH₂, —CH—CH—C₂H₄—CH=CH₂, —CH₂—C(CH₃)₂—CH=CH₂, —C(CH₃)₂—CH₂—CH=CH₂, —CH₂—C(CH₃)₂—CH=CH₂, —CH₂—C(CH₃)=C(CH₃)₂,    —CH(CH₃)—CH=C(CH₃)₂, —C(CH₃)₂—CH=CH—CH₃, —CH=CH—CH₂—CH=CH—CH₃,    —CH(CH₃)—C(CH₃)=CH—CH₃, —CH=C(CH₃)—CH(CH₃)₂, —C(CH₃)=CH—CH(CH₃)₂,    —C(CH₃)=C(CH₃)—C₂H₅,
—CH=CH—C(CH₃)₃,    —C(CH₃)₂—C(CH₃)=CH₂, —CH(C₂H₅)—C(CH₃)=CH₂,    —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃,    —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂,    —CH₂—CH=CH—CH₂—CH=CH₂, —C₃H₆—C≡C—CH₃,    —CH₂—CH=CH—CH=CH—CH₃,    —CH=CH—CH=CH—C₂H₅, —CH₂—CH=CH—C(CH₃)=CH₂, —CH₂—CH=C(CH₃)—CH=CH₂,    —CH₂—C(CH₃)=CH—CH=CH₂,    —CH(CH₃)—CH₂—C≡CH, —CH(CH₃)—CH=CH—CH=CH₂, —CH=CH—CH₂—C(CH₃)=CH₂,    —CH(CH₃)—C≡C—CH₃, —CH=CH—CH(CH₃)—CH=CH₂,    —CH=C (CH₃)—CH₂—CH═CH₂, —C₂H₄—CH(CH₃)—C≡CH, —C(CH₃)═CH—CH₂—CH═CH₂, —CH═CH—CH═C(CH₃)₂, —CH₂—CH(CH₃)—CH₂—C≡CH, —CH═CH—C(CH₃)═CH—CH₃, —CH═C(CH₃)—CH═CH—CH₃, —CH₂—CH(CH₃)—C≡CH, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—CH₂—C≡CH, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃;

R^N represents —H, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CHO, —COCH₃, —COC₂H₅, —COC₃H₇, —CO-cyclo-C₃H₅, —COCH(CH₃)₂, —COC(CH₃)₃, —COCN, —COOCH₃, —COOC₂H₅, —COOC₃H₇, —COO-cyclo-C₃H₅, —COOCH(CH₃)₂, —COOC(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —SO₂CH₃, —SO₂C₂H₅, —SO₂C₃H₇, —SO₂-cyclo-C₃H₅, —SO₂CH(CH₃)₂, —SO₂C(CH₃)₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂—CH₂-Ph, —CH═CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)₂, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH═CH₂, —CH₂—CH═CH₂, —C(CH₃)═CH₂, —CH═CH—CH₃, —C₂H₄—CH═CH₂, —CH₂—CH═CH—CH₃, —CH═CH—C₂H₅, —CH₂—C(CH₃)═CH₂, —CH(CH₃)—CH═CH, —CH═C(CH₃)₂, —C(CH₃)═CH—CH₃, —CH═CH—CH═CH₂, —C₃H₆—CH═CH₂, —C₂H₄—CH═CH—CH₃, —CH₂—CH═CH—C₂H₅, —CH═CH—C₃H₇, —CH₂—CH═CH—CH═CH₂, —CH═CH—CH═CH—CH₃, —CH═CH—CH₂—CH═CH₂, —C(CH₃)═CH—CH═CH₂, —CH═C(CH₃)—CH═CH₂, —CH═CH—C(CH₃)═CH₂, —C₂H₄—C(CH₃)═CH₂, —CH₂—CH(CH₃)—CH═CH₂, —CH(CH₃)—CH₂—CH═CH₂, —CH═C(CH₃)₂, —CH₂—CH═CH—CH₃, —CH(CH₃)—CH═CH—CH₃, —CH₂—CH═CH(CH₃)₂, —CH₂—CH═C(CH₃)—C₂H₅, —C(CH₃)═CH—C₂H₅, —C(CH₃)═C(CH₃)₂, —C(CH₃)₂—CH═CH₂, —CH(CH₃)—C(CH₃)═CH₂, —CH═C(CH₃)—CH═CH₂, —CH═CH—C(CH₃)═CH₂, —CH═CH—C(CH₃)═CH—CH₂, —C₄H₈—CH═CH₂, —C₃H₅—CH═CH—CH₃, —C₂H₄—CH═CH—C₂H₅, —CH₂—CH═CH—C₃H₇, —CH═CH—C₄H₉, —C₃H₆—C(CH₃)═CH₂, —C₂H₄—CH(CH₃)—CH═CH₂, —CH₂—CH(CH₃)—CH₂—CH═CH₂, —C₂H₄—CH═C(CH₃)₂, —CH(CH₃)—C₂H₄—CH═CH₂, —C₂H₄—C(CH₃)═CH—CH₃, —CH₂—CH(CH₃)—CH═CH—CH₃, —CH(CH₃)—CH₂—CH═CH—CH₃, —CH₂—CH═CH—CH(CH₃)₂, —CH₂—CH═C(CH₃)—C₂H₅, —CH₂—C(CH₃)═CH—C₂H₅, —CH(CH₃)—CH═CH—C₂H₅, —CH═CH—CH₂—CH(CH₃)₂, —CH═CH—CH(CH₃)—C₂H₅, —CH═C(CH₃)—C₃H₇, —C(CH₃)═CH—C₃H₇, —CH═C(CH₃)—C₃H₇, —CH₂—CH(C₂H₅)—CH═CH₂, —C[C(CH₃)₃]═CH₂, —CH(CH₃)—CH₂—C(CH₃)═CH₂, —CH(CH₃)—CH(CH₃)—CH═CH₂, —CH═CH—C₂H₄—CH═CH₂, —CH₂—C(CH₃)₂—CH═CH₂, —C(CH₃)₂—CH₂—CH═CH₂, —CH₂—C(CH₃)═C(CH₃)₂, —CH(CH₃)—CH═C(CH₃)₂, —C(CH₃)₂—CH═CH—CH₃, —CH═CH—CH₂—CH═CH—CH₃, —CH(CH₃)—C(CH₃)═CH—CH₃, —CH═C(CH₃)—CH(CH₃)₂, —C(CH₃)═CH—CH(CH₃)₂, —C(CH₃)═C(CH₃)—C₂H₅, —CH═CH—C(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[CH(CH₃)(C₂H₅)]═CH₂, —C[CH₂—CH(CH₃)₂]═CH₂, —C₂H₄—CH═CH—CH═CH₂, —CH₂—CH═CH—CH₂—CH═CH₂, —C₃H₆—C≡C—CH₃, —CH₂—CH═CH—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—

CH=CH₂, —CH(CH₃)—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH(CH₃)—CH=CH₂, —CH=C(CH₃)—CH₂—CH=CH₂, —C₂H₄—CH(CH₃)—C≡CH, —C(CH₃)=CH—CH₂—CH=CH₂, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃;

R⁴⁴ and R⁴⁴' represent independently of each other R⁴⁵, —H, —CH₃, —CH(CH₃)—CH₂—CH₃, —CH₂—CH(CH₃)₂, —CH₂—CH₂—S—CH₃, —CH(CH₃)₂, —CH₂-Ph, —CH₂-Ph-ortho-OH, —CH₂-Ph-meta-OH, —CH₂-Ph-para-OH, —CH₂—CONH₂, —CH₂SH, —CH₂—CH₂—CONH₂, —CH₂—OH, —CH₂—CH(CH₃)(OH), —CH₂—CH₂—CH₂—NH—C(=NH)(—NH₂), —CH₂—CH₂—CH₂—CH₂—NH₂, —CH₂—CH₂—COOH, —CH₂—COOH,

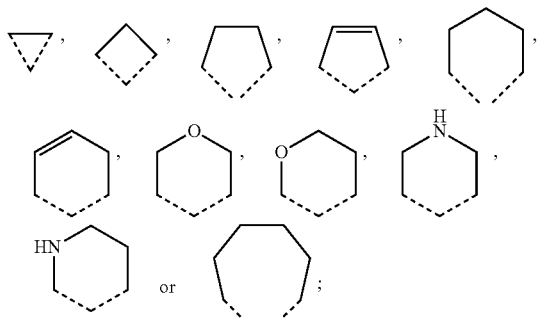

—CH₂—C₆H₅F, —CH₂-cyclo-C₃H₅, —CH₂—OCH₃, —C₂H₄—OCH₃;

R⁴⁴ and R⁴⁴' can form together a cyclic ring selected from the group consisting of:

X2, X3, X4 and X5 represent independently of each other:
a bond, —CH₂—, —C₂H₄—, —C₃H₈—, —C₄H₈—, —C₅H₁₀—, —C₆H₁₂—, —C₇H₁₄—, —C₈H₁₆—, —C₉H₁₈—, —C₁₀H₂₀—, —CH(CH₃)—, —C[(CH₃)₂]—, —CH₂—CH(CH₃)—, —CH(CH₃)—CH₂—, —CH(CH₃)—C₂H₄—, —CH₂—CH(CH₃)—CH₂—, —C$_2$H$_4$—CH(CH$_3$)—, —CH$_2$—C[(CH$_3$)$_2$]—,
—C[(CH$_3$)$_2$]—CH$_2$—, —CH(CH$_3$)—CH(CH$_3$)—,
—C[(C$_2$H$_5$)(CH$_3$)]—, —CH(C$_3$H$_7$)—, —CH$_2$CH$_2$O—,
—(CH$_2$—CH$_2$—O)$_m$—CH$_2$—CH$_2$—, —C(CH$_3$)
=CH—C(CH$_3$)=CH—, —C$_2$H$_4$—CH=CH—
CH=CH—, —CH$_2$—CH=CH—CH$_2$—CH=CH—,
—C$_3$H$_6$—C≡C—CH$_2$—, —CH$_2$—CH=CH—
CH=CH—CH$_2$—, —CH=CH—CH=CH—C$_2$H$_4$—,
—CH$_2$—CH=CH—C(CH$_3$)=CH—, —CH$_2$—
CH=C(CH$_3$)—CH=CH—, —CH$_2$—C(CH$_3$)
=CH—CH=CH—, —CH(CH$_3$)—CH=CH—
CH=CH—, —CH=CH—CH$_2$—C(CH$_3$)=CH—,
—CH(CH$_3$)—C≡C—CH$_2$—, —CONH—,
—NHCO—, —CH$_2$—CONH—, —CONH—CH$_2$—,
—NHCO—CH$_2$—, —CH$_2$—NHCO—;

wherein m is an integer from 1 to 10; or

X$^4$—R$^A$ and X$^3$—R$^B$ can form together a cyclic ring selected from the group consisting of:

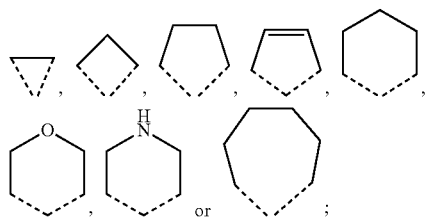

and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

In fact, it is a finding of this invention that a connection at R$^C$—R$^L$-position results in macrocyclic molecules which are more stabilized against metabolism as well as structurally more rigid, and at the same time maintain the selective binding to FKBP51, e.g. they discriminate not only against FKBP52.

The term "ligand capable of binding" herein means any molecule, which is capable to bind to the target molecule with an affinity of at least 10 μM, preferable <1 μM, more preferable <100 nM and most preferably <10 nM.

In one embodiment, the linker L of the HAM-FKB51-Inhibitor of the present invention is represented by:

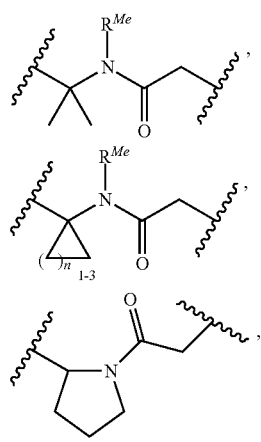

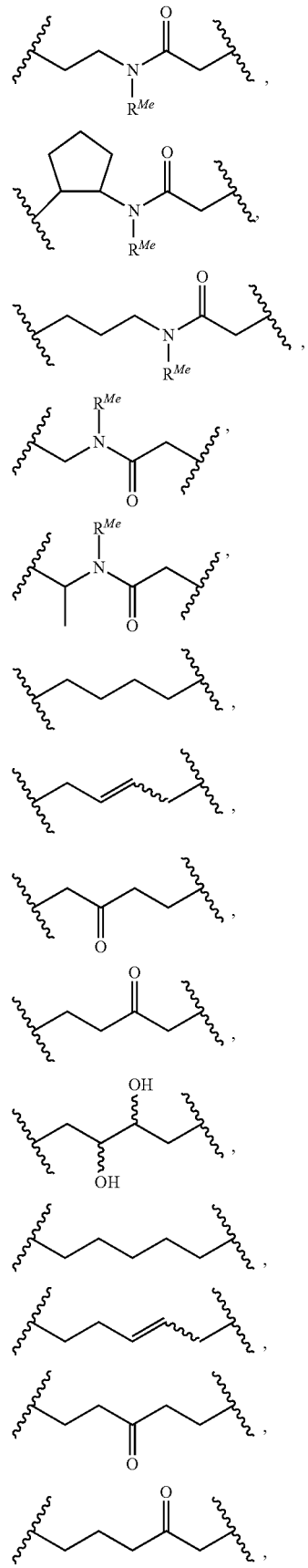

-continued

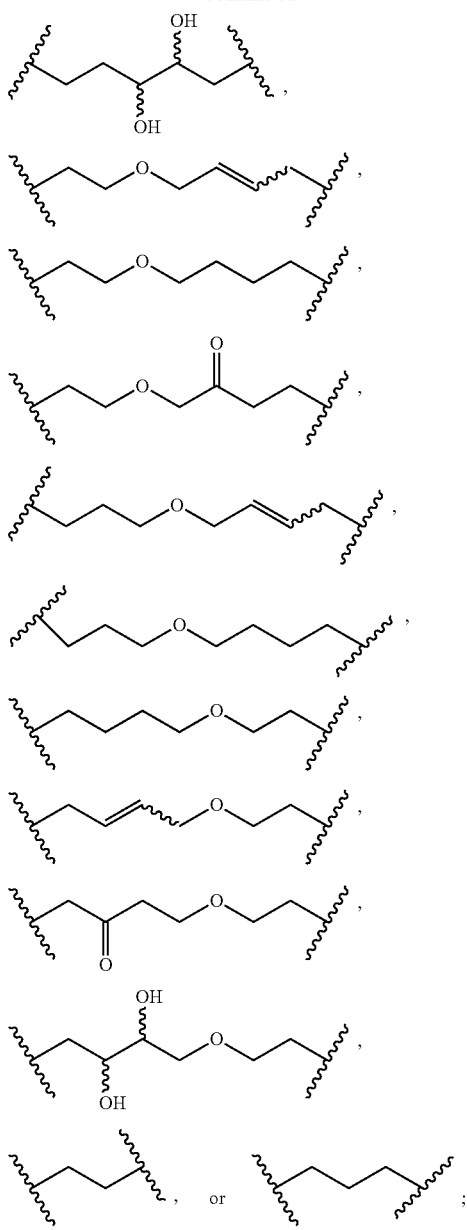

wherein L can be connected to $R^C$ and $R^L$ as follows: $R^C$-L-$R^L$ or $R^L$-L-$R^c$.

In one embodiment, the HAM-FKB51-Inhibitor of the present invention is represented by the core structures:

(Subformula I)

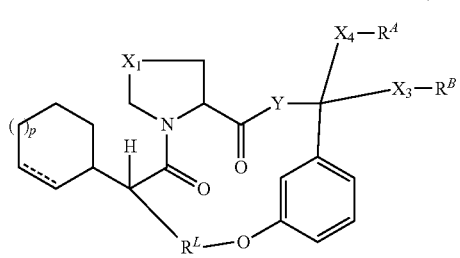

-continued (Subformula II)

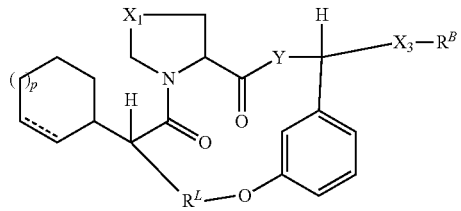

(Subformula III)

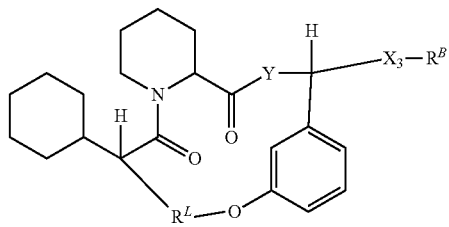

(Subformula IV)

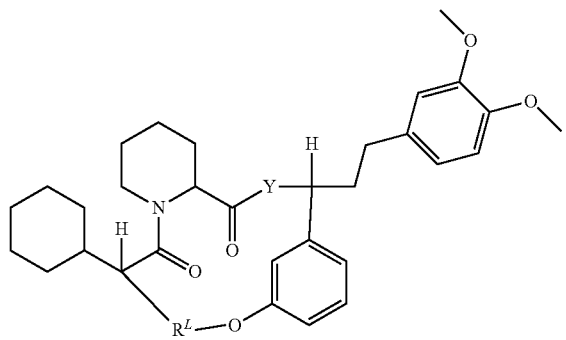

In another embodiment, the HAM-FKB51-Inhibitor of the present invention is selected from a group comprising the structures:

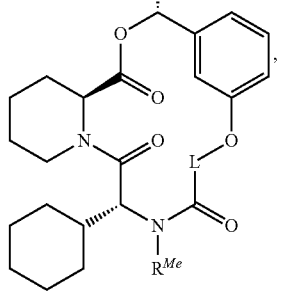

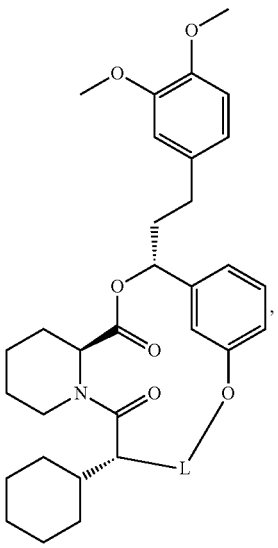

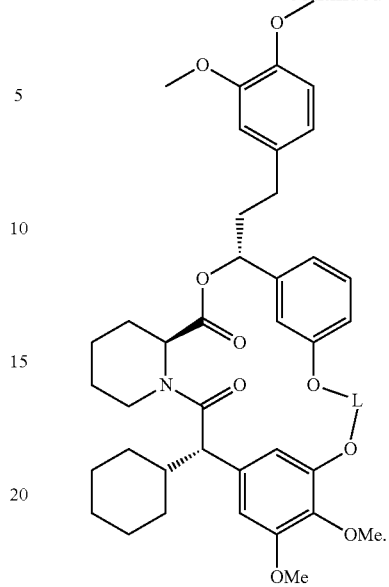

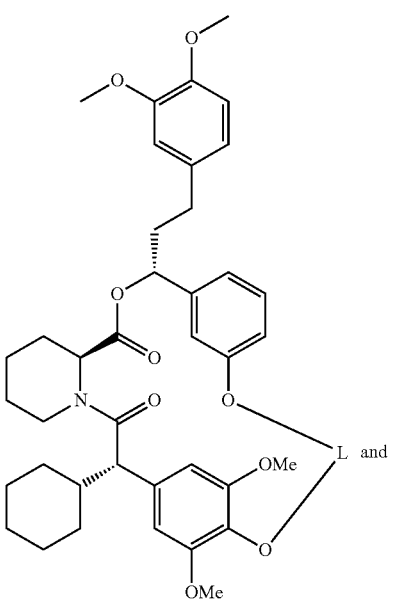

and

In further embodiments enantiomers, stereoisomeric forms, mixtures of enantiomers, anomers, deoxy-forms, diastereomers, mixtures of diastereomers, prodrugs, tautomers, hydrates, solvates and racemates of the above mentioned compounds are also encompassed, as well as pharmaceutically acceptable salts thereof.

Pharmaceutical Compositions

The present invention also comprises pharmaceutically acceptable salts of the compounds according to the general formula (I) and the subformulas (II)-(IV), all stereoisomeric forms of the compound as well as solvates, especially hydrates, tautomers or prodrugs thereof.

The expression "tautomer" is defined as an organic compound that is interconvertible by a chemical reaction called tautomerization. Tautomerization can be catalyzed preferably by bases or acids or other suitable compounds.

The expression "prodrug" is defined as a pharmacological substance, a drug, which is administered in an inactive or significantly less active form. Once administered, the prodrug is metabolized in the body in vivo into the active compound.

In case, the inventive compounds bear basic and/or acidic substituents, they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, mandelic acid, o-methylmandelic acid, hydrogen-benzenesulfonic acid, picric acid, adipic acid, tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) and the subformulas (II)-(IV), with a solution of an acid, selected out of the group mentioned above.

Some of the compounds of the present invention may be crystallised or re-crystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain compounds of the general formula (I) and the subformulas (II)-(IV) may exist in the form of optical isomers if substituents with at least one asymmetric center are present, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Where a compound according to the general formula (I) and the subformulas (II)-(IV) contains an alkene moiety, the alkene can be presented as a cis- or trans-isomer or a mixture thereof.

When an isomeric form of a compound of the invention is provided substantially free of other isomers, it will preferably contain less than 5% w/w, more preferably less than 2% w/w and especially less than 1% w/w of the other isomers.

Another aspect of the present invention relates to the use of the HAM-FKB51-Inhibitor of the present invention as drugs, i.e. as pharmaceutically active agents applicable in medicine.

Therefore, one aspect of the present invention is that the compounds according to the general formula (I) and the subformulas (II)-(IV) are suitable for use to eliminate of FKBP-function in an organism. It is preferred if said compound is suitable to eliminate the function of the FK506-binding protein 51 (FKBP51).

FKBP51 has been implicated in numerous in human diseases. Consequently, FKBP51 is a target which is addressed in order to prevent and/or treat the diseases disclosed in the literature.

Thus, HAM-FKB51-Inhibitor of the present invention can be used as pharmaceutically active agent in medicine.

Preferred, the HAM-FKB51-Inhibitor of the present invention can be used for treatment, or for the preparation of a pharmaceutical formulation for prophylaxis and/or treatment of these FKBP51-associated diseases.

The inventive compound of any one of general formula (I) and/or the subformulas (I)-(IV) is used in the manufacture of a medicament or of a pharmaceutical composition for the treatment and/or prevention of FKBP51-associated diseases.

Another aspect of the present invention relates to a method of treating FKBP51-associated diseases comprising administration a therapeutically effective amount of at least one inventive compound or a pharmaceutical composition comprising at least one inventive compound.

These FKBP51-associated diseases include psychiatric and neurodegenerative diseases, disorders and conditions, metabolic diseases such as localized adiposity or obesity, diabetes or obesity-induced complications, pain disorders, especially neuropathic pain, inflammatory pain, drug-induced pain, diabetic pain; sleep disorders, neuroprotection or neuroregeneration, the treatment of neurological disorders, the treatment of diseases relating to neurodegeneration, the treatment of cancers such as malignant melanoma, glioma or acute lymphoblastic leukaemia and especially steroid-hormone dependent cancers such as prostate cancer, the treatment of glucocorticoid hyposensitivity syndromes and peripheral glucocorticoid resistance, asthma, especially steroid-resistant asthma, and the treatment of infectious diseases, stimulating neurite growth or neuroregeneration, neuroprotection, the use as wound healing agents for treating wounds resulting from injury or surgery; the use in limiting or preventing hemorrhage or neovascularization; for treating macular degeneration, and for treating oxidative damage to eye tissues, for treating a metabolic disorder or for pain relief.

The HAM-FKB51-inhibitor of the present invention are preferably suitable for treatment, or for the preparation of a pharmaceutical formulation for prophylaxis and treatment of psychiatric diseases. It is especially preferred if this psychiatric disease is an affective disorder (ICD-10 classification: F30-F39) or an anxiety disorder.

Among the hundreds of different neurodegenerative disorders, the attention has been given only to a handful, including Alzheimer's disease, Parkinson's Disease, and amyotrophic lateral sclerosis.

Among the glucocorticoid hyposensitivity syndromes, the attention has been given to the group of related diseases enclosing resistant asthma, eosinophilic esophagitis, AIDS, rheumatoid arthritis, hypertension.

Among the metabolic disorders, the attention has been given to obesity and diabetes.

Among the cancers, the attention has been given to malignant melanoma, acute lymphoblastic leukaemia, gliomas, idiopathic myelofibrosis, pancreatic and breast cancers, steroid-hormone dependent cancers or prostate cancer.

Among the pain indications, the attention has been given to chronic pain, neuropathic pain and to fibromyalgia.

Therefore, another aspect of the present invention is directed to pharmaceutical compositions comprising at least one compound of the present invention as active ingredient, together with at least one pharmaceutically acceptable carrier, excipient and/or diluents. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention, and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 wt. % of the benzothiophene-1,1-dioxide derived compound and/or the respective pharmaceutically active salt as active ingredient.

Suitable binders include starch, gelatine, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may comprise an additional pharmaceutically active compound or drug. The pharmaceutically active compound or drug may belong to the group of glucocorticoids. Thus, an embodiment of the current invention comprises the administration of a compound of the current invention in addition to a co-administration of glucocorticoids.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and pacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatines or starch for holding or containing compositions comprising the active ingredient(s). Capsules with hard shells are typically made of blended of relatively high gel strength gelatines from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 wt. %, and more preferably from about 30 to about 60 wt. %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 wt. % of the composition, more preferably from about 5 to about 10 wt. %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatine and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 wt. % of the composition, preferably from about 3 to about 10 wt. %, and more preferably from about 3 to about 6 wt. %.

Lubricants refer to a class of substances, which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D-,L-leucine. Lubricants are usually added at the very last step before compression, since they must be present at the surface of the granules. The amount of lubricant in the composition may range from about 0.2 to about 5 wt. % of the composition, preferably from about 0.5 to about 2 wt. %, and more preferably from about 0.3 to about 1.5 wt. % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 wt. % of the final composition, preferably from about 0.5 to about 2 wt. %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 wt. % of the composition, preferably from about 0.1 to about 1 wt. %.

Said pharmaceutical compositions may further comprise at least one HAM-FKB51-Inhibitor of the present invention of the general formula (I) and the subformulas (II)-(IV).

The pharmaceutical compositions may further comprise at least one further active agent. It is preferred if this active agent is selected from the group consisting of anti-depressant and other psychotropic drugs. It is further preferred if the anti-depressant is selected from amitriptyline, amioxide clomipramine, doxepine, duloxetine, imipramine trimipramine, mirtazapine, reboxetine, citaloprame, fluoxetine, moclobemide and sertraline.

Medical Uses

Another aspect of the invention is to provide compounds and/or pharmaceutically acceptable salts thereof, which can be used as pharmaceutically active agents, especially for the treatment of psychiatric disorders and neurodegenerative diseases, disorders and conditions, for treating vision disorders and/or improving vision; for treating memory impairment and/or enhancing memory performance and for treating alopecia, as well as compositions comprising at least one of those compounds and/or pharmaceutically acceptable salts thereof as pharmaceutically active ingredients.

A further aspect of the invention is to provide methods for preparing said compounds.

The object of the present invention is solved by the teaching of the independent claims. Further advantageous features, aspects and details of the invention are evident from the dependent claims, the description, and the examples of the present application.

Methods of Production

Another aspect of the invention is to provide methods for production of the compounds of the present invention as well as pharmaceutical compositions. The details of synthesis-steps are outlined in the example section.

DETAILED DESCRIPTION OF THE INVENTION

Examples

Figure 1:
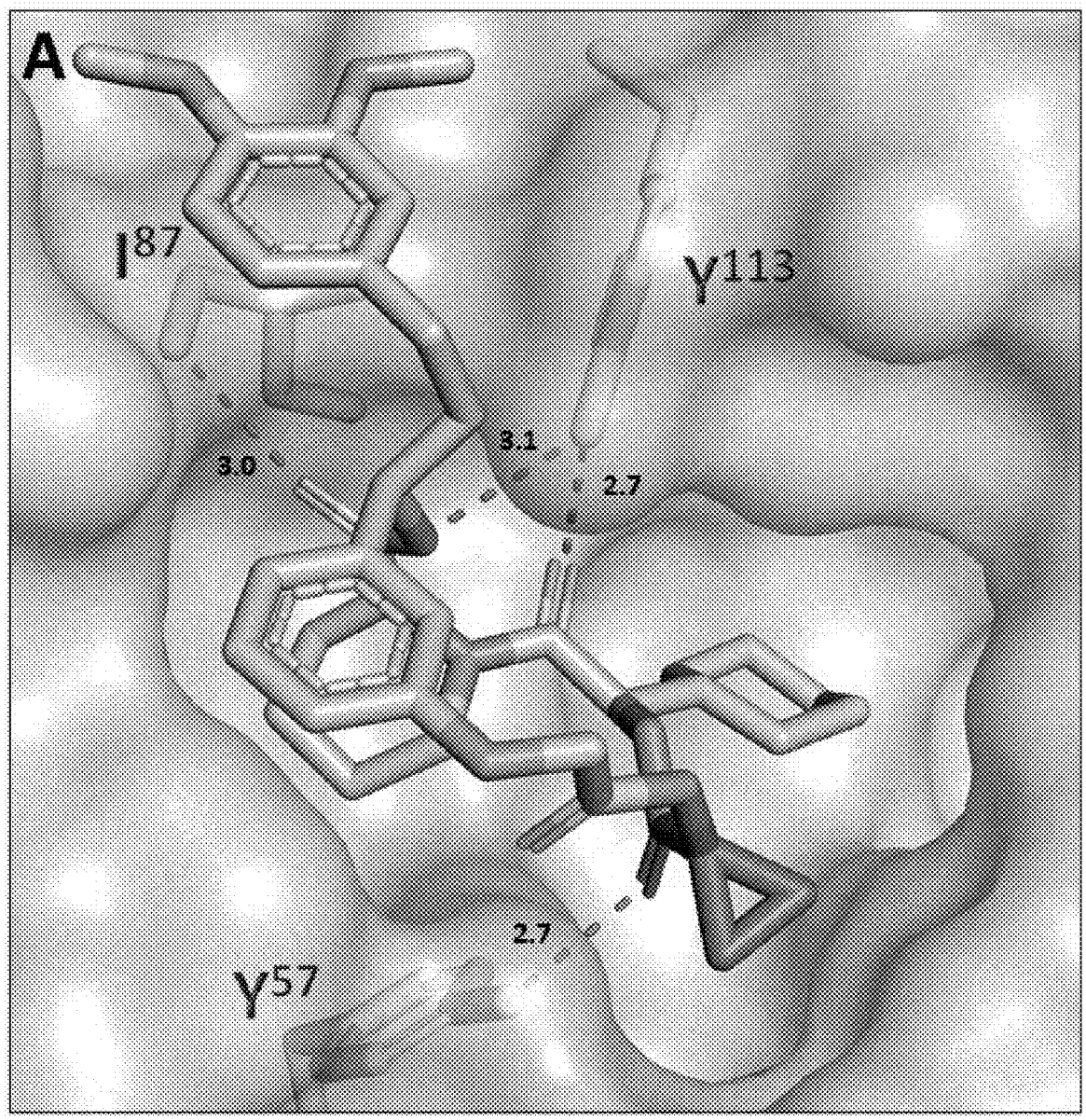
FIG. 1 A) Crystal structure of the FK1 domain of FKBP51 in complex with the macrocycle (2'R,5'S,12'R)-12'-cyclohexyl-2'-[2-(3,4-dimethoxyphenyl)ethyl]-3',19'-dioxa-10', 13',16'-triazaspiro[cyclopropane-1,15'-tricyclo[18.3.1.0$^{5,10}$] tetracosane]-1'(24'),20',22'-triene-4',11',14',17'-tetrone 86, key interactions with the residues $I^{87}$, $Y^{113}$ and $Y^{57}$ indicated as broken line (distance annotated in Å)
Figure 2:
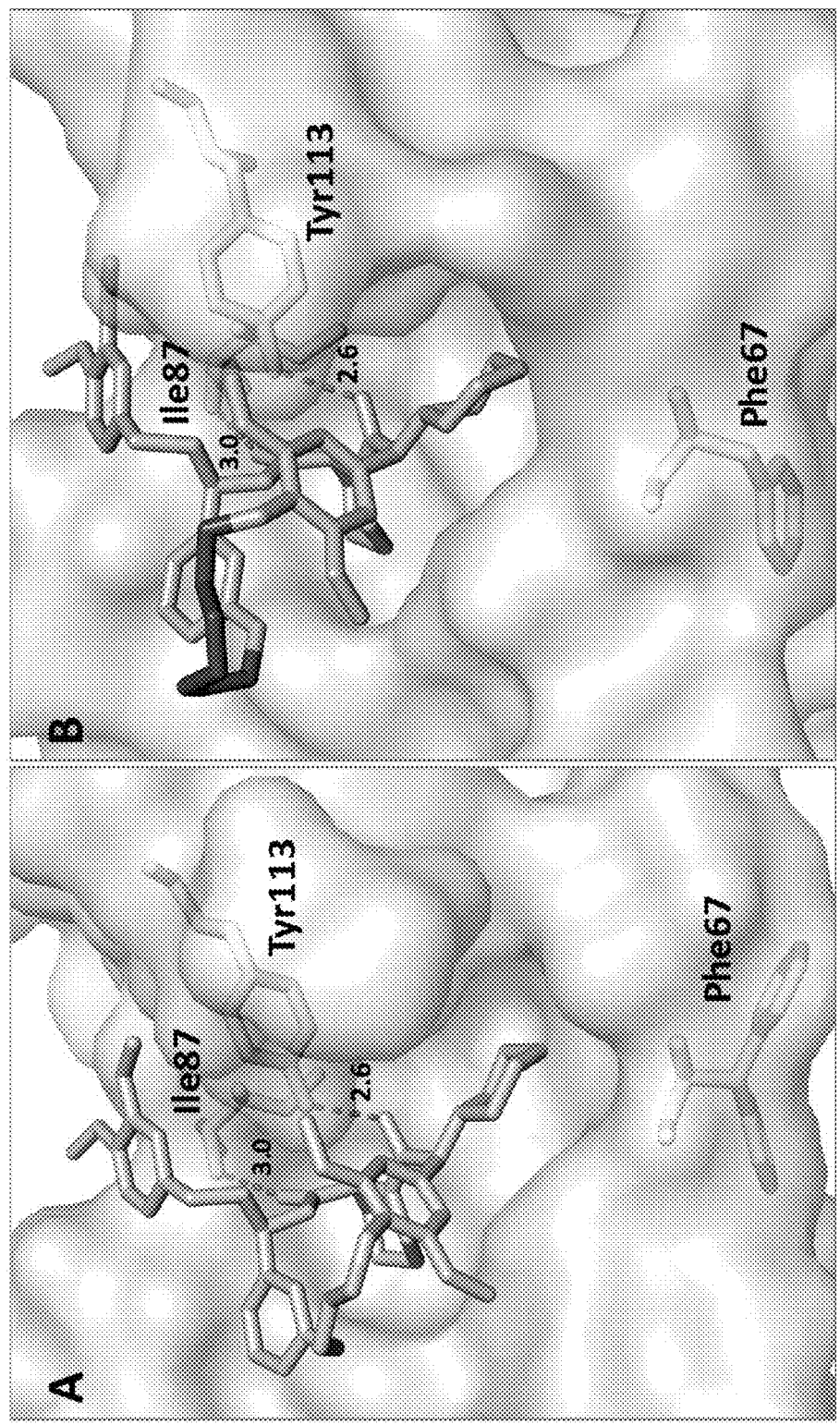
FIG. 2 X-ray structures of macrocyclic ligands in complex with the FK506-binding domain of FKBP51; Lys121 has been omitted for clarity. Hydrogen bonds to Ile87 and Tyr113 are indicated as dotted lines. Phe67 has been displaced by the cyclohexyl moiety upon binding of the ligands (and adopts two rotamers in representation A). Novel linker moieties are highlighted in black. (A) Surface representation of FKBP51 in complex with macrocycle 56 (PDB: 7A6X). (B) Surface representation of FKBP51 in complex with macrocycle 33-(Z) (PDB: 7A6W).

Example 1: Crystallographic Analysis and Design of the Macrocyclization Strategy We used existing 3D information of high-affinity inhibitors in complex with the FK1 domain of FKBP51 to identify promising attachment points for the design of macrocyclic SAFit analogs. The crystal structures of known, selective FKBP51 inhibitors served as templates for our structure-based rigidification strategy. The FKBP51-iFit4 complex (pdb: 4TW7) illustrates two aryl rings (A and B) which are directly appended to the core binding elements of pipecolate and cyclohexyl ring, but projecting away from the protein binding surface and thereby presenting possible sites for a linkage. X-ray analysis and modeling led us to postulate that macrocyclization within this structural framework of the known inhibitor series would lead to macrocyclic ligands that could maintain all the binding interactions observed for the existing acyclic analogs. Pursuing this idea, we designed and synthesized macrocycles with different connection points in the ring A and applied different linkers that seemed suitable to fit the targeted binding site for the first macrocyclic FKBP51 inhibitors.

Example 2: Synthesis of Para- and Meta-Aryl-Substituted Cyclization Precursors

The synthetic path towards the cyclization precursors for para-aryl-linked macrocycles starts with commercially available phenol 1 (Scheme 1). After TPDBS protection of the para hydroxyl group, the carboxylic acid was pre-activated to introduced the chiral auxiliary. The key step in this sequence is the introduction of the cyclohexene ring via α-alkylation of the enolate derived through deprotonation of 2. Hydrogenation of the alkene followed by hydrolysis affords the chiral TBDPS-protected intermediate 6 in 33% yield over six steps. Amide coupling with amine 15 and TBAF-mediated desilylation provides the phenol 8, which is further derivatized to the cyclization precursors (9-12) through alkylation with the corresponding allyl-containing building blocks.

The synthesis of the RCM precursors for meta-aryl-linked macrocycles turned out to be far more challenging, since six steps were necessary to prepare the hydroxy group in meta-position of the aryl ring accessible for later derivatizations. 18 was synthesized over five steps in 51% yield

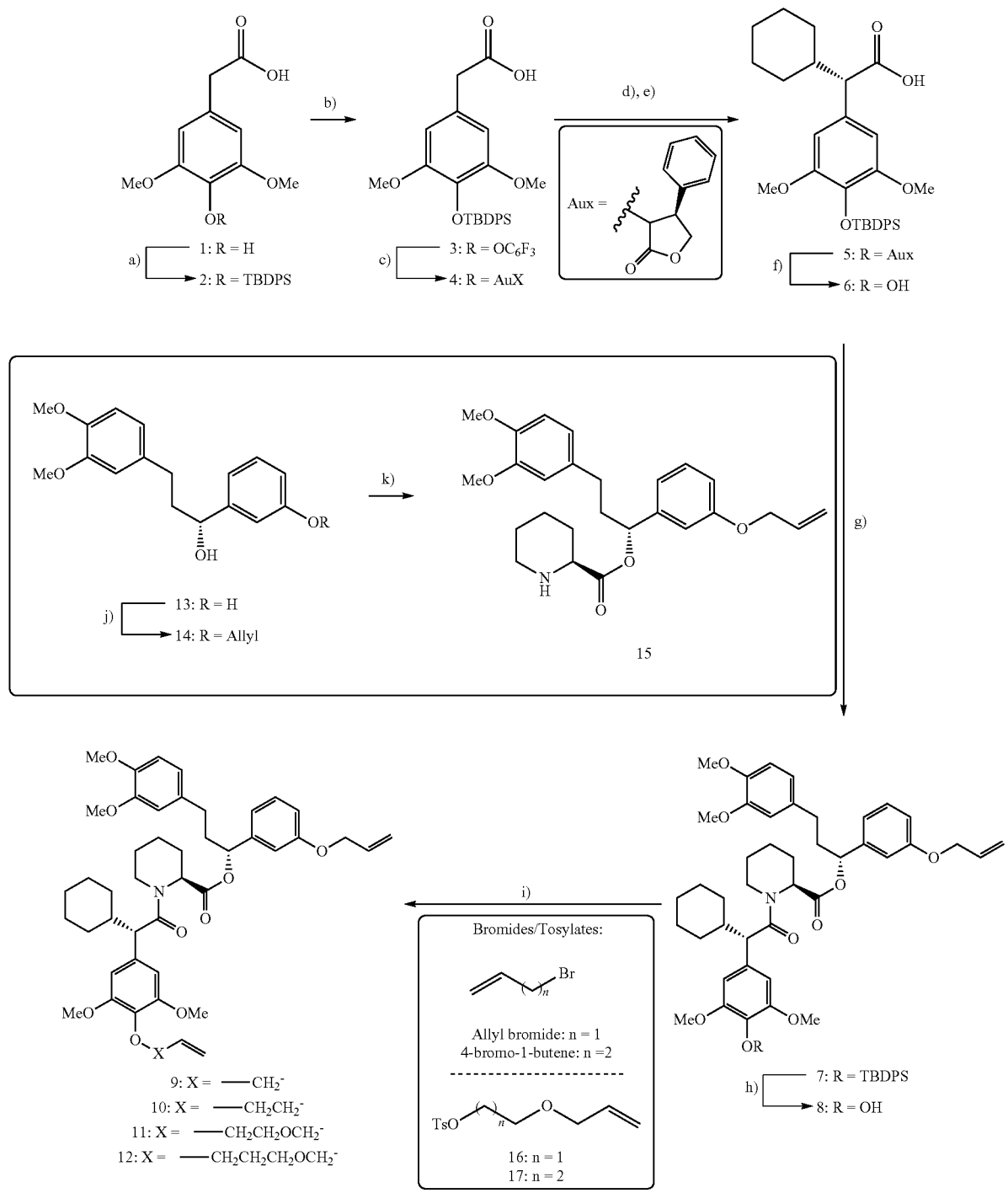

Scheme 1. Synthesis of para-aryl-substituted cyclization precursors[a]

[a]Reagents and conditions: a) TBDPSCl, imidazole, DCM/DMF, rt; then K$_2$CO$_3$, THF/H$_2$O, rt, 93%; b) C$_6$F$_5$OH, EDC, 4-DMAP, DCM, rt, 92%; c) (S)-4-phenyloxazolidin-2-one, n-BuLi THF, 0° C. - rt, 81%; d) 3-bromocyclohexene, LiHMDS, THF, -78° C. - rt, 50%; e) Pd/C, H$_2$, CH/EA, rt, 99%; f) LiOH, H$_2$O$_2$, THF/H$_2$O, rt, 95%; g) 15, HATU, DIPEA, DCM/DMF, rt, 88%; h) TBAF, THF, 0° C. - rt, 95%; i) Bromide or tosylate, K$_2$CO$_3$, MeCN, reflux, 92-98%; j) Allyl bromide, K$_2$CO$_3$, acetone, reflux, 96%; k) (S)-Fmoc-Pip-OH, DCC, 4-DMAP, DCM, 0° C. - rt; then 4-methylpiperidine, DCM, rt, 67% (2 steps);

from commercially available 3,4,5-trimethoxyphenylacetic acid following literature known procedures. Methylation of the remaining hydroxy groups in 18 afforded 19 in a good yield of 93%. After substantial exploration of several alkylation conditions, we referred to a direct racemic alkylation protocol, where the carboxylic ester 19 is converted to the corresponding enolate with LiHMDS, alkylated with 3-bromocyclohexene and the methyl ester 20 is afterwards hydrolyzed in a mixture of aqueous LiOH and THF, to generate carboxylic acid 21. Conversion to the corresponding acyl chloride with SOCl$_2$ and subsequent Schotten-Baumann reaction with L-Pipecolic acid and aqueous KOH in 1,4-dioxane provided the corresponding amide as a mixture of four diastereomers (not shown). Fortunately, the acyl chloride-activation/amidation sequence provides a good yield of 71% with additional 28% of recovered 21 after hydrolysis of the Schotten-Baumann reaction. Pd/C-catalyzed hydrogenation effected alkene reduction and simultaneous deprotection of the benzyl ether to afford 22b and desired 22a as a 1:1 mixture of diastereomers that could be separated by silica gel chromatography. Alkylation to install the alkene for later RCM followed by ester cleavage afforded the carboxylic acids 23-26 in very good yields (81-96%) over two steps. After substantial optimization to minimize epimerization, esterification with alcohol 14 was achieved with EDC and an excess of 4-pyrrolidinopyridine, which afforded 59-64% of the desired esters 27-30 with low amounts of epimerization (<5%).

Two key findings substantially contributed to the optimized conditions: (a) the excess use of 4-pyrrolidinopyridine, a more reactive analogue to standard DMAP and (b) the use of toluene as a non-polar solvent, probably due to decreased stabilization of the polar intermediates that lead to epimerization.

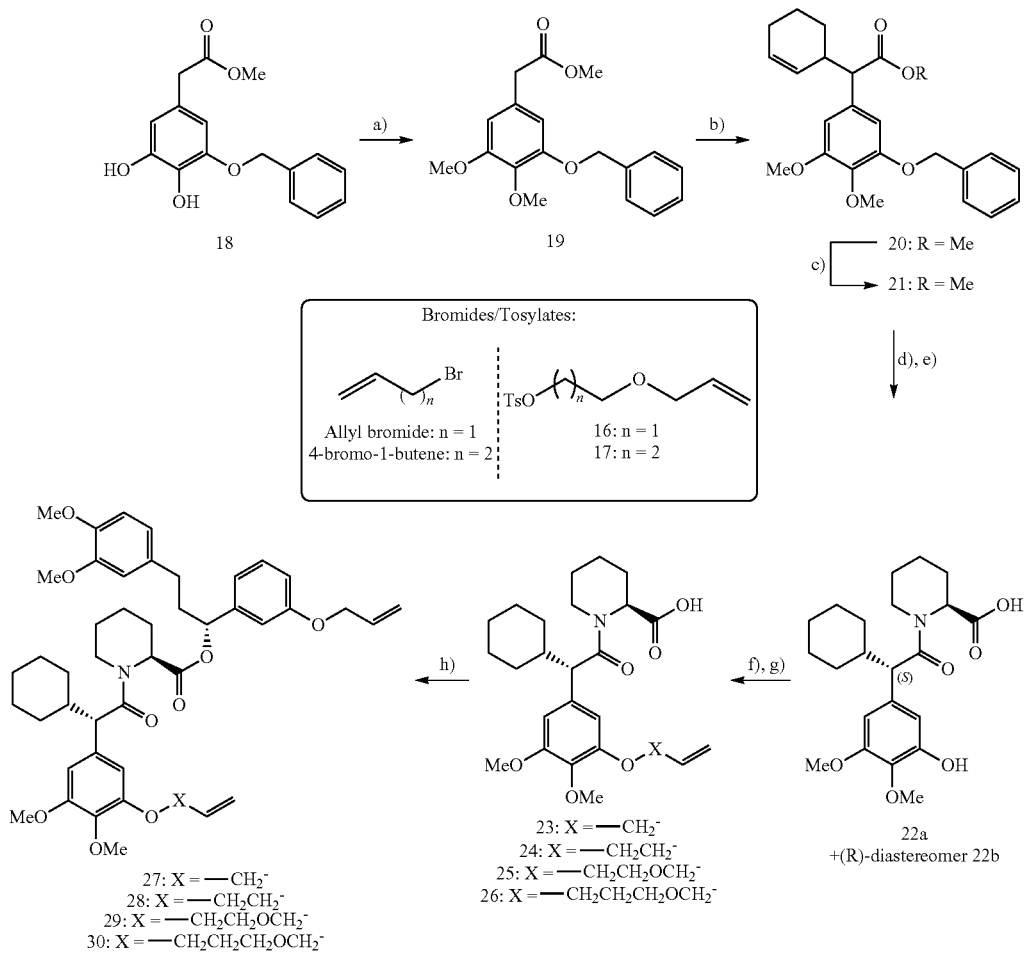

Scheme 2. Synthesis of meta-aryl-substituted cyclization precursors$^a$ $^a$Reagents and conditions: a) MeI, K$_2$CO$_3$, DMF, rt, 93%; b) 3-Bromocyclohexene, LiHMDS, THF, -78° C.-rt, 94%; c) LiOH, THF/H$_2$O, rt, 91%; d) SOCl$_2$, DCM, reflux; then L-Pipecolic acid, KOH aq, 1,4-dioxane, 0° C.-rt, 71% + 28% of recovered substrate 21; e) Pd/C, H$_2$, THF/MeOH, rt, 44% for 22b, 41% for 22a, separation of isomers by flash column chromatography; f) Bromide or Tosylate, K$_2$CO$_3$, MeCN, reflux, 87-99%; g) LiOH, THF/MeOH/H$_2$O, rt, 90-97%; h) 14, EDC, 4-(pyrrolidin-1-yl)pyridine, toluene, 0° C.-rt, 59-64%;

Example 3: Synthesis of Macrocyclic FKBP51 Ligands

The precursors for the para- (9-12) and the meta-series (27-30) were cyclized via ring-closing metathesis to give the macrocycles (31-38, Scheme 3 and 73-75 Scheme 4). The RCM always afforded mixtures of E/Z alkene isomers, except for the longest linker of each series (34, 38 and 75), where only the E-alkenes were observed. Fortunately, we were able to separate all E/Z-alkene mixtures and hence tested the influence of alkene geometry on FKBP51 binding affinity.

The geometry of the alkene bonds was determined by $^1$H-$^1$H-homonuclear decoupling of the two sets of vicinal methylene protons, providing informative coupling constants between the double bond protons for at least one of the two isomers.

Hydrogenation of the alkenes afforded the saturated macrocycles (39-46, 76 and 80).

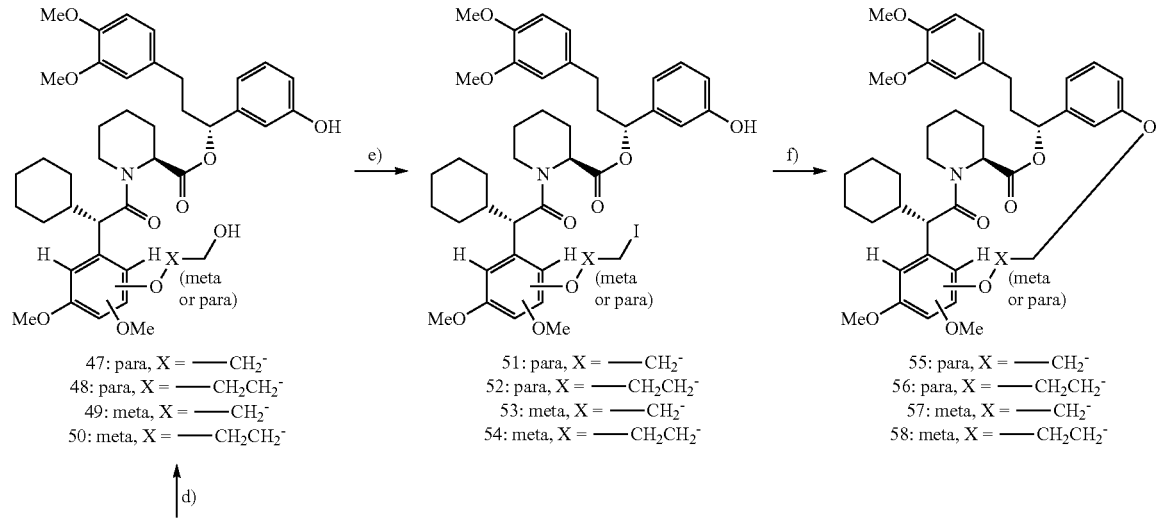

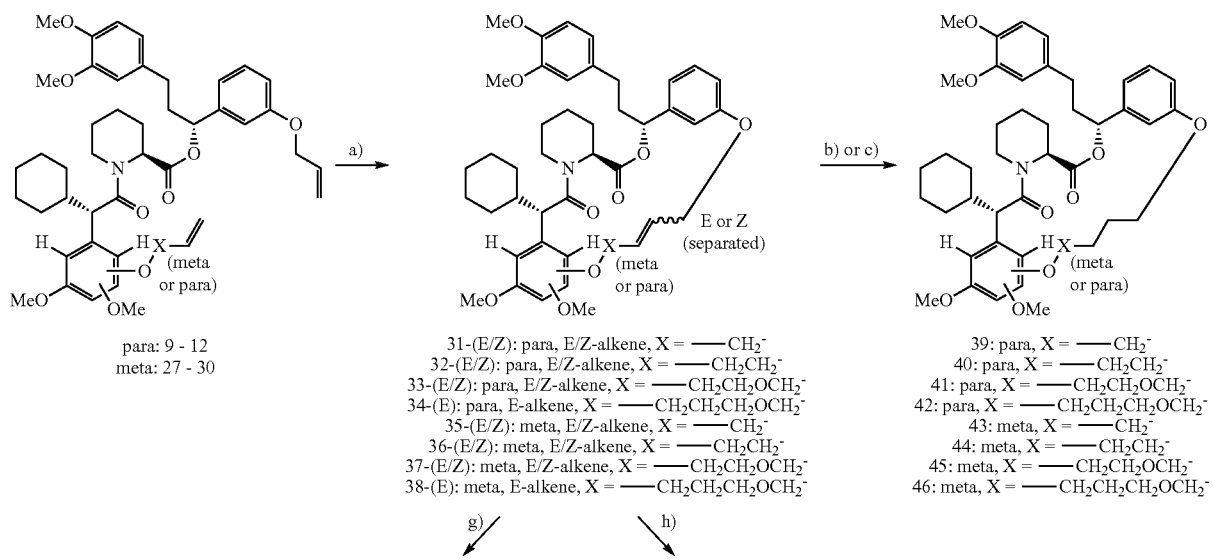

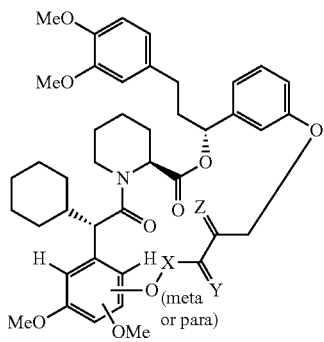

59: para, X = —CH$_2$-, Y = none, Z = O
60: meta, X = —CH$_2$-, Y = none, Z = O
61a: meta, X = —CH$_2$CH$_2$-, Y = O, Z = none
61b: meta, X = —CH$_2$CH$_2$-, Y = none, Z = O
62: meta, X = —CH$_2$CH$_2$OCH$_2$-, Y = O, Z = none

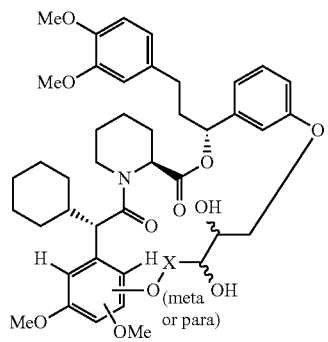

63: para (isomer mixture, 2:1)
64a/64b: meta (two pure isomers)

[a]Reagents and conditions: a) Grubbs-II, DCM, reflux, 33-78%; b) Pd/C, H$_2$, MeOH, rt, 37-45% (for 39 and 40); c) RhCl(PPh$_3$)$_3$, H$_2$, toluene or MeOH/THF, rt, 66-87% (for 41-46); d) RhCl(PPh$_3$)$_3$, DABCO, EtOH/H$_2$O, reflux, 16-47%; e) I$_2$, PPh$_3$, imidazole, toluene or DCM, rt, 38-85%; f) K$_2$CO$_3$, MeCN, reflux, 26-81%; g) Pd(OAc)$_2$, p-BQ, HBF$_4$, MeCN/H$_2$O, rt, 33-67%; h) OsO$_4$, HMO, H$_2$O/acetone. 0° C. - rt, 26-40%

The shorter variants of alkene macrocycles (31-(E), 35-(Z), 73 and 75) were applied to Upjohn dihydroxylation to introduce additional functionality into the macrocyclic frame. Fortunately, we were able to separate the resulting pair of isomers for the meta-series (64a/b) and for 73 (resulting in 78 and 79), but not for the para-series (63) and 75 (resulting in 82). Furthermore, the alkenes 31-(E), 35-(Z), 36-(E), 37-(E), 73 and 75 were oxidized under Wacker conditions to obtain the corresponding ketones (59, 60, 61a/b, 62, 77 and 81). Interestingly, the oxidation of the short-chain alkenes (31-(E) and 35-(Z)) resulted in ketones 59 and 60 as the sole products of two possible regioisomers. Oxidation of the medium-length linker (36-(E)) provided major and minor product regioisomers (61a and 61b), whereas oxidation of the longest linker resulted in a single isolable product isomer (62).

The bis-O-allyl intermediates bearing an alkyl O-allyl moiety (11, 12, 29 and 30) offered the potential for an additional approach towards cyclization. Global deallylation of these intermediates with Wilkinson catalyst yielded the diols (47-50), which were transformed into the corresponding mono-iodides (51-54). Subsequent ring-closure was achieved through intramolecular $S_N^2$ reaction under high dilution to yield the smallest macrocycles of the para- (55 and 56) and meta-series (57 and 58).

Scheme 4 Synthetic pathway towards macrocyclic FKBP51 ligands[a]

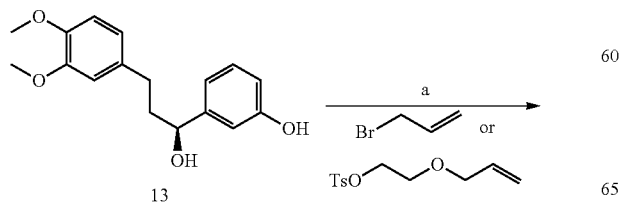

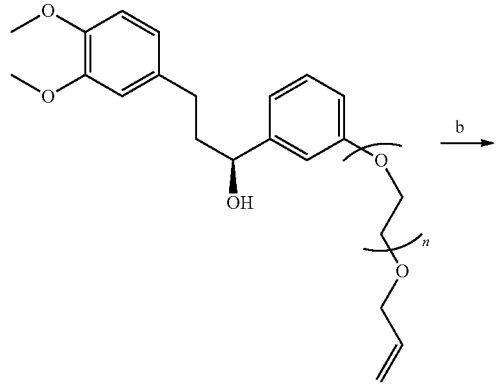

65 n = 0
66, n = 1

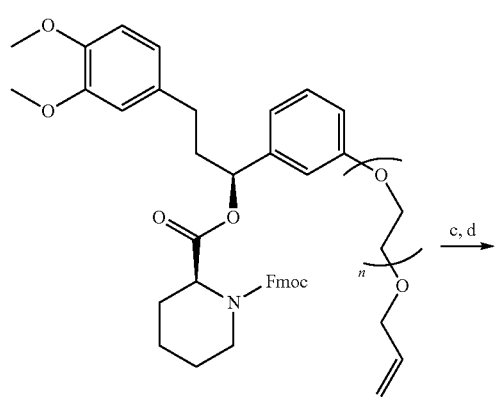

67 n = 0
68, n = 1

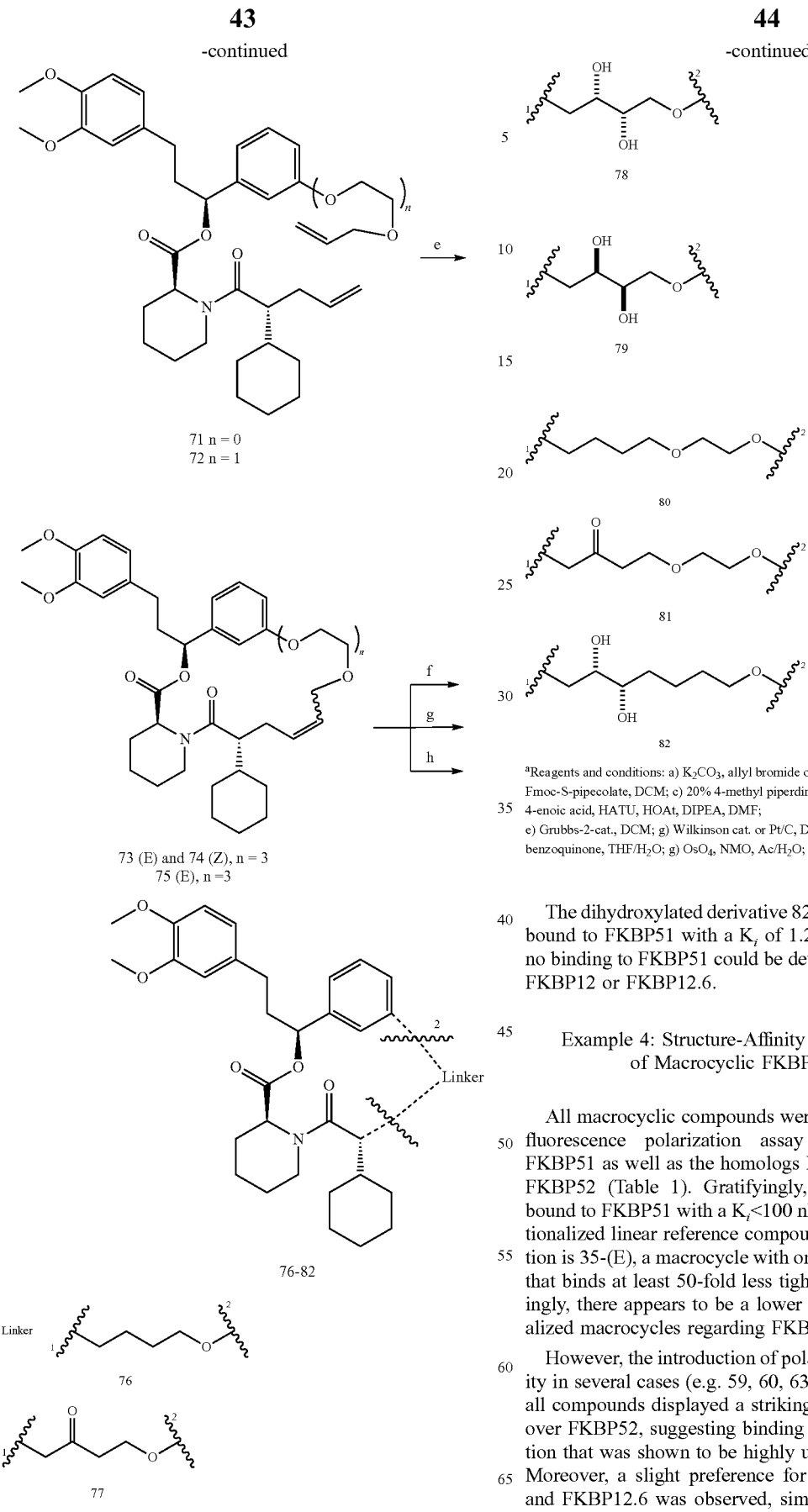

The dihydroxylated derivative 82 of the larger macrocycle bound to FKBP51 with a $K_i$ of 1.2 µM, whereas for 76-81 no binding to FKBP51 could be detected. 82 did not bind to FKBP12 or FKBP12.6.

Example 4: Structure-Affinity Relationship (SAR) of Macrocyclic FKBP51 Ligands

All macrocyclic compounds were tested in a competitive fluorescence polarization assay for binding towards FKBP51 as well as the homologs FKBP12, FKBP12.6 and FKBP52 (Table 1). Gratifyingly, almost all compounds bound to FKBP51 with a $K_i$<100 nM, similar to the unfunctionalized linear reference compound A1. A notable exception is 35-(E), a macrocycle with one of the smallest linkers, that binds at least 50-fold less tightly to FKBP51. Interestingly, there appears to be a lower limit for the unfunctionalized macrocycles regarding FKBP51 binding affinity.

However, the introduction of polar groups increased affinity in several cases (e.g. 59, 60, 63, or 64a/b). Gratifyingly, all compounds displayed a striking selectivity for FKBP51 over FKBP52, suggesting binding to a Phe67$^{out}$ conformation that was shown to be highly unfavorable for FKBP52. Moreover, a slight preference for FKBP51 over FKBP12 and FKBP12.6 was observed, similar to previous findings for acyclic SAFit analogs.

TABLE 1
FKBP51 Binding Affinities of macrocyclic ligands[a]
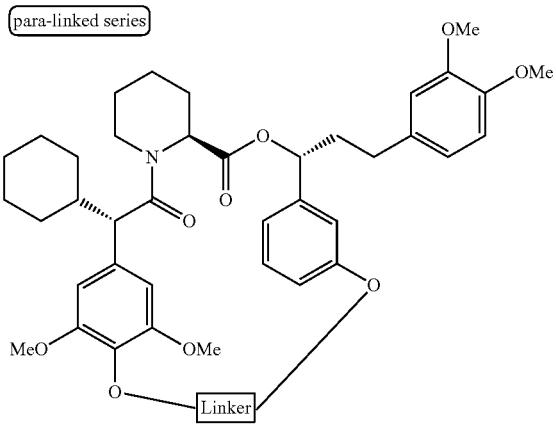 [SMILES: COc1cccc([C@@H](CCc2ccc(OC)c(OC)c2)OC(=O)[C@@H]2CCCCN2C(=O)[C@H](c2cc(OC)c(OC)c(OC)c2)C2CCCCC2)c1]
para-linked series
| LINKER | Cpd | $K_i$ [nM] FKBP51FK1 | $K_i$ [nM] FKBP12 | $K_i$ [nM] FKBP12.6 |
|---|---|---|---|---|
| 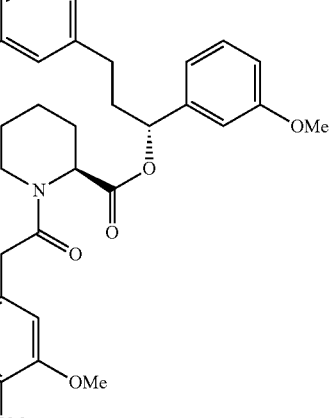 | A1 (ACYCLIC REFERENCE) | 94 | 222 | 199 |
|  | 55 | 64 | 412 | 190 |
|  | 56 | 67 | 384 | 211 |
|  | 31-(E) | 56 | 289 | 263 |
|  | 31-(Z) | 70 | 261 | 328 |
|  | 39 | 53 | 159 | 191 |

TABLE 1-continued

| Structure | Col1 | Col2 | Col3 | Col4 |
|---|---|---|---|---|
| (ketone, CH2CH2-C(=O)-CH2CH2) | 59 | 8 | 53 | 30 |
| (diol, CH2CH(OH)CH(OH)CH2) | 63[b] | 11 | 97 | 83 |
| (diol stereoisomer) | — | — | — | — |
| (E-alkene, CH2CH2CH=CHCH2CH2) | 32-(E) | 126 | 404 | 347 |
| (Z-alkene) | 32-(Z) | 80 | 189 | 237 |
| (hexamethylene) | 40 | 102 | 204 | 198 |
| (ketone, longer) | — | — | — | — |
| (ketone, CH2CH2CH2-C(=O)-CH2CH2) | — | — | — | — |
| (E-ether-alkene) | 33-(E) | 131 | 534 | 361 |
| (Z-ether-alkene) | 33-(Z) | 76 | 309 | 186 |
| (ether alkyl) | 41 | 118 | 449 | 230 |
| (ether ketone) | — | — | — | — |
| (E-ether-alkene, longer) | 34-(E) | 94 | 430 | 315 |

TABLE 1-continued
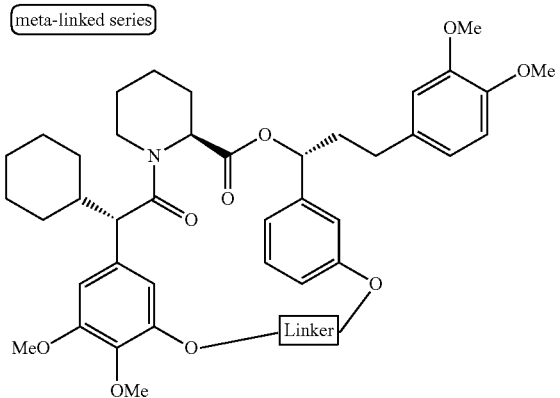 [SMILES: COc1cccc([C@@H](CCc2ccc(OC)c(OC)c2)OC(=O)[C@@H]2CCCCN2C(=O)[C@H](c2cc(OC)c(OC)c(OC)c2)C2CCCCC2)c1]
| LINKER | Cpd | $K_i$ [nM] FKBP51FK1 | $K_i$ [nM] FKBP12 | $K_i$ [nM] FKBP12.6 |
|---|---|---|---|---|
| (ether linker) | 42 | 70 | 350 | 187 |
| (meta-linked series reference) | — | — | — | — |
| (propyl) | 57 | 47 | 308 | 78 |
| (butyl) | 58 | 54 | 401 | 87 |
| (E-alkene) | 35-(E) | >5 μM | >100 μM | >100 μM |
| (Z-alkene) | 35-(Z) | 93 | 173 | 192 |
| (pentyl) | 43 | 30 | 92 | 62 |

TABLE 1-continued
| Structure | # | | | |
|---|---|---|---|---|
| 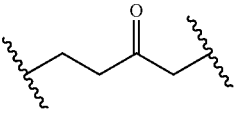 [SMILES: *CCC(=O)C*] | 60 | 10 | 54 | 28 |
| 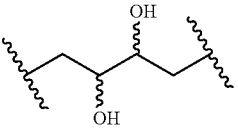 [SMILES: *CC(O)C(O)C*] | 64a | 4 | 23 | 10 |
| 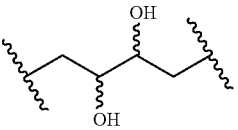 [SMILES: *CC(O)C(O)C*] | 64b | 13 | 34 | 17 |
| 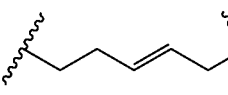 | 36-(E) | 89 | 154 | 157 |
| 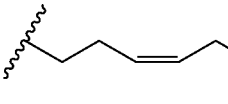 | 36-(Z) | 77 | 118 | 96 |
| 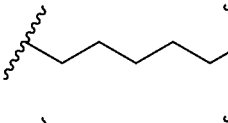 | 44 | 43 | 88 | 65 |
| 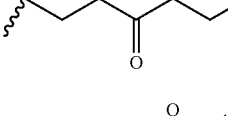 | 61a | 8 | 38 | 22 |
| 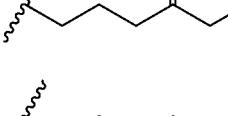 | 61b | 28 | 58 | 37 |
| 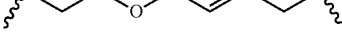 | 37-(E) | 46 | 182 | 74 |
| 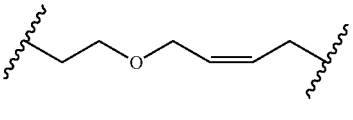 [SMILES: *C/C=C\COCC*] | 37-(Z) | 113 | 270 | 190 |
| 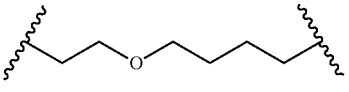 [SMILES: *CCCCOCC*] | 45 | 48 | 123 | 84 |
| 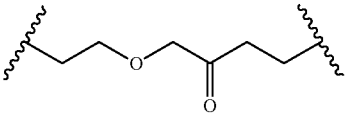 [SMILES: *CCOCC(=O)CC*] | 62 | 23 | 39 | 57 |
| 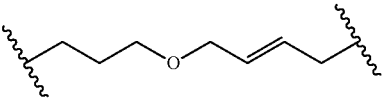 [SMILES: *C/C=C/COCCC*] | 38-(E) | 93 | 269 | 144 |

TABLE 1-continued

| | | | |
|---|---|---|---|
| (linker structure) | 46 | 80 | 449 | 116 |

[a] $K_i$ values were determined by a competitive Fluorescence Polarization Assay.
[b] Compound 63 was tested as a diastereomeric mixture (dr = 34:66).

Example 5: Co-Crystal Structures

To understand the molecular binding mode of our macrocyclic FKBP51 inhibitors and to evaluate the role of the linker, we solved cocrystal structures of 33-(Z) (PDB: 7A6W) and 56 (PDB: 7A6X) in complex with the FK506-binding domain of FKBP51 (

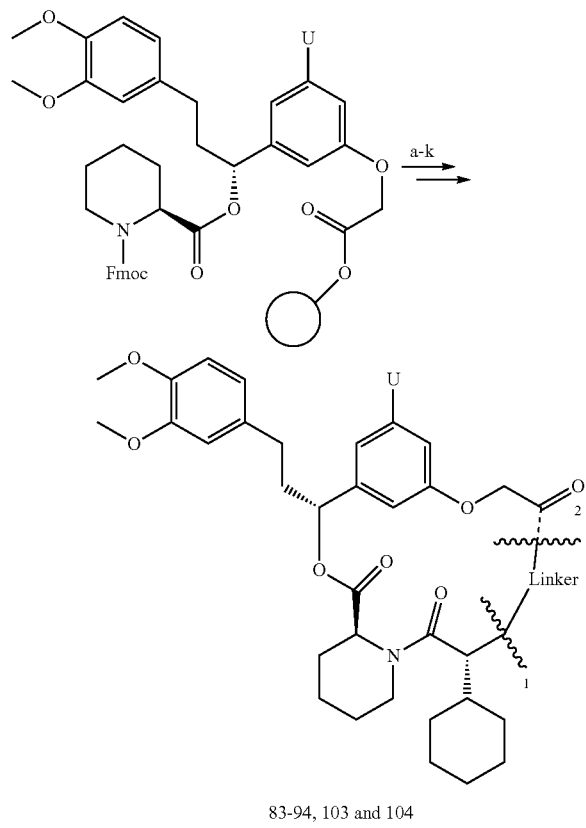

83-94, 103 and 104

Linker
83-94, 103 and 104

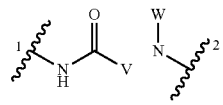

U = ––H, ––OH, ––OMe,
V = amino acid residues see example 7
W = ––H, or ––Me

Both the 19-membered, saturated macrocycle 56 as well as the 23-membered, macrocyclic alkene 33-(Z) show binding modes consistent with those of linear FKBP51-selective ligands (pdb: 4TW6, 4TW7, 5DIT, 5DIU, 5 DIV, 6SAF and 6TXX), including the conformational rearrangement of Phe67, which underlies the strong selectivity vs the highly homologous FKBP52.

Gratifyingly, the conformations of the linkers in 56 and 33-(Z) were well defined, although neither of them directly contacts FKBP51.

Figure 3:
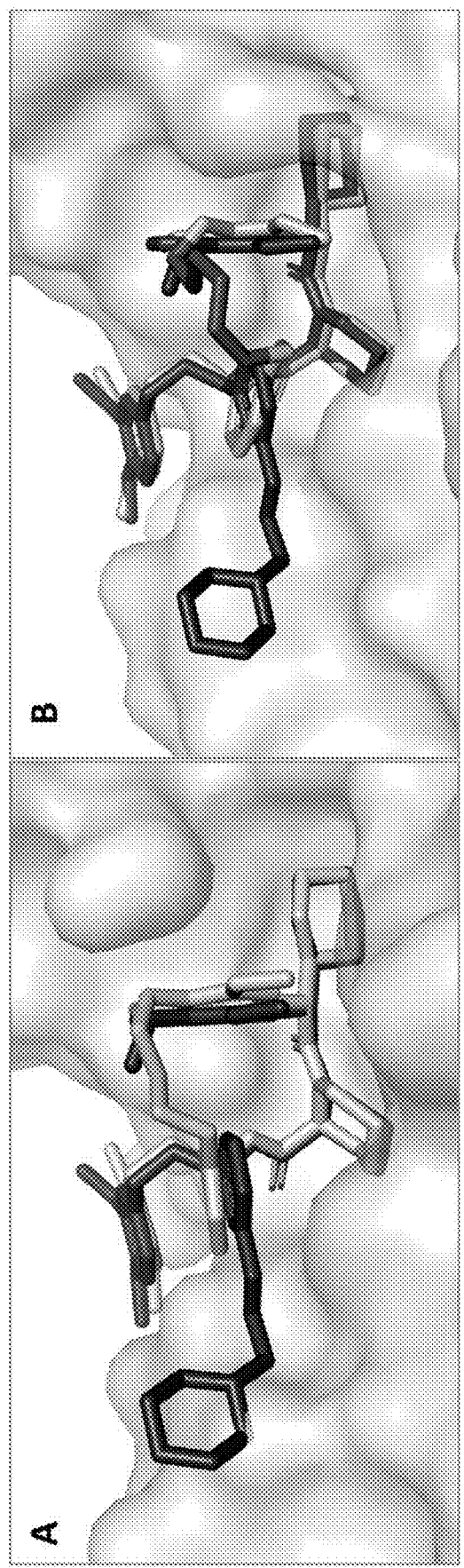
FIG. 3. X-ray structures of macrocyclic ligands in complex with the FK506-binding domain of FKBP51 (gray surface); Lys121 has been omitted for clarity. The overlay of newly discovered macrocyclic ligands with iFit4 is based solely on protein atoms from the complex structures. Novel linker moieties are highlighted in black. (A) Surface representations of FKBP51 in complex with macrocycle 56 (PDB: 7A6X). iFit4 bound to FKBP51 is superimposed in red. (B) Surface representations of FKBP51 in complex with macrocycle 33-(Z) (PDB: 7A6W). iFit4 bound to FKBP51 is superimposed.

A superposition of the cocrystallized macrocycles 33-(Z) and 56 with cocrystallized iFit4 (FIG. 3) reveals almost identical binding modes of the pipecolate core, the cyclohexyl ring, and ring C of the top group. The macrocyclization slightly influenced the conformation of the A and B rings compared to linear SAFit analogs. The A ring slightly shifts outwards (0.5 Å for 56, 0.4 Å for 33-(Z)) and the B ring is either shifted outwards (0.8 Å for 56) or rotated by 5.6° (for 33-(Z)), suggesting plasticity for the interactions of these residues.

Example 6: General Procedures

General Procedure A—Alkylation with Bromides or Tosylates

To a stirred solution of the substrate and K2CO3 in the solvent was added the corresponding bromide or tosylate and the reaction mixture was heated at reflux until completion of the reaction. The resulting suspension was filtered through Celite, washed with EA and the solvent was removed under reduced pressure. The crude product was purified by flash column chromatography.

General Procedure B—Ring-Closing Metathesis

A stirred solution of the substrate in DCM was degassed by sparging with Argon for 15 minutes. Then Grubbs 2nd Generation catalyst and 1,4-benzoquinone (if indicated) were added and the mixture was heated at reflux. After completion of the reaction the mixture is either a) filtered through silica and the solvent removed under reduced pressure or b) quenched by the addition of tris(hydroxymethyl) phosphine solution (1 M in iPrOH) and washed with brine. The organic phase was dried over $MgSO_4$, filtered, and concentrated under reduced pressure. The crude product was purified by flash column chromatography or semi-preparative HPLC.

General Procedure C—Nucleophilic Substitution with Iodine (Appel-Like Reaction)

To a stirred solution of the substrate, $PPh_3$ and base in anhydrous solvent was added iodine. The mixture was stirred at room temperature until completion of the reaction. The reaction mixture was diluted with DCM or $Et_2O$ and washed with aqueous $Na_2S_2O_3$. The organic phase was washed with 1 M HCl solution and brine, dried over $MgSO_4$ and concentrated under reduced pressure. The crude product was purified by flash column chromatography or semi-preparative HPLC.

General Procedure D—Intramolecular Nucleophilic Substitution

To a stirred solution of the substrate in MeCN was added $K_2CO_3$ and the mixture was degassed by sparging with Argon for 15 minutes. The resulting mixture was then heated at reflux until completion of the reaction. After cooling to room temperature, the suspension was filtered through Celite, washed with EA and the solvent was removed under reduced pressure. The crude product was purified by flash column chromatography or semi-preparative HPLC.

General Procedure E—Double Bond Hydrogenation

A stirred solution of the substrate in the solvent was degassed by sparging with Argon for 10 minutes. After addition of Wilkinson's catalyst [RhCl(PPh$_3$)$_3$] the solution was sparged with hydrogen for 15 minutes and was then stirred under a hydrogen atmosphere at room temperature. When the reaction was deemed complete by LC-MS analysis, the solvent was removed under reduced pressure. The crude product was purified by flash column chromatography or semi-preparative HPLC.

General Procedure F—Ester Hydrolysis

To a stirred solution of the substrate in H$_2$O/MeOH/THF (v/v/v=1:1:2) was added lithium hydroxide. The mixture was stirred at room temperature until completion of the reaction. The reaction mixture was extracted with Et$_2$O. The organic layer was removed and the aqueous layer acidified with 1 M HCl solution (pH=1-2). After extraction with Et$_2$O, the organic phase was washed with brine, dried over MgSO$_4$ and concentrated under reduced pressure. The crude product was purified by flash column chromatography.

General Procedure G—Esterification with Alcohol 14

To a stirred solution of the substrate, 14 and 4-(1-Pyrrolidinyl)pyridine in dry toluene at 0° C. was added EDC. After stirring for one hour at 0° C., the reaction mixture was allowed to reach ambient temperature and left stirring for the indicated time span. During this time, the reaction was controlled via LC-MS and HPLC to monitor product formation and epimerization. Then the reaction mixture was acidified with 1 M HCl solution and extracted with DCM. The organic phase was washed with brine, dried over MgSO$_4$ and concentrated under reduced pressure. The crude product was purified by flash column chromatography.

General Procedure H—Wacker Oxidation of Internal Alkenes

Palladium acetate (Pd(OAc)$_2$) and 1,4-benzoquinone were charged in a flask under air. A mixture of MeCN and water (v/v=9:1) was added, followed by the addition of aqueous HBF$_4$. After the addition of the corresponding substrate, the mixture was stirred at room temperature until completion of the reaction. The reaction mixture was diluted with brine and extracted with DCM. The combined organic phases were dried over MgSO$_4$ and concentrated under reduced pressure. The crude product was purified by flash column chromatography or semi-preparative HPLC.

Example 7: Synthesis of Macrocyclic FKBP51 Ligands by Solid Phase Peptide Synthesis (SPPS)

a) Resin loading: Resin loading with 2-(3-((R)-1-(((S)-1-(((9H-fluoren-9-yl)methoxy)carbonyl)piperidine-2-carbonyl)oxy)-3-(3,4-dimethoxyphenyl)propyl)phenoxy)acetic acid or 102 was done as described by Gopalakrishnan et al.[1] 2-Chlorotrityl chloride resin (2.0 eq) is placed into a dried and heated flask and swelled for 30 min in dry DCM (30 mL/g resin) at r.t. under argon protection. The compound being loaded (1.0 eq) is dissolved in a minimum amount of dry DCM, mixed with DIPEA (4 eq) and the resulting mixture is then added to the resin and stirred at r.t. overnight. After complete loading (TLC check of the solution) the resin is capped for 30 min by addition of 100 µL/g resin dry MeOH and 1 eq DIPEA. The resin is then filtered, washed with DMF (3×), DCM (3×) and dried in the desiccator overnight. The loading l is determined as follows:

$$((m\_total - m\_resin) \cdot 10^3) / ((MW - 36.46) \cdot m\_total) = l \text{ mmol/g}$$

b) 1st deprotection: The needed amount of resin calculated by the resin loading is transferred to a syringe with a fritted-glass filter. The resin is swelled for 20 min in DCM, then washed with DMF 3×. The pipecolate is Fmoc-deprotected by shaking in 20% 4-methyl piperidine in DMF (3×10 min). The completion of the reaction is monitored on LCMS by test cleavage as well as by Chloranil-test.

c) 1st AA coupling: Fmoc-AA-OH, (3.0 eq respectively to the resin loading), HATU (3.0 eq) and HOAt (3.0 eq) are dissolved in a minimum amount of DMF by sonication. Then DIPEA (6.0 eq) is added and the mixture is drawn up into the filter syringe filled with loaded resin. The syringe is mixed by shaking for 2 h or with especially hindered substrates overnight. Finally, the solvent is removed and the resin is washed with DMF (3×), THF (3×), DCM (3×). The coupling is confirmed via test cleavage and/or by Chloranil-test.

d) 2nd deprotection: The Fmoc protecting group is removed by the addition of 5% 4-methyl piperidine in DMF solution pre-cooled in an ice bath to 4° C. to the filter syringes. After 5 min the deprotection solution is removed and the resin is washed with DMF (1×). The completion of the reaction is confirmed via test cleavage and/or by Kaiser-test. The deprotection procedure is repeated two times if needed. After the final step the resin is washed with DMF (3×), then DCM (3×).

e) 2nd AA coupling: Repeat entry c). in case of an N-methylation Fmoc-sarcosin is coupled or steps g) to i) applied.

f) 3rd deprotection: Repeat entry d); in case of the meta OH B ring derivative 23 an additional deprotection for the allyl is done by the addition of Pd(OAc)2 (0.1 eq), PPh3 (1.0 eq) and morpholine (2.0 eq) in THF. After addition to the syringe the resin is mixed for 20 min. The completion of the reaction is confirmed via test cleavage.

g) Nosyl protection (optional for N-methylation): o-Nitrobenzene sulfonychloride (4 eq) is dissolved in NMP and 2, 4, 6-collidine (10.0 eq) is added. The mixture is drawn up into the syringe with resin and reacted for 15 min. This procedure is repeated 2×. After the final step the resin is washed with DMF (3×), then DCM (3×). The completion of the reaction is confirmed via test cleavage and/or by Kaiser-test.

h) N-methylation (optional for N-methylation): The resin is washed with dry THF (3×) and a solution of PPh3 (5.0 eq) and dry MeOH (10.0 eq) in dry THF are added. Then DIAD (5.0 eq) diluted in dry THF is added portion wise (Caution! Exothermic reaction!). After 10 min the reaction mixture is discarded, the resin washed with dry THF and the procedure repeated 2×. After the final step the resin is washed with DMF (3×), then DCM (3×). The completion of the reaction is confirmed via test cleavage.

i) Nosyl deprotection (optional for N-methylation): DBU (5.0 eq) and beta-mercaptoethanol (10.0 eq) are dissolved in NMP. The mixture is drawn up into the syringe with resin and reacted for 10 min. This procedure is repeated if needed. After the final step the resin is washed with DMF (3×), then DCM (3×). The completion of the reaction is confirmed via test cleavage and/or by Chloranil-test.

j) Cleavage from resin: The resin is transferred to a round bottom flask and stirred in 20 mL/g resin 20% HFIP in DCM for 2 h. The resin is filtered off and washed with DCM. The solvent is removed and the crude linear product identified by LCMS.

k) Macrocyclization: The crude linear product is dissolved in DMF (1.0 mM calculated as if pure compound) and HATU (3 eq) and DIPEA (5.0 eq) added. In case of the meta OH B ring derivative 25 another method is used: HATU (1.0 eq), DIPEA (3.0 eq) pentafluoro phenol (10.0 eq) in NMP (1 mM). The reaction is stirred at r.t. overnight and the solvent removed under reduced pressure. The crude product is purified by silica column chromatography and/or semi-preparative HPLC.

Scheme 5. Synthesis of macrocyclic FKBP51 ligands by SPPS, a) Synthesis procedure see a)-k) above.

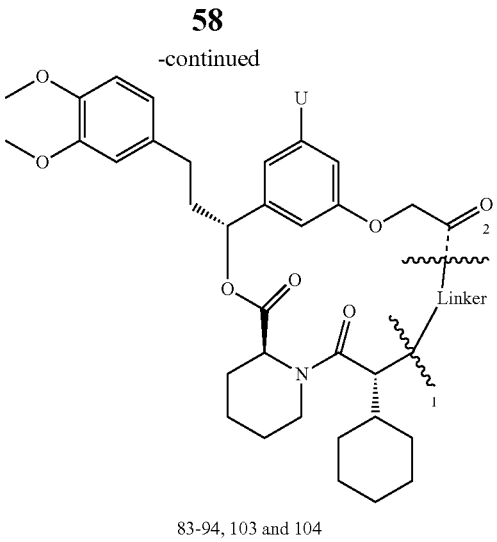

83-94, 103 and 104

Linker 83-94, 103 and 104

U = —H, —OH, —OMe,
V = amino acid residues see example 7
W = —H, or —Me

Example 8: Fluorescence Polarisation Assay of the Macrocyclic FKBP51 Ligands by SPPS

TABLE 2

Binding affinities of macrocyclic ligands, [a] standard error from three independent measurements; [b] values derived from literature[2,3]; [c] error from two independent measurements.

| Cmpd. | Linker (Scheme 5) | U (Scheme 5) | FKBP51FK1 | FKBP12 $K_i$ [μM] | FKBP12.6 |
|---|---|---|---|---|---|
| SAFit1 | No linker | H | 0.004 ± 0.001[a] | 0.163 ± 0.009[a] | 0.019 ± 0.002[a] |
| FK506 | | H | 0.104[b] | 0.0006[b] | 0.004[b] |
| 83 | | H | 2.30 ± 0.05[c] | >80 | >80 |
| 84 | | H | 1.00 | >80 | >80 |

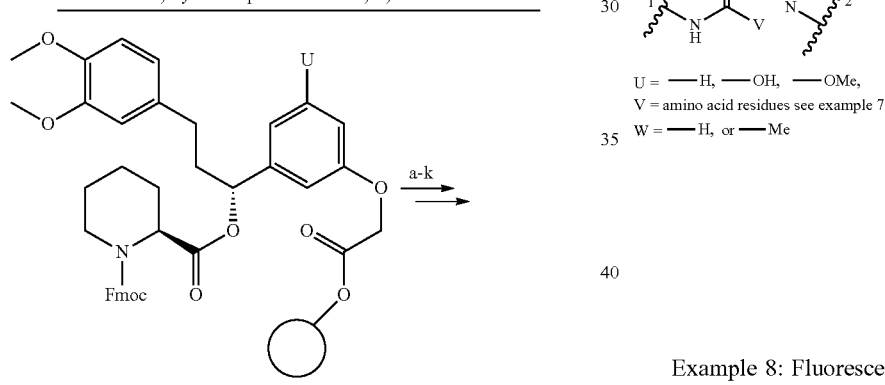

TABLE 2-continued

Binding affinities of macrocyclic ligands, [a] standard error from three independent measurements; [b] values derived from literature[2,3]; [c] error from two independent measurements.

| Cmpd. | Linker (Scheme 5) | U (Scheme 5) | FKBP51FK1 $K_i$ [μM] | FKBP12 | FKBP12.6 |
|---|---|---|---|---|---|
| 85 | | H | 0.29 ± 0.05[a] | >80 | >80 |
| 86 | | H | 0.40 ± 0.05[a] | >80 | >80 |
| 87 | | H | 0.40 | >80 | >80 |
| 88 | | H | 1.30 | >80 | >80 |
| 89 | | H | 3.10 | >80 | >80 |
| 90 | | H | 0.80 | >80 | >80 |
| 91 | | H | 17 | >80 | >80 |
| 92 | | H | 5.10 | >80 | >80 |
| 93 | | H | 7.40 | >80 | >80 |
| 94 | | H | 1.80 | >80 | >80 |

TABLE 2-continued

Binding affinities of macrocyclic ligands, [a] standard error from three independent measurements; [b] values derived from literature[2,3]; [c] error from two independent measurements.

| Cmpd. | Linker (Scheme 5) | U (Scheme 5) | FKBP51FK1 | FKBP12 $K_i$ [μM] | FKBP12.6 |
|---|---|---|---|---|---|
| 103 | | OH | 0.37 | | |
| 104 | | OMe | 0.39 | | |

The glycine derivative 83 had an affinity of 2.3 μM. With increasing substitution (84 (D-Ala): 1.0 μM, 85 (Aib): 0.29 μM) the affinity increased as well. The affinity for geminal cyclic amino acids slightly decreased with their ring size (86: 0.40 μM, 87: 0.40 μM, 88: 1.3 μM). N-methylation and N-cyclization did not substantially affect affinity [89 (R2=Me): 3.1 μM, 90 (D-Pro): 0.8 μM]. The L-Ala derivative 91 bound more weakly, consistent with the substantially reduced affinity of the L-Pro derivative 92. Linkers with increased length such as β-Ala 93 and GABA 95 (no binding, not shown) displayed reduced affinity, which could be compensated by rigidification as in 94 (1.8 μM; other diastereomers were inactive, not shown). Meta substituted macrocycles 103 and 104 bound similarly to the glycine derivative 83.

Example 9: Production and Analysis of Specific Compounds 2-(4-((tert-butyldiphenylsilyl)oxy)-3,5-dimethoxyphenyl)acetic acid (2)

3,5-Dimethoxy-4-hydroxyphenylacetic acid 1 (10.00 g, 47.1 mmol, 1 equiv) and imidazole (12.83 g, 188.5 mmol, 4 equiv) were dissolved in a mixture of DCM/DMF (v/v=2:1, 150 mL). TBDPSCI (38.87 g, 141.4 mmol, 3 equiv) is added dropwise and the reaction mixture was stirred at room temperature for 20 h. The reaction was quenched by the addition of water and stirred for 5 mins. The layers were separated, and the organic phase was washed with water for another three times. The organic layer was then washed with 1 M HCl and brine, dried over MgSO$_4$, filtered, and concentrated under reduced pressure to give 51.2 g crude product of the bis-protected compound as a brown oil. The crude was dissolved in THF/H$_2$O (v/v=2:1, 150 mL), K$_2$CO$_3$ (13.03 g, 94.2 mmol, 2 equiv) was added and the reaction mixture was stirred at room temperature for 16 h. 0.1 M HCL was added to adjust a neutral pH and the reaction mixture was extracted with Et$_2$O. The combined organic phases were washed with brine, dried over MgSO$_4$, filtered, and concentrated under reduced pressure. The crude product was purified by flash column chromatography (CH/EA=5:1) to yield 2 (19.81 g, 93%) as white solid over two steps. $^1$H NMR (500 MHz, CDCl$_3$): δ 7.78-7.64 (m, 4H), 7.40-7.29 (m, 6H), 6.35 (s, 2H), 3.51 (s, 2H), 3.43 (s, 6H), 1.11 (s, 9H). LC-MS (m/z): (ESI$^+$) calculated for C$_{26}$H$_{31}$O$_5$Si [M+H]$^+$: 451.19, found 451.13.

Perfluorophenyl 2-(4-((tert-butyldiphenylsilyl)oxy)-3,5-dimethoxyphenyl)acetate (3)

To a stirred solution of 2 (19.81 g, 44.0 mmol, 1 equiv) and 2,3,4,5,6-pentafluorophenol (8.90 g, 48.4 mmol, 1.1 equiv) in DCM (220 mL, 0.2 M) were added EDC hydrochloride (9.27 g, 48.4 mmol, 1.1 equiv) and DMAP (1.61 g, 13.2 mmol, 0.3 equiv) and the reaction mixture was stirred at room temperature overnight. The reaction mixture was washed with 1 M HCl and brine, dried over MgSO$_4$, filtered, and concentrated under reduced pressure. The crude product was purified by flash column chromatography (CH/EA=20:1) to yield 3 (24.90 g, 92%) as colorless oil. $^1$H NMR (300 MHz, CDCl$_3$): δ 7.86-7.60 (m, 4H), 7.49-7.29 (m, 6H), 6.43 (s, 2H), 3.83 (s, 2H), 3.47 (s, 6H), 1.13 (s, 9H).

(S)-3-(2-(4-((tert-butyldiphenylsilyl)oxy)-3,5-dimethoxyphenyl)acetyl)-4-phenyloxazo-lidin-2-one (4)

(S)-4-phenyloxazolidin-2-one (6.72 g, 40.8 mmol, 1.01 equiv) was dissolved in dry THF (350 mL, c=0.1 M) and cooled in an ice bath to 0° C. n-Butyllithium (2.3 M in Hexanes, 1.01 equiv) was added dropwise and the reaction mixture was stirred for 1 h at 0° C. Afterwards, 3 (24.90 g, 40.4 mmol, 1 equiv) dissolved in dry THE (50 mL) was added to the above solution and stirred for 3 h at 0° C. and then overnight at room temperature. The reaction mixture was quenched by the addition of saturated NH$_4$Cl solution and the aqueous phase was extracted by Et$_2$O. The combined organic phases were dried over MgSO$_4$, filtered, and concentrated under reduced pressure. The crude product was purified by flash column chromatography (CH/EA=8:1) to yield 4 (19.58 g, 81%) as white solid. $^1$H NMR (300 MHz, CDCl$_3$): δ 7.77-7.61 (m, 4H), 7.41-7.25 (m, 9H), 7.15-7.08 (m, 2H), 6.31 (s, 2H), 5.40 (dd, J=4.2, 8.8 Hz, 1H), 4.65 (t, J=8.8 Hz, 1H), 4.30-4.12 (m, 2H), 4.05 (d, J=14.4 Hz, 1H), 3.36 (s, 6H), 1.09 (s, 9H). LC-MS (m/z): (ESI$^+$) calculated for C$_{35}$H$_{38}$NO$_6$Si [M+H]$^+$: 596.25, found 596.11.

(S)-3-((S)-2-(4-((tert-butyldiphenylsilyl)oxy)-3,5-dimethoxyphenyl)-2-cyclohexylacetyl)-4-phenyloxazolidin-2-one (5)

To a stirred solution of 4 (19.58 g, 32.9 mmol, 1.0 equiv) was added LiHMDS (1 M in THF, 39.4 mL, 1.2 equiv) at 0° C. and the reaction mixture was stirred at this temperature for 1 h. The mixture was then cooled to −78° C. and 3-bromocyclohex-1-ene (11.14 g, 65.7 mmol, 2 equiv) was added dropwise. The reaction mixture was stirred at −78° C. for 5 h and was then allowed to warm to room temperature overnight. The reaction mixture was quenched by the addition of saturated NH₄Cl solution and the aqueous phase was extracted by Et₂O. The combined organic phases were washed with brine, dried over MgSO₄, filtered, and concentrated under reduced pressure. The crude product was purified by flash column chromatography (CH/EA=10:1) to yield S1 (11.12 g, 50%) as white solid and a mixture of diastereomers (analytics shown in Supporting Information). Subsequently, a stirred solution of S1 (11.09 g, 16.41 mmol, 1 equiv) in a mixture of CH/EA/MeOH (v/v/v=2:1:1, 400 mL) was degassed by sparging with Argon for 15 minutes. After addition of Pd/C (10 wt.-%, 1.74 g, 1.64 mmol, 0.1 equiv) the solution was sparged with hydrogen for 15 minutes and was then stirred under a hydrogen atmosphere at room temperature overnight. The dark suspension was filtered through Celite and the solvent was removed under reduced pressure to yield 5 (11.10 g, 99%) as white solid without further purification. $^1$H NMR (500 MHz, CDCl₃): δ 7.76-7.60 (m, 4H), 7.43-7.26 (m, 11H), 6.45 (s, 2H), 5.33 (dd, J=3.4, 8.7 Hz, 1H), 4.69 (d, J=10.6 Hz, 1H), 4.54 (t, J=8.8 Hz, 1H), 4.19 (dd, J=3.5, 8.8 Hz, 1H), 3.42 (s, 6H), 1.95-1.80 (m, 1H), 1.66-1.44 (m, 4H), 1.39-1.28 (m, 1H), 1.20-1.04 (m, 12H), 0.96-0.83 (m, 1H), 0.79-0.59 (m, 1H). LC-MS (m/z): (ESI⁺) calculated for $C_{41}H_{48}NO_6Si$ [M+H]⁺: 678.33, found 678.29.

(S)-2-(4-((tert-butyldiphenylsilyl)oxy)-3,5-dimethoxyphenyl)-2-cyclohexylacetic acid (6)

To a stirred solution of 5 (11.21 g, 16.54 mmol, 1 equiv) in THF/H₂O (v/v=8:5, 130 mL) at 0° C. under air is added lithium hydroxide (792 mg, 33.07 mmol, 2 equiv) and H₂O₂ (30% w/w in water, 8.45 mL, 82.68 mmol, 5 equiv). After stirring overnight at room temperature, the reaction mixture was quenched by the addition of 1.5 M Na₂SO₃ solution and extracted with Et₂O. The aqueous phase was acidified with 1 M HCl (pH<2) and extracted with Et₂O. The combined organic phases were washed with brine, dried over MgSO₄, filtered, and concentrated under reduced pressure. The crude product was purified by flash column chromatography (CH/EA=8:1+1% HCOOH) to afford 6 (8.36 g, 95%) as white solid. $^1$H NMR (500 MHz, CDCl₃): δ 7.71-7.65 (m, 4H), 7.36-7.30 (m, 2H), 7.30-7.25 (m, 4H), 6.36 (s, 2H), 3.41 (s, 6H), 3.02 (d, J=10.5 Hz, 1H), 1.89-1.80 (m, 2H), 1.76-1.70 (m, 1H), 1.68-1.58 (m, 2H), 1.33-1.24 (m, 2H), 1.17-1.08 (m, 11H), 1.06-0.96 (m, 1H), 0.73-0.58 (m, 1H). HRMS (m/z): (ESI⁺) calculated for $C_{32}H_{41}O_5Si$ [M+H]⁺: 533.2718, found 533.2718.

(S)-(R)-1-(3-(allyloxy)phenyl)-3-(3,4-dimethoxyphenyl)propyl-1-((S)-2-(4-((tert-butyldiphenyl-silyl)oxy)-3,5-dimethoxyphenyl)-2-cyclohexylacetyl) piperidine-2-carboxylate (7)

To a stirred solution of 6 (1.82 g, 3.42 mmol, 1 equiv) in a mixture of DCM/DMF (v/v=1:1, 100 mL) at room temperature were added HATU (1.37 g, 3.59 mmol, 1.05 equiv) and DIPEA (1.33 g, 10.25 mmol, 3 equiv) and stirred for 30 mins, before 15 (1.65 g, 3.76 mmol, 1.1 equiv, synthesis and analytics shown in Supporting Information) was added. After stirring overnight, additional portions of HATU (0.2 equiv), DIPEA (1 equiv) and 15 (0.1 equiv) were added and the reaction was stirred for another 4 hours. Then the reaction mixture was diluted with DCM, washed with 1 M HCl and H₂O. The organic phase was washed with brine, dried over MgSO₄, filtered, and concentrated under reduced pressure. The crude product was purified by flash column chromatography (CH/EA=10:1) to yield 7 (2.86 g, 88%) as colorless resin. $^1$H NMR (500 MHz, CDCl₃, mixture of rotamers 0.76:1, A:B): δ 7.75-7.68 (m, 2.92H, A+B), 7.68-7.65 (m, 1.15H, A+B), 7.40-7.21 (m, 6.92H, A+B), 7.16 (t, J=7.9 Hz, 0.57H, A), 6.98-6.87 (m, 1.33H, A+B), 6.84-6.75 (m, 2.21H, A+B), 6.74-6.70 (m, 0.44H, A), 6.69-6.67 (m, 0.44H, A), 6.67-6.63 (m, 1.16H, B), 6.57-6.53 (m, 0.56H, A), 6.29 (d, J=1.0 Hz, 1.15H, B), 6.24 (d, J=1.1 Hz, 0.87H, A), 6.14-5.98 (m, 0.94H, A+B), 5.82 (t, J=6.9 Hz, 0.42H, A), 5.63 (dd, J=5.5, 8.0 Hz, 0.56H, B), 5.49-5.43 (m, 1.10H, B), 5.43-5.38 (m, 0.47H, A), 5.35-5.25 (m, 0.99H, A+B), 4.73-4.67 (m, 0.42H, A), 4.60-4.47 (m, 2.51H, A+B), 3.88 (d, J=1.5 Hz, 3.00H, A+B), 3.86 (d, J=2.2 Hz, 3.88H, A+B), 3.44 (s, 2.71H, A+B), 3.29 (s, 3.34H, A+B), 3.27 (d, J=10.0 Hz, 0.83H, A+B), 2.93 (d, J=9.4 Hz, 0.43H, A), 2.79 (m, 0.54H, B), 2.67-2.41 (m, 2.48H, A+B), 2.34-2.23 (m, 1.04H, A+B), 2.18-2.09 (m, 0.43H, A), 2.06-1.95 (m, 2.11H, A+B), 1.94-1.84 (m, 1.71H, A+B), 1.75-1.50 (m, 6.79H, A+B), 1.47-1.22 (m, 6.04H, A+B), 1.18-1.13 (m, 5.74H, A+B), 1.13-1.09 (m, 6.60H, A+B), 1.04-0.77 (m, 6.03H, A+B), 0.73-0.62 (m, 1.13H, A+B), 0.61-0.51 (m, 0.46H, A). LC-MS (m/z): (ESI⁺) calculated for $C_{58}H_{72}NO_9Si$ [M+H]⁺: 954.50, found 954.28.

(S)-(R)-1-(3-(allyloxy)phenyl)-3-(3,4-dimethoxyphenyl)propyl 1-((S)-2-cyclohexyl-2-(4-hydroxy-3,5-dimethoxyphenyl)acetyl)piperidine-2-carboxylate (8)

To a stirred solution of 7 (2.86 g, 3.00 mmol, 1 equiv) in THF (50 mL, c=0.06 M) at 0° C. was added TBAF (1 M in THF, 3 mL, 3.00 mmol, 1 equiv) and the reaction was allowed to warm to room temperature and stirred overnight. The reaction was quenched by the addition of H₂O and extracted with Et₂O. The combined organic phases were washed with brine, dried over MgSO₄, filtered, and concentrated under reduced pressure. The crude product was purified by flash column chromatography (CH/EA=4:1) to afford 8 (2.04 g, 95%) as light pink solid. $^1$H NMR (500 MHz, CDCl₃, mixture of rotamers 0.37:1, A:B): δ 7.28 (t, J=7.9 Hz, 0.28H, A), 7.10 (t, J=7.9 Hz, 0.73H, B), 6.97-6.91 (m, 0.59H, A+B), 6.89-6.85 (m, 0.3H, A), 6.82-6.74 (m, 1.81H, A+B), 6.73-6.67 (m, 1.06H, A+B), 6.66-6.59 (m, 1.81H, A+B), 6.50-6.41 (m, 2.83H, A+B), 6.10-5.96 (m, 0.95H, A+B), 5.81 (dd, J=6.3, 7.7 Hz, 0.27H, A), 5.58 (dd, J=5.6, 8.0 Hz, 0.74H, B), 5.48-5.34 (m, 2.70H, A+B), 5.31-5.23 (m, 1.01H, A+B), 4.71 (d, J=5.6 Hz, 0.27H, A), 4.61-4.45 (m, 2.40H, A+B), 3.96-3.89 (m, 0.77H, B), 3.88-3.81 (m, 8.16H, A+B), 3.71 (s, 4.52H, A+B), 3.34 (d, J=9.8 Hz, 0.72H, B), 2.95 (d, J=9.6 Hz, 0.27H, A), 2.79 (td, J=3.0, 13.3 Hz, 0.72H, B), 2.65-2.51 (m, 0.87H, A+B), 2.50-2.34 (m, 1.50H, A+B), 2.32-2.23 (m, 1.03H, A+B), 2.15-2.01 (m, 2.04H, A+B), 2.01-1.92 (m, 0.76H, A+B), 1.92-1.79 (m, 1.86H, A+B), 1.73-1.49 (m, 6.52H, A+B), 1.48-1.04 (m, 8.43H, A+B), 1.04-0.68 (m, 3.22H, A+B), 0.67-0.52 (m, 0.58H, B). HRMS (m/z): (ESI⁺) calculated for $C_{42}H_{54}NO_9$ [M+H]⁺: 716.37931, found 716.37915.

(S)-(R)-1-(3-(allyloxy)phenyl)-3-(3,4-dimethoxyphenyl)propyl 1-((S)-2-(4-(allyloxy)-3,5-dimethoxyphenyl)-2-cyclohexylacetyl)piperidine-2-carboxylate (9)

The substrate 8 (400 mg, 0.56 mmol, 1 equiv) was applied to general procedure A with K₂CO₃ (116 mg, 0.84 mmol, 1.5 equiv) and allyl bromide (76 mg, 0.62 mmol, 1.1 equiv) in MeCN (20 mL). Additional portions of $K_2CO_3$ (1 equiv) and allyl bromide (2×2 equiv) were added until completion of the reaction. 9 (411 mg, 97%) was obtained after purification by flash column chromatography (CH/EA=4:1). $^1$H NMR (500 MHz, CDCl$_3$, mixture of rotamers 0.38:1, A:B): δ 7.26-7.23 (m, 0.27H, A), 7.06 (t, J=7.9 Hz, 0.71H, B), 6.93-6.88 (m, 0.58H, A+B), 6.85-6.82 (m, 0.28H, A), 6.77-6.70 (m, 1.78H, A+B), 6.68-6.64 (m, 1.03H, B), 6.64-6.58 (m, 1.80H, A+B), 6.47 (s, 1.47H, A+B), 6.42-6.38 (m, 1.32H, A+B), 6.08-5.94 (m, 1.93H, A+B), 5.78 (dd, J=6.2, 7.7 Hz, 0.28H, A), 5.54 (dd, J=5.6, 8.1 Hz, 0.72H, B), 5.46-5.42 (m, 0.72H, B), 5.40-5.32 (m, 1.02H, A+B), 5.27-5.19 (m, 2.28H, A+B), 5.14-5.05 (m, 1.01H, A+B), 4.70-4.66 (m, 0.27H, A), 4.56-4.44 (m, 3.02H, A+B), 4.42-4.38 (m, 1.47H, A+B), 3.96-3.89 (m, 0.77H, B), 3.83-3.76 (m, 8.23H, A+B), 3.66 (s, 4.49H, A+B), 3.35 (d, J=9.8 Hz, 0.72H, B), 2.95 (d, J=9.6 Hz, 0.27H, A), 2.77 (td, J=2.9, 13.4 Hz, 0.71H, B), 2.61-2.49 (m, 0.86H, A+B), 2.47-2.31 (m, 1.49H, A+B), 2.29-2.21 (m, 1.05H, A+B), 2.12-1.99 (m, 1.76H, A+B), 1.96-1.75 (m, 2.66H, A+B), 1.70-1.46 (m, 6.38H, A+B), 1.44-1.02 (m, 8.83H, A+B), 1.01-0.67 (m, 3.33H, A+B), 0.65-0.52 (m, 0.59H, B). HRMS (m/z): (ESI$^+$) calculated for $C_{45}H_{58}NO_9$ [M+H]$^+$: 756.41061, found 756.40996.

(S)-(R)-1-(3-(allyloxy)phenyl)-3-(3,4-dimethoxyphenyl)propyl 1-((S)-2-(4-(but-3-en-1-yloxy)-3,5-dimethoxyphenyl)-2-cyclohexylacetyl)piperidine-2-carboxylate (10)

The substrate 8 (300 mg, 0.42 mmol, 1 equiv) was applied to general procedure A with $K_2CO_3$ (174 mg, 1.26 mmol, 3 equiv) and 4-bromo-1-butene (146 mg, 1.05 mmol, 2.5 equiv) in MeCN (10 mL). Additional portions of $K_2CO_3$ (2 equiv) and 4-bromo-1-butene (3×3 equiv) were added until completion of the reaction. 10 (307 mg, 95%) was obtained after purification by flash column chromatography (CH/EA=5:1). $^1$H NMR (500 MHz, CDCl$_3$, mixture of rotamers 0.38:1, A:B): δ 7.29-7.24 (m, 0.35H, A), 7.07 (t, J=7.9 Hz, 0.72H, B), 6.94-6.89 (m, 0.59H, A+B), 6.87-6.83 (m, 0.3H, A), 6.79-6.71 (m, 1.81H, A+B), 6.69-6.58 (m, 2.86H, A+B), 6.47 (s, 1.49H, A+B), 6.45-6.38 (m, 1.34H, A+B), 6.06-5.96 (m, 0.96H, A+B), 5.93-5.76 (m, 1.26H, A+B), 5.54 (dd, J=5.6, 8.1 Hz, 0.73H, B), 5.47-5.43 (m, 0.72H, B), 5.41-5.33 (m, 1.00H, A+B), 5.28-5.20 (m, 1.07H, A+B), 5.13-5.07 (m, 0.29H, A), 5.07-4.95 (m, 1.72H, A+B), 4.69 (d, J=5.7 Hz, 0.27H, A), 4.57-4.44 (m, 2.40H, A+B), 4.01-3.89 (m, 2.96H, A+B), 3.86-3.76 (m, 8.39H, A+B), 3.67 (s, 4.55H, A+B), 3.36 (d, J=9.7 Hz, 0.72H, B), 2.95 (d, J=9.6 Hz, 0.28H, A), 2.78 (td, J=2.9, 13.3 Hz, 0.71H, B), 2.61-2.32 (m, 4.61H, A+B), 2.30-2.22 (m, 1.08H, A+B), 2.12-2.00 (m, 2.17H, A+B), 1.98-1.75 (m, 2.67H, A+B), 1.70-1.48 (m, 6.32H, A+B), 1.45-1.03 (m, 7.64H, A+B), 1.01-0.80 (m, 1.32H, A+B), 0.78-0.68 (m, 0.76H, B), 0.66-0.52 (m, 0.57H, A). HRMS (m/z): (ESI$^+$) calculated for $C_{46}H_{60}NO_9$ [M+H]$^+$: 770.42626, found 770.42659.

(S)-(R)-1-(3-(allyloxy)phenyl)-3-(3,4-dimethoxyphenyl)propyl 1-((S)-2-(4-(2-(allyloxy)ethoxy)-3,5-dimethoxyphenyl)-2-cyclohexylacetyl)piperidine-2-carboxylate (11)

The substrate 8 (500 mg, 0.7 mmol, 1 equiv) was applied to general procedure A (Supporting Information) with $K_2CO_3$ (290 mg, 2.1 mmol, 3 equiv) and 16 (718 mg, 2.8 mmol, 4 equiv) in MeCN (25 mL). 11 (550 mg, 98%) was obtained after purification by flash column chromatography (CH/EA=4:1) as light yellow resin. $^1$H NMR (500 MHz, CDCl$_3$, mixture of rotamers 0.44:1, A:B): δ 7.29 (t, J=7.9 Hz, 0.33H, A), 7.10 (t, J=7.9 Hz, 0.70H, B), 6.97-6.91 (m, 0.64H, A+B), 6.90-6.85 (m, 0.32H, A), 6.81-6.74 (m, 1.79H, A+B), 6.71-6.67 (m, 1.03H, B), 6.66-6.61 (m, 1.80H, A+B), 6.48 (s, 1.41H, A+B), 6.46-6.43 (m, 0.75H, A+B), 6.41 (s, 0.63H, A), 6.09-5.99 (m, 0.97H, A+B), 5.97-5.86 (m, 0.93H, A+B), 5.81 (dd, J=6.2, 7.7 Hz, 0.31H, A), 5.56 (dd, J=5.5, 8.2 Hz, 0.71H, B), 5.49-5.44 (m, 0.69H, B), 5.44-5.36 (m, 1.05H, A+B), 5.31-5.22 (m, 2.27H, A+B), 5.18-5.12 (m, 0.98H, A+B), 4.70 (d, J=5.7 Hz, 0.29H, A), 4.59-4.47 (m, 2.42H, A+B), 4.16-4.12 (m, 0.64H, A), 4.10-4.02 (m, 3.47H, A+B), 3.97-3.90 (m, 0.71H, B), 3.87-3.79 (m, 8.42H, A+B), 3.77-3.73 (m, 0.68H, A), 3.72-3.67 (m, 5.73H, A+B), 3.37 (d, J=9.8 Hz, 0.70H, B), 2.97 (d, J=9.6 Hz, 0.30H, A), 2.80 (td, J=2.9, 13.3 Hz, 0.70H, B), 2.65-2.51 (m, 0.94H, A+B), 2.50-2.35 (m, 1.54H, A+B), 2.32-2.24 (m, 1.07H, A+B), 2.15-2.00 (m, 1.77H, A+B), 1.99-1.78 (m, 2.58H, A+B), 1.74-1.50 (m, 6.80H, A+B), 1.47-1.05 (m, 6.92H, A+B), 1.04-0.85 (m, 1.18H, A+B), 0.79-0.69 (m, 0.75H, A+B), 0.67-0.53 (m, 0.65H, A+B). HRMS (m/z): (ESI$^+$) calculated for $C_{47}H_{62}NO_{10}$ [M+H]$^+$: 800.43682, found 800.43719.

(S)-(R)-1-(3-(allyloxy)phenyl)-3-(3,4-dimethoxyphenyl)propyl 1-((S)-2-(4-(3-(allyloxy)propoxy)-3,5-dimethoxyphenyl)-2-cyclohexylacetyl)piperidine-2-carboxylate (12)

The substrate 8 (550 mg, 0.77 mmol, 1 equiv) was applied to general procedure A (Supporting Information) with $K_2CO_3$ (213 mg, 1.54 mmol, 2.5 equiv) and 17 (625 mg, 2.31 mmol, 3 equiv, synthesis and analytics shown in Supporting Information) in MeCN (20 mL). Additional portions of $K_2CO_3$ (1 equiv) and 17 (1 equiv) were added until completion of the reaction. 12 (576 mg, 92%) was obtained after purification by flash column chromatography (CH/EA=4:1) as colorless resin. $^1$H NMR (500 MHz, CDCl$_3$, mixture of rotamers 0.42:1, A:B): δ 7.30-7.26 (m, 0.25H, A), 7.11-7.06 (m, 0.69H, B), 6.95-6.90 (m, 0.62H, B), 6.88-6.85 (m, 0.31H, A), 6.80-6.73 (m, 1.77H, A+B), 6.70-6.66 (m, 1.04H, B), 6.66-6.60 (m, 1.80H, A+B), 6.47 (s, 1.43H, B), 6.46-6.42 (m, 0.75H, A+B), 6.41-6.39 (m, 0.63H, A), 6.08-5.98 (m, 0.96H, A+B), 5.95-5.83 (m, 0.95H, A+B), 5.80 (t, J=6.9 Hz, 0.31H, A), 5.58-5.53 (m, 0.71H, B), 5.45 (d, J=5.5 Hz, 0.70H, B), 5.43-5.35 (m, 1.04H, A+B), 5.30-5.20 (m, 2.05H, A+B), 5.17-5.10 (m, 1.01H, A+B), 4.72-4.68 (m, 0.30H, A), 4.58-4.46 (m, 2.42H, A+B), 4.07-4.02 (m, 0.70H, B), 4.01-3.90 (m, 4.42H, A+B), 3.86-3.77 (m, 8.55H, A+B), 3.70-3.63 (m, 5.14H, A+B), 3.63-3.58 (m, 1.51H), A+B, 3.36 (d, J=9.7 Hz, 0.70H, B), 2.96 (d, J=9.5 Hz, 0.3H, A), 2.83-2.75 (m, 0.69H, B), 2.64-2.50 (m, 0.96H, A+B), 2.49-2.34 (m, 1.46H, A+B), 2.31-2.23 (m, 1.06H, A+B), 2.13-2.04 (m, 1.58H, A+B), 2.01-1.90 (m, 2.71H, A+B), 1.90-1.78 (m, 2.00H, A+B), 1.72-1.49 (m, 6.50H, A+B), 1.46-1.25 (m, 3.15H, A+B), 1.20-1.06 (m, 2.98H, A+B), 1.03-0.82 (m, 1.21H, A+B), 0.79-0.68 (m, 0.69H, A+B), 0.66-0.52 (m, 0.57H, A+B). HRMS (m/z): (ESI$^+$) calculated for $C_{48}H_{64}NO_{10}$ [M+H]$^+$: 814.45247, found 814.45247.

Methyl 2-(3-(benzyloxy)-4,5-dihydroxyphenyl)acetate (18)

To a stirred solution of Methyl 2-(7-(benzyloxy)-2,2-dimethylbenzo[d][1,3]dioxol-5-yl)acetate (7.23 g, 22.0 mmol, 1 equiv, synthesis and analytics shown in Supporting Information) in MeCN/H$_2$O (70 mL, v/v=1:1) was added trifluoroacetic acid (170 mL) and the reaction mixture was stirred at room temperature for 4 hours. The reaction mixture was quenched by the addition of saturated aq. NaHCO$_3$ solution. The aqueous phase was extracted with EA and the combined organic phase subsequently washed with brine, dried over MgSO$_4$, filtered, and concentrated under reduced pressure. The crude product was purified by flash column chromatography (CH/EA=4:1→3:1) to yield 18 (5.13 g, 81%) as yellow oil. $^1$H NMR (500 MHz, CDCl$_3$): δ 7.43-7.32 (m, 5H), 6.54 (d, J=1.9 Hz, 1H), 6.50 (d, J=1.9 Hz, 1H), 5.49-5.36 (m, 2H), 5.07 (s, 2H), 3.68 (s, 3H), 3.49 (s, 2H). LC-MS (m/z): (ESI$^+$) calculated for C$_{16}$H$_{17}$O$_5$ [M+H]$^+$: 289.11, found 289.16.

Methyl
2-(3-(benzyloxy)-4,5-dimethoxyphenyl)acetate (19)

To a stirred solution of 18 (5.13 g, 17.8 mmol, 1 equiv) in degassed DMF (60 mL, 0.3 M) were added K$_2$CO$_3$ (7.37 g, 53.3 mmol, 3 equiv) and methyl iodide (10.10 g, 71.1 mmol, 4 equiv) and the reaction mixture was stirred at room temperature overnight. The resulting red solution was diluted with water and then extracted with Et$_2$O. The combined organic phases were washed with brine, dried over MgSO$_4$, filtered, and concentrated under reduced pressure. The crude product was purified by flash column chromatography (CH/EA=6:1→3:1) to yield 19 (5.25 g, 93%) as light yellow oil. $^1$H NMR (500 MHz, CDCl$_3$): b 7.46-7.43 (m, 2H), 7.39-7.36 (m, 2H), 7.33-7.29 (m, 1H), 6.55 (d, J=1.9 Hz, 1H), 6.51 (d, J=1.9 Hz, 1H), 5.12 (s, 2H), 3.86 (s, 6H), 3.68 (s, 3H), 3.52 (s, 2H). HRMS (m/z): (ESI$^+$) calculated for C$_{18}$H$_{21}$O$_5$ [M+H]$^+$: 317.13835, found 317.13795.

Methyl 2-(3-(benzyloxy)-4,5-dimethoxyphenyl)-2-(cyclohex-2-en-1-yl)acetate (20)

To a stirred solution of 19 (4.85 g, 15.3 mmol, 1.0 equiv) was added LiHMDS (1 M in THF, 16.9 mL, 1.1 equiv) dropwise at −78° C. and the reaction mixture was stirred at this temperature for 20 minutes. Then 3-bromocyclohex-1-ene (5.20 g, 30.7 mmol, 2 equiv) was added dropwise. The reaction mixture was allowed to warm to −40° C. over a period of 3 hours (TLC indicated full conversion) before the reaction mixture was quenched by the addition of saturated NH$_4$Cl solution. The aqueous phase was extracted with Et$_2$O and the combined organic phases were washed with brine, dried over MgSO$_4$, filtered, and concentrated under reduced pressure. The crude product was purified by flash column chromatography (CH/EA=10:1) to yield 20 (5.72 g, 94%) as light yellow oil and mixture of diastereomers. $^1$H NMR (500 MHz, CDCl$_3$, mixture of diastereomers): δ 7.47-7.41 (m, 3.07H), 7.38-7.33 (m, 3.00H), 7.32-7.27 (m, 1.40H), 6.62 (d, J=1.9 Hz, 0.53H), 6.58-6.57 (m, 1.44H), 6.54-6.52 (m, 1.00H), 5.80-5.74 (m, 1.14H), 5.67-5.61 (m, 0.48H), 5.60-5.53 (m, 1.10H), 5.18-5.10 (m, 2.19H), 3.91-3.81 (m, 9.92H), 3.67-3.62 (m, 4.53H), 3.21-3.14 (m, 1.59H), 2.82-2.66 (m, 1.67H), 2.01-1.93 (m, 3.12H), 1.90-1.83 (m, 0.54H), 1.79-1.53 (m, 3.17H), 1.47-1.37 (m, 1.46H), 1.36-1.27 (m, 1.82H), 1.04-0.94 (m, 1.17H), 0.91-0.82 (m, 0.41H). HRMS (m/z): (ESI$^+$) calculated for C$_{24}$H$_{29}$O$_5$ [M+H]$^+$: 397.20095, found 397.20114.

2-(3-(benzyloxy)-4,5-dimethoxyphenyl)-2-(cyclohex-2-en-1-yl)acetic acid (21)

To a stirred solution of 20 (1147 mg, 2.90 mmol, 1 equiv) in THF/H$_2$O (v/v=1:1, 50 mL) under air at room temperature was added lithium hydroxide (348 mg, 14.50 mmol, 5 equiv) and the mixture was heated at reflux overnight. The reaction mixture was extracted with Et$_2$O. The organic layer was removed, and the aqueous layer acidified with 1 M HCl solution (pH=1-2). After extraction with Et$_2$O, the organic phase was washed with brine, dried over MgSO$_4$, and concentrated under reduced pressure. The crude product was purified by flash column chromatography (CH/EA=6:1+ 0.2% HCOOH) to afford 21 (1010 mg, 91%) as colorless resin. $^1$H NMR (500 MHz, CDCl$_3$, mixture of diastereomers): 7.45-7.40 (m, 2H), 7.38-7.31 (m, 2H), 7.30-7.25 (m, 1H), 6.67-6.65 (m, 0.5H), 6.62-6.58 (m, 1H), 6.57-6.54 (m, 0.5H), 5.83-5.77 (m, 0.5H), 5.70-5.63 (m, 1H), 5.18-5.10 (m, 2.5H), 3.89-3.83 (m, 6H), 3.19 (t, J=11.3 Hz, 1H), 2.81-2.67 (m, 1H), 2.02-1.93 (m, 2.5H), 1.81-1.73 (m, 0.5H), 1.63-1.55 (m, 1H), 1.45-1.32 (m, 1.5H), 1.03-0.95 (m, 0.5H). HRMS (m/z): (ESI$^+$) calculated for C$_{23}$H$_{27}$O$_5$ [M+H]$^+$: 383.18530, found 383.18513.

(S)-1-((S)-2-cyclohexyl-2-(3-hydroxy-4,5-dimethoxyphenyl)acetyl)piperidine-2-carboxylic acid (22a) and (S)-1-((R)-2-cyclohexyl-2-(3-hydroxy-4,5-dimethoxyphenyl)acetyl)piperidine-2-carboxylic acid (22b)

To a stirred solution of 21 (3.11 g, 8.14 mmol, 1 equiv) in DCM (125 mL) at 0° C. was added DMF (6 μL, 0.08 mmol, 0.01 equiv) and thionyl chloride (0.89 mL, 12.21 mmol, 1.5 equiv) and the reaction was stirred at 0° C. overnight. Then additional portions of DMF (0.05 equiv) and thionyl chloride (0.2 equiv) were added and the reaction was stirred for one more hour. The volatiles were removed under reduced pressure to yield the crude acid chloride as a yellow oil, which was used in the following step without further purification. (S)-piperidine-2-carboxylic acid (1168 mg, 8.95 mmol, 1.1 equiv) was dissolved in 1 M KOH aqueous solution (18 mL, 17.9 mmol, 2.2 equiv) and cooled to 0° C. In a separate flask, the crude acid chloride was dissolved in 1,4-dioxane (25 mL) and was added to the above aqueous solution at 0° C. After stirring for one hour at 0° C., the reaction mixture was allowed to reach ambient temperature and left stirring overnight. The reaction mixture was quenched and acidified with 1 M HCL solution (pH=1-2), extracted with EA, dried over MgSO$_4$, and concentrated under reduced pressure. The crude product was purified by flash column chromatography (CH/EA=5:1+1% HCOOH) to afford product S7 (2858 mg, 71%, white solid, analytics shown in Supporting Information) and recovered starting material 21 (885 mg, 28%). Subsequently, a stirred solution of S7 (6.15 g, 12.46 mmol, 1 equiv) in THF/MeOH (v/v=1: 1, 300 mL) was degassed by sparging with Argon for 15 minutes. After addition of Pd/C (10 wt. %, 1330 mg, 1.25 mmol, 0.1 equiv) the solution was sparged with hydrogen for 15 minutes and was then stirred under a hydrogen atmosphere at room temperature overnight. The dark suspension was filtered through Celite and the solvent was removed under reduced pressure. The crude product was purified by flash column chromatography (DCM/MeOH/HCOOH=90: 1:1) to afford the desired product 22a (2089 mg, 41%) and the corresponding diastereomer 22b (2210 mg, 44%) as white solids. Data for 22a: $^1$H NMR (500 MHz, CDCl$_3$, mixture of rotamers 0.32:1, A:B): δ 6.47-6.34 (m, 1.96H, A+B), 4.78 (d, J=5.5 Hz, 0.17H, A), 4.58 (d, J=13.7 Hz, 0.13H, A), 3.95-3.66 (m, 6.90H, A+B), 3.30 (d, J=9.6 Hz, 0.76H, B), 3.10 (d, J=9.7 Hz, 0.24H, A), 2.97-2.85 (m, 0.70H, B), 2.64 (td, J=2.8, 13.4 Hz, 0.22H, A), 2.29-2.17 (m, 0.75H, B), 2.12-1.97 (m, 1.30H, A+B), 1.92-1.76 (m, 1.22H, A+B), 1.75-1.50 (m, 6.15H, A+B), 1.50-1.00 (m, 7.50H, A+B), 0.98-0.63 (m, 2.32H, A+B). HRMS (m/z): (ESI$^+$) calculated for $C_{22}H_{32}NO_6$ [M+H]$^+$: 406.22241, found 406.22231. Data for 22b: $^1$H NMR (500 MHz, CDCl$_3$, mixture of rotamers 0.12:1, A:B): δ 6.51-6.47 (m, 0.84H, A+B), 6.47-6.43 (m, 0.86H, A+B), 6.42-6.39 (m, 0.34H, A), 5.48-5.43 (m, 0.82H, B), 4.94-4.90 (m, 0.10H, A), 4.53 (d, J=13.4 Hz, 0.08H, A), 4.01-3.94 (m, 0.86H, B), 3.87-3.84 (m, 2.56H, A+B), 3.84-3.77 (m, 3.43H, A+B), 3.36 (d, J=10.0 Hz, 0.84H, B), 3.23 (td, J=3.1, 13.1 Hz, 0.99H, A+B), 2.80-2.72 (m, 0.10H, A), 2.30-2.14 (m, 1.03H, A+B), 2.14-2.01 (m, 1.04H, A+B), 1.89 (d, J=12.7 Hz, 1.00H, A+B), 1.74-1.42 (m, 6.60H, A+B), 1.42-1.20 (m, 4.08H, A+B), 1.19-0.93 (m, 3.33H, A+B), 0.93-0.79 (m, 1.25H, A+B), 0.79-0.65 (m, 1.05H). HRMS (m/z): (ESI$^+$) calculated for $C_{22}H_{32}NO_6$ [M+H]$^+$: 406.22241, found 406.22269.

(S)-1-((S)-2-(3-(allyloxy)-4,5-dimethoxyphenyl)-2-cyclohexylacetyl)piperidine-2-carboxylic acid (23)

The substrate 22a (350 mg, 0.86 mmol, 1 equiv) was applied to general procedure A (Supporting Information) with $K_2CO_3$ (358 mg, 2.59 mmol, 3 equiv) and allyl bromide (313 mg, 2.59 mmol, 3 equiv) in MeCN (20 mL). An additional portion of allyl bromide (0.5 equiv) was added until completion of the reaction. The product S8 (390 mg, 93%, analytics shown in Supporting Information) was obtained after purification by flash column chromatography (CH/EA=6:1) as light yellow oil. Subsequently, S8 (390 mg, 0.80 mmol, 1 equiv) was applied to general procedure F (Supporting Information) with LiOH (78 mg, 3.20 mmol, 4 equiv) in $H_2O$/MeOH/THF (12 mL). 23 (322 mg, 90%) was obtained after purification by flash column chromatography (CH/EA=3:1+0.2% HCOOH) as white solid. $^1$H NMR (500 MHz, CDCl$_3$, mixture of rotamers 0.36:1, A:B): δ 8.31 (br s, 0.79H, A+B), 6.47-6.40 (m, 2.12H, A+B), 6.07-5.95 (m, 0.99H, A+B), 5.39-5.33 (m, 1.03H, A+B), 5.29 (dd, J=2.4, 6.1 Hz, 0.74H, B), 5.25-5.19 (m, 1.04H, A+B), 4.75 (d, J=5.6 Hz, 0.26H, A), 4.63-4.49 (m, 2.41H, A+B), 3.90-3.73 (m, 7.19H, A+B), 3.32 (d, J=9.6 Hz, 0.74H, B), 3.09 (d, J=9.7 Hz, 0.26H, A), 2.94-2.85 (m, 0.73H, B), 2.67-2.59 (m, 0.26H, A), 2.26-2.19 (m, 0.73H, B), 2.11-1.99 (m, 1.48H, A+B), 1.93-1.79 (m, 1.06H, A+B), 1.72-1.52 (m, 6.16H, A+B), 1.51-1.24 (m, 3.90H, A+B), 1.21-0.97 (m, 3.11H, A+B), 0.96-0.85 (m, 0.82H, A+B), 0.83-0.64 (m, 1.38H, A+B). HRMS (m/z): (ESI$^+$) calculated for $C_{25}H_{36}NO_6$ [M+H]$^+$: 446.25371, found 446.25383.

(S)-1-((S)-2-(3-(but-3-en-1-yloxy)-4,5-dimethoxyphenyl)-2-cyclohexylacetyl)piperidine-2-carboxylic acid (24)

The substrate S9 (360 mg, 0.70 mmol, 1 equiv) was applied to general procedure F with LiOH (67 mg, 2.80 mmol, 4 equiv) in $H_2O$/MeOH/THF (16 mL). 24 (298 mg, 93%) was obtained after purification by flash column chromatography (CH/EA=4:1+0.5% HCOOH). $^1$H NMR (500 MHz, CDCl$_3$, mixture of rotamers 0.36:1, A:B): δ 8.52 (br s, 0.81H, A+B), 6.51-6.37 (m, 2.16H, A+B), 5.97-5.83 (m, 0.99H, A+B), 5.33-5.27 (m, 0.73H, B), 5.18-5.03 (m, 2.08H, A+B), 4.76 (d, J=5.7 Hz, 0.26H, A), 4.63-4.55 (m, 0.26H, A), 4.01 (q, J=6.6 Hz, 2.21H, A+B), 3.92-3.84 (m, 0.77H, B), 3.83-3.72 (m, 6.23H, A+B), 3.32 (d, J=9.6 Hz, 0.76H, B), 3.10 (d, J=9.7 Hz, 0.26H, A), 2.95-2.86 (m, 0.71H, B), 2.68-2.60 (m, 0.28H, A), 2.57-2.47 (m, 2.15H, A+B), 2.26-2.19 (m, 0.76H, B), 2.12-1.99 (m, 1.46H, A+B), 1.93-1.79 (m, 1.09H, A+B), 1.73-1.52 (m, 6.21H, A+B), 1.50-0.98 (m, 7.17H, A+B), 0.96-0.85 (m, 0.87H, B), 0.83-0.65 (m, 1.38H, A+B). HRMS (m/z): (ESI$^+$) calculated for $C_{26}H_{38}NO_6$ [M+H]$^+$: 460.26936, found 460.26956.

(S)-1-((S)-2-(3-(2-(allyloxy)ethoxy)-4,5-dimethoxyphenyl)-2-cyclohexylacetyl)piperidine-2-carboxylic acid (25)

The substrate S10 (635 mg, 1.11 mmol, 1 equiv) was applied to general procedure F with LiOH (106 mg, 4.43 mmol, 4 equiv) in $H_2O$/MeOH/THF (20 mL). 25 (511 mg, 94%) was obtained after purification by flash column chromatography (CH/EA=5:1+0.5% HCOOH). $^1$H NMR (500 MHz, CDCl$_3$, mixture of rotamers 0.34:1, A:B): δ 9.33 (br s, 0.90H, A+B), 6.48-6.43 (m, 2.11H, A+B), 5.96-5.85 (m, 1.06H, A+B), 5.33-5.24 (m, 1.89H, A+B), 5.20-5.14 (m, 1.07H, A+B), 4.75 (d, J=5.6 Hz, 0.26H, A), 4.62-4.56 (m, 0.26H, A), 4.17-4.05 (m, 4.11H, A+B), 3.88-3.74 (m, 10.02H, A+B), 3.32 (d, J=9.5 Hz, 0.75H, B), 3.10 (d, J=9.6 Hz, 0.24H, A), 2.91-2.82 (m, 0.75H, B), 2.67-2.60 (m, 0.25H, A), 2.27-2.19 (m, 0.77H, B), 2.11-2.00 (m, 1.33H, A+B), 1.90-1.81 (m, 0.96H, A+B), 1.70-1.56 (m, 5.93H, A+B), 1.47-1.02 (m, 7.05H, A+B), 0.95-0.67 (m, 2.01H, A+B). HRMS (m/z): (ESI$^+$) calculated for $C_{27}H_{40}NO_7$ [M+H]$^+$: 490.27993, found 490.28008.

(S)-1-((S)-2-(3-(3-(allyloxy)propoxy)-4,5-dimethoxyphenyl)-2-cyclohexylacetyl)piperidine-2-carboxylic acid (26)

The substrate S11 (694 mg, 1.15 mmol, 1 equiv) was applied to general procedure F with LiOH (110 mg, 4.60 mmol, 4 equiv) in $H_2O$/MeOH/THF (20 mL). 26 (563 mg, 97%) was obtained after purification by flash column chromatography (CH/EA=4:1+0.5% HCOOH). 1H NMR (500 MHz, CDCl$_3$, mixture of rotamers 0.33:1, A:B): δ 8.73 (br s, 0.81H, A+B), 6.49-6.40 (m, 2.01H, A+B), 5.92-5.83 (m, 1.04H, A+B), 5.30 (dd, J=2.3, 6.0 Hz, 0.74H, B), 5.27-5.21 (m, 1.09H, A+B), 5.16-5.11 (m, 1.04H, A+B), 4.77-4.74 (m, 0.23H, A), 4.61-4.55 (m, 0.23H, A), 4.09-4.02 (m, 2.00H, A+B), 4.00-3.94 (m, 2.45H, A+B), 3.87-3.73 (m, 7.33H, A+B), 3.64-3.58 (m, 2.14H, A+B), 3.32 (d, J=9.4 Hz, 0.72H, B), 3.11 (d, J=9.7 Hz, 0.24H, A), 2.88-2.81 (m, 0.70H, B), 2.63 (td, J=2.6, 13.3 Hz, 0.23H, A), 2.24-2.19 (m, 0.71H, B), 2.08-1.99 (m, 3.12H, A+B), 1.91-1.80 (m, 1.27H, A+B), 1.68-1.54 (m, 6.02H, A+B), 1.46-1.25 (m, 3.49H, A+B), 1.22-1.01 (m, 2.50H, A+B), 0.94-0.86 (m, 0.80H, B), 0.81-0.67 (m, 1.19H, A+B). HRMS (m/z): (ESI$^+$) calculated for $C_{28}H_{42}NO_7$ [M+H]$^+$: 504.29558, found 504.29563.

(S)-(R)-1-(3-(allyloxy)phenyl)-3-(3,4-dimethoxyphenyl)propyl 1-((S)-2-(3-(allyloxy)-4,5-dimethoxyphenyl)-2-cyclohexylacetyl)piperidine-2-carboxylate (27)

The substrate 23 (246 mg, 0.55 mmol, 1 equiv) was applied to general procedure G (Supporting Information) with 14 (181 mg, 0.55 mmol, 1 equiv, synthesis and analytics shown in Supporting Information), 4-(1-Pyrrolidinyl)pyridine (334 mg, 2.21 mmol, 4 equiv) and EDC (119 mg, 0.61 mmol, 1.1 equiv) in toluene (40 mL). After stirring at room temperature for 3 hours, 27 (267 mg, 64%) was obtained after purification by flash column chromatography (CH/EA=4:1+1% MeOH) as light yellow resin. $^1$H NMR (500 MHz, CDCl$_3$, mixture of rotamers, major rotamer A): δ 7.29 (t, J=7.9 Hz, 0.31H), 7.21-7.17 (m, 0.12H), 7.11 (t, J=7.9 Hz, 0.58H, A), 6.97-6.90 (m, 0.66H, A), 6.90-6.85 (m, 0.33H), 6.81-6.74 (m, 2.03H, A), 6.71-6.67 (m, 0.93H, A), 6.67-6.58 (m, 1.80H, A), 6.53-6.48 (m, 1.42H, A), 6.46-6.40 (m, 1.21H, A), 6.09-5.93 (m, 1.95H, A), 5.82-5.78 (m, 0.29H), 5.58 (dd, J=5.6, 8.1 Hz, 0.70H, A), 5.48-5.44 (m, 0.59H, A), 5.44-5.34 (m, 1.87H, A), 5.33-5.17 (m, 2.38H, A), 4.73-4.67 (m, 0.34H), 4.60-4.45 (m, 4.48H, A), 3.97-3.90 (m, 0.78H, A), 3.88-3.75 (m, 10.90H, A), 3.69 (s, 1.79H, A), 3.38-3.32 (m, 0.70H, A), 3.09 (d, J=9.5 Hz, 0.04H), 3.01-2.91 (m, 0.37H), 2.80 (td, J=2.9, 13.3 Hz, 0.58H, A), 2.65-2.50 (m, 1.01H, A), 2.50-2.34 (m, 1.42H, A), 2.32-2.23 (m, 1.05H, A), 2.15-1.79 (m, 4.32H, A), 1.72-1.51 (m, 6.67H, A), 1.47-1.05 (m, 6.68H, A), 1.04-0.84 (m, 1.19H, A), 0.80-0.68 (m, 0.81H, A), 0.65-0.50 (m, 0.55H). HRMS (m/z): (ESI$^+$) calculated for $C_{45}H_{58}NO_9$ [M+H]$^+$: 756.41061, found 756.41056.

(S)-(R)-1-(3-(allyloxy)phenyl)-3-(3,4-dimethoxyphenyl)propyl 1-((S)-2-(3-(but-3-en-1-yloxy)-4,5-dimethoxyphenyl)-2-cyclohexylacetyl)piperidine-2-carboxylate (28)

The substrate 24 (289 mg, 0.63 mmol, 1 equiv) was applied to general procedure G with 14 (207 mg, 0.63 mmol, 1 equiv), 4-(1-Pyrrolidinyl)pyridine (380 mg, 2.52 mmol, 4 equiv) and EDC (135 mg, 0.69 mmol, 1.1 equiv) in toluene (50 mL). After stirring at room temperature for 4 hours, 28 (287 mg, 59%) was obtained after purification by flash column chromatography (CH/EA=4:1+1% MeOH). $^1$H NMR (500 MHz, CDCl$_3$, mixture of rotamers): δ 7.28 (t, J=7.9 Hz, 0.29H), 7.19 (t, J=8.1 Hz, 0.10H), 7.10 (t, J=7.9 Hz, 0.60H, A), 6.96-6.90 (m, 0.61H, A), 6.89-6.85 (m, 0.32H), 6.80-6.73 (m, 2.04H, A), 6.71-6.58 (m, 2.51H, A), 6.52-6.48 (m, 1.41H, A), 6.43-6.39 (m, 1.10H, A), 6.08-5.98 (m, 0.91H, A), 5.94-5.78 (m, 1.16H, A), 5.57 (dd, J=5.6, 8.0 Hz, 0.72H, A), 5.48-5.45 (m, 0.60H, A), 5.43-5.36 (m, 1.01H, A), 5.31-5.23 (m, 1.01H, A), 5.19-5.03 (m, 2.03H, A), 4.73-4.68 (m, 0.28H), 4.58-4.46 (m, 2.39H, A), 4.06-4.01 (m, 0.62H), 4.01-3.91 (m, 2.26H, A), 3.87-3.80 (m, 8.47H, A), 3.79-3.76 (m, 2.56H, A), 3.69 (s, 1.87H, A), 3.39-3.33 (m, 0.73H, A), 2.98-2.93 (m, 0.30H, A), 2.79 (td, J=2.9, 13.3 Hz, 0.59H, A), 2.63-2.34 (m, 4.30H, A), 2.31-2.24 (m, 0.96H, A), 2.14-2.03 (m, 1.63H, A), 1.99-1.79 (m, 2.18H, A), 1.71-1.51 (m, 5.98H, A), 1.47-1.06 (m, 6.21H, A), 1.02-0.85 (m, 0.99H, A), 0.79-0.70 (m, 0.71H, A), 0.64-0.53 (m, 0.44H, A). HRMS (m/z): (ESI$^+$) calculated for $C_{46}H_{60}NO_9$ [M+H]$^+$: 770.42626, found 770.42648.

(S)-(R)-1-(3-(allyloxy)phenyl)-3-(3,4-dimethoxyphenyl)propyl 1-((S)-2-(3-(2-(allyloxy)ethoxy)-4,5-dimethoxyphenyl)-2-cyclohexylacetyl)piperidine-2-carboxylate (29)

The substrate 25 (508 mg, 1.04 mmol, 1 equiv) was applied to general procedure G with 14 (341 mg, 1.04 mmol, 1 equiv), 4-(1-Pyrrolidinyl)pyridine (628 mg, 4.15 mmol, 4 equiv) and EDC (223 mg, 1.14 mmol, 1.1 equiv) in toluene (75 mL). After stirring at room temperature for 4 hours and performing the standard work-up procedure, the crude product was reacted with acetic anhydride (234 mg), pyridine (75 μL) and DMAP (11 mg) in DCM (15 mL) to convert unreacted 14 into the corresponding acetate and thereby facilitating the purification of 29. 29 (524 mg, 63%) was obtained after purification by flash column chromatography (CH/EA=5:1). $^1$H NMR (500 MHz, CDCl$_3$, mixture of rotamers): δ 7.29 (t, J=7.8 Hz, 0.30H), 7.21-7.17 (m, 0.10H), 7.11 (t, J=7.9 Hz, 0.58H, A), 6.97-6.90 (m, 0.67H, A), 6.89-6.85 (m, 0.34H, A), 6.81-6.73 (m, 2.13H, A), 6.72-6.57 (m, 2.88H, A), 6.54-6.49 (m, 1.51H, A), 6.47-6.39 (m, 1.23H, A), 6.09-5.98 (m, 1.01H, A), 5.96-5.85 (m, 0.98H, A), 5.82-5.77 (m, 0.30H), 5.60-5.54 (m, 0.72H, A), 5.48-5.44 (m, 0.62H, A), 5.44-5.35 (m, 1.20H, A), 5.33-5.24 (m, 2.12H, A), 5.21-5.14 (m, 1.02H, A), 4.74-4.64 (m, 0.35H), 4.58-4.45 (m, 2.47H, A), 4.18-4.02 (m, 4.36H, A), 3.98-3.62 (m, 16.72H, A), 3.39-3.32 (m, 0.75H, A), 3.09 (d, J=9.6 Hz, 0.04H), 3.01-2.91 (m, 0.36H), 2.78 (td, J=2.9, 13.3 Hz, 0.59H, A), 2.65-2.52 (m, 1.03H, A), 2.50-2.33 (m, 1.46H, A), 2.33-2.21 (m, 1.12H, A), 2.15-1.77 (m, 4.52H, A), 1.76-1.48 (m, 7.00H, A), 1.48-1.04 (m, 6.93H, A), 1.03-0.84 (m, 1.22H, A), 0.80-0.68 (m, 0.85H, A), 0.65-0.49 (m, 0.54H). HRMS (m/z): (ESI$^+$) calculated for $C_{47}H_{62}NO_{10}$ [M+H]$^+$: 800.43682, found 800.43680.

(S)-(R)-1-(3-(allyloxy)phenyl)-3-(3,4-dimethoxyphenyl)propyl 1-((S)-2-(3-(3-(allyloxy)propoxy)-4,5-dimethoxyphenyl)-2-cyclohexylacetyl)piperidine-2-carboxylate (30)

The substrate 26 (545 mg, 1.08 mmol, 1 equiv) was applied to general procedure G with 14 (355 mg, 1.08 mmol, 1 equiv), 4-(1-Pyrrolidinyl)pyridine (640 mg, 4.32 mmol, 4 equiv) and EDC (228 mg, 1.19 mmol, 1.1 equiv) in toluene (75 mL). After stirring at room temperature for 4 hours and performing the standard work-up procedure, the crude product was reacted with acetic anhydride (166 mg), pyridine (53 μL) and DMAP (8 mg) in DCM (10 mL) to convert unreacted 14 into the corresponding acetate and thereby facilitating the purification of 30. 30 (522 mg, 59%) was obtained after purification by flash column chromatography (CH/EA=4:1). $^1$H NMR (500 MHz, CDCl$_3$, mixture of rotamers): δ 7.30-7.26 (m, 0.19H), 7.20-7.16 (m, 0.10H), 7.09 (t, J=7.9 Hz, 0.56H, A), 6.96-6.89 (m, 0.55H, A), 6.88-6.84 (m, 0.29H), 6.79-6.73 (m, 1.88H, A), 6.70-6.56 (m, 2.55H, A), 6.52-6.48 (m, 1.38H, A), 6.42 (s, 0.55H, A), 6.40-6.37 (m, 0.54H), 6.07-5.97 (m, 0.92H, A), 5.93-5.84 (m, 0.93H, A), 5.79 (dd, J=6.2, 7.6 Hz, 0.27H), 5.55 (dd, J=5.6, 8.1 Hz, 0.68H, A), 5.46 (d, J=5.4 Hz, 0.55H, A), 5.42-5.35 (m, 1.09H, A), 5.29-5.22 (m, 2.01H, A), 5.16-5.11 (m, 0.99H, A), 4.70 (d, J=5.6 Hz, 0.27H), 4.57-4.46 (m, 2.25H, A), 4.10-3.91 (m, 5.04H, A), 3.86-3.79 (m, 8.36H, A), 3.77-3.74 (m, 2.42H, A), 3.67-3.53 (m, 3.89H, A), 3.37-3.33 (m, 0.71H, A), 2.95 (d, J=9.7 Hz, 0.30H), 2.78 (td, J=2.8, 13.4 Hz, 0.54H, A), 2.62-2.50 (m, 0.80H, A), 2.48-2.33 (m, 1.22, A), 2.30-2.23 (m, 0.94H, A), 2.12-1.79 (m, 6.01H, A), 1.70-1.52 (m, 5.93H, A), 1.44-1.06 (m, 6.25H, A), 1.03-0.82 (m, 1.01H, A), 0.79-0.68 (m, 0.70H, A), 0.63-0.52 (m, 0.37H). HRMS (m/z): (ESI$^+$) calculated for $C_{48}H_{63}NO_{10}Na$ [M+Na]$^+$: 836.43442, found 836.43489.

Macrocycles 31-(Z) and 31-(E)

The substrate 9 (357 mg, 0.47 mmol, 1 equiv) was applied to general procedure B with Grubbs 2$^{nd}$ Generation catalyst (40 mg, 0.05 mmol, 0.1 equiv) in DCM (1000 mL, 0.5 mM). After work-up procedure a), 31-(Z) (16 mg, 5%) and 31-(E) (132 mg, 38%) were obtained as pure isomers after purification by flash column chromatography (CH/EA=5:1) and semi-preparative HPLC (70-100% Solvent B). Another product fraction was obtained as a mixture of E/Z isomers (77 mg, 22%) and not further purified. Data for Macrocycle 31-(Z): $^1$H NMR (500 MHz, CDCl$_3$): δ 7.15 (t, J=7.7 Hz, 1H), 6.84-6.81 (m, 1H), 6.80-6.75 (m, 3H), 6.74 (d, J=1.9 Hz, 1H), 6.72-6.68 (m, 1H), 6.32-6.29 (m, 2H), 6.06-5.99 (m, 1H), 5.89-5.79 (m, 2H), 5.50 (d, J=5.4 Hz, 1H), 4.65-4.54 (m, 2H), 4.09-4.03 (m, 1H), 3.88 (s, 3H), 3.85 (s, 3H), 3.84-3.78 (m, 4H), 3.62 (s, 3H), 3.56-3.51 (m, 1H), 3.27 (d, J=9.3 Hz, 1H), 2.69-2.62 (m, 1H), 2.58-2.49 (m, 2H), 2.33-2.27 (m, 1H), 2.19-2.10 (m, 1H), 2.09-1.92 (m, 2H), 1.89-1.82 (m, 1H), 1.72-1.60 (m, 5H), 1.57-1.48 (m, 1H), 1.48-1.28 (m, 3H), 1.24-1.18 (m, 1H), 1.18-1.07 (m, 2H), 0.98-0.88 (m, 1H), 0.81-0.71 (m, 1H). HRMS (m/z): (ESI$^+$) calculated for $C_{43}H_{54}NO_9$ [M+H]$^+$: 728.37931, found 728.37972. Data for Macrocycle 31-(E): $^1$H NMR (500 MHz, CDCl$_3$): δ 7.17 (t, J=7.9 Hz, 1H), 6.84-6.81 (m, 1H), 6.80-6.76 (m, 2H), 6.71-6.65 (m, 3H), 6.42-6.39 (m, 1H), 6.27 (d, J=1.8 Hz, 1H), 5.86 (ddd, J=5.9, 7.4, 15.5 Hz, 1H), 5.70-5.60 (m, 2H), 5.49-5.44 (m, 1H), 4.63 (ddd, J=1.1, 6.7, 25.9 Hz, 1H), 4.40-4.37 (m, 2H), 3.97-3.90 (m, 1H), 3.86 (s, 3H), 3.84 (s, 3H), 3.82 (s, 3H), 3.53 (s, 3H), 3.30 (d, J=9.9 Hz, 1H), 2.88-2.79 (m, 1H), 2.64-2.46 (m, 2H), 2.29-2.22 (m, 1H), 2.13-2.02 (m, 2H), 1.94-1.82 (m, 2H), 1.72-1.54 (m, 6H), 1.48-1.38 (m, 1H), 1.37-1.23 (m, 3H), 1.17-1.06 (m, 2H), 0.94-0.84 (m, 1H), 0.78-0.67 (m, 1H). HRMS (m/z): (ESI$^+$) calculated for $C_{43}H_{54}NO_9$ [M+H]$^+$: 728.37931, found 728.37955.

Macrocycles 32-(Z) and 32-(E)

The substrate 10 (304 mg, 0.40 mmol, 1 equiv) was applied to general procedure B with Grubbs 2$^{nd}$ Generation catalyst (34 mg, 0.04 mmol, 0.1 equiv) in DCM (800 mL, 0.5 mM). After work-up procedure a), 32-(Z) (50 mg, 17%) and 32-(E) (62 mg, 21%) were obtained as pure isomers after purification by flash column chromatography (CH/EA=5:1). Another product fraction was obtained as a mixture of E/Z isomers (118 mg, 40%) and not further purified. Data for Macrocycle 32-(Z): $^1$H NMR (500 MHz, CDCl$_3$): δ 7.15 (t, J=7.9 Hz, 1H), 6.86-6.82 (m, 1H), 6.80-6.75 (m, 2H), 6.71-6.63 (m, 3H), 6.39-6.36 (m, 1H), 6.32 (br s, 1H), 5.73-5.67 (m, 2H), 5.64 (dd, J=6.4, 8.1 Hz, 1H), 5.46-5.43 (m, 1H), 4.45 (dd, J=5.7, 12.5 Hz, 1H), 4.34 (dd, J=3.9, 12.6 Hz, 1H), 4.20-4.13 (m, 1H), 4.07-4.00 (m, 1H), 3.94 (d, J=13.8 Hz, 1H), 3.88-3.80 (m, 6H), 3.54 (br s, 3H), 3.32 (d, J=9.9 Hz, 1H), 2.72 (td, J=2.8, 13.4 Hz, 1H), 2.60-2.50 (m, 1H), 2.49-2.40 (m, 3H), 2.31-2.25 (m, 1H), 2.16-2.05 (m, 2H), 1.95-1.84 (m, 2H), 1.71-1.52 (m, 6H), 1.46-1.07 (m, 6H), 0.93-0.83 (m, 1H), 0.79-0.68 (m, 1H). HRMS (m/z): (ESI$^+$) calculated for $C_{44}H_{56}NO_9$ [M+H]$^+$: 742.39496, found 742.39492. Data for Macrocycle 32-(E): $^1$H NMR (500 MHz, CDCl$_3$): δ 7.15 (t, J=7.9 Hz, 1H), 6.83-6.75 (m, 3H), 6.66-6.61 (m, 2H), 6.57-6.23 (m, 3H), 5.70 (dt, J=6.3, 15.6 Hz, 1H), 5.56-5.44 (m, 3H), 4.50-4.44 (m, 1H), 4.35-4.28 (m, 2H), 4.09-4.03 (m, 1H), 4.02-3.96 (m, 1H), 3.85-3.84 (m, 6H), 3.79-3.53 (m, 6H), 3.35 (d, J=9.9 Hz, 1H), 2.99 (td, J=2.7, 13.3 Hz, 1H), 2.56-2.48 (m, 1H), 2.47-2.37 (m, 2H), 2.34-2.22 (m, 2H), 2.12-2.03 (m, 2H), 1.92-1.82 (m, 2H), 1.72-1.56 (m, 6H), 1.49-1.38 (m, 1H), 1.37-1.21 (m, 3H), 1.17-1.06 (m, 2H), 0.94-0.83 (m, 1H), 0.81-0.70 (m, 1H). HRMS (m/z): (ESI$^+$) calculated for $C_{44}H_{56}NO_9$ [M+H]$^+$: 742.39496, found 742.39481.

Macrocycles 33-(Z) and 33-(E)

The substrate 11 (170 mg, 0.21 mmol, 1 equiv) was applied to general procedure B (Supporting Information) with Grubbs 2$^{nd}$ Generation catalyst (18 mg, 0.02 mmol, 0.1 equiv) in DCM (450 mL, 0.5 mM). After work-up procedure a), 33-(Z) (11 mg, 7%) and 33-(E) (91 mg, 56%) were obtained after purification by flash column chromatography (CH/EA=3:1) as colorless resins. Data for Macrocycle 33-(Z): $^1$H NMR (500 MHz, CDCl$_3$): δ 7.17 (t, J=7.9 Hz, 1H), 6.87-6.84 (m, 1H), 6.83-6.79 (m, 1H), 6.79-6.75 (m, 1H), 6.66-6.63 (m, 2H), 6.53-6.50 (m, 1H), 6.37 (s, 2H), 5.91 (ddd, J=5.3, 6.8, 11.9 Hz, 1H), 5.87-5.81 (m, 1H), 5.49 (dd, J=5.6, 8.7 Hz, 1H), 5.45 (d, J=5.1 Hz, 1H), 4.63 (dd, J=6.9, 11.9 Hz, 1H), 4.54 (ddd, J=6.0, 12.2, 19.4 Hz, 2H), 4.23 (dd, J=5.6, 12.7 Hz, 1H), 4.16-4.05 (m, 2H), 3.93 (d, J=13.6 Hz, 1H), 3.87-3.84 (m, 6H), 3.80-3.68 (m, 2H), 3.58 (s, 6H), 3.34 (d, J=10.1 Hz, 1H), 2.75 (td, J=3.0, 13.3 Hz, 1H), 2.58-2.51 (m, 1H), 2.45-2.38 (m, 1H), 2.35-2.29 (m, 1H), 2.14-2.06 (m, 1H), 2.04-1.95 (m, 1H), 1.92-1.85 (m, 2H), 1.71-1.58 (m, 6H), 1.46-1.08 (m, 6H), 0.91-0.82 (m, 1H), 0.79-0.70 (m, 1H). HRMS (m/z): (ESI$^+$) calculated for $C_{45}H_{58}NO_{10}$ [M+H]$^+$: 772.4055, found 772.4050. Data for Macrocycle 33-(E): $^1$H NMR (500 MHz, CDCl$_3$, mixture of rotamers 0.58:1, A:B): δ 7.30-7.27 (m, 0.30H, A), 7.16-7.11 (m, 0.99H, A+B), 6.90-6.87 (m, 0.37H, A), 6.81-6.67 (m, 3.52H, A+B), 6.65-6.61 (m, 1.26H, A+B), 6.52-6.45 (m, 2.58H, A+B), 5.83 (dt, J=5.6, 17.0 Hz, 1.00H, A+B), 5.75 (dt, J=5.1, 16.0 Hz, 0.59H, B), 5.66-5.63 (m, 0.65H, B), 5.51-5.46 (m, 0.63H, B), 5.41 (dd, J=5.5, 8.5 Hz, 0.62H, B), 4.80-4.76 (m, 0.41H, A), 4.64-4.59 (m, 0.62H, B), 4.55-4.50 (m, 0.61H, B), 4.45-4.38 (m, 0.74H, A), 4.28-4.24 (m, 0.72H, A), 4.16 (dd, J=4.8, 10.1 Hz, 0.41H, A), 4.12-4.00 (m, 2.61H, A+B), 3.98-3.83 (m, 10.46H, A+B), 3.67-3.52 (m, 5.57H, A+B), 3.39 (d, J=9.9 Hz, 0.61H, B), 3.01-2.93 (m, 0.99H, A+B), 2.71 (ddd, J=5.4, 9.1, 14.3 Hz, 0.36H, A), 2.61 (ddd, J=7.1, 8.8, 14.1 Hz, 0.37H, A), 2.51-2.38 (m, 1.30H, B), 2.35 (d, J=10.1 Hz, 0.37H, A), 2.29-2.23 (m, 1.26H, A+B), 2.12-2.05 (m, 0.93H, A+B), 1.96-1.85 (m, 1.65H, A+B), 1.79-1.62 (m, 6.10H, A+B), 1.49-0.77 (m, 8.30H, A+B), 0.66-0.57 (m, 0.34H, A), −0.14 (qd, J=3.7, 12.7 Hz, 0.34H, A), −0.22--0.31 (m, 0.34H, A). HRMS (m/z): (ESI$^+$) calculated for $C_{45}H_{58}NO_{10}$ [M+H]$^+$: 772.40552, found 772.40455.

Macrocycle 34-(E)

The substrate 12 (125 mg, 0.15 mmol, 1 equiv) was applied to general procedure B with Grubbs 2$^{nd}$ Generation catalyst (13 mg, 0.015 mmol, 0.1 equiv) in DCM (310 mL, 0.5 mM). After work-up procedure a), 34-(E) (53 mg, 44%) was obtained after purification by flash column chromatography (CH/EA=4:1). The corresponding Z-alkene was only observed in trace amounts during the reaction control via LC-MS and could not be isolated. $^1$H NMR (500 MHz, $C_6D_6$): δ 7.08 (t, J=7.9 Hz, 1H), 6.74-6.70 (m, 5H), 6.64-6.59 (m, 2H), 6.52-6.47 (m, 1H), 5.91-5.87 (m, 1H), 5.84 (dd, J=5.3, 8.1 Hz, 1H), 5.56-5.48 (m, 2H), 4.33-4.24 (m, 2H), 4.13-4.07 (m, 1H), 3.99-3.94 (m, 1H), 3.91-3.86 (m, 1H), 3.70-3.64 (m, 2H), 3.55 (s, 3H), 3.46-3.43 (m, 9H), 3.35-3.28 (m, 3H), 2.97-2.90 (m, 1H), 2.60-2.51 (m, 3H), 2.33-2.28 (m, 1H), 2.25-2.21 (m, 1H), 2.08-1.99 (m, 3H), 1.91-1.85 (m, 1H), 1.77-1.73 (m, 1H), 1.67-1.62 (m, 2H), 1.56-1.52 (m, 1H), 1.44-1.28 (m, 4H), 1.20-1.14 (m, 4H), 0.97-0.91 (m, 1H), 0.87-0.78 (m, 1H). HRMS (m/z): (ESI$^+$) calculated for $C_{46}H_{60}NO_{10}$ [M+H]$^+$: 786.42117, found 786.42139.

Macrocycles 35-(Z) and 35-(E)

The substrate 27 (261 mg, 0.35 mmol, 1 equiv) was applied to general procedure B (Supporting Information) with Grubbs 2$^{nd}$ Generation catalyst (30 mg, 0.04 mmol, 0.1 equiv) in DCM (700 mL, 0.5 mM). After work-up procedure b), 35-(Z) (57 mg, 23%) and 35-(E) (28 mg, 11%) were obtained as white, solid product isomers after purification by flash column chromatography (CH/EA=5:1). Another product fraction was obtained as a mixture of E/Z isomers (69 mg, 28%) and not further purified. Data for Macrocycle 35-(E): $^1$H NMR (500 MHz, CDCl$_3$): δ 7.20 (d, J=1.7 Hz, 1H), 7.07-7.02 (m, 1H), 6.79-6.75 (m, 2H), 6.55-6.49 (m, 3H), 6.46-6.43 (m, 1H), 6.29 (d, J=1.8 Hz, 1H), 6.24 (d, J=16.3 Hz, 1H), 5.68-5.61 (m, 1H), 5.59 (d, J=5.1 Hz, 1H), 5.28 (dd, J=3.4, 10.1 Hz, 1H), 4.87-4.74 (m, 3H), 4.66 (dd, J=9.9, 13.4 Hz, 1H), 4.40 (d, J=13.4 Hz, 1H), 3.86 (s, 3H), 3.85 (s, 3H), 3.74 (s, 3H), 3.71 (s, 3H), 3.57 (d, J=10.3 Hz, 1H), 3.11 (td, J=2.5, 13.1 Hz, 1H), 2.39-2.30 (m, 2H), 2.23-2.12 (m, 2H), 1.92-1.87 (m, 1H), 1.85-1.78 (m, 2H), 1.74-1.65 (m, 3H), 1.58-1.50 (m, 2H), 1.44-1.35 (m, 4H), 1.26-1.17 (m, 2H), 1.11-1.04 (m, 1H), 0.99-0.91 (m, 1H), 0.82-0.74 (m, 1H). HRMS (m/z): (ESI$^+$) calculated for C$_{43}$H$_{54}$NO$_9$ [M+H]$^+$: 728.37931, found 728.37950. Data for Macrocycle 35-(Z): $^1$H NMR (500 MHz, CDCl$_3$, mixture of rotamers 0.16:1, A:B): δ 7.24 (t, J=7.8 Hz, 0.15H, A), 7.09 (t, J=7.8 Hz, 0.85H, B), 7.04-7.01 (m, 0.14H, A), 6.92-6.87 (m, 0.30H, A), 6.81-6.74 (m, 2.59H, A+B), 6.70-6.51 (m, 4.36H, A+B), 6.47-6.43 (m, 0.84H, B), 6.16-6.13 (m, 0.14H, A), 6.08-5.80 (m, 2.39H, A+B), 5.56-5.52 (m, 0.85H, B), 5.33 (dd, J=4.2, 9.8 Hz, 0.88H, B), 4.88-4.80 (m, 0.85H, B), 4.78-4.65 (m, 2.35H, A+B), 4.58-4.53 (m, 0.16H, A), 4.49-4.35 (m, 1.05H, A+B), 4.27 (d, J=13.2 Hz, 0.85H, B), 3.87-3.82 (m, 7.03H, A+B), 3.79 (s, 0.61H, A), 3.74 (s, 5.06H, A+B), 3.50 (d, J=10.2 Hz, 0.79H, B), 3.20 (td, J=2.6, 13.1 Hz, 0.85H, B), 2.93 (td, J=3.5, 12.8 Hz, 0.14H, A), 2.63-2.50 (m, 0.35H, A), 2.42-2.17 (m, 3.57H, A+B), 2.15-2.09 (m, 0.30H, A), 1.88 (d, J=12.4 Hz, 0.97H, A+B), 1.76-1.46 (m, 8.06H, A+B), 1.43-1.31 (m, 3.08H, A+B), 1.28-1.11 (m, 3.00H, A+B), 0.98-0.83 (m, 1.20H, A+B), 0.80-0.68 (m, 0.84H, B), 0.41-0.31 (m, 0.15H, A), 0.10--0.01 (m, 0.14H, A). HRMS (m/z): (ESI$^+$) calculated for C$_{43}$H$_{54}$NO$_9$ [M+H]$^+$: 728.37931, found 728.37963.

Macrocycles 36-(Z) and 36-(E)

The substrate 28 (224 mg, 0.29 mmol, 1 equiv) was applied to general procedure B with Grubbs 2$^{nd}$ Generation catalyst (25 mg, 0.03 mmol, 0.1 equiv) and 1,4-benzoquinone (4 mg, 0.03 mmol, 0.1 equiv) in DCM (1 mM, 300 mL). After work-up procedure b), 36-(Z) (28 mg, 13%) and 36-(E) (115 mg, 53%) were obtained as product isomers after purification by flash column chromatography (CH/EA=4:1) and semi-preparative HPLC (80-100% Solvent B). Data for Macrocycle 36-(Z): $^1$H NMR (500 MHz, CDCl$_3$, mixture of rotamers 0.16:1, A:B): δ 7.29 (t, J=7.9 Hz, 0.15H, A), 7.15 (t, J=8.3 Hz, 0.85H, B), 7.08-7.06 (m, 0.14H, A), 6.94-6.88 (m, 0.32H, A), 6.81-6.74 (m, 2.73H, A+B), 6.69-6.61 (m, 2.75H, A+B), 6.56-6.51 (m, 0.22H, A), 6.43-6.40 (m, 0.80H, B), 6.31-6.28 (m, 0.81H, B), 6.21-6.19 (m, 0.13H, A), 6.02-5.95 (m, 0.15H, A), 5.93-5.78 (m, 1.87H, A+B), 5.55-5.46 (m, 1.77H, B), 4.62-4.42 (m, 0.65H, A), 4.34-4.23 (m, 2.52H, A+B), 4.12-4.00 (m, 1.79H, B), 3.88-3.82 (m, 6.69H, A+B), 3.80-3.76 (m, 3.00H, A+B), 3.64 (s, 2.42H, B), 3.37 (d, J=10.0 Hz, 0.84H, B), 2.81-2.71 (m, 1.73H, A+B), 2.66-2.54 (m, 0.38H, A), 2.52-2.34 (m, 3.01H, A+B), 2.31-2.24 (m, 1.02H, A+B), 2.20-2.06 (m, 1.21H, A+B), 1.92-1.84 (m, 1.64H, A+B), 1.80-1.53 (m, 7.03H, A+B), 1.50-1.24 (m, 3.83H, A+B), 1.19-1.07 (m, 2.59H, A+B), 0.92-0.82 (m, 1.05H, A+B), 0.78-0.69 (m, 0.82H, B), 0.30-0.21 (m, 0.13H, A), 0.14-0.05 (m, 0.18H, A). HRMS (m/z): (ESI$^+$) calculated for C$_{44}$H$_{56}$NO$_9$ [M+H]$^+$: 742.39496, found 742.39491. Data for Macrocycle 36-(E): $^1$H NMR (500 MHz, THF-d$_8$, mixture of rotamers 0.18:1, A:B): δ 7.20 (t, J=7.8 Hz, 0.90H, B), 7.11-7.08 (m, 0.14H, A), 6.99-6.92 (m, 0.81H, B), 6.92-6.83 (m, 0.31H, A), 6.81-6.75 (m, 1.85H, B), 6.73-6.70 (m, 0.99H, B), 6.69 (d, 0.82H, B), 6.67-6.60 (m, 1.17H, A+B), 6.46 (d, J=1.8 Hz, 0.80H, B), 6.37 (d, J=1.9 Hz, 0.14H, A), 6.33 (d, J=1.8 Hz, 0.79H, B), 5.97-5.89 (m, 0.28H, A), 5.79 (dt, J=4.9, 16.2 Hz, 0.15H, A), 5.72-5.61 (m, 1.69H, A+B), 5.56 (dd, J=4.8, 9.2 Hz, 0.82H, B), 5.29-5.25 (m, 0.80H, B), 4.74 (d, J=5.8 Hz, 0.14H, A), 4.69-4.53 (m, 2.01H, A+B), 4.24-4.17 (m, 0.14H, A), 3.98-3.92 (m, 0.16H, A), 3.89-3.81 (m, 1.75H, A+B), 3.76-3.67 (m, 13.11H, A+B), 3.43 (d, J=8.7 Hz, 0.87H, B), 2.84 (d, J=9.9 Hz, 0.14H, A), 2.74 (td, J=3.1, 13.3 Hz, 0.97H, B), 2.61-2.54 (m, 0.99H, A+B), 2.50-2.34 (m, 3.56H, A+B), 2.11-2.03 (m, 1.01H, A+B), 1.99-1.89 (m, 1.76H, A+B), 1.85-1.79 (m, 1.00H, A+B), 1.70-1.55 (m, 5.22H, A+B), 1.46-1.37 (m, 0.94H, A+B), 1.33-0.76 (m, 8.59H, A+B), 0.55-0.45 (m, 0.25H, A). HRMS (m/z): (ESI$^+$) calculated for C$_{44}$H$_{56}$NO$_9$ [M+H]$^+$: 742.39496, found 742.39517.

Macrocycles 37-(E) and 37-(Z)

The substrate 29 (201 mg, 0.25 mmol, 1 equiv) was applied to general procedure B with Grubbs 2$^{nd}$ Generation catalyst (21 mg, 0.03 mmol, 0.1 equiv) and 1,4-benzoquinone (3 mg, 0.03 mmol, 0.1 equiv) in DCM (1 mM, 250 mL). After work-up procedure b), 37-(E) (58 mg, 30%) and 37-(Z) (7 mg, 4%) were obtained as pure product isomers after purification by flash column chromatography (CH/EA=4:1) and semi-preparative HPLC (80-100% Solvent B). Another product fraction was obtained as a mixture of E/Z isomers (75 mg, 39%) and not further purified. Data for Macrocycle 37-(E): $^1$H NMR (500 MHz, CDCl$_3$, mixture of rotamers 0.34:1, A:B): δ 7.28-7.23 (m, 0.40H, A), 7.19-7.15 (m, 0.78H, B), 7.05-7.02 (m, 0.23H, A), 6.91-6.87 (m, 0.28H, A), 6.86-6.72 (m, 2.99H, A+B), 6.71-6.61 (m, 2.06H, A+B), 6.57-6.55 (m, 0.71H, B), 6.43-6.37 (m, 1.34H, A+B), 6.33-6.30 (m, 0.23H, A), 6.00 (dt, J=4.9, 17.3 Hz, 0.32H, A), 5.93-5.90 (m, 0.17H, A), 5.87 (dt, J=5.2, 16.5 Hz, 1.15H, B), 5.83-5.80 (m, 0.40H, A), 5.58 (dd, J=5.3, 8.5 Hz, 0.74H, B), 5.49 (d, J=5.5 Hz, 0.78H, B), 4.65-4.54 (m, 1.05H, A+B), 4.53-4.42 (m, 1.57H, A+B), 4.31-4.18 (m, 0.79H, A), 4.15-4.03 (m, 2.82H, A+B), 4.00-3.88 (m, 2.20H, A+B), 3.86-3.79 (m, 11.69H, A+B), 3.74-3.61 (m, 4.92H, A+B), 3.33 (d, J=9.5 Hz, 0.72H, B), 2.85-2.76 (m, 0.98H, A+B), 2.69 (d, J=9.7 Hz, 0.24H, A), 2.65-2.48 (m, 1.31H, A+B), 2.45-2.38 (m, 0.77H, B), 2.32-2.18 (m, 1.51H, A+B), 2.10-1.96 (m, 2.00H, A+B), 1.90-1.83 (m, 1.51H, A+B), 1.70-1.56 (m, 5.38H, A+B), 1.51-1.23 (m, 5.20H, A+B), 1.17-0.99 (m, 2.30H, A+B), 0.94-0.85 (m, 0.96H, A+B), 0.77-0.69 (m, 0.82H, B), 0.48-0.38 (m, 0.23H, A), 0.26-0.17 (m, 0.25H, A). HRMS (m/z): (ESI$^+$) calculated for C$_{45}$H$_{58}$NO$_{10}$ [M+H]$^+$: 772.40552, found 772.40598. Data for Macrocycle 37-(Z): $^1$H NMR (500 MHz, CDCl$_3$, mixture of rotamers): δ 7.28-7.24 (m, 0.98H), 7.16 (dt, J=7.9, 10.4 Hz, 0.72H), 7.01 (t, J=2.0 Hz, 0.15H), 6.97 (t, J=2.0 Hz, 0.16H), 6.92 (dd, J=2.1, 8.0 Hz, 0.29H), 6.89-6.73 (m, 3.01H), 6.72-6.66 (m, 1.03H), 6.65-6.55 (m, 2.97H), 6.50 (d, J=1.9 Hz, 0.36H), 6.35 (d, J=1.9 Hz, 0.30H), 6.23 (d, J=2.0 Hz, 0.14H), 6.01-5.74 (m, 2.45H), 5.52 (dd, J=5.6, 8.7 Hz, 0.36H), 5.45-5.36 (m, 1.00H), 4.79-4.57 (m, 2.38H), 4.52 (d, J=13.7 Hz, 0.17H), 4.30-4.20 (m, 1.49H), 4.19-3.97 (m, 2.86H), 3.89-3.75 (m, 14.09H), 3.72-3.69 (m, 0.35H), 3.65-3.60 (m, 0.30H), 3.57-3.51 (m, 0.29H), 3.39 (dd, J=5.7, 9.4 Hz, 0.60H), 3.25 (d, J=9.6 Hz, 0.17H), 2.93-2.83 (m, 0.55H), 2.77 (td, J=3.1, 13.3 Hz, 0.32H), 2.68-2.51 (m, 1.32H), 2.48-2.40 (m, 0.65H), 2.38-2.19 (m, 1.39H), 2.16-2.02 (m, 1.70H), 1.98-1.75 (m, 2.19H), 1.72-1.55 (m, 6.00H), 1.47-1.27 (m, 4.00H), 1.19-1.00 (m, 2.99H), 0.92-0.73 (m, 2.06H), 0.40-0.30 (m, 0.17H), 0.27-0.18 (m, 0.15H). HRMS (m/z): (ESI$^+$) calculated for C$_{45}$H$_{58}$NO$_{10}$ [M+H]$^+$: 772.40552, found 772.40547.

Macrocycle 38-(E)

The substrate 30 (134 mg, 0.17 mmol, 1 equiv) was applied to general procedure B with Grubbs 2$^{nd}$ Generation catalyst (15 mg, 0.017 mmol, 0.1 equiv) and 1,4-benzoquinone (2 mg, 0.017 mmol, 0.1 equiv) in DCM (1 mM, 175 mL). After work-up procedure b), 38-(E) (43 mg, 33%) was obtained as pure product isomer after purification by semi-preparative HPLC (85-100% Solvent B). Another product fraction was obtained as a mixture of the E-alkene and an unidentified isomer (probably the Z-alkene due to same m/z on HPLC-MS; 75 mg, 58%, ratio 1:4, unidentified isomer/ E-alkene). Unfortunately, we were not able to obtain the unidentified isomer as a pure product by column chromatography or semi-preparative HPLC. $^1$H NMR (500 MHz, CDCl$_3$, mixture of rotamers 0.36:1, A:B): δ 7.29-7.26 (m, 0.22H, A), 7.14 (t, J=7.9 Hz, 0.86H, B), 7.03-7.01 (m, 0.23H, A), 6.89-6.87 (m, 0.24H, A), 6.87-6.84 (m, 0.24H, A), 6.80-6.72 (m, 2.87H, A+B), 6.69-6.64 (m, 2.16H, A+B), 6.63-6.59 (m, 1.23H, A+B), 6.47-6.43 (m, 1.48H, A+B), 6.28 (d, J=1.9 Hz, 0.21H, A), 5.95-5.89 (m, 0.39H, A), 5.87-5.80 (m, 1.12H, A+B), 5.77 (dt, J=5.1, 16.0 Hz, 0.92H, B), 5.58 (dd, J=5.6, 8.3 Hz, 0.75H, B), 5.51 (d, J=5.6 Hz, 0.73H, B), 4.64-4.56 (m, 0.95H, A+B), 4.40-4.36 (m, 1.43H, A+B), 4.14-4.04 (m, 2.40H, A+B), 4.02-3.97 (m, 1.07H, A+B), 3.96-3.90 (m, 1.70H, A+B), 3.87-3.83 (m, 6.67H, A+B), 3.82 (s, 0.81H, A), 3.81-3.79 (m, 0.93H, A), 3.78 (s, 2.32H, B), 3.66 (s, 2.67H, A+B), 3.58-3.53 (m, 0.90H, A+B), 3.35 (d, J=9.8 Hz, 0.74H, B), 2.92 (td, J=2.8, 13.5 Hz, 0.77H, B), 2.83-2.74 (m, 0.50H, A), 2.65-2.59 (m, 0.38H, A), 2.55-2.37 (m, 2.20H, A+B), 2.32-2.23 (m, 1.00H, A+B), 2.21-2.14 (m, 0.30H, A), 2.11-1.97 (m, 3.64H, A+B), 1.93-1.83 (m, 1.37H, A+B), 1.72-1.58 (m, 5.21H, A+B), 1.54-1.40 (m, 1.19H, A+B), 1.36-1.25 (m, 3.38H, A+B), 1.17-1.07 (m, 2.20H, A+B), 0.95-0.83 (m, 1.22H, A+B), 0.78-0.70 (m, 0.81H, B), 0.61-0.51 (m, 0.22H, A), 0.39-0.30 (m, 0.23H, A). HRMS (m/z): (ESI$^+$) calculated for C$_{46}$H$_{60}$NO$_{10}$ [M+H]$^+$: 786.42117, found 786.42154.

Macrocycle 39

A stirred solution of 31 (E/Z-alkene mixture, 44 mg, 0.06 mmol, 1 equiv) in MeOH (3 mL) was degassed by sparging with Argon for 15 minutes. After addition of Pd/C (10 wt.-%, 6.4 mg, 0.006 mmol, 0.1 equiv) the solution was sparged with hydrogen for 15 minutes and was then stirred under a hydrogen atmosphere at room temperature for 45 minutes. The dark suspension was filtered through Celite and the solvent was removed under reduced pressure. The crude product was purified by flash column chromatography (CH/ EA=5:1) to afford 39 (20 mg, 45%). $^1$H NMR (500 MHz, CDCl$_3$): δ 7.15 (t, J=7.9 Hz, 1H), 6.79-6.71 (m, 5H), 6.70-6.66 (m, 1H), 6.33 (d, J=1.8 Hz, 1H), 6.18-6.15 (m, 1H), 5.74 (dd, J=5.8, 8.1 Hz, 1H), 5.48 (d, J=5.7 Hz, 1H), 4.38-4.32 (m, 1H), 4.20-4.12 (m, 1H), 4.07-4.01 (m, 1H), 3.95-3.90 (m, 1H), 3.88 (s, 3H), 3.86 (s, 3H), 3.85 (s, 3H), 3.77 (td, J=3.0, 8.9 Hz, 1H), 3.56 (s, 3H), 3.28 (d, J=9.9 Hz, 1H), 2.66-2.55 (m, 2H), 2.50-2.42 (m, 1H), 2.33-2.27 (m, 1H), 2.24-2.16 (m, 1H), 2.16-2.06 (m, 2H), 2.00-1.83 (m, 3H), 1.76-1.52 (m, 8H), 1.46-1.25 (m, 4H), 1.18-1.09 (m, 2H), 0.95-0.84 (m, 1H), 0.80-0.69 (m, 1H). HRMS (m/z): (ESI$^+$) calculated for C$_{43}$H$_{56}$NO$_9$ [M+H]$^+$: 730.39496, found 730.39464.

Macrocycle 40

A stirred solution of 32 (E/Z-alkene mixture, 118 mg, 0.16 mmol, 1 equiv) in MeOH (3 mL) was degassed by sparging with Argon for 15 minutes. After addition of Pd/C (10 wt. %, 20 mg, 0.02 mmol, 0.1 equiv) the solution was sparged with hydrogen for 15 minutes and was then stirred under a hydrogen atmosphere at room temperature for 15 minutes. The dark suspension was filtered through Celite and the solvent was removed under reduced pressure. The crude product was purified by flash column chromatography (CH/ EA=6:1) to afford 40 (44 mg, 37%). $^1$H NMR (500 MHz, CDCl$_3$): δ 7.16 (t, J=7.9 Hz, 1H), 6.84-6.80 (m, 1H), 6.78-6.73 (m, 2H), 6.69-6.59 (m, 3H), 6.44-6.40 (m, 1H), 6.30 (br s, 1H), 5.59 (dd, J=6.0, 8.3 Hz, 1H), 5.47-5.42 (m, 1H), 4.22-4.15 (m, 1H), 4.10-4.04 (m, 1H), 3.99-3.89 (m, 3H), 3.88-3.80 (m, 9H), 3.51 (br s, 3H), 3.33 (d, J=9.8 Hz, 1H), 2.82 (td, J=2.8, 13.4 Hz, 1H), 2.58 (ddd, J=5.5, 9.6, 14.6 Hz, 1H), 2.46 (ddd, J=6.6, 9.4, 13.9 Hz, 1H), 2.32-2.22 (m, 1H), 2.22-2.02 (m, 2H), 1.97-1.90 (m, 1H), 1.86 (d, J=12.5 Hz, 1H), 1.76-1.50 (m, 12H), 1.45-1.38 (m, 1H), 1.35-1.23 (m, 3H), 1.19-1.06 (m, 2H), 0.95-0.83 (m, 1H), 0.79-0.68 (m, 1H). HRMS (m/z): (ESI$^+$) calculated for C$_{44}$H$_{58}$NO$_9$ [M+H]$^+$: 744.41061, found 744.41050.

Macrocycle 41

The substrate 33-(E) (40 mg, 0.05 mmol, 1 equiv) was applied to general procedure E with RhCl(PPh$_3$)$_3$ (10 mg, 0.01 mmol, 0.2 equiv) in toluene (2 mL). Additional portions of RhCl(PPh$_3$)$_3$ (2×0.1 eq.) and sparging with hydrogen were applied until completion of the reaction. 41 (30 mg, 75%) was obtained after purification by flash column chromatography (CH/EA=2:1). $^1$H NMR (500 MHz, CDCl$_3$, mixture of rotamers 0.63:1, A:B): δ 7.31-7.26 (m, 0.34H, A), 7.15 (t, J=7.9 Hz, 0.62H, B), 7.13-7.11 (m, 0.36H, A), 6.92-6.88 (m, 0.38H, A), 6.83-6.74 (m, 2.80H, A+B), 6.72-6.63 (m, 2.10H, A+B), 6.51-6.44 (m, 1.32H, A+B), 6.36 (s, 1.23H, A+B), 5.81 (dd, J=5.3, 8.7 Hz, 0.39H, A), 5.46 (q, J=5.2 Hz, 1.25H, B), 4.77 (dd, J=2.4, 7.0 Hz, 0.37H, A), 4.38 (d, J=13.4 Hz, 0.38H, A), 4.32-4.26 (m, 0.39H, A), 4.22-4.17 (m, 0.42H, A), 4.16-4.10 (m, 0.67H, B), 4.09-3.79 (m, 12.23H, A+B), 3.75-3.60 (m, 2.77H, A+B), 3.57 (s, 4.20H, A+B), 3.47-3.41 (m, 0.43H, A), 3.34 (d, J=9.9 Hz, 0.62H, B), 3.19-3.12 (m, 0.43H, A), 3.06-2.96 (m, 0.39H, A), 2.81 (td, J=3.0, 13.3 Hz, 0.60H, B), 2.73-2.65 (m, 0.39H, A), 2.63-2.51 (m, 0.99H, A+B), 2.47-2.39 (m, 0.63H, B), 2.34-2.26 (m, 1.29H, A+B), 2.20 (d, J=13.8 Hz, 0.39H, A+B), 2.12-1.99 (m, 1.60H, A+B), 1.94-1.55 (m, 10.94H, A+B), 1.51-1.00 (m, 7.52H, A+B), 0.96-0.68 (m, 2.00H, A+B), 0.64-0.54 (m, 0.36H, A), −0.11-−0.22 (m, 0.38H, A), −0.25-−0.37 (m, 0.38H, A). HRMS (m/z): (ESI$^+$) calculated for C$_{45}$H$_{60}$NO$_{10}$ [M+H]$^+$: 774.42117, found 774.42144.

Macrocycle 42

The substrate 34-(E) (31 mg, 0.04 mmol, 1 equiv) was applied to general procedure E with RhCl(PPh$_3$)$_3$ (15 mg, 0.016 mmol, 0.4 equiv) in toluene (2 mL). 42 (27 mg, 87%) was obtained after purification by flash column chromatography (CH/EA=3:1). $^1$H NMR (500 MHz, CDCl$_3$, mixture of rotamers 0.08:1. Only major rotamer is reported here): δ 7.13 (t, J=7.9 Hz, 1H), 6.77-6.62 (m, 5H), 6.52-6.48 (m, 1H), 6.41 (s, 2H), 5.50-5.44 (m, 2H), 3.97-3.84 (m, 11H), 3.69-3.65 (m, 1H), 3.60-3.48 (m, 9H), 3.36 (d, J=9.9 Hz, 1H), 2.85 (td, J=2.9, 13.3 Hz, 1H), 2.54-2.41 (m, 2H), 2.30-2.26 (m, 1H), 2.11-2.05 (m, 1H), 1.96-1.82 (m, 6H), 1.74-1.60 (m, 8H), 1.44-1.11 (m, 7H), 0.92-0.85 (m, 1H), 0.77-0.71 (m, 1H). HRMS (m/z): (ESI⁺) calculated for $C_{46}H_{62}NO_{10}$ [M+H]⁺: 788.43682, found 788.43728.

Macrocycle 43

The substrate 35 (E/Z-alkene mixture, 30 mg, 0.04 mmol, 1 equiv) was applied to general procedure E (Supporting Information) with RhCl(PPh₃)₃ (20 mg, 0.021 mmol, 0.5 equiv) in THF/MeOH (v/v=1:1, 10 mL). 43 (20 mg, 66%) was obtained after purification by flash column chromatography (CH/EA=5:1) as white solid. ¹H NMR (500 MHz, CDCl₃, mixture of rotamers 0.22:1, A:B): δ 7.29 (t, J=7.9 Hz, 0.22H, A), 7.15-7.10 (m, 0.97H, A+B), 6.93-6.90 (m, 0.18H, A), 6.84-6.79 (m, 0.29H, A), 6.79-6.75 (m, 0.95H, A+B), 6.74-6.68 (m, 2.59H, A+B), 6.68-6.66 (m, 0.19H, A), 6.65-6.61 (m, 1.58H, A+B), 6.48 (d, J=1.7 Hz, 0.18H, A), 6.38 (d, J=1.9 Hz, 0.75H, B), 6.29 (d, J=1.8 Hz, 0.17H, A), 5.92-5.87 (m, 0.75H, B), 5.78 (dd, J=5.2, 8.6 Hz, 0.18H, A), 5.61 (dd, J=6.6, 7.7 Hz, 0.82H, B), 5.53 (d, J=5.5 Hz, 0.80H, B), 4.78 (td, J=4.2, 11.3 Hz, 0.17H, A), 4.54-4.48 (m, 0.16H, A), 4.43-4.40 (m, 0.17H, A), 4.25-4.09 (m, 2.98H, A+B), 4.00 (d, J=13.7 Hz, 0.82H, B), 3.96-3.90 (m, 0.81H, B), 3.87-3.78 (m, 10.08H, A+B), 3.59 (s, 2.43H, B), 3.33 (d, J=10.2 Hz, 0.80H, B), 2.87-2.79 (m, 0.16H, A), 2.71-2.55 (m, 0.38H, A), 2.54-2.11 (m, 6.59H, A+B), 1.97-1.78 (m, 3.90H, A+B), 1.77-1.49 (m, 7.01H, A+B), 1.46-1.07 (m, 6.33H, A+B), 0.99-0.92 (m, 0.37H, A), 0.88-0.80 (m, 1.17H, A+B), 0.76-0.68 (m, 0.73H, B), 0.22-0.13 (m, 0.16H, A), 0.09-0.00 (m, 0.16H, A). HRMS (m/z): (ESI⁺) calculated for $C_{43}H_{56}NO_9$ [M+H]⁺: 730.39496, found 730.39472.

Macrocycle 44

The substrate 36-(E) (25 mg, 0.034 mmol, 1 equiv) was applied to general procedure E with RhCl(PPh₃)₃ (16 mg, 0.017 mmol, 0.5 equiv) in THF/MeOH (v/v=1:1, 10 mL). 44 (18 mg, 72%) was obtained after purification by semi-preparative HPLC (85-100% Solvent B). ¹H NMR (500 MHz, CDCl₃, mixture of rotamers 0.32:1, A:B): δ 7.28 (d, J=8.0 Hz, 0.21H, A), 7.14 (t, J=7.9 Hz, 0.75H, B), 7.09-7.07 (m, 0.24H, A), 6.90-6.85 (m, 0.52H, A), 6.81-6.72 (m, 2.64H, A+B), 6.71-6.69 (m, 0.30H, A), 6.67-6.61 (m, 2.88H, A+B), 6.43 (d, J=1.8 Hz, 0.75H, B), 6.23-6.20 (m, 1.01H, A+B), 5.87 (dd, J=5.4, 8.5 Hz, 0.25H, A), 5.54-5.49 (m, 1.54H, A+B), 4.56-4.47 (m, 0.57H, A), 4.24-4.17 (m, 1.33H, A+B), 4.12-3.91 (m, 3.11H, A+B), 3.87-3.82 (m, 7.90H, A+B), 3.80 (s, 0.81H, A), 3.75 (s, 2.29H, B), 3.65 (s, 2.30H, B), 3.39 (d, J=10.1 Hz, 0.76H, B), 2.94-2.86 (m, 0.24H, A), 2.75 (td, J=2.6, 13.3 Hz, 0.75H, B), 2.68-2.53 (m, 0.49H, A), 2.51-2.33 (m, 1.64H, B), 2.32-2.19 (m, 1.24H, A+B), 2.14-2.07 (m, 1.00H), 2.01-1.93 (m, 1.29H, A+B), 1.90-1.55 (m, 12.08H, A+B), 1.51-1.25 (m, 4.00H, A+B), 1.20-1.07 (m, 2.19H, A+B), 1.03-0.82 (m, 1.59H, A+B), 0.78-0.69 (m, 0.77H, B), 0.28-0.18 (m, 0.51H, A+B). HRMS (m/z): (ESI⁺) calculated for $C_{44}H_{58}NO_9$ [M+H]⁺: 744.41061, found 744.40994.

Macrocycle 45

The substrate 37-(E) (30 mg, 0.04 mmol, 1 equiv) was applied to general procedure E with RhCl(PPh₃)₃ (18 mg, 0.02 mmol, 0.5 equiv) in THF/MeOH (v/v=1:1, 10 mL). 45 (25 mg, 83%) was obtained after purification by semi-preparative HPLC (80-100% Solvent B). ¹H NMR (500 MHz, CDCl₃, mixture of rotamers 0.48:1, A:B): δ 7.26-7.23 (m, 0.30H, A), 7.18 (t, J=7.9 Hz, 0.59H, B), 7.01-6.99 (m, 0.29H, A), 6.90-6.83 (m, 1.25H, A+B), 6.81-6.73 (m, 1.93H, A+B), 6.71-6.61 (m, 2.15H, A+B), 6.60-6.56 (m, 0.78H, A+B), 6.52-6.49 (m, 0.59H, B), 6.38-6.34 (m, 0.69H, B), 6.28 (d, J=2.0 Hz, 0.29H, A), 5.84 (dd, J=5.5, 8.3 Hz, 0.29H, A), 5.52 (dd, J=5.4, 8.7 Hz, 0.60H, B), 5.45-5.42 (m, 0.63H, B), 4.64-4.60 (m, 0.28H, A), 4.53 (d, J=13.6 Hz, 0.26H, A), 4.27-4.21 (m, 0.34H, A), 4.16-3.91 (m, 4.67H, A+B), 3.87-3.79 (m, 9.44H, A+B), 3.76-3.73 (m, 3.09H, A+B), 3.70-3.64 (m, 2.06H, A+B), 3.36 (d, J=9.7 Hz, 0.64H, A+B), 2.88 (td, J=3.0, 13.1 Hz, 0.27H, A), 2.82 (td, J=3.0, 13.4 Hz, 0.61H, B), 2.66-2.60 (m, 0.65H, B), 2.58-2.46 (m, 0.98H, A+B), 2.43-2.37 (m, 0.63H, B), 2.31-2.25 (m, 1.13H, A+B), 2.19-2.05 (m, 1.96H, A+B), 1.96-1.77 (m, 6.13H, A+B), 1.69-1.57 (m, 4.99H, A+B), 1.52-1.25 (m, 4.86H, A+B), 1.20-1.01 (m, 3.13H, A+B), 0.95-0.85 (m, 1.06H, A+B), 0.77-0.69 (m, 0.70H, B), 0.45-0.37 (m, 0.26H, A), 0.28-0.19 (m, 0.26H, A). HRMS (m/z): (ESI⁺) calculated for $C_{45}H_{60}NO_{10}$ [M+H]⁺: 774.42117, found 774.42152.

Macrocycle 46

The substrate 38-(E) (75 mg, 0.095 mmol, 1 equiv) was applied to general procedure E with RhCl(PPh₃)₃ (44 mg, 0.048 mmol, 0.5 equiv) in THF/MeOH (v/v=1:1, 10 mL). 46 (33 mg, 44%) was obtained after purification by semi-preparative HPLC (85-100% Solvent B). ¹H NMR (500 MHz, CDCl₃, mixture of rotamers 0.55:1, A:B): δ 7.29-7.24 (m, 0.64H, A), 7.17-7.11 (m, 0.66H, B), 7.01-6.98 (m, 0.36H, A), 6.90-6.87 (m, 0.38H, A), 6.86-6.83 (m, 0.39H, A), 6.81-6.72 (m, 2.27H, A+B), 6.71-6.68 (m, 0.34H, A), 6.67-6.62 (m, 2.22H, A+B), 6.59 (d, J=1.8 Hz, 0.35H, A), 6.50-6.47 (m, 0.65H, B), 6.43 (d, J=1.8 Hz, 0.64H, B), 6.29 (d, J=1.8 Hz, 0.37H, A), 5.77 (dd, J=5.6, 8.2 Hz, 0.37H, A), 5.52-5.48 (m, 1.35H, B), 4.65-4.61 (m, 0.35H, A), 4.52 (br d, J=13.8 Hz, 0.36H, A), 4.37 (br s, 0.66H, B), 4.26-4.20 (m, 0.39H, A), 4.15-4.02 (m, 2.40H, A+B), 3.97-3.88 (m, 1.27H, A+B), 3.87-3.78 (m, 10.32H, A+B), 3.72-3.47 (m, 6.29H, A+B), 3.41 (d, J=10.0 Hz, 0.63H, B), 3.00 (td, J=2.7, 13.3 Hz, 0.64H, B), 2.87 (td, J=3.1, 13.3 Hz, 0.35H, A), 2.68-2.53 (m, 1.11H, A+B), 2.49-2.33 (m, 1.32H, A+B), 2.32-2.25 (m, 1.00H, A+B), 2.19-1.57 (m, 15.12H, A+B), 1.51-1.02 (m, 7.50H, A+B), 0.95-0.85 (m, 1.00H, A+B), 0.79-0.70 (m, 0.63H, B), 0.48-0.39 (m, 0.34H, A), 0.18-0.09 (m, 0.36H, A). HRMS (m/z): (ESI⁺) calculated for $C_{46}H_{62}NO_{10}$ [M+H]⁺: 788.43682, found 788.43647.

(S)-(R)-3-(3,4-dimethoxyphenyl)-1-(3-hydroxyphenyl)propyl 1-((S)-2-cyclohexyl-2-(4-(2-hydroxyethoxy)-3,5-dimethoxyphenyl)acetyl)piperidine-2-carboxylate (47)

A solution of 11 (200 mg, 0.25 mmol, 1 equiv), diazabicyclo[2.2.2]octane (9 mg, 0.08 mmol, 0.3 equiv) and RhCl(PPh₃)₃ (23 mg, 0.03 mmol, 0.1 equiv) in EtOH/H₂O (v/v=9:1, 15 mL) was heated at reflux. The reaction was assayed by TLC and LC-MS analysis and was quenched by the addition of 1 M HCl solution at room temperature when the reaction progress had stopped. After stirring at room temperature for 2 hours, the reaction mixture was extracted with EA, dried over MgSO₄, filtered, and concentrated under reduced pressure. The crude product was purified by flash column chromatography (CH/EA=2:1+1% MeOH) to yield 47 (85 mg, 47%). ¹H NMR (500 MHz, CDCl₃, mixture of rotamers 0.22:1, A:B): δ 7.78 (s, 0.13H, A), 7.40 (s, 0.71H, B), 7.18 (t, J=7.8 Hz, 0.18H, A), 7.03 (t, J=7.9 Hz, 0.81H, B), 6.90-6.81 (m, 0.60H, B), 6.79-6.70 (m, 1.90H, A+B), 6.69-6.58 (m, 2.16H, A+B), 6.54-6.41 (m, 3.83H, A+B), 5.80 (t, J=6.6, 14.1 Hz, 0.17H, A), 5.57 (dd, J=5.7, 8.0 Hz, 0.82H, B), 5.47-5.42 (m, 0.82H, B), 4.74-4.68 (m, 0.17H, A), 4.57-4.49 (m, 0.17H, A), 4.14-3.99 (m, 2.17H, A+B), 3.95-3.88 (m, 0.92H, A+B), 3.88-3.76 (m, 7.78H, A+B), 3.76-3.57 (m, 8.43H, A+B), 3.38 (d, J=9.9 Hz, 0.82H, B), 3.04 (d, J=9.7 Hz, 0.18H, A), 2.77-2.68 (m, 0.82H, B), 2.63-2.34 (m, 2.78H, A+B), 2.32-2.21 (m, 1.06H, A+B), 2.15-2.03 (m, 1.48H, A+B), 1.98-1.78 (m, 2.80H, A+B), 1.70-1.48 (m, 6.29H, A+B), 1.46-1.04 (m, 6.77H, A+B), 1.04-0.82 (m, 1.14H, A+B), 0.80-0.55 (m, 1.25H, A+B). HRMS (m/z): (ESI$^+$) calculated for $C_{41}H_{54}NO_{10}$ [M+H]$^+$: 720.37422, found 720.37412.

(S)-(R)-3-(3,4-dimethoxyphenyl)-1-(3-hydroxyphenyl)propyl 1-((S)-2-cyclohexyl-2-(4-(3-hydroxypropoxy)-3,5-dimethoxyphenyl)acetyl)piperidine-2-carboxylate (48)

A solution of 12 (100 mg, 0.12 mmol, 1 equiv), diazabicyclo[2.2.2]octane (6 mg, 0.055 mmol, 0.45 equiv) and RhCl(PPh$_3$)$_3$ (17 mg, 0.02 mmol, 0.15 equiv) in EtOH/H$_2$O (v/v=9:1, 10 mL) was heated at reflux. The reaction was assayed by TLC and LC-MS analysis and was quenched by the addition of 1 M HCl solution at room temperature when the reaction progress had stopped. After stirring at room temperature for 20 minutes, the reaction mixture was extracted with EA, dried over MgSO$_4$, filtered, and concentrated under reduced pressure. The crude product was purified by flash column chromatography (CH/EA=2:1) to yield 48 (20 mg, 22%) as white solid. R$_f$=0.32. $^1$H NMR (500 MHz, CDCl$_3$, mixture of rotamers 0.21:1, A:B): δ 7.21 (t, J=8.1 Hz, 0.15H, A), 7.06 (t, J=7.8 Hz, 0.81H, B), 6.88-6.81 (m, 0.50H, A), 6.80-6.71 (m, 1.85H, A+B), 6.71-6.60 (m, 2.00H, A+B), 6.57-6.52 (m, 0.82H, B), 6.49 (s, 1.60H, B), 6.43 (s, 0.29H, A), 6.33 (t, J=2.1 Hz, 0.79H, B), 5.81 (dd, J=6.2, 7.6 Hz, 0.13H, A), 5.59 (dd, J=5.7, 8.1 Hz, 0.79H, B), 5.48-5.43 (m, 0.80H, B), 4.72 (d, J=5.5 Hz, 0.13H, A), 4.54 (d, J=13.6 Hz, 0.11H, A), 4.15-4.04 (m, 1.98H, A+B), 3.95-3.78 (m, 9.91H, A+B), 3.67 (s, 4.90H, A+B), 3.38 (d, J=9.9 Hz, 0.82H, B), 3.06 (d, J=9.6 Hz, 0.18H, A), 2.69 (td, J=3.0, 13.3 Hz, 0.93H, B), 2.63-2.53 (m, 0.44H, A), 2.53-2.34 (m, 1.98H, A+B), 2.32-2.22 (m, 1.00H, A+B), 2.18-2.02 (m, 1.42H, A+B), 2.00-1.86 (m, 3.86H, A+B), 1.86-1.75 (m, 0.90H, A+B), 1.74-1.49 (m, 6.10H, A+B), 1.47-0.95 (m, 7.18H, A+B), 0.95-0.58 (m, 2.51H, A+B). HRMS (m/z): (ESI$^+$) calculated for $C_{42}H_{56}NO_{10}$ [M+H]$^+$: 734.38987, found 734.38989.

(S)-(R)-3-(3,4-dimethoxyphenyl)-1-(3-hydroxyphenyl)propyl 1-((S)-2-cyclohexyl-2-(3-(2-hydroxyethoxy)-4,5-dimethoxyphenyl)acetyl)piperidine-2-carboxylate (49)

A solution of 29 (233 mg, 0.29 mmol, 1 equiv), diazabicyclo[2.2.2]octane (10 mg, 0.09 mmol, 0.3 equiv) and RhCl(PPh$_3$)$_3$ (27 mg, 0.03 mmol, 0.1 equiv) in EtOH/H$_2$O (v/v=9:1, 30 mL) was heated at reflux. The reaction was assayed by TLC and LC-MS analysis and was quenched by the addition of 1 M HCl solution at room temperature when the reaction progress had stopped. After stirring at room temperature for 6 hours, the reaction mixture was extracted with EA, dried over MgSO$_4$, filtered, and concentrated under reduced pressure. The crude product was purified by flash column chromatography (CH/EA=1:2) to yield 49 (79 mg, 38%). $^1$H NMR (500 MHz, CDCl$_3$, mixture of rotamers): δ 7.24-7.19 (m, 0.19H), 7.12-7.06 (m, 0.88H, A), 7.00 (br s, 0.51H, A), 6.88-6.85 (m, 0.24H), 6.84-6.72 (m, 2.21H, A), 6.70-6.54 (m, 4.27H, A), 6.52-6.43 (m, 1.25H, A), 6.23-6.20 (m, 0.74H, A), 5.84-5.77 (m, 0.10H, A), 5.62 (dd, J=5.9, 8.1 Hz, 0.75H, A), 5.54 (t, J=6.8 Hz, 0.13H, A), 5.48-5.41 (m, 0.93H, A), 4.75-4.62 (m, 0.14H), 4.53 (d, J=13.7 Hz, 0.09H), 4.14-3.97 (m, 2.42H, A), 3.96-3.73 (m, 13.96H, A), 3.66 (s, 2.33H, A), 3.43 (d, J=9.9 Hz, 0.17H), 3.36 (d, J=10.1 Hz, 0.78H, A), 3.23-3.01 (m, 0.48H, A), 3.00-2.89 (m, 0.37H), 2.57 (td, J=3.0, 13.3 Hz, 1.05H, A), 2.49-2.25 (m, 3.05H, A), 2.19-1.84 (m, 4.21H, A), 1.84-1.74 (m, 1.00H, A), 1.73-1.52 (m, 6.02H, A), 1.42-1.08 (m, 8.03H, A), 0.94-0.71 (m, 3.01H, A). HRMS (m/z): (ESI$^+$) calculated for $C_{41}H_{54}NO_{10}$ [M+H]$^+$: 720.3742, found 720.3742.

(S)-(R)-3-(3,4-dimethoxyphenyl)-1-(3-hydroxyphenyl)propyl 1-((S)-2-cyclohexyl-2-(3-(3-hydroxypropoxy)-4,5-dimethoxyphenyl)acetyl)piperidine-2-carboxylate (50)

A solution of 30 (257 mg, 0.32 mmol, 1 equiv), diazabicyclo[2.2.2]octane (11 mg, 0.10 mmol, 0.3 equiv) and RhCl(PPh$_3$)$_3$ (29 mg, 0.03 mmol, 0.1 equiv) in EtOH/H$_2$O (v/v=9:1, 30 mL) was heated at reflux. The reaction was assayed by TLC and LC-MS analysis and was quenched by the addition of 1 M HCl solution at room temperature when the reaction progress had stopped. After stirring at room temperature for 2 hours, the reaction mixture was extracted with EA, dried over MgSO$_4$, filtered, and concentrated under reduced pressure. The crude product was purified by semi-preparative HPLC (50-100% Solvent B) and flash column chromatography (CH/EA=1:1) to yield 50 (36 mg, 16%). $^1$H NMR (500 MHz, CDCl$_3$, mixture of rotamers): δ 7.30 (br s, 0.52H, A), 7.19 (t, J=7.8 Hz, 0.15H), 7.06 (t, J=7.9 Hz, 0.84H, A), 6.87-6.81 (m, 0.47H), 6.79-6.70 (m, 2.06H, A), 6.69-6.61 (m, 2.27H, A), 6.60-6.47 (m, 2.99H, A), 6.45-6.41 (m, 0.33H), 6.32-6.30 (m, 0.73H, A), 5.82 (dd, J=6.0, 7.7 Hz, 0.13H), 5.60 (dd, J=5.6, 8.1 Hz, 0.74H, A), 5.52 (dd, J=4.8, 8.6 Hz, 0.13H), 5.47-5.43 (m, 0.90H, A), 4.74-4.70 (m, 0.12H), 4.52 (d, J=13.5 Hz, 0.12H), 4.17-4.13 (m, 0.38H), 4.11-4.00 (m, 1.69H, A), 3.95-3.88 (m, 1.07H, A), 3.87-3.74 (m, 12.73H, A), 3.73-3.64 (m, 2.83H, A), 3.44 (d, J=10.0 Hz, 0.15H), 3.37 (d, J=10.0 Hz, 0.74H, A), 3.10-2.92 (m, 1.01H, A), 2.68 (td, J=2.9, 13.3 Hz, 0.77H, A), 2.60-2.53 (m, 0.42H), 2.50-2.34 (m, 1.63H, A), 2.31-2.22 (m, 1.47H, A), 2.13-2.03 (m, 1.47H, A), 1.97-1.86 (m, 3.40H, A), 1.85-1.78 (m, 0.77H, A), 1.72-1.53 (m, 6.00H, A), 1.45-1.36 (m, 0.76H, A), 1.34-1.07 (m, 4.95H, A), 0.93-0.84 (m, 0.93H, A), 0.79-0.71 (m, 0.90H, A). HRMS (m/z): (ESI$^+$) calculated for $C_{42}H_{56}NO_{10}$ [M+H]$^+$: 734.38987, found 734.39029.

(S)-(R)-3-(3,4-dimethoxyphenyl)-1-(3-hydroxyphenyl)propyl 1-((S)-2-cyclohexyl-2-(4-(2-iodoethoxy)-3,5-dimethoxyphenyl)acetyl)piperidine-2-carboxylate (51)

The substrate 47 (76 mg, 0.11 mmol, 1 equiv) was applied to general procedure C with PPh$_3$ (36 mg, 0.14 mmol, 1.3 equiv), imidazole (15 mg, 0.21 mmol, 2 equiv) and iodine (38 mg, 0.15 mmol, 1.4 equiv) in DCM (3 mL). Additional portions of PPh$_3$ (1.3+0.5 equiv), imidazole (2 equiv) and iodine (1.5+0.5 equiv) were added until completion of the reaction. 51 (41 mg, 47%) was obtained after purification by flash column chromatography (CH/EA=3:1). $^1$H NMR (500 MHz, CDCl$_3$, mixture of rotamers 0.2:1, A:B): δ 7.23 (t, J=7.8 Hz, 0.19H, A), 7.07 (t, J=7.9 Hz, 0.77H, B), 6.91-6.87 (m, 0.18H, A), 6.86-6.81 (m, 0.36H, A), 6.81-6.73 (m, 1.86H, A+B), 6.70-6.68 (m, 0.20H, A), 6.67-6.61 (m, 1.85H, A+B), 6.59-6.53 (m, 0.9H, A+B), 6.52 (s, 1.59H, B), 6.43 (s, 0.29H, A), 6.29-6.27 (m, 0.07H, A), 6.23 (t, J=2.0 Hz, 0.79H, B), 5.81 (dd, J=6.2, 7.7 Hz, 0.17H, A), 5.61 (dd, J=6.0, 7.9 Hz, 0.83H, B), 5.47 (q, J=2.0 Hz, 0.84H, B), 4.72 (d, J=5.6 Hz, 0.14H, A), 4.54 (d, J=13.7 Hz, 0.16H, A), 4.23-4.11 (m, 2.01H, A+B), 3.97-3.89 (m, 0.98H, A+B), 3.88-3.79 (m, 6.93H, A+B), 3.68 (s, 4.79H, A+B), 3.50 (s, 0.11H, A), 3.42-3.27 (m, 2.81H, A+B), 3.06 (d, J=9.6 Hz, 0.14H, A), 2.66 (td, J=2.9, 13.3 Hz, 0.86H, B), 2.63-2.52 (m, 0.39H, A), 2.52-2.33 (m, 1.91H, A+B), 2.32-2.23 (m, 1.05H, A+B), 2.19-2.03 (m, 1.58H, A+B), 1.96-1.83 (m, 2.10H, A+B), 1.83-1.49 (m, 7.28H, A+B), 1.47-1.07 (m, 7.28H, A+B), 1.05-0.82 (m, 1.38H, A+B), 0.82-0.57 (m, 1.21H, A+B). HRMS (m/z): (ESI$^+$) calculated for $C_{41}H_{53}NO_9$ [M+H]$^+$: 830.27598, found 830.27529.

(S)-(R)-3-(3,4-dimethoxyphenyl)-1-(3-hydroxyphenyl)propyl 1-((S)-2-cyclohexyl-2-(4-(3-iodopropoxy)-3,5-dimethoxyphenyl)acetyl)piperidine-2-carboxylate (52)

The substrate 48 (41 mg, 0.06 mmol, 1 equiv) was applied to general procedure C (Supporting Information) with PPh$_3$ (28 mg, 0.11 mmol, 1.9 equiv), pyridine (13 μL, 0.17 mmol, 3 equiv) and iodine (23 mg, 0.09 mmol, 1.6 equiv) in toluene (3 mL). Additional portions of PPh$_3$ (1.5+0.7 equiv) and iodine (1+0.5 equiv) were added until completion of the reaction. 52 (18 mg, 38%) was obtained after purification by flash column chromatography (CH/EA=3:1) as light yellow solid. $^1$H NMR (500 MHz, CDCl$_3$, mixture of rotamers 0.16:1, A:B): δ 7.22 (t, J=7.8 Hz, 0.16H, A), 7.07 (t, J=7.8 Hz, 0.83H, B), 6.88 (d, J=7.7 Hz, 0.15H, A), 6.86-6.81 (m, 0.32H, A), 6.80-6.72 (m, 1.87H, A+B), 6.71-6.67 (m, 0.19H, A), 6.67-6.62 (m, 1.87H, A+B), 6.57-6.51 (m, 2.51H, A+B), 6.42 (s, 0.31H, A), 6.31 (s, 0.76H, B), 6.17 (t, J=1.9 Hz, 0.81H, B), 5.81 (dd, J=6.1, 7.7 Hz, 0.14H, A), 5.61 (dd, J=6.0, 8.0 Hz, 0.85H, B), 5.49-5.44 (m, 0.83H, B), 4.73 (d, J=5.5 Hz, 0.14H, A), 4.55 (d, J=13.6 Hz, 0.14H, A), 4.03-3.96 (m, 2.03H, A+B), 3.96-3.89 (m, 0.93H, A+B), 3.89-3.80 (m, 7.03H, A+B), 3.69 (s, 5.09H, A+B), 3.48 (t, J=6.8 Hz, 0.32H, A), 3.43 (t, J=6.8 Hz, 1.71H, B), 3.37 (d, J=10.1 Hz, 0.86H, B), 3.07 (d, J=9.6 Hz, 0.14H, A), 2.65-2.55 (m, 1.10H, A+B), 2.51-2.42 (m, 0.99H, A+B), 2.41-2.32 (m, 0.89H, A+B), 2.32-2.25 (m, 1.05H, A+B), 2.24-2.02 (m, 3.46H, A+B), 1.96-1.48 (m, 9.94H, A+B), 1.45-0.97 (m, 6.81H, A+B), 0.95-0.83 (m, 0.95H, A+B), 0.82-0.70 (m, 1.02H, A+B), 0.69-0.58 (m, 0.18H, A). HRMS (m/z): (ESI$^+$) calculated for $C_{42}H_{55}NIO_9$ [M+H]$^+$: 844.2916, found 844.2906.

(S)-(R)-3-(3,4-dimethoxyphenyl)-1-(3-hydroxyphenyl)propyl 1-((S)-2-cyclohexyl-2-(3-(2-iodoethoxy)-4,5-dimethoxyphenyl)acetyl)piperidine-2-carboxylate (53)

The substrate 49 (88 mg, 0.12 mmol, 1 equiv) was applied to general procedure C with PPh$_3$ (42 mg, 0.16 mmol, 1.3 equiv), imidazole (17 mg, 0.24 mmol, 2 equiv) and iodine (44 mg, 0.17 mmol, 1.4 equiv) in DCM (5 mL). Additional portions of PPh$_3$ (0.5 equiv), imidazole (0.5 equiv) and iodine (0.5 equiv) were added until completion of the reaction. 53 (74 mg, 73%) was obtained after purification by semi-preparative HPLC (70-100% Solvent B). $^1$H NMR (500 MHz, CDCl$_3$, mixture of rotamers): δ 7.24-7.20 (m, 0.21H), 7.13-7.05 (m, 0.90H, A), 6.89-6.83 (m, 0.51H), 6.80-6.73 (m, 1.83H, A), 6.71-6.60 (m, 1.92H, A), 6.57-6.47 (m, 2.78H, A), 6.43-6.41 (m, 0.13H, A), 6.30-6.25 (m, 0.66H, A), 5.82 (t, J=7.0 Hz, 0.13H), 5.63-5.56 (m, 0.86H, A), 5.49-5.44 (m, 0.85H, A), 4.78-4.73 (m, 0.15H), 4.52 (d, J=13.6 Hz, 0.13H), 4.30-4.23 (m, 0.35H), 4.19-4.05 (m, 1.73H, A), 3.99-3.90 (m, 0.73H, A), 3.89-3.75 (m, 10.85H, A), 3.70-3.65 (m, 2.20H, A), 3.46-3.36 (m, 1.26H, A), 3.34-3.25 (m, 1.75H, A), 3.11 (d, J=9.6 Hz, 0.04H), 3.06 (d, J=9.9 Hz, 0.13H), 2.98 (td, J=2.6, 13.4 Hz, 0.14H), 2.70-2.50 (m, 1.19H, A), 2.48-2.23 (m, 2.75H, A), 2.14-2.02 (m, 1.10H, A), 1.93-1.84 (m, 1.38H, A), 1.82-1.52 (m, 7.08H, A), 1.47-1.09 (m, 5.95H, A), 0.95-0.85 (m, 0.85H, A), 0.81-0.59 (m, 1.14H, A). HRMS (m/z): (ESI$^+$) calculated for $C_{41}H_{53}INO_9$ [M+H]$^+$: 830.27596, found 830.27584.

(S)-(R)-3-(3,4-dimethoxyphenyl)-1-(3-hydroxyphenyl)propyl 1-((S)-2-cyclohexyl-2-(3-(3-iodopropoxy)-4,5-dimethoxyphenyl)acetyl)piperidine-2-carboxylate (54)

The substrate 50 (34 mg, 0.05 mmol, 1 equiv) was applied to general procedure C with PPh$_3$ (19 mg, 0.07 mmol, 1.5 equiv), imidazole (8 mg, 0.12 mmol, 2.5 equiv) and iodine (22 mg, 0.09 mmol, 1.8 equiv) in DCM (5 mL). 54 (33 mg, 85%) was obtained after purification by flash column chromatography (CH/EA=2:1). $^1$H NMR (500 MHz, THF-d$_8$, mixture of rotamers): δ 8.39 (s, 0.18H), 8.33 (s, 0.03H), 8.23 (s, 0.10H), 8.16 (s, 0.54H, A), 7.15 (t, J=7.8 Hz, 0.23H), 7.05 (t, J=7.8 Hz, 0.11H), 6.99 (t, J=7.8 Hz, 0.63H, A), 6.85-6.75 (m, 1.54H, A), 6.73-6.65 (m, 1.54H, A), 6.64-6.55 (m, 3.65H, A), 6.53-6.51 (m, 0.65H, A), 6.32-6.26 (m, 0.64H, A), 5.79 (dd, J=5.9, 7.7 Hz, 0.24H, A), 5.54 (dd, J=5.2, 8.3 Hz, 0.76H, A), 5.43-5.40 (m, 0.63H, A), 5.35 (d, J=4.8 Hz, 0.12H), 4.89-4.85 (m, 0.21H), 4.53 (d, J=13.5 Hz, 0.20H), 4.08 (d, J=13.5 Hz, 0.71H, A), 4.04-3.98 (m, 0.50H), 3.96-3.83 (m, 1.52H, A), 3.78-3.72 (m, 7.03H, A), 3.70 (s, 1.11H, A), 3.66-3.61 (m, 3.98H, A), 3.51 (d, J=9.9 Hz, 0.80H, A), 3.41 (td, J=1.2, 6.8 Hz, 0.49H), 3.36-3.25 (m, 1.55H, A), 3.14 (d, J=9.8 Hz, 0.20H), 2.90 (dd, J=11.7, 14.4 Hz, 0.11H), 2.77 (td, J=2.8, 13.3 Hz, 0.63H, A), 2.59-2.32 (m, 2.00H, A), 2.29-2.20 (m, 1.60H, A), 2.17-2.02 (m, 3.04H, A), 1.95-1.85 (m, 1.98H, A), 1.84-1.76 (m, 0.55H), 1.70-1.54 (m, 5.16H, A), 1.51-1.06 (m, 7.20H, A), 0.97-0.77 (m, 1.65H, A), 0.74-0.64 (m, 0.35H). HRMS (m/z): (ESI$^+$) calculated for $C_{42}H_{55}NO_9$ [M+H]$^+$: 844.29161, found 844.29172.

Macrocycle 55

The substrate 51 (41 mg, 0.05 mmol, 1 equiv) was applied to general procedure D with K$_2$CO$_3$ (14 mg, 0.10 mmol, 2 equiv) in MeCN (c=1 mM, 50 mL). 55 (19 mg, 54%) was obtained after purification by flash column chromatography (CH/EA=5:1). $^1$H NMR (500 MHz, CDCl$_3$): δ 7.17 (t, J=7.9 Hz, 1H), 6.78-6.69 (m, 5H), 6.66 (dd, J=2.0, 8.2 Hz, 1H), 6.33 (d, J=1.8 Hz, 1H), 6.04-5.98 (m, 1H), 5.89 (t, J=6.1 Hz, 1H), 5.58 (d, J=5.0 Hz, 1H), 4.47-4.35 (m, 3H), 4.22-4.15 (m, 1H), 4.04-3.97 (m, 1H), 3.88 (s, 3H), 3.85 (s, 3H), 3.84 (s, 3H), 3.56 (s, 3H), 3.29 (d, J=10.0 Hz, 1H), 2.69-2.61 (m, 1H), 2.53-2.41 (m, 2H), 2.38-2.32 (m, 1H), 2.22-2.01 (m, 2H), 2.01-1.89 (m, 2H), 1.76-1.52 (m, 6H), 1.48-1.28 (m, 4H), 1.15 (td, J=9.3, 12.3 Hz, 2H), 0.94-0.71 (m, 2H). HRMS (m/z): (ESI$^+$) calculated for $C_{41}H_{52}NO_9$ [M+H]$^+$: 702.36366, found 702.36395.

Macrocycle 56

The substrate 52 (16 mg, 0.02 mmol, 1 equiv) was applied to general procedure D (Supporting Information) with K₂CO₃ (5 mg, 0.04 mmol, 2 equiv) in MeCN (c=0.5 mM, 40 mL). 56 (11 mg, 81%) was obtained after purification by flash column chromatography (CH/EA=4:1) as white solid. $^1$H NMR (500 MHz, CDCl$_3$): δ 7.14 (t, J=7.8 Hz, 1H), 6.78-6.66 (m, 6H), 6.38-6.34 (m, 1H), 6.25-6.21 (m, 1H), 5.76 (t, J=6.9 Hz, 1H), 5.51 (d, J=5.4 Hz, 1H), 4.44-4.30 (m, 2H), 3.94-3.83 (m, 9H), 3.77 (s, 3H), 3.68 (s, 3H), 3.25 (d, J=9.8 Hz, 1H), 2.59-2.43 (m, 3H), 2.31 (d, J=13.5 Hz, 1H), 2.24-2.17 (m, 1H), 2.13-2.07 (m, 3H), 2.01-1.94 (m, 1H), 1.88 (d, J=12.4 Hz, 1H), 1.68-1.56 (m, 6H), 1.42-1.28 (m, 4H), 1.18-1.09 (m, 2H), 0.91-0.84 (m, 1H), 0.77-0.70 (m, 1H). HRMS (m/z): (ESI$^+$) calculated for C$_{42}$H$_{54}$NO$_9$ [M+H]$^+$: 716.37931, found 716.38054.

Macrocycle 57

The substrate 53 (49 mg, 0.06 mmol, 1 equiv) was applied to general procedure D with K₂CO₃ (16 mg, 0.12 mmol, 2 equiv) in MeCN (c=1 mM, 60 mL). 57 (17 mg, 42%) was obtained after purification by semi-preparative HPLC (85-100% Solvent B). $^1$H NMR (500 MHz, CDCl$_3$): δ 7.14 (t, J=7.9 Hz, 1H), 6.78-6.74 (m, 3H), 6.72-6.69 (m, 1H), 6.65-6.61 (m, 3H), 6.28-6.24 (m, 1H), 5.64 (dd, J=5.5, 7.8 Hz, 1H), 5.58 (d, J=5.5 Hz, 1H), 4.51-4.47 (m, 2H), 4.45-4.40 (m, 1H), 4.27 (dt, J=4.3, 11.6 Hz, 1H), 4.11 (d, J=13.7 Hz, 1H), 3.86 (s, 3H), 3.85 (s, 3H), 3.68 (s, 3H), 3.64 (s, 3H), 3.44 (d, J=10.3 Hz, 1H), 2.89-2.82 (m, 1H), 2.44-2.38 (m, 2H), 2.26-2.13 (m, 2H), 1.90-1.78 (m, 3H), 1.72-1.58 (m, 6H), 1.47-1.30 (m, 4H), 1.21-1.10 (m, 2H), 0.92-0.85 (m, 1H), 0.79-0.71 (m, 1H). HRMS (m/z): (ESI$^+$) calculated for C$_{41}$H$_{52}$NO$_9$ [M+H]$^+$: 702.36366, found 702.36404.

Macrocycle 58

The substrate 54 (32 mg, 0.04 mmol, 1 equiv) was applied to general procedure D with K₂CO₃ (11 mg, 0.08 mmol, 2 equiv) in MeCN (c=0.3 mM, 125 mL). 58 (7 mg, 26%) was obtained after purification by semi-preparative HPLC (85-90% Solvent B). $^1$H NMR (500 MHz, CDCl$_3$, rotamers are present): δ 7.16-7.12 (m, 1H), 6.82-6.79 (m, 1H), 6.78-6.75 (m, 2H), 6.71 (d, J=1.9 Hz, 1H), 6.63-6.61 (m, 2H), 6.51 (d, J=1.8 Hz, 1H), 6.30-6.27 (m, 1H), 5.58-5.52 (m, 2H), 4.47-4.43 (m, 1H), 4.36-4.31 (m, 1H), 4.17-4.12 (m, 1H), 4.10-4.03 (m, 2H), 3.86-3.84 (m, 6H), 3.74 (s, 3H), 3.66 (s, 3H), 3.41 (d, J=10.2 Hz, 1H), 2.76 (td, J=2.6, 13.3 Hz, 1H), 2.43-2.26 (m, 6H), 2.20-2.15 (m, 2H), 1.88 (br d, J=12.6 Hz, 1H), 1.80-1.75 (m, 1H), 1.71-1.58 (m, 6H), 1.41-1.30 (m, 3H), 1.22-1.11 (m, 3H), 0.90-0.84 (m, 1H), 0.78-0.70 (m, 1H). HRMS (m/z): (ESI$^+$) calculated for C$_{42}$H$_{54}$NO$_9$ [M+H]$^+$: 716.37931, found 716.38019.

Macrocycle 59

The substrate 31-(E) (27 mg, 0.04 mmol, 1 equiv) was applied to general procedure H with Pd(OAc)$_2$ (0.5 mg, 0.002 mmol, 0.05 equiv), 1,4-benzoquinone (4 mg, 0.04 mmol, 1 equiv) and aqueous HBF$_4$ (48 wt. %, 10 μL, 0.05 mmol, 1.4 equiv) in MeCN/H$_2$O (v/v=7:1, 800 μL). Additional portions of Pd(OAc)$_2$ (0.05 equiv) and 1,4-benzoquinone (0.3 equiv) were added until completion of the reaction. 59 (14 mg, 52%) was obtained after purification by flash column chromatography (CH/EA=4:1) as single product isomer. $^1$H NMR (500 MHz, CDCl$_3$): δ 7.21 (t, J=7.9 Hz, 1H), 6.88-6.85 (m, 1H), 6.78-6.74 (m, 2H), 6.72-6.70 (m, 1H), 6.69-6.65 (m, 2H), 6.44-6.42 (m, 1H), 6.29 (d, J=1.8 Hz, 1H), 5.64 (dd, J=5.5, 8.1 Hz, 1H), 5.51-5.47 (m, 1H), 4.50 (dt, J=6.7, 11.4 Hz, 1H), 4.44-4.36 (m, 3H), 3.94 (d, J=13.9 Hz, 1H), 3.87 (s, 3H), 3.84 (s, 3H), 3.80 (s, 3H), 3.52 (s, 3H), 3.35 (d, J=9.9 Hz, 1H), 2.86-2.79 (m, 3H), 2.60-2.46 (m, 2H), 2.33-2.27 (m, 1H), 2.18-2.07 (m, 2H), 1.99-1.92 (m, 1H), 1.88 (d, J=12.4 Hz, 1H), 1.71-1.61 (m, 6H), 1.49-1.41 (m, 1H), 1.38-1.29 (m, 3H), 1.17-1.09 (m, 2H), 0.94-0.86 (m, 1H), 0.78-0.70 (m, 1H). HRMS (m/z): (ESI$^+$) calculated for C$_{43}$H$_{54}$NO$_{10}$ [M+H]$^+$: 744.37422, found 744.37440.

Macrocycle 60

The substrate 35-(Z) (32 mg, 0.04 mmol, 1 equiv) was applied to general procedure H (Supporting Information) with Pd(OAc)$_2$ (1 mg, 0.004 mmol, 0.1 equiv), 1,4-benzoquinone (6 mg, 0.05 mmol, 1.2 equiv) and aqueous HBF$_4$ (48 wt.-%, 8 μL, 0.06 mmol, 1.4 equiv) in MeCN/H$_2$O (v/v=7:1, 3 mL). Additional portions of Pd(OAc)$_2$ (3×0.1 equiv), 1,4-benzoquinone (2×1.2 equiv) and aqueous HBF$_4$ (4×3 equiv) were added until completion of the reaction. 60 (15 mg, 45%) was obtained after purification by semi-preparative HPLC (70-100% Solvent B) as white solid and single product isomer. $^1$H NMR (500 MHz, CDCl$_3$): δ 7.19 (t, J=7.9 Hz, 1H), 6.83-6.80 (m, 1H), 6.78-6.75 (m, 1H), 6.74-6.70 (m, 1H), 6.68 (d, J=1.8 Hz, 1H), 6.64-6.61 (m, 2H), 6.45 (d, J=1.8 Hz, 1H), 6.13-6.09 (m, 1H), 5.57 (dd, J=5.9, 8.2 Hz, 1H), 5.52 (d, J=5.5 Hz, 1H), 4.57-4.42 (m, 4H), 4.08 (d, J=13.8 Hz, 1H), 3.86-3.84 (m, 6H), 3.67 (s, 3H), 3.63 (s, 3H), 3.43 (d, J=10.2 Hz, 1H), 3.41-3.33 (m, 1H), 2.83-2.67 (m, 2H), 2.52-2.44 (m, 1H), 2.41-2.33 (m, 1H), 2.30 (d, J=14.0 Hz, 1H), 2.15-2.03 (m, 1H), 1.96-1.74 (m, 3H), 1.73-1.59 (m, 6H), 1.49-1.40 (m, 1H), 1.37-1.22 (m, 3H), 1.20-1.08 (m, 2H), 0.94-0.83 (m, 1H), 0.80-0.70 (m, 1H). HRMS (m/z): (ESI$^+$) calculated for C$_{43}$H$_{53}$NO$_{10}$Na [M+Na]$^+$: 766.35617, found 766.35619.

Macrocycles 61a and 61b

The substrate 36-(E) (35 mg, 0.047 mmol, 1 equiv) was applied to general procedure H with Pd(OAc)$_2$ (1.0 mg, 0.005 mmol, 0.1 equiv), 1,4-benzoquinone (6.1 mg, 0.056 mmol, 1.2 equiv) and aqueous HBF$_4$ (48 wt. %, 12 μL, 0.066 mmol, 1.4 equiv) in MeCN/H$_2$O (v/v=7:1, 4 mL). The two product isomers 61a (19 mg, 53%) and 61b (5 mg, 14%) were obtained after purification by semi-preparative HPLC (70-100% Solvent B). Data for Macrocycle 61a: $^1$H NMR (500 MHz, CDCl$_3$, mixture of rotamers 0.18:1, A:B): δ 7.30-7.26 (m, 0.12H, A), 7.16-7.11 (m, 0.88H, B), 7.05-7.01 (m, 0.15H, A), 6.90-6.87 (m, 0.16H, A), 6.86-6.83 (m, 0.16H, A), 6.81-6.75 (m, 1.04H, A+B), 6.74-6.66 (m, 2.91H, A+B), 6.64-6.60 (m, 1.81H, A+B), 6.41 (d, J=1.8 Hz, 0.86H, B), 6.23 (d, J=2.0 Hz, 0.15H, A), 5.88 (t, J=2.0 Hz, 0.85H, B), 5.85 (dd, J=4.9, 8.6 Hz, 0.17H, A), 5.55-5.49 (m, 1.78H, A+B), 4.60-4.54 (m, 0.31H, A), 4.51-4.41 (m, 0.98H, A+B), 4.40-4.34 (m, 0.17H, A), 4.34-4.28 (m, 1.19H, A+B), 4.27-4.22 (m, 0.87H, B), 4.17-4.12 (m, 0.94H, A+B), 4.11-3.98 (m, 3.04H, A+B), 3.87-3.83 (m, 6.21H, A+B), 3.81 (s, 0.49H, A), 3.68 (s, 2.60H, B), 3.54 (s, 2.59H, B), 3.40 (d, J=10.3 Hz, 0.86H, B), 3.15-3.08 (m, 0.85H, B), 3.08-3.01 (m, 0.88H, B), 2.94-2.87 (m, 1.60H, A+B), 2.85-2.79 (m, 0.87H, B), 2.70-2.62 (m, 0.96H, A+B), 2.46-2.38 (m, 1.01H, A+B), 2.34-2.26 (m, 1.75H, A+B), 2.23-2.10 (m, 1.05H, A+B), 1.93-1.88 (m, 0.84H, B), 1.82-1.74 (m, 0.86H, A+B), 1.72-1.53 (m, 6.86H, A+B), 1.50-1.26 (m, 3.92H, A+B), 1.22-1.10 (m, 2.79H, A+B), 1.05-0.97 (m, 0.32H, A), 0.91-0.82 (m, 1.04H, A+B), 0.78-0.70 (m, 0.89H, B), 0.32-0.15 (m, 0.31H, A). HRMS (m/z): (ESI$^+$) calculated for C$_{44}$H$_{56}$NO$_{10}$ [M+H]$^+$: 758.38987, found 758.39061. Data for Macrocycle 61b: $^1$H NMR (500 MHz, CDCl$_3$, mixture of rotamers 0.21:1, A:B): δ 7.32 (t, J=7.9 Hz, 0.20H, A), 7.19 (t, J=7.9 Hz, 0.80H, B), 7.03-7.00 (m, 0.20H, A), 6.98-6.95 (m, 0.21H, A), 6.91-6.87 (m, 0.22H, A), 6.85-6.82 (m, 0.80H, B), 6.81-6.75 (m, 1.78H, A+B), 6.71-6.59 (m, 3.20H, A+B), 6.38 (d, J=1.8 Hz, 0.75H, B), 6.25-6.22 (m, 0.94H, A+B), 5.88 (dd, J=5.5, 8.3 Hz, 0.20H, A), 5.53-5.46 (m, 1.56H, B), 4.61-4.49 (m, 1.63H, A+B), 4.40 (d, J=15.1 Hz, 0.72H, B), 4.18-4.11 (m, 0.19H, A), 4.05-3.98 (m, 2.53H, A+B), 3.88-3.83 (m, 6.76H, A+B), 3.80 (s, 0.68H, A), 3.78 (s, 2.34H, B), 3.67 (s, 2.38H, B), 3.37 (d, J=10.0 Hz, 0.77H, B), 3.18 (dt, J=7.0, 16.5 Hz, 0.20H, A), 3.05-2.98 (m, 0.78H, B), 2.87-2.80 (m, 0.19H, A), 2.70-2.34 (m, 7.46H, A+B), 2.31-2.01 (m, 4.54H, A+B), 1.91-1.81 (m, 1.54H, A+B), 1.76-1.52 (m, 6.83H, A+B), 1.45-1.24 (m, 4.25H, A+B), 1.19-1.10 (m, 2.57H, A+B), 0.92-0.83 (m, 1.39H, A+B), 0.78-0.69 (m, 0.85H, B), 0.36-0.21 (m, 0.40H, A). HRMS (m/z): (ESI$^+$) calculated for C$_{44}$H$_{56}$NO$_{10}$ [M+H]$^+$: 758.38987, found 758.39032.

Macrocycle 62

The substrate 37-(E) (38 mg, 0.05 mmol, 1 equiv) was applied to general procedure H with Pd(OAc)$_2$ (1.1 mg, 0.005 mmol, 0.1 equiv), 1,4-benzoquinone (6.4 mg, 0.06 mmol, 1.2 equiv) and aqueous HBF$_4$ (48 wt. %, 13 μL, 0.07 mmol, 1.4 equiv) in MeCN/H$_2$O (v/v=7:1, 5 mL). Additional portions of Pd(OAc)$_2$ (0.1 equiv), 1,4-benzoquinone (1.2 equiv) and aqueous HBF$_4$ (2 equiv) were added until completion of the reaction. 62 (13 mg, 33%) was obtained after purification by semi-preparative HPLC (80-90% Solvent B) as single product isomer. $^1$H NMR (500 MHz, CDCl$_3$, mixture of rotamers 0.24:1, A:B): δ 7.29-7.26 (m, 0.16H, A), 7.17 (t, J=7.9 Hz, 0.83H, B), 7.00-6.97 (m, 0.19H, A), 6.92-6.89 (m, 0.22H, A), 6.87-6.84 (m, 0.25H, A), 6.83-6.73 (m, 2.79H, A+B), 6.71-6.63 (m, 2.75H, A+B), 6.59-6.52 (m, 0.29H, A), 6.39-6.34 (m, 1.00H, A+B), 6.27-6.23 (m, 0.77H, B), 5.80 (dd, J=5.3, 8.4 Hz, 0.18H, A), 5.56 (dd, J=5.9, 8.3 Hz, 0.80H, B), 5.46 (d, J=5.5 Hz, 0.79H, B), 5.43-5.40 (m, 0.26H, A), 4.65-4.59 (m, 0.24H, A), 4.52 (d, J=13.7 Hz, 0.21H, A), 4.41-4.10 (m, 6.04H, A+B), 4.03 (dt, J=3.4, 10.9 Hz, 0.88H, A+B), 3.98-3.90 (m, 2.18H, A+B), 3.85 (d, J=4.0 Hz, 6.61H, A+B), 3.80 (d, J=10.6 Hz, 3.16H, A+B), 3.64 (s, 2.40H, B), 3.35 (d, J=9.8 Hz, 0.80H, B), 3.14-3.03 (m, 1.00H, A+B), 2.90-2.81 (m, 1.11H, A+B), 2.72-2.56 (m, 3.02H, A+B), 2.52-2.36 (m, 1.96H, A+B), 2.32-2.25 (m, 1.09H, A+B), 2.13-2.04 (m, 1.09H, A+B), 1.97-1.76 (m, 3.05H, A+B), 1.72-1.57 (m, 5.97H, A+B), 1.48-1.25 (m, 4.99H, A+B), 1.21-1.09 (m, 2.19H, A+B), 0.95-0.83 (m, 1.09H, A+B), 0.79-0.70 (m, 1.00H, A+B), 0.39-0.30 (m, 0.17H, A), 0.15-0.06 (m, 0.15H, A). HRMS (m/z): (ESI$^+$) calculated for C$_{45}$H$_{58}$NO$_{11}$H [M+H]$^+$: 788.40044, found 788.40094.

Macrocycle 63

To a stirred solution of 31-(E) (51 mg, 0.07 mmol, 1 equiv) in acetone (1 mL) at 0° C. was added N-methylmorpholine N-oxide (13 mg, 0.11 mmol, 1.5 equiv). The mixture was treated with OsO$_4$ (2.5 wt. % in tBuOH, 144 μL, 0.014 mmol, 0.2 equiv) and H$_2$O (1 mL). The resulting mixture was stirred at room temperature overnight. Then the reaction mixture was diluted with EA, layers separated, and the organic phase extracted with H$_2$O. The organic phase was dried over MgSO$_4$ and concentrated under reduced pressure. The crude product was purified by flash column chromatography (CH/EA=2:3 and DCM/MeOH=50:1) to afford the desired product 63 (14 mg, 26%) as a mixture of diastereomers (dr=34:66, determined via HPLC). $^1$H NMR (500 MHz, CDCl$_3$, mixture of diastereomers 0.5:1, A:B): δ 7.23-7.13 (m, 1.54H, A+B), 6.89-6.83 (m, 1.15H, A+B), 6.84-6.80 (m, 1.63H, A+B), 6.80-6.75 (m, 3.05H, A+B), 6.75-6.68 (m, 3.63H, A+B), 6.41-6.36 (m, 0.95H, B), 6.33-6.30 (m, 0.91H, A), 6.26-6.22 (m, 0.96H, B), 5.80-5.71 (m, 1.60H, A+B), 5.51-5.44 (m, 1.54H, A+B), 4.37 (dd, J=3.0, 11.9 Hz, 0.50H, A), 4.23 (dd, J=4.7, 10.3 Hz, 1.00H, B), 4.19-4.09 (m, 2.36H, A+B), 4.06-3.99 (m, 2.45H, A+B), 3.92-3.83 (m, 16.74H, A+B), 3.79 (dd, J=3.6, 10.4 Hz, 1.20H, B), 3.72-3.67 (m, 1.61H, A+B), 3.60 (s, 1.30H, A), 3.52 (s, 2.84H, A+B), 3.34-3.28 (m, 1.49H, A+B), 3.00 (br s, 0.95H, A+B), 2.74-2.61 (m, 2.44H, A+B), 2.55-2.46 (m, 1.49H, A+B), 2.36-2.26 (m, 1.61H, A+B), 2.17-2.05 (m, 2.85H, A+B), 1.96-1.85 (m, 2.76H, A+B), 1.76-1.54 (m, 10.94H, A+B), 1.46-1.27 (m, 6.55H, A+B), 1.21-1.09 (m, 2.93H, A+B), 0.98-0.86 (m, 1.45H, A+B), 0.85-0.71 (m, 1.44H, A+B). HRMS (m/z): (ESI$^+$) calculated for C$_{43}$H$_{56}$NO$_{11}$ [M+H]$^+$: 762.38479, found 762.38530.

Macrocycles 64a and 64b

To a stirred solution of 35-(Z) (35 mg, 0.05 mmol, 1 equiv) in acetone (1 mL) at 0° C. was added N-methylmorpholine N-oxide (8 mg, 0.07 mmol, 1.5 equiv). The mixture was treated with OsO$_4$ (2.5 wt. % in tBuOH, 100 μL, 0.01 mmol, 0.2 equiv) and H$_2$O (1 mL). The resulting mixture was stirred at room temperature overnight. Then the reaction mixture was diluted with EA, layers separated, and the organic phase extracted with H$_2$O. The organic phase was dried over MgSO$_4$ and concentrated under reduced pressure. The crude product was purified by flash column chromatography (CH/EA=2:3) and semi-preparative HPLC (70-100% Solvent B) to afford the desired product diastereomers 64a (8 mg, 22%) and 64b (7 mg, 18%) as white solids. Data for Macrocycle 64a: $^1$H NMR (500 MHz, CDCl$_3$, rotamers are present): δ 7.16 (t, J=7.9 Hz, 1H), 6.79-6.72 (m, 4H), 6.65-6.60 (m, 2H), 6.41 (d, J=1.8 Hz, 1H), 5.90-5.87 (m, 1H), 5.61 (dd, J=6.4, 7.8 Hz, 1H), 5.53 (d, J=5.5 Hz, 1H), 4.40-4.31 (m, 2H), 4.25 (dd, J=3.0, 10.2 Hz, 1H), 4.20 (dd, J=3.5, 9.6 Hz, 1H), 4.00 (br d, J=13.9 Hz, 1H), 3.86 (s, 3H), 3.85 (s, 3H), 3.74 (s, 3H), 3.59 (s, 3H), 3.36 (d, J=10.3 Hz, 1H), 3.11 (br s, 1H), 2.55 (t, J=13.2 Hz, 1H), 2.48-2.41 (m, 1H), 2.37-2.24 (m, 2H), 2.19-2.11 (m, 1H), 1.91-1.84 (m, 2H), 1.75-1.52 (m, 9H), 1.40-1.11 (m, 7H), 0.90-0.81 (m, 2H), 0.76-0.68 (m, 1H). HRMS (m/z): (ESI$^+$) calculated for C$_{43}$H$_{56}$NO$_{11}$ [M+H]$^+$: 762.38479, found 762.38489. Data for Macrocycle 64b: $^1$H NMR (500 MHz, CDCl$_3$): δ 7.15 (t, J=7.9 Hz, 1H), 6.79-6.72 (m, 4H), 6.65-6.61 (m, 2H), 6.37 (d, J=1.8 Hz, 1H), 5.72-5.68 (m, 1H), 5.61 (t, J=7.2 Hz, 1H), 5.50 (d, J=5.4 Hz, 1H), 4.41 (ddd, J=4.7, 8.6, 20.4 Hz, 2H), 4.27-4.19 (m, 2H), 4.13 (dd, J=4.5, 9.8 Hz, 1H), 4.08-4.04 (m, 1H), 3.99-3.93 (m, 1H), 3.87 (s, 3H), 3.85 (s, 3H), 3.80 (s, 3H), 3.54 (s, 3H), 3.33 (d, J=10.2 Hz, 1H), 2.58 (br s, 2H), 2.47-2.40 (m, 2H), 2.36-2.25 (m, 2H), 2.19-2.10 (m, 1H), 1.93-1.85 (m, 2H), 1.71-1.53 (m, 6H), 1.41-1.31 (m, 2H), 1.25-1.11 (m, 4H), 0.88-0.82 (m, 1H), 0.76-0.68 (m, 1H). HRMS (m/z): (ESI$^+$) calculated for C$_{43}$H$_{56}$NO$_{11}$ [M+H]$^+$: 762.38479, found 762.38465.

(R)-1-(3-(allyloxy)phenyl)-3-(3,4-dimethoxyphenyl) propan-1-ol (65)

(R)-3-(3-(3,4-dimethoxyphenyl)-1-hydroxypropyl)phenol (2.16 g, 7.49 mmol, 1.0 eq), K$_2$CO$_3$ (1.14 g, 8.24 mmol, 1.1 eq) and allyl bromide (997 mg, 8.24 mmol, 1.1 eq) are dissolved in 70 mL MeCN. The reaction is stirred overnight at r.t. After complete conversion, the mixture is filtered over celite and washed with MeCN. The solvent is removed under reduced pressure and the crude product purified by silica filtration (CH/EE, 3/2). Compound 65 is obtained as a white solid. Yield 2.31 g (94%). $^1$H-NMR (300 MHz, CDCl$_3$): δ 7.24 (ddd, J=1.0, 7.0, 8.2 Hz, 1H), 6.91 (dd, J=1.4, 7.3 Hz, 2H), 6.86-6.78 (m, 1H), 6.77 (d, J=0.8 Hz, 1H), 6.73 (d, J=1.8 Hz, 1H), 6.71 (s, 1H), 6.13-5.98 (m, 1H), 5.41 (dq, J=1.6, 17.3 Hz, 1H), 5.28 (dq, J=1.4, 10.5 Hz, 1H), 4.64 (dd, J=5.3, 7.7 Hz, 1H), 4.52 (dt, J=1.5, 5.2 Hz, 2H), 3.84 (d, J=1.5 Hz, 6H), 2.65 (qdd, J=6.4, 9.2, 13.8 Hz, 2H), 2.20-1.91 (m, 2H). LC-MS: m/z: calculated=311.17 [M-OH]$^+$, found=311.03 [M-OH]$^+$.

(R)-1-(3-(2-(allyloxy)ethoxy)phenyl)-3-(3,4-dimethoxyphenyl)propan-1-ol (66)

(R)-3-(3-(3,4-dimethoxyphenyl)-1-hydroxypropyl)phenol (969 mg, 3.36 mmol, 1.0 eq), K$_2$CO$_3$ (697 g, 5 mmol, 1.5 eq) and 2-(allyloxy)ethyl 4-methylbenzenesulfonate (861 mg, 3.4 mmol, 1.1 eq) are dissolved in 20 mL MeCN. The reaction is stirred overnight after heating to reflux. After complete conversion, the mixture is filtered over celite and washed with acetone. The solvent is removed under reduced pressure and the crude product purified by column chromatography (CH/EE, 3/1). Compound 66 is obtained as a beige oil. Yield 1.18 g (94%). $^1$H-NMR (300 MHz, CDCl$_3$): δ 7.26 (td, J=2.8, 7.9 Hz, 1H), 6.99-6.90 (m, 2H), 6.89-6.77 (m, 1H), 6.77-6.66 (m, 2H), 5.95 (ddt, J=5.0, 10.1, 16.2 Hz, 1H), 5.32 (dd, J=2.7, 17.2 Hz, 1H), 5.22 (d, J=10.3 Hz, 1H), 4.72-4.60 (m, 1H), 4.19-4.03 (m, 5H), 3.86 (d, J=2.9 Hz, 6H), 3.84-3.72 (m, 2H), 2.66 (qdd, J=2.7, 8.4, 13.8, 16.1 Hz, 2H), 2.13-1.92 (m, 3H). LC-MS: m/z: calculated=354.17 [M-OH]$^+$, 390.22 [M+NH$_4$]$^+$, found=355.10 [M-OH]$^+$, 390.04 [M+NH$_4$]$^+$.

(S)-1-((9H-fluoren-9-yl)methyl) 2-((R)-1-(3-(allyloxy)phenyl)-3-(3,4-dimethoxyphenyl)propyl) piperidine-1,2-dicarboxylate (67)

65 (1.29 g, 3.47 mmol, 1.0 eq) and Fmoc-S-pipecolate (1.99 g, 5.66 mmol, 1.1 eq) are dissolved in 40 mL dry DCM and cooled to 0° C. for 15 min. DMAP (70 mg, 0.57 mmol, 0.1 eq) is added and stirred until dissolved, then DCC (1.17 g, 5.66 mmol, 1.0 eq) is added. The mixture is stirred for 15 min under cooling. Finally, the ice bath is removed and the reaction stirred overnight at r.t. The reaction mixture is filtered, washed with DCM and the solvent removed under reduced pressure. The crude product is purified by silica column chromatography (CH/EE, 5/1) and pure product 67 obtained as white foam. Yield 3.16 g (93%). LC-MS: m/z: calculated=679.30 [M+H]$^+$, found=679.02 [M+H]$^+$.

(S)-1-((9H-fluoren-9-yl)methyl) 2-((R)-1-(3-(2-(allyloxy)ethoxy)phenyl)-3-(3,4-dimethoxyphenyl)propyl) piperidine-1,2-dicarboxylate (68)

66 (1.29 g, 3.47 mmol, 1.0 eq) and Fmoc-S-pipecolate (1.30 g, 3.81 mmol, 1.1 eq) are dissolved in 20 mL dry DCM and cooled to 0° C. for 15 min. DMAP (50 mg, 0.38 mmol, 0.1 eq) is added and stirred until dissolved, then DCC (0.8 g, 3.81 mmol, 1.1 eq) is added. The mixture is stirred for 15 min under cooling. Finally, the ice bath is removed and the reaction stirred overnight at r.t. The reaction mixture is filtered, washed with DCM and the solvent removed under reduced pressure. The crude product is purified by silica column chromatography (CH/EE, 4/1) and pure product 68 obtained as white foam. Yield 2.17 g (89%). LC-MS: m/z: calculated=723.36 [M+NH$_4$]$^+$, found=723.07 [M+NH$_4$]$^+$.

(S)-(R)-1-(3-(allyloxy)phenyl)-3-(3,4-dimethoxyphenyl)propyl piperidine-2-carboxylate (69)

67 (3.15 g, 4.76 mmol, 1.0 eq) is dissolved in 40 mL DCM and 10% 4-methylpiperidine (4.4 mL) is added. The reaction is stirred at r.t. for 2 h, then diluted with 50 mL DCM, washed with 1 M HCl (4×50 mL) and brine (1×50 mL). The organic phase is dried with MgSO$_4$, filtered and the solvent removed. The crude product is purified by silica column chromatography (CH/EE, 2/1+1% TEA+2% MeOH) and the pure product 69 obtained as colorless oil.
Yield 1.85 g (89%). $^1$H-NMR (300 MHz, Chloroform-d): δ 7.24 (t, J=7.8 Hz, 1H), 6.96-6.85 (m, 2H), 6.83 (ddd, J=1.0, 2.6, 8.3 Hz, 1H), 6.78 (d, J=7.9 Hz, 1H), 6.67 (d, J=7.9 Hz, 2H), 6.05 (ddt, J=5.3, 10.5, 17.1 Hz, 1H), 5.77 (dd, J=5.7, 7.9 Hz, 1H), 5.41 (dq, J=1.6, 17.2 Hz, 1H), 5.28 (dq, J=1.4, 10.5 Hz, 1H), 4.52 (dt, J=1.5, 5.3 Hz, 2H), 3.85 (s, 3H), 3.84 (s, 3H), 3.37 (dd, J=3.2, 9.7 Hz, 1H), 3.07 (dt, J=3.4, 11.9 Hz, 1H), 2.72-2.45 (m, 3H), 2.34-2.15 (m, 1H), 2.15-1.96 (m, 3H), 1.87-1.74 (m, 1H), 1.70-1.37 (m, 4H). LC-MS m/z: calculated=440.24 [M+H]$^+$, found=440.23 [M+H]$^+$.

((S)-(R)-1-(3-(2-(allyloxy)ethoxy)phenyl)-3-(3,4-dimethoxyphenyl)propyl piperidine-2-carboxylate (70)

68 (2.17 g, 3.08 mmol, 1.0 eq) is dissolved in 30 mL DCM and 10% 4-methylpiperidine (3.3 mL) is added. The reaction is stirred at r.t. for 2 h, then diluted with 50 mL DCM, washed with 1 M HCl (4×50 mL) and brine (1×50 mL). The organic phase is dried with MgSO$_4$, filtered and the solvent removed. The crude product is purified by silica column chromatography (CH/EE, 2/1+1% TEA+2% MeOH) and the pure product 70 obtained as colorless oil. Yield 1.23 g (83%). $^1$H-NMR (300 MHz, Chloroform-d): δ 7.23 (t, J=8.0 Hz, 1H), 6.90 (dt, J=1.2, 5.6 Hz, 2H), 6.83 (ddd, J=1.0, 2.6, 8.2 Hz, 1H), 6.77 (d, J=7.9 Hz, 1H), 6.66 (d, J=7.8 Hz, 2H), 5.93 (ddt, J=5.7, 10.4, 17.3 Hz, 1H), 5.76 (dd, J=5.7, 7.9 Hz, 1H), 5.37-5.25 (m, 1H), 5.20 (dq, J=1.4, 10.4 Hz, 1H), 4.16-4.05 (m, 4H), 3.85 (s, 3H), 3.84 (s, 3H), 3.82-3.74 (m, 2H), 3.36 (dd, J=3.2, 9.7 Hz, 1H), 3.11-3.00 (m, 1H), 2.70-2.44 (m, 3H), 2.31-2.16 (m, 1H), 2.12-1.96 (m, 4H), 1.80 (dt, J=3.8, 7.8 Hz, 1H), 1.69-1.36 (m, 3H). LC-MS m/z: calculated=484.26 [M+H]$^+$, found=484.18 [M+H]$^+$.

(S)-(R)-1-(3-(allyloxy)phenyl)-3-(3,4-dimethoxyphenyl)propyl 1-((R)-2-cyclohexylpent-4-enoyl) piperidine-2-carboxylate (71)

(R)-2-cyclohexylpent-4-enoic acid[4] (456 mg, 2.50 mmol, 1.1 eq) is dissolved in 5 mL DMF, HATU (951 mg, 2.50 mmol, 1.1 eq) and DIPEA (1160 µL, 6.83 mmol, 3.0 eq) are added and the mixture stirred for 5 min. Then a solution of 69 (1.0 g, 2.28 mmol, 1.0 eq) in 15 mL DMF is added. The reaction is stirred at r.t overnight. The solvent is removed under reduced pressure. The crude product is purified by silica column chromatography (CH/EE, 7/1) to obtain pure product 71 as a sticky resin. Yield 900 mg (68%). $^1$H-NMR (300 MHz, Chloroform-d): δ 7.27-7.19 (m, 1H), 6.93-6.81 (m, 3H), 6.80-6.73 (m, 1H), 6.71-6.62 (m, 2H), 6.11-5.98 (m, 1H), 5.93-5.81 (m, 1H), 5.81-5.72 (m, 1H), 5.64-5.53 (m, 1H), 5.46-5.36 (m, 1H), 5.32-5.24 (m, 2H), 5.10-4.96

(m, 1H), 4.96-4.88 (m, 1H), 4.56-4.49 (m, 2H), 3.98-3.87 (m, 1H), 3.84 (d, J=2.2 Hz, 6H), 3.15-3.01 (m, 1H), 2.66-2.39 (m, 3H), 2.38-2.17 (m, 3H), 2.13-1.94 (m, 1H), 1.87 LC-MS: m/z: calculated=604.36 [M+H]$^+$, found=604.13 [M+H]$^+$.

(S)-(R)-1-(3-(2-(allyloxy)ethoxy)phenyl)-3-(3,4-dimethoxyphenyl)propyl 1-((R)-2-cyclohexylpent-4-enoyl)piperidine-2-carboxylate (72)

(R)-2-cyclohexylpent-4-enoic acid[4] (415 mg, 2.27 mmol, 1.1 eq) is dissolved in 5 mL DMF, HATU (865 mg, 2.27 mmol, 1.1 eq) and DIPEA (1055 μL, 6.20 mmol, 3.0 eq) are added and the mixture stirred for 5 min. Then a solution of 70 (1.0 g, 2.07 mmol, 1.0 eq) in 10 mL DMF is added. The reaction is stirred at r.t overnight. The solvent is removed under reduced pressure. The crude product is purified by silica column chromatography (CH/EE, 7/1) to obtain pure product 72 as a sticky resin. Yield 1.20 g (90%). $^1$H-NMR (300 MHz, Chloroform-d): δ 7.23 (t, J=7.4, 8.3 Hz, 1H), 6.93-6.87 (m, 2H), 6.86-6.80 (m, 1H), 6.80-6.73 (m, 1H), 6.69-6.61 (m, 2H), 6.01-5.86 (m, 1H), 5.85-5.71 (m, 2H), 5.59 (d, J=5.7 Hz, 1H), 5.35-5.24 (m, 1H), 5.24-5.15 (m, 1H), 5.09-4.95 (m, 1H), 4.95-4.87 (m, 1H), 4.15-4.03 (m, 6H), 3.95-3.88 (m, 1H), 3.86-3.81 (m, 6H), 3.81-3.72 (m, 2H), 3.14-3.01 (m, 1H), 2.74-2.13 (m, 7H), 1.93-1.79 (m, 1H), 1.79-1.50 (m, 9H), 1.42-1.01 (m, 4H), 1.01-0.66 (m, 2H). LC-MS: m/z: calculated=648.38 [M+H]$^+$, found=648.06 [M+H]$^+$.

(2R,5S,12R,14Z)-12-cyclohexyl-2-[2-(3,4-dimethoxyphenyl)ethyl]-3,17-dioxa-10-azatricyclo[16.3.1.0$^{5,10}$]docosa-1(22),14,18,20-tetraene-4,11-dione (73 and 74)

71 (536 mg, 0.89 mmol, 1.0 eq) is dissolved in 1.8 L dry DCM (0.5 mM) in a dried flask with condenser. The solution is sparged continuously with argon and heated to 30° C. The system is equilibrated for 45 min, then Grubbs 2$^{nd}$ generation catalyst (75 mg, 0.089, 0.1 eq) is added. After 2.5 h the solution is filtered through a silica plug and the product eluted with 300 mL EE. The solvent is removed under reduced pressure and the crude mixture purified by manual silica column chromatography (CH/EE, 4/1) to obtain pure products 73 (E-isomer) and 74 (Z-isomer). Yield (73) 441 mg (86%), (74) 44 mg (9%). $^1$H-NMR (500 MHz, THF-d$_8$, 73): δ 7.10 (t, J=7.3 Hz, 1H), 7.05-7.01 (m, 1H), 6.80-6.73 (m, 1H), 6.75 (d, J=8.1 Hz, 1H), 6.72 (d, J=2.0 Hz, 1H), 6.72-6.66 (m, 1H), 6.62 (dd, J=2.1, 8.1 Hz, 1H), 5.91 (dt, J=6.6, 8.0, 15.5 Hz, 1H), 5.64 (dd, J=4.9, 8.3 Hz, 1H), 5.64-5.58 (m, 1H), 5.56 (ddd, J=4.7, 7.4, 15.7 Hz, 1H), 4.64-4.49 (m, 2H), 3.73 (d, J=13.1 Hz, 6H), 3.68-3.60 (m, 1H), 2.57-2.30 (m, 6H), 2.27-2.19 (m, 1H), 2.12-2.03 (m, 1H), 2.04-1.93 (m, 1H), 1.80-1.66 (m, 4H), 1.67-1.54 (m, 4H), 1.52-1.45 (m, 1H), 1.44-1.33 (m, 1H), 1.32-1.24 (m, 1H), 1.24-1.09 (m, 3H), 1.07-0.96 (m, 1H), 0.92-0.83 (m, 1H). $^1$H-NMR (500 MHz, THF-d$_8$, 74): δ 7.11 (t, J=7.9 Hz, 1H), 6.79-6.75 (m, 2H), 6.74 (d, J=2.0 Hz, 1H), 6.70 (d, 1H), 6.69-6.65 (m, 2H), 5.73 (dd, J=3.7, 8.5 Hz, 1H), 5.49-5.44 (m, 1H), 5.36-5.28 (m, 1H), 5.23 (dt, J=2.1, 4.0, 11.3 Hz, 1H), 5.10 (dt, J=2.6, 4.3, 11.0 Hz, 1H), 4.63 (dq, J=2.8, 16.0 Hz, 1H), 3.98-3.91 (m, 1H), 3.75 (s, 3H), 3.72 (s, 3H), 3.50 (td, J=3.0, 13.0 Hz, 1H), 2.76-2.68 (m, 1H), 2.66-2.60 (m, 2H), 2.56-2.45 (m, 1H), 2.29-2.17 (m, 1H), 2.17-2.10 (m, 1H), 2.10-2.00 (m, 2H), 1.90-1.82 (m, 1H), 1.80-1.62 (m, 10H), 1.62-1.41 (m, 1H), 1.34-0.95 (m, 4H). LC-MS (73): m/z calculated=576.32 [M+H]$^+$, found=576.05 [M+H]$^+$, (74): m/z calculated=576.32 [M+H]$^+$, found=576.35 [M+H]$^+$. HRMS (ESI, 73): calculated=576.33196 [M+H]$^+$, found=576.33201 [M+H]$^+$, err [ppm]=0.08. HRMS (ESI, 74): calculated=576.33196 [M+H]$^+$, found=576.33236 [M+H]$^+$, err [ppm]=0.69.

(2R,5S,12R,14E)-12-cyclohexyl-2-[2-(3,4-dimethoxyphenyl)ethyl]-3,17,20-trioxa-10-azatricyclo[19.3.1.0$^{5,10}$]pentacosa-1(25),14,21,23-tetraene-4,11-dione (75)

72 (592 mg, 0.91 mmol, 1.0 eq) is dissolved in 1.8 L dry DCM (0.5 mM) in a dried flask with condenser. The solution is sparged continuously with argon and heated to 30° C. The system is equilibrated for 45 min, then Grubbs 2$^{nd}$ generation catalyst (78 mg, 0.091, 0.1 eq) is added. After 2.5 h the solution is filtered through a silica plug and the product eluted with 200 mL EE. The solvent is removed under reduced pressure and the crude mixture purified by manual silica column chromatography (CH/EE, 4/1) to obtain pure product 75. Yield 519 mg (92%). $^1$H-NMR (500 MHz, CD$_2$Cl$_2$): δ 7.28-7.19 (m, 1H), 7.11 (t, J=2.1 Hz, 1H), 6.94-6.90 (m, 1H), 6.85 (ddd, J=0.9, 2.5, 8.2 Hz, 1H), 6.82-6.77 (m, 1H), 6.75-6.68 (m, 2H), 5.69 (dd, J=5.1, 8.8 Hz, 1H), 5.64 (ddd, J=1.3, 5.8, 15.0 Hz, 1H), 5.59 (d, J=5.9 Hz, OH), 5.52 (dt, J=5.7, 15.4 Hz, 1H), 5.47 (d, 1H), 5.44-5.36 (m, OH), 4.23-4.18 (m, 2H), 3.90 (d, 2H), 3.81 (d, J=5.3 Hz, 6H), 3.72-3.57 (m, 2H), 3.18 (td, J=3.1, 12.8 Hz, 1H), 2.71-2.63 (m, 1H), 2.63-2.52 (m, 2H), 2.47-2.40 (m, 1H), 2.31-2.21 (m, 3H), 2.14-2.03 (m, 1H), 1.87-1.81 (m, 1H), 1.79-1.53 (m, 8H), 1.48-1.35 (m, 2H), 1.31-1.20 (m, 3H), 1.20-1.08 (m, 1H), 1.04-0.91 (m, 2H). LC-MS: m/z: calculated=620.35 [M+H]$^+$, found=620.39 [M+H]$^+$. HRMS (ESI): calculated=620.35818 [M+H]$^+$, found=620.35870 [M+H]$^+$, err [ppm]=0.84.

(2R,5S,12R)-12-cyclohexyl-2-[2-(3,4-dimethoxyphenyl)ethyl]-3,17-dioxa-10-azatricyclo[16.3.1.0$^{5,10}$]docosa-1(22),18,20-triene-4,11-dione (76)

73 (48 mg, 0.083 mmol, 1.0 eq) is dissolved in 3 mL dry MeOH and the solvent sparged with argon for 5 min, Then Pt/C (2 mg, 0.0008 mmol, 0.01 eq) is added and the slurry sparged with H$_2$ for 10 min. Then the reaction is stirred at 1 bar H$_2$ for 2 h. The mixture is filtered over SiO$_2$ and eluted with MeOH. The solvent is removed and the crude product purified by semi-preparative HPLC. Yield 16 mg (33%). $^1$H-NMR (500 MHz, THF-d$_8$): δ 7.12 (d, J=7.4 Hz, 1H), 7.04 (dd, J=1.5, 2.6 Hz, 1H), 6.77 (dd, J=2.6, 7.7 Hz, 2H), 6.74 (d, J=2.1 Hz, 1H), 6.72 (dt, J=1.2, 7.5 Hz, 1H), 6.64 (dd, J=2.1, 8.1 Hz, 1H), 5.70 (dd, J=6.2, 7.4 Hz, 1H), 5.66 (d, J=5.1 Hz, 1H), 4.28-4.16 (m, 1H), 4.17-4.01 (m, 1H), 3.78 (d, J=15.2 Hz, 4H), 3.75 (s, 3H), 3.73 (s, 3H), 2.72-2.59 (m, 1H), 2.57-2.50 (m, 1H), 2.53-2.44 (m, 2H), 2.39-2.28 (m, 1H), 2.21-2.13 (m, 1H), 2.09-1.98 (m, 1H), 1.79 (ddd, J=7.0, 10.3, 14.4 Hz, 2H), 1.70 (d, J=13.8 Hz, 3H), 1.68-1.56 (m, 6H), 1.56-1.44 (m, 2H), 1.46-1.34 (m, 2H), 1.35-1.24 (m, 1H), 1.26-1.18 (m, 1H), 1.21-1.07 (m, 1H), 1.09-0.88 (m, 2H). LC-MS: m/z: calculated=578.34 [M+H]$^+$, found=578.42 [M+H]$^+$. HRMS (ESI): calculated=578.34761 [M+H]$^+$, found=578.34766 [M+H]$^+$, err [ppm]=0.08.

(2R,5S,12R)-12-cyclohexyl-2-[2-(3,4-dimethoxyphenyl)ethyl]-3,17-dioxa-10-azatricyclo[16.3.1.0$^{5,10}$]docosa-1(22),18,20-triene-4,11,14-trione (77)

73 (34 mg, 0.059 mmol, 1.0 eq) is dissolved in 0.7 mL THF and 0.1 mL H$_2$O (7/1, ratio) added. p-benzoquinone (7 mg, 0.06 mmol, 1.1 eq), then PdCl$_2$ (2 mg, 0.01 mmol, 0.2 eq) are added. The reaction is stirred over night at r.t. The solvent is removed under reduced pressure and the crude product is purified by silica column chromatography (CH/EE, 3/1) and pure 77 is obtained. Yield 27 mg (77%). $^1$H-NMR (500 MHz, CDCl$_3$): δ 7.19 (t, J=7.8 Hz, 1H), 6.87 (t, J=2.1 Hz, 1H), 6.81-6.75 (m, 3H), 6.71-6.65 (m, 2H), 5.65 (dd, J=5.3, 7.9 Hz, 1H), 5.39-5.33 (m, 1H), 4.46-4.33 (m, 2H), 3.91-3.87 (m, 1H), 3.86 (s, 3H), 3.85 (s, 3H), 3.36 (td, J=2.8, 13.3 Hz, 1H), 3.15-3.08 (m, 1H), 3.08-3.02 (m, 2H), 2.92 (ddd, J=5.8, 8.2, 16.7 Hz, 1H), 2.67-2.58 (m, 2H), 2.54 (dt, J=4.9, 16.7 Hz, 1H), 2.49-2.43 (m, 1H), 2.33-2.21 (m, 1H), 2.15-2.05 (m, 2H), 1.80-1.60 (m, 5H), 1.59-1.47 (m, 1H), 1.33-1.16 (m, 2H), 1.16-1.06 (m, 1H), 1.06-0.85 (m, 2H). LC-MS m/z: calculated=592.32 [M+H]$^+$, found=592.34 [M+H]$^+$. HRMS (ESI): calculated=592.32688 [M+H]$^+$, found=592.32709 [M+H]$^+$, err [ppm]=0.35.

(2R,5S,12R)-12-cyclohexyl-2-[2-(3,4-dimethoxyphenyl)ethyl]-14,15-dihydroxy-3,17-dioxa-10-azatricyclo[16.3.1.0$^{5,10}$]docosa-1(22),18,20-triene-4,11-dione (78 and 79)

73 (53 mg, 0.092 mmol, 1.0 eq) is dissolved in 2 mL acetone and 220 μL H$_2$O (9/1, ratio) added. NMO (16 mg, 0.14 mmol, 1.5 eq), then OsO$_4$ (23 μL, 0.002 mmol, 0.02 eq) of a 2.5 w % solution in tBuOH are added. The reaction is stirred overnight at r.t. The reaction is quenched with 1 mL sat. Na$_2$S$_2$O$_{3(aq)}$ solution and stirred for 15 min. The mixture is diluted with H$_2$O and extracted with DCM (3×15 mL). The organic phase is washed with 15 mL sat. CuSO$_{4(aq)}$ solution, dried over MgSO$_4$, filtered and the solvent removed under reduced pressure. The crude product is purified by semi-preparative HPLC and pure diastereomers 78 and 79 obtained. Yield (78) 15 mg (26%), (79) 13 mg (23%). $^1$H-NMR (500 MHz, CDCl$_3$, 78): δ 7.24-7.22 (m, 1H), 7.17 (dd, J=7.4, 8.3 Hz, 1H), 6.89-6.83 (m, 1H), 6.77 (d, J=7.9 Hz, 1H), 6.75-6.71 (m, 1H), 6.69-6.64 (m, 2H), 5.67 (dd, J=5.6, 8.3 Hz, 1H), 5.63 (d, J=4.6 Hz, 1H), 4.44 (dd, J=6.1, 12.8 Hz, 1H), 4.10 (dd, J=5.7, 12.8 Hz, 1H), 3.85 (s, 3H), 3.83 (s, 3H), 3.76-3.72 (m, 1H), 3.72-3.63 (m, 2H), 3.27 (s, 3H), 2.66-2.56 (m, 2H), 2.53-2.44 (m, 2H), 2.44-2.35 (m, 1H), 2.35-2.23 (m, 1H), 2.14-2.01 (m, 2H), 1.90-1.81 (m, 1H), 1.79-1.52 (m, 7H), 1.54-1.31 (m, 2H), 1.28-0.89 (m, 4H). $^1$H-NMR (500 MHz, CDCl$_3$, 79): δ 7.24 (t, J=7.8 Hz, 1H), 7.09-7.07 (m, 1H), 6.93-6.89 (m, 1H), 6.88-6.85 (m, 1H), 6.79 (d, J=7.9 Hz, 1H), 6.70-6.65 (m, 2H), 5.65 (t, J=7.1 Hz, 1H), 5.54-5.49 (m, 1H), 4.36 (dd, J=2.8, 12.6 Hz, 1H), 4.24 (dd, J=6.1, 12.6 Hz, 1H), 3.90-3.88 (m, 1H), 3.86 (s, 3H), 3.85 (s, 3H), 3.68-3.63 (m, 1H), 3.61-3.56 (m, 1H), 2.96 (td, J=2.7, 13.4 Hz, 1H), 2.76-2.68 (m, 1H), 2.61-2.52 (m, 2H), 2.46-2.35 (m, 1H), 2.20-2.14 (m, 1H), 2.14-2.06 (m, 1H), 1.83 (d, J=12.9 Hz, 1H), 1.77-1.55 (m, 4H), 1.55-1.36 (m, 1H), 1.29-1.04 (m, 3H), 1.04-0.83 (m, 2H). LC-MS (78): m/z: calculated=610.33 [M+H]$^+$, found=610.40 [M+H]$^+$, (79): m/z: calculated=610.33 [M+H]$^+$, found=610.44 [M+H]$^+$. HRMS (ESI, 78): calculated=610.33744 [M+H]$^+$, found=610.33760 [M+H]$^+$, err [ppm]=0.26. HRMS (ESI, 79): calculated=610.33744 [M+H]$^+$, found=610.33762 [M+H]$^+$, err [ppm]=0.28.

(2R,5S,12R)-12-cyclohexyl-2-[2-(3,4-dimethoxyphenyl)ethyl]-3,17,20-trioxa-10-azatricyclo[19.3.1.0$^{5,10}$]pentacosa-1(25),21,23-triene-4,11-dione (80)

75 (30 mg, 0.048 mmol, 1.0 eq), RuCl(PPh$_3$)$_3$ (22 mg, 0.024 mmol, 0.5 eq) is dissolved in 3 mL toluene. The solution is sparged with H$_2$ for 10 min, then reacted under 1 bar H$_2$ atmosphere over night at r.t. The solvent is removed and the crude product purified by silica column chromatography (CH/EE, 3/1) to obtain pure product 80. Yield 28 mg (93%). $^1$H-NMR (500 MHz, CD$_2$Cl$_2$): δ 7.23 (t, J=7.9 Hz, 1H), 7.20 (t, J=2.1 Hz, 1H), 6.92-6.89 (m, 1H), 6.89-6.86 (m, 1H), 6.77 (d, J=8.6 Hz, 1H), 6.71-6.65 (m, 2H), 5.81 (dd, J=5.6, 8.3 Hz, 1H), 5.66-5.61 (m, 1H), 4.26-4.11 (m, 2H), 3.97-3.91 (m, 1H), 3.86 (s, 3H), 3.85 (s, 3H), 3.67 (ddd, J=2.7, 4.9, 11.5 Hz, 1H), 3.59-3.48 (m, 2H), 3.39 (ddd, J=4.8, 7.2, 9.3 Hz, 1H), 3.02-2.94 (m, 1H), 2.68-2.57 (m, 1H), 2.57-2.47 (m, 2H), 2.32-2.26 (m, 1H), 2.26-2.18 (m, 1H), 2.09-1.99 (m, 1H), 1.91-1.83 (m, 1H), 1.82-1.48 (m, 11H), 1.46-1.33 (m, 5H), 1.30-1.17 (m, 2H), 1.17-1.06 (m, 1H), 1.01-0.84 (m, 2H). LC-MS m/z: calculated=622.37 [M+H]$^+$, found=622.50 [M+H]$^+$. HRMS (ESI): calculated=622.37383 [M+H]$^+$, found=622.37352 [M+H]$^+$, err [ppm]=0.50.

(2R,5S,12R)-12-cyclohexyl-2-[2-(3,4-dimethoxyphenyl)ethyl]-3,17,20-trioxa-10-azatricyclo[19.3.1.0$^{5,10}$]pentacosa-1(25),21,23-triene-4,11,14-trione (81)

75 (50 mg, 0.081 mmol, 1.0 eq) is dissolved in 0.7 mL THF and 0.1 mL H$_2$O (7/1 ratio) added. p-benzoquinone (10 mg, 0.09 mmol, 1.1 eq), then PdCl$_2$ (4 mg, 0.016 mmol, 0.4 eq) are added. The reaction is stirred over night at r.t. The solvent is removed under reduced pressure and the crude product is purified by semi-preparative HPLC and pure 81 obtained. Yield 23 mg (45%). $^1$H-NMR (500 MHz, CDCl$_3$): δ 7.20 (t, J=7.9 Hz, 1H), 7.05 (t, J=2.0 Hz, 1H), 6.83 (d, J=1.2, 7.8 Hz, 1H), 6.82-6.76 (m, 2H), 6.71-6.66 (m, 2H), 5.73 (dd, J=5.4, 8.1 Hz, 1H), 5.45 (d, 1H), 4.16-4.09 (m, 2H), 3.93 (d, J=13.3 Hz, 1H), 3.90-3.81 (m, 6H), 3.76-3.70 (m, 2H), 3.69-3.61 (m, 1H), 3.25-3.18 (m, 1H), 3.16-3.08 (m, 1H), 2.83 (dd, J=6.0, 17.9 Hz, 1H), 2.76 (ddd, J=4.9, 8.3, 16.4 Hz, 1H), 2.66 (dd, J=6.1, 18.1 Hz, 1H), 2.63-2.50 (m, 2H), 2.43 (dt, J=5.0, 16.4 Hz, 1H), 2.31-2.16 (m, 2H), 2.13-2.01 (m, 1H), 1.91-1.82 (m, 1H), 1.77-1.57 (m, 7H), 1.57-1.50 (m, 1H), 1.49-1.35 (m, 2H), 1.31-1.18 (m, 2H), 1.19-1.05 (m, 1H), 1.03-0.79 (m, 2H). LC-MS m/z: calculated=636.35 [M+H]$^+$, found=636.44 [M+H]$^+$. HRMS (ESI): calculated=636.35309 [M+H]$^+$, found=636.35343 [M+H]$^+$, err [ppm]=0.52.

(2R,5S,12R)-12-cyclohexyl-2-[2-(3,4-dimethoxyphenyl)ethyl]-14,15-dihydroxy-3,17,20-trioxa-10-azatricyclo[19.3.1.0$^{5,10}$]pentacosa-1(25),21,23-triene-4,11-dione (82)

75 (53 mg, 0.086 mmol, 1.0 eq) is dissolved in 2 mL acetone and 220 μL H$_2$O (9/1, ratio) added. NMO (12 mg, 0.1 mmol, 1.2 eq), then OSO$_4$ (21 μL, 0.002 mmol, 0.02 eq) of a 2.5 w % solution in tBuOH are added. The reaction is stirred overnight at r.t. The reaction is quenched with 1 mL sat. Na$_2$S$_2$O$_{3(aq)}$ solution and stirred for 15 min. The mixture is diluted with H$_2$O and extracted with DCM (3×15 mL). The organic phase is washed with 15 mL sat. CuSO$_{4(aq)}$ solution, dried over MgSO$_4$, filtered and the solvent removed under reduced pressure. The crude product is purified by semi-preparative HPLC and pure 82 obtained. (Diastereomers could not be separated on either prep. HPLC or RP-HPLC). Yield 19 mg (34%). $^1$H-NMR (500 MHz, CDCl$_3$): δ 7.29-7.26 (m, 1H), 7.25-7.21 (m, 1H), 7.01 (t, J=2.0 Hz, 1H), 6.93-6.85 (m, 2H), 6.81-6.74 (m, 1H), 6.71-6.65 (m, 2H), 5.76 (dd, J=5.9, 8.1 Hz, 0.57H), 5.70 (dd, J=5.2, 8.3 Hz, 0.43H), 5.58 (d, J=1.9, 6.2 Hz, 0.50H), 5.55 (d, 0.64H), 4.35-4.15 (m, 2H), 4.05 (d, J=13.6 Hz, 0.42H), 3.91-3.81 (m, 6H), 3.79-3.42 (m, 6H), 3.40-3.29 (m, 0.53H), 3.24-3.09 (m, 0.51H), 3.03-2.85 (m, 1H), 2.82-2.46 (m, 2H), 2.40-2.20 (m, 2H), 2.17-1.95 (m, 1H), 1.95-1.80 (m, 1H), 1.80-1.34 (m, 8H), 1.30-0.87 (m, 4H). LC-MS m/z: calculated=654.36 [M+H]$^+$, found=654.51 [M+H]$^+$. HRMS (ESI): calculated=654.36366 [M+H]$^+$, found=654.36352 [M+H]$^+$, err [ppm]=0.21.

(2R,5S,12R)-12-cyclohexyl-2-[2-(3,4-dimethoxyphenyl)ethyl]-3,19-dioxa-10,13,16-triazatricyclo[18.3.1.0$^{5,10}$]tetracosa-1(24),20,22-triene-4,11,14,17-tetrone (83)

Procedure as described in Example 7. Starting materials: Resin: (0.17 mmol), 1$^{st}$ AA: Fmoc-D-Chg-OH, 2$^{nd}$ AA: Fmoc-Gly-OH. Yield 11 mg (10%). $^1$H-NMR (500 MHz, CDCl$_3$): δ 7.29-7.21 (m, 1H), 7.14 (d, J=9.1 Hz, 1H), 6.96-6.87 (m, 3H), 6.88-6.82 (m, 1H), 6.77 (d, J=7.6 Hz, 1H), 6.69-6.61 (m, 2H), 5.67-5.59 (m, 1H), 5.26-5.18 (m, 1H), 4.82-4.74 (m, 1H), 4.69-4.57 (m, 2H), 4.57-4.43 (m, 1H), 3.86 (s, 3H), 3.84 (s, 3H), 3.80-3.73 (m, 1H), 3.37 (dd, J=4.3, 14.8 Hz, 1H), 3.16 (td, J=2.9, 13.2 Hz, 1H), 2.66-2.39 (m, 1H), 2.37-2.22 (m, 1H), 2.21-2.11 (m, 1H), 2.10-1.98 (m, 1H), 1.94-1.79 (m, 2H), 1.80-1.67 (m, 2H), 1.69-1.53 (m, 8H), 1.54-1.34 (m, 1H), 1.30-1.10 (m, 2H), 1.09-0.93 (m, 2H). LC-MS m/z: calculated=636.33 [M+H]$^+$, found=636.07 [M+H]$^+$. HRMS (ESI): calculated=636.32794 [M+H]$^+$, found=636.32770 [M+H]1, err [ppm]=0.37.

(2R,5S,12R,15R)-12-cyclohexyl-2-[2-(3,4-dimethoxyphenyl)ethyl]-15-methyl-3,19-dioxa-10,13,16-triazatricyclo[18.3.1.0$^{5,10}$]tetracosa-1(24),20,22-triene-4,11,14,17-tetrone (84)

Procedure as described in Example 7. Starting materials: Resin: (0.14 mmol), 1$^{st}$ AA: Fmoc-D-Chg-OH, 2$^{nd}$ AA: Fmoc-D-Ala-OH. Yield 17 mg (19%). $^1$H-NMR (800 MHz, DMSO-d$_6$+CD$_2$Cl$_2$): δ 8.31 (d, J=7.2 Hz, 1H), 7.75 (d, J=9.0 Hz, 1H), 7.20 (t, J=7.8 Hz, 1H), 6.90-6.86 (m, 1H), 6.87-6.82 (m, 3H), 6.78 (d, J=2.0 Hz, 1H), 6.67 (dd, J=2.0, 8.1 Hz, 1H), 5.62 (dd, J=5.0, 8.6 Hz, 1H), 5.08-5.04 (m, 1H), 4.73 (d, J=15.8 Hz, 1H), 4.61 (d, J=15.8 Hz, 1H), 4.48 (dd, J=7.0, 9.1 Hz, 1H), 4.08 (p, J=7.3 Hz, 1H), 3.73 (s, 3H), 3.71 (s, 3H), 3.70-3.65 (m, 1H), 3.00-2.93 (m, 1H), 2.59-2.52 (m, 1H), 2.49-2.43 (m, 1H), 2.17-2.10 (m, 1H), 2.06-1.99 (m, 2H), 1.79-1.72 (m, 1H), 1.72-1.68 (m, 1H), 1.67-1.58 (m, 6H), 1.58-1.54 (m, 1H), 1.40-1.33 (m, 2H), 1.31 (d, J=7.3 Hz, 3H), 1.22-1.11 (m, 2H), 1.09-1.03 (m, 1H), 0.98-0.89 (m, 2H). LC-MS m/z: calculated=650.34 [M+H]$^+$, found=650.09 [M+H]$^+$. HRMS (ESI): calculated=650.34359 [M+H]$^+$, found=650.34361 [M+H]$^+$, err [ppm]=0.03.

(2R,5S,12R)-12-cyclohexyl-2-[2-(3,4-dimethoxyphenyl)ethyl]-15,15-dimethyl-3,19-dioxa-10,13,16-triazatricyclo[18.3.1.0$^{5,10}$]tetracosa-1(24),20,22-triene-4,11,14,17-tetrone (85)

Procedure as described in Example 7. Starting materials: Resin: (0.47 mmol), 1$^{st}$ AA: Fmoc-D-Chg-OH, 2$^{nd}$ AA: Fmoc-Aib-OH. Yield 257 mg (83%). $^1$H-NMR (500 MHz, CDCl$_3$): δ 7.73 (d, J=9.0 Hz, 1H), 7.25-7.19 (m, 1H), 6.99-6.96 (m, 1H), 6.85-6.80 (m, 2H), 6.77 (d, J=8.0 Hz, 1H), 6.68-6.62 (m, 2H), 6.48 (s, 1H), 5.65 (dd, J=5.7, 7.6 Hz, 1H), 5.25-5.20 (m, 1H), 4.69 (dd, J=6.1, 9.1 Hz, 1H), 4.64 (d, J=16.1 Hz, 1H), 4.54 (d, J=16.1 Hz, 1H), 3.86 (s, 3H), 3.84 (s, 3H), 3.81-3.75 (m, 1H), 3.28 (td, J=3.1, 13.1 Hz, 1H), 2.62-2.44 (m, 2H), 2.31-2.20 (m, 1H), 2.16-2.10 (m, 1H), 2.08-2.00 (m, 1H), 1.99 (s, 1H), 1.82 (s, 1H), 1.78 (s, 3H), 1.77-1.60 (m, 10H), 1.41 (s, 3H), 1.30-1.17 (m, 2H), 1.16-0.97 (m, 2H). LC-MS (50-100% B, 19 min): t$_R$ (13c) =8.25 min, m/z: calculated=664.35 [M+H]$^+$, found=664.32 [M+H]$^+$. HRMS (ESI): calculated=664.35924 [M+H]$^+$, found=664.36019 [M+H]$^+$, err [ppm]=1.42.

(2'R,5'S,12'R)-12'-cyclohexyl-2'-[2-(3,4-dimethoxyphenyl)ethyl]-3', 19'-dioxa-10', 13', 16'-triazaspiro[cyclopropane-1,15'-tricyclo[18.3.1.0$^{5,10}$]tetracosane]-1'(24'),20', 22'-triene-4', 11', 14', 17'-tetrone (86)

Procedure as described in Example 7. Starting materials: Resin (0.05 mmol), 1$^{st}$ AA: Fmoc-D-Chg-OH, 2$^{nd}$ AA: Fmoc-1-amino-1-cyclopropanecarboxylic acid. Yield 27 mg (77%). $^1$H-NMR (599 MHz, DMSO-d$_6$+CD$_2$Cl$_2$): δ 8.12 (s, 1H), 7.46 (d, J=9.0 Hz, 1H), 6.77 (t, J=7.8 Hz, 1H), 6.51 (d, J=2.4 Hz, 1H), 6.43-6.38 (m, 3H), 6.35-6.31 (m, 1H), 6.24 (dd, J=2.1, 8.0 Hz, 1H), 5.22 (dd, J=5.3, 8.3 Hz, 1H), 4.61 (dd, J=2.7, 6.3 Hz, 1H), 4.34 (d, J=16.0 Hz, 1H), 4.10 (d, J=15.9 Hz, 1H), 4.04 (t, J=8.2 Hz, 1H), 3.30 (s, 3H), 3.27 (s, 4H), 3.17 (d, J=13.7 Hz, 1H), 2.50 (t, J=12.5 Hz, 1H), 2.05-1.96 (m, 1H), 1.75-1.67 (m, 1H), 1.66-1.54 (m, 3H), 1.40-1.28 (m, 1H), 1.30-1.13 (m, 6H), 1.13-1.03 (m, 2H), 0.98-0.86 (m, 2H), 0.85-0.66 (m, 2H), 0.66-0.55 (m, 1H), 0.55-0.41 (m, 3H), 0.39-0.29 (m, 1H). LC-MS m/z: calculated=662.34 [M+H]$^+$, found=662.32 [M+H]$^+$. HRMS (ESI): calculated=662.34359 [M+H]$^+$, found=662.34412 [M+H]$^+$, err [ppm]=0.79.

(2'R,5'S,12'R)-12'-cyclohexyl-2'-[2-(3,4-dimethoxyphenyl)ethyl]-3', 19'-dioxa-10', 13', 16'-triazaspiro[cyclobutane-1,15'-tricyclo[18.3.1.0$^{5,10\circ}$ ]tetracosane]-1'(24'),20', 22'-triene-4', 11', 14', 17'-tetrone (87)

Procedure as described in Example 7. Starting materials: Resin: (0.19 mmol), 1$^{st}$ AA: Fmoc-D-Chg-OH, 2$^{nd}$ AA: Fmoc-1-amino-1-cyclobutanecarboxylic acid. Yield 38 mg (29%). $^1$H-NMR (500 MHz, CDCl$_3$): δ 7.87 (d, J=9.5 Hz, 1H), 7.23-7.17 (m, 1H), 6.89-6.83 (m, 2H), 6.81-6.72 (m, 2H), 6.64-6.61 (m, 2H), 6.57 (s, 1H), 5.60 (t, J=6.6 Hz, 1H), 5.26 (q, J=2.1 Hz, 1H), 4.75 (d, J=16.5 Hz, 1H), 4.71 (dd, J=6.4, 9.5 Hz, 1H), 4.58 (d, J=16.6 Hz, 1H), 3.84 (s, 3H), 3.82 (s, 3H), 3.81-3.77 (m, 1H), 3.22-3.14 (m, 1H), 2.94-2.85 (m, 1H), 2.78-2.69 (m, 1H), 2.59-2.52 (m, 1H), 2.52-2.40 (m, 1H), 2.29-2.17 (m, 1H), 2.14-2.06 (m, 1H), 2.03-1.81 (m, 4H), 1.80-1.59 (m, 11H), 1.51-1.38 (m, 1H), 1.31-1.19 (m, 2H), 1.19-1.09 (m, 1H), 1.08-1.00 (m, 1H). LC-MS m/z: calculated=676.36 [M+H]$^+$, found=676.48 [M+H]$^+$. HRMS (ESI): calculated=676.35924 [M+H]$^+$, found=676.35936 [M+H]$^+$, err [ppm]=0.17.

(2'R,5'S,12'R)-12'-cyclohexyl-2'-[2-(3,4-dimethoxyphenyl)ethyl]-3', 19'-dioxa-10', 13', 16'-triazaspiro[cyclopentane-1,15'-tricyclo[18.3.1.0$^{5,10}$]tetracosane]-1'(24'),20', 22'-triene-4', 11', 14', 17'-tetrone (88)

Procedure as described in Example 7. Starting materials: Resin: (0.14 mmol), 1$^{st}$ AA: Fmoc-D-Chg-OH, 2$^{nd}$ AA: Fmoc-1-amino-1-cyclopentanecarboxylic acid. Yield 4 mg (4%). LC-MS (50-100% B, 19 min): $t_R$ (13f)=13.04 min, m/z: calculated=690.38 [M+H]$^+$, found=690.36 [M+H]$^+$. HRMS (ESI): calculated=690.37487 [M+H]$^+$, found=690.37549 [M+H]$^+$, err [ppm]=0.90.

(2R,5S,12R)-12-cyclohexyl-2-[2-(3,4-dimethoxyphenyl)ethyl]-16-methyl-3,19-dioxa-10,13,16-triazatricyclo[18.3.1.0$^{5,10}$]tetracosa-1(24),20,22-triene-4,11,14,17-tetrone (89)

Procedure as described in Example 7. Starting materials: Resin: (0.24 mmol), 1$^{st}$ AA: Fmoc-D-Chg-OH, 2$^{nd}$ AA: Fmoc-Gly-OH. Yield 30 mg (19%). $^1$H-NMR (500 MHz, CDCl$_3$): δ 7.23 (t, J=7.9 Hz, 1H), 6.96 (s, 1H), 6.80-6.73 (m, 3H), 6.69-6.61 (m, 2H), 5.73-5.67 (m, 1H), 5.41-5.35 (m, 1H), 4.89 (t, J=7.8 Hz, 1H), 4.72 (d, J=12.6 Hz, 1H), 4.49 (d, J=12.6 Hz, 1H), 4.06 (q, J=17.3 Hz, 2H), 3.92-3.85 (m, 1H), 3.85 (s, 3H), 3.84 (s, 3H), 3.28-3.18 (m, 1H), 3.07 (s, 3H), 2.62-2.51 (m, 2H), 2.25-2.02 (m, 2H), 1.83-1.62 (m, 12H), 1.54-1.38 (m, 1H), 1.30-0.98 (m, 5H). LC-MS m/z: calculated=650.34 [M+H]$^+$, found=650.51 [M+H]$^+$. HRMS (ESI): calculated=650.34359 [M+H]$^+$, found=650.34345 [M+H]$^+$, err [ppm]=0.22.

(9R,12R,19S,22R)-12-cyclohexyl-22-[2-(3,4-dimethoxyphenyl)ethyl]-2,21-dioxa-5,11,14-triazatetracyclo[21.3.1.0$^{5,9}$.0$^{14,19}$]heptacosa-1(26),23(27),24-triene-4,10,13,20-tetrone (90)

Procedure as described in Example 7. Starting materials: Resin: (0.15 mmol), 1$^{st}$ AA: Fmoc-D-Chg-OH, 2$^{nd}$ AA: Fmoc-D-Pro-OH. Yield 7 mg (7%). LC-MS m/z: calculated=676.36 [M+H]$^+$, found=676.18 [M+H]$^+$. HRMS (ESI): calculated=676.35924 [M+H]$^+$, found=676.35889 [M+H]$^+$, err [ppm]=0.52.

(2R,5S,12R,15S)-12-cyclohexyl-2-[2-(3,4-dimethoxyphenyl)ethyl]-15-methyl-3,19-dioxa-10,13,16-triazatricyclo[18.3.1.0$^{5,10}$]tetracosa-1(24),20,22-triene-4,11,14,17-tetrone (91)

Procedure as described in Example 7. Starting materials: Resin: (0.15 mmol), 1$^{st}$ AA: Fmoc-D-Chg-OH, 2$^{nd}$ AA: Fmoc-L-Ala-OH. Yield 27 mg (28%). $^1$H-NMR (800 MHz, DMSO-d$_6$+CD$_2$Cl$_2$): δ 8.30 (d, J=9.0 Hz, 1H), 7.68 (d, J=8.5 Hz, 1H), 7.29-7.25 (m, 1H), 6.96 (ddd, J=1.0, 2.6, 8.2 Hz, 1H), 6.93-6.89 (m, 1H), 6.83 (d, J=8.1 Hz, 1H), 6.75 (d, J=2.0 Hz, 1H), 6.74-6.71 (m, 1H), 6.65 (dd, J=2.0, 8.1 Hz, 1H), 5.73 (t, J=7.1 Hz, 1H), 5.23-5.20 (m, 1H), 4.68 (d, J=16.1 Hz, 1H), 4.64-4.58 (m, 1H), 4.46 (t, J=9.0 Hz, 1H), 4.42 (d, J=16.1 Hz, 1H), 3.99-3.92 (m, 1H), 3.73 (s, 3H), 3.71 (s, 3H), 2.64-2.56 (m, 1H), 2.48-2.37 (m, 2H), 2.15-2.07 (m, 2H), 2.06-1.99 (m, 1H), 1.74-1.60 (m, 5H), 1.60-1.54 (m, 2H), 1.52-1.42 (m, 2H), 1.40-1.21 (m, 2H), 1.16 (d, J=6.8 Hz, 3H), 1.14-1.07 (m, 2H), 0.97-0.80 (m, 2H). LC-MS m/z: calculated=650.34 [M+H]$^+$, found=650.07 [M+H]$^+$. HRMS (ESI): calculated=650.34359 [M+H]$^+$, found=650.34358 [M+H]$^+$, err [ppm]=0.01.

(9S,12R,19S,22R)-12-cyclohexyl-22-[2-(3,4-dimethoxyphenyl)ethyl]-2,21-dioxa-5,11,14-triazatetracyclo[21.3.1.0$^{5,9}$.0$^{14,19}$]heptacosa-1(26),23(27),24-triene-4,10,13,20-tetrone (92)

Procedure as described in Example 7. Starting materials: Resin: (0.15 mmol), 1$^{st}$ AA: Fmoc-D-Chg-OH, 2$^{nd}$ AA: Fmoc-L-Pro-OH. Yield 4 mg (4%). LC-MS m/z: calculated=676.36 [M+H]$^+$, found=676.18 [M+H]$^+$. HRMS (ESI): calculated=676.35924 [M+H]$^+$, found=676.35941 [M+H]$^+$, err [ppm]=0.24.

(2R,5S,12R)-12-cyclohexyl-2-[2-(3,4-dimethoxyphenyl)ethyl]-3,20-dioxa-10,13,17-triazatricyclo[19.3.1.0$^{5,10}$]pentacosa-1(25),21,23-triene-4,11,14,18-tetrone (93)

Procedure as described in Example 7. Starting materials: Resin: (0.13 mmol), 1$^{st}$ AA: Fmoc-D-Chg-OH, 2$^{nd}$ AA: Fmoc-β-Ala-OH. Yield 14 mg (16%). $^1$H-NMR (800 MHz, DMSO-d$_6$+CD$_2$Cl$_2$): δ 7.93 (d, J=9.1 Hz, 1H), 7.82-7.78 (m, 1H), 7.24 (t, J=7.9 Hz, 1H), 6.89-6.86 (m, 1H), 6.86-6.82 (m, 2H), 6.77 (d, J=2.0 Hz, 1H), 6.74-6.71 (m, 1H), 6.69 (dd, J=2.0, 8.1 Hz, 1H), 5.58 (dd, J=5.3, 8.2 Hz, 1H), 5.17-5.13 (m, 1H), 4.71-4.67 (m, 1H), 4.46 (d, J=15.4 Hz, 1H), 4.40 (d, J=15.4 Hz, 1H), 4.03-3.97 (m, 1H), 3.74 (s, 3H), 3.71 (s, 3H), 3.59-3.53 (m, 1H), 3.18-3.13 (m, 1H), 3.13-3.06 (m, 1H), 2.58-2.52 (m, 1H), 2.48-2.40 (m, 2H), 2.32-2.27 (m, 1H), 2.10-2.05 (m, 1H), 2.05-1.98 (m, 2H), 1.77-1.69 (m, 3H), 1.69-1.64 (m, 1H), 1.64-1.56 (m, 5H), 1.42-1.32 (m, 1H), 1.28-1.06 (m, 5H), 1.05-0.92 (m, 2H). LC-MS m/z: calculated=650.35 [M+H]$^+$, found=650.04 [M+H]$^+$. HRMS (ESI): calculated=650.34359 [M+H]$^+$, found=650.34363 [M+H]$^+$, err [ppm]=0.05.

(2R,5S,12R,15R,19R)-12-cyclohexyl-2-[2-(3,4-dimethoxyphenyl)ethyl]-3,23-dioxa-10,13,20-triazatetracyclo[22.3.1.0$^{5,10}$.0$^{15,19}$]octacosa-1(28),24,26-triene-4,11,14,21-tetrone (94)

Procedure as described in Example 7. Starting materials: Resin: (0.14 mmol), 1$^{st}$ AA: Fmoc-D-Chg-OH, 2$^{nd}$ AA: (1R,2R)-Fmoc-2-amino-1-cyclopentanecarboxylic acid. Yield 3 mg (3%). LC-MS m/z: calculated=690.37 [M+H]$^+$, found=690.32 [M+H]$^+$. HRMS (ESI): calculated=690.37489 [M+H]$^+$, found=690.37473 [M+H]$^+$, err [ppm]=0.23.

(2R,5S,12R)-12-cyclohexyl-2-[2-(3,4-dimethoxyphenyl)ethyl]-3,21-dioxa-10,13,18-triazatricyclo[20.3.1.0$^{5,10}$]hexacosa-1(26),22,24-triene-4,11,14,19-tetrone (95)

Procedure as described in Example 7. Starting materials: Resin: (0.24 mmol), 1$^{st}$ AA: Fmoc-D-Chg-OH, 2$^{nd}$ AA: Fmoc-GABA-OH. Yield 8 mg (5%). LC-MS m/z: calculated=664.35 [M+H]$^+$, found=664.31 [M+H]$^+$. HRMS (ESI): calculated=664.35924 [M+H]$^+$, found=664.35929 [M+H]$^+$, err [ppm]=0.07.

(2R,5S,12R,15S,19R)-12-cyclohexyl-2-[2-(3,4-dimethoxyphenyl)ethyl]-3,23-dioxa-10,13,20-triazatetracyclo[22.3.1.0$^{5,10}$.0$^{15,19}$]octacosa-1(28),24,26-triene-4,11,14,21-tetrone (96)

Procedure as described in Example 7. Starting materials: Resin: (0.07 mmol), 1$^{st}$ AA: Fmoc-D-Chg-OH, 2$^{nd}$ AA: (1S,2R)-Fmoc-2-amino-1-cyclopentanecarboxylic acid. Yield 2 mg (4%). LC-MS m/z: calculated=690.37 [M+H]$^+$, found=690.28 [M+H]$^+$. HRMS (ESI): calculated=690.37489 [M+H]$^+$, found=690.37455 [M+H]$^+$, err [ppm]=0.50.

(E)-1-(3,5-dihydroxyphenyl)-3-(3,4-dimethoxyphenyl)prop-2-en-1-one (97)

3,5-Dihydroxyacetophenon (6.00 g, 39 mmol, 1.0 eq) and 3,4-dimethoxybenzaldehyde (6.55 g, 39 mol, 1.0 eq) are dissolved in 120 mL EtOH and sparged with argon for 20 min. The solution is cooled to 0° C. and cooled NaOH (10.40 g, 350 mmol, 9.0 eq) dissolved in 120 mL H$_2$O is slowly added in 10 min. The reaction is stirred under argon at slowly rising temperature to r.t. overnight. The mixture is acidified with conc. HCl and extracted with EE (3×150 mL). The combined organic layers are dried with MgSO$_4$, filtered and the solvent removed under reduced pressure. The crude product is purified by silica filtration (EE). The pure product 97 is obtained as yellow foam. Yield 8.75 g (74%). $^1$H-NMR (500 MHz, DMSO-d$_6$): δ 9.61 (s, 2H), 7.67-7.60 (m, 2H), 7.50 (d, J=2.0 Hz, 1H), 7.34 (dd, J=2.0, 8.4 Hz, 1H), 7.03-6.93 (m, 3H), 6.80 (d, J=2.2 Hz, 1H), 6.51 (t, J=2.2 Hz, 1H), 3.85 (s, 3H), 3.81 (s, 3H). LC-MS m/z: calculated=301.10 [M+H]$^+$, found=301.22 [M+H]$^+$.

1-(3,5-dihydroxyphenyl)-3-(3,4-dimethoxyphenyl) propan-1-one (98)

Zn powder (1.4 g, 21 mmol, 5.0 eq) and NH$_4$Cl (5.5 g, 126 mmol, 30.0 eq) are added to a flask and suspended in 50 mL MeOH. 97 (1.22 g, 4 mmol, 1.0 eq) is dissolved in 30 mL MeOH and added dropwise to the vigorously stirring suspension in 1.5 h. After complete addition, the mixture is filtered and washed with MeOH. The solvent is removed under reduced pressure, then the solid dissolved in 100 mL H$_2$O and extracted with EE (3×100 mL). The combined organic layers are dried with MgSO$_4$, filtered and the solvent removed under reduced pressure. The crude product is purified by column chromatography (CH/EE, 1/1). The pure product 98 is obtained as beige-white solid. Yield 350 mg (28%). $^1$H-NMR (500 MHz, DMSO-d$_6$) δ 9.54 (s, 2H), 6.86 (d, J=2.0 Hz, 1H), 6.83 (d, J=8.2 Hz, 1H), 6.80 (d, J=2.2 Hz, 2H), 6.74 (dd, J=2.0, 8.2 Hz, 1H), 6.44 (t, J=2.2 Hz, 1H), 3.73 (s, 3H), 3.70 (s, 3H), 3.18 (dd, J=7.0, 8.0 Hz, 2H), 2.83 (t, J=7.5 Hz, 2H). LC-MS m/z: calculated=303.12 [M+H]$^+$, found=302.92 [M+H]$^+$.

(R)-5-(3-(3,4-dimethoxyphenyl)-1-hydroxypropyl) benzene-1,3-diol (99)

98 (2.10 g, 6.95 mmol, 1.0 eq) is dissolved in 50 mL THF and added to an autoclave (Roth, model II). The solution is sparged with argon for 10 min, then 100 mL iPrOH is added and the solution further sparged with argon for 5 min. RuCl$_2$[(S)-(DM-SEGPHOS)][(S)-DAIPEN] (84 mg, 0.07 mmol, 0.01 eq) and 1 M KOtBu in tBuOH (7 mL, 7 mmol, 1.0 eq) is added and the autoclave closed, then flushed 3× with H$_2$ and finally 10 bar H$_2$ applied. After reaction overnight, the mixture is transferred to a flask and the solvent is removed under reduced pressure. The crude product is dissolved in 200 mL EE and washed with 100 mL sat. NH$_4$Cl solution. The aqueous phase is extracted with EE (3×100 ml). The combined organic layers are dried with MgSO$_4$, filtered and the solvent removed under reduced pressure. The crude product is purified by column chromatography (CH/EE, 1/2). The pure product 99 is obtained as a white solid. Yield 1.37 g (65%). $^1$H-NMR (500 MHz, DMSO-d$_6$) δ 9.03 (s, 2H), 6.83 (d, J=8.2 Hz, 1H), 6.76 (d, J=2.0 Hz, 1H), 6.68 (dd, J=2.0, 8.1 Hz, 1H), 6.20 (d, J=2.2 Hz, 2H), 6.06 (t, J=2.2 Hz, 1H), 5.03 (d, J=4.3 Hz, 1H), 4.32 (dt, J=4.8, 7.4 Hz, 1H), 3.73 (s, 3H), 3.70 (s, 3H), 2.62-2.51 (m, 2H), 2.47 (s, OH), 1.79 (ddt, J=5.6, 9.0, 11.9 Hz, 2H). LC-MS m/z: calculated=287.11 [M-OH]$^+$, found=287.12 [M-OH]$^+$.

(R)-3-(3-(3,4-dimethoxyphenyl)-1-hydroxypropyl)-5-(trityloxy)phenol (100)

99 (680 mg, 2.23 mmol, 1.0 eq) is dissolved in 50 mL dry MeCN and added to a dried flask under argon atmosphere. Then K$_2$CO$_3$ (308 mg, 2.23 mmol, 1.0 eq) and trityl chloride (466 mg, 1.67 mmol, 0.75 eq) are added. The reaction is stirred at r.t. over night. The mixture is filtered and the solvent removed. The crude product is purified by column chromatography (CH/EE, 2/1 gradient to EE). The pure product 100 is obtained as yellow solid. Yield 431 mg (47%). $^1$H-NMR $^1$H NMR (500 MHz, DMSO-d$_6$) δ 9.01 (s, 1H), 7.41-7.38 (m, 6H), 7.30 (dd, J=7.0, 8.5 Hz, 7H), 7.24-7.19 (m, 3H), 6.83 (d, J=8.1 Hz, 1H), 6.68 (d, J=2.0 Hz, 1H), 6.58 (dd, J=2.0, 8.2 Hz, 1H), 6.22 (t, J=1.7 Hz, 1H), 6.06 (d, J=2.0 Hz, 1H), 5.98 (t, J=2.2 Hz, 1H), 4.97 (d, J=4.4 Hz, 1H), 4.14 (dt, J=4.7, 7.6 Hz, 1H), 3.72 (d, J=5.2 Hz, 6H), 2.32 (dddd, J=6.2, 9.7, 13.9, 23.5 Hz, 2H), 1.64-1.47 (m, 2H). LC-MS m/z: calculated=569.23 [M+Na]$^+$, found=596.11 [M+Na]$^+$.

(R)-allyl 2-(3-(3-(3,4-dimethoxyphenyl)-1-hydroxypropyl)-5-(trityloxy)phenoxy)acetate (101)

100 (1000 mg, 1.83 mmol, 1.0 eq) is dissolved in 50 mL MeCN. K$_2$CO$_3$ (1000 mg, 7.32 mmol, 4.0 eq) and allyl 2-bromoacetate (570 mg, 3.20 mmol, 1.75 eq) is added. The reaction is stirred at r.t. night. After complete conversion, the suspension is filtered, washed with MeCN and the solvent removed under reduced pressure. The crude product is purified by column chromatography (CH/EE, 3/1 then 2/1). The pure product 101 is obtained as yellow solid. Yield 910 mg (77%). $^1$H-NMR (500 MHz, DMSO-d$_6$) δ 7.41-7.37 (m, 6H), 7.30 (dd, J=7.0, 8.5 Hz, 6H), 7.25-7.20 (m, 3H), 6.83 (d, J=8.2 Hz, 1H), 6.68 (d, J=2.0 Hz, 1H), 6.58 (dd, J=2.0, 8.2 Hz, 1H), 6.36 (dd, J=1.2, 2.5 Hz, 1H), 6.24 (t, J=1.7 Hz, 1H), 6.07 (t, J=2.3 Hz, 1H), 5.86 (ddt, J=5.4, 10.7, 17.3 Hz, 1H), 5.30-5.17 (m, 2H), 5.06 (d, J=4.5 Hz, 1H), 4.57-4.53 (m, 4H), 4.21 (dt, J=4.9, 7.6 Hz, 1H), 3.73 (s, 3H), 3.71 (s, 3H), 2.32 (dddd, J=6.1, 9.7, 13.9, 23.6 Hz, 2H), 1.64-1.48 (m, 1H). LC-MS m/z: calculated=667.27 [M+Na]$^+$, found=667.16 [M+Na]$^+$.

(S)-1-((9H-fluoren-9-yl)methyl) 2-((R)-1-(3-(2-(allyloxy)-2-oxoethoxy)-5-hydroxyphenyl)-3-(3,4-dimethoxyphenyl)propyl) piperidine-1,2-dicarboxylate (102)

101 (910 mg, 1.41 mmol, 1.0 eq) and Fmoc-S-pipecolate (546 mg, 1.55 mmol, 1.1 eq) are dissolved in 50 mL dry DCM and cooled to 0° C. for 15 min. DMAP (57 mg, 0.47 mmol, 0.3 eq) is added and stirred until dissolved, then DCC (320 mg, 1.55 mmol, 1.1 eq) is added. The mixture is stirred for 15 min under cooling. Finally, the ice bath is removed and the reaction stirred overnight at r.t. The reaction mixture is filtered, washed with DCM and the solvent removed under reduced pressure. The crude product is dissolved in 30 mL DCM+1% TFA and stirred for 5 min. The solvent is removed under reduced pressure and the crude product purified by silica column chromatography (CH/EE, 2/1) and the pure product 102 is obtained as colorless oil. Yield 1.05 g (92%). $^1$H-NMR (500 MHz, Chloroform-d): δ 7.79-7.72 (m, 1H), 7.71 (d, J=7.6 Hz, 1H), 7.57 (dd, J=7.6, 11.5 Hz, 1H), 7.46 (dd, J=7.5, 26.6 Hz, 1H), 7.34 (ddt, J=7.6, 16.1, 33.4 Hz, 3H), 7.20 (t, J=7.5 Hz, 1H), 6.77-6.70 (m, 1H), 6.68-6.53 (m, 2H), 6.45-6.41 (m, 2H), 6.30 (d, J=17.0 Hz, 1H), 5.94-5.82 (m, 1H), 5.74-5.62 (m, 1H), 5.33-5.27 (m, 1H), 5.23 (d, J=10.5 Hz, 1H), 5.04-4.86 (m, 1H), 4.68-4.63 (m, 2H), 4.57 (s, 1H), 4.50 (s, 1H), 4.48-4.41 (m, 1H), 4.38-4.22 (m, 2H), 4.06 (d, J=16.4 Hz, 1H), 3.87-3.74 (m, 6H), 3.22-3.13 (m, 1H), 2.90 (t, J=13.1 Hz, OH), 2.62-2.38 (m, 2H), 2.34-2.25 (m, 1H), 2.21-1.90 (m, 1H), 1.72 (t, J=14.4 Hz, 4H), 1.52-1.39 (m, 1H), 1.31 (s, 1H). LC-MS m/z: calculated=753.33 [M+NH$_4$]$^+$, found=753.73 [M+NH$_4$]$^+$.

(2R,5S,12R)-12-cyclohexyl-2-[2-(3,4-dimethoxyphenyl)ethyl]-22-hydroxy-15,15-dimethyl-3,19-dioxa-10,13,16-triazatricyclo[18.3.1.0$^{5,10}$]tetracosa-1(24),20,22-triene-4,11,14,17-tetrone (103)

Procedure as described in Example 7. Starting materials: Resin: (0.66 mmol), 1$^{st}$ AA: Fmoc-D-Chg-OH, 2$^{nd}$ AA: Fmoc-Aib-OH. Yield 90 mg (20%). $^1$H-NMR (500 MHz, CDCl$_3$): δ 7.78 (d, J=8.8 Hz, 1H), 6.78 (d, J=8.0 Hz, 1H), 6.68 (d, J=2.0 Hz, 1H), 6.67-6.62 (m, 1H), 6.61-6.52 (m, 2H), 6.35-6.32 (m, 2H), 5.57-5.51 (m, 1H), 5.25-5.21 (m, 1H), 4.70 (s, 1H), 4.64 (d, J=16.4 Hz, 1H), 4.53 (d, J=16.3 Hz, 1H), 3.86 (s, 3H), 3.85 (s, 3H), 3.85-3.81 (m, 1H), 3.31 (t, J=13.1 Hz, 1H), 2.57-2.48 (m, 2H), 2.29-2.19 (m, 1H), 2.17-2.10 (m, 1H), 2.08-1.99 (m, 1H), 1.77 (s, 3H), 1.77-1.61 (m, 8H), 1.53-1.44 (m, 1H), 1.43 (s, 3H), 1.31-1.16 (m, 3H), 1.18-1.09 (m, 1H), 1.08-0.93 (m, 2H). LC-MS m/z: calculated=680.35 [M+H]$^+$, found=680.49 [M+H]$^+$. HRMS (ESI): calculated=680.35416 [M+H]$^+$, found=680.35433 [M+H]$^+$, err [ppm]=0.25.

(2R,5S,12R)-12-cyclohexyl-2-[2-(3,4-dimethoxyphenyl)ethyl]-22-methoxy-15,15-dimethyl-3,19-dioxa-10,13,16-triazatricyclo[18.3.1.0$^{5,10}$]tetracosa-1(24),20,22-triene-4,11,14,17-tetrone (104)

103 (5 mg, 0.01 mmol, 1.0 eq) is dissolved in 1 mL dry MeCN and K$_2$CO$_3$ (10 mg, 0.1 mmol, 10.0 eq) is added. Then MeI (5 μL, 0.1 mmol, 10.0 eq) is added and the mixture stirred at r.t. over night. The mixture is diluted with DCM and extracted 1× with 1 M NaOH$_{aq}$. The organic solvent is removed and the crude product purified by semi preparative HPLC. Yield 1 mg (19%). LC-MS m/z: calculated=694.36 [M+H]$^+$, found=694.47 [M+H]$^+$. HRMS (ESI): calculated=694.36981 [M+H]$^+$, found=694.36967 [M+H]$^+$, err [ppm]=0.20.

[1] Gopalakrishnan, R., et al., Exploration of pipecolate sulfonamides as binders of the FK506-binding proteins 51 and 52. *J Med Chem*, 2012. 55(9): p. 4123-31.

[2] Banaszynski, L. A., C. W. Liu, and T. J. Wandless, Characterization of the FKBP.rapamycin.FRB ternary complex. *J Am Chem Soc*, 2005. 127(13): p. 4715-21.

[3] Blackburn, E. A. and M. D. Walkinshaw, Targeting FKBP isoforms with small-molecule ligands. *Curr Opin Pharmacol*, 2011. 11(4): p. 365-71.

[4] Feng, X., et al., Structure-Affinity Relationship Analysis of Selective FKBP51 Ligands. *J Med Chem*, 2015. 58(19): p. 7796-806.

What is claimed is:

1. A compound with the structure of formula I:

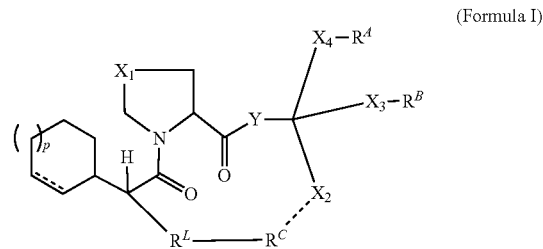

(Formula I)

wherein

X1 represents —CH$_2$—, —CH$_2$CH$_2$—, —CH=CH—, —CH$_2$—S—, or —S—CH$_2$—;

Y represents —NH—, or —O—;

p is an integer of 0 or 1;

⇌ represents a C=C bond or a C—C bond;

⋯ represents a bond between R$^C$ and X$_2$;

R$^L$ represents:

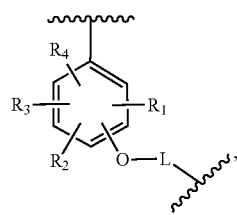

or —NR$^{Me}$—C(=O)-L-, —NR$^{Me}$-L-, or L;

R$^C$ represents: -Q-L, or

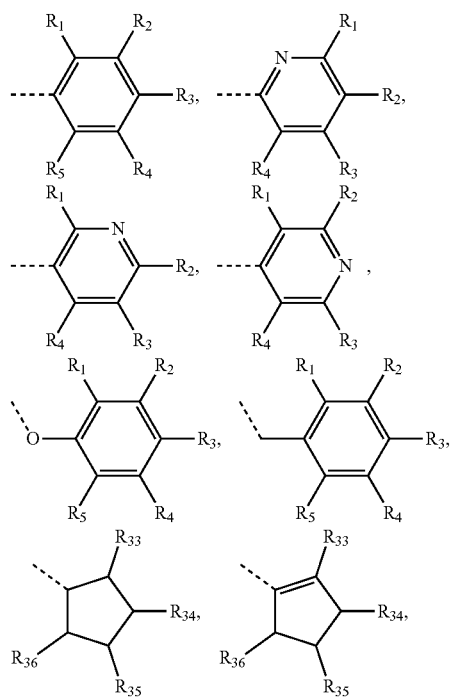

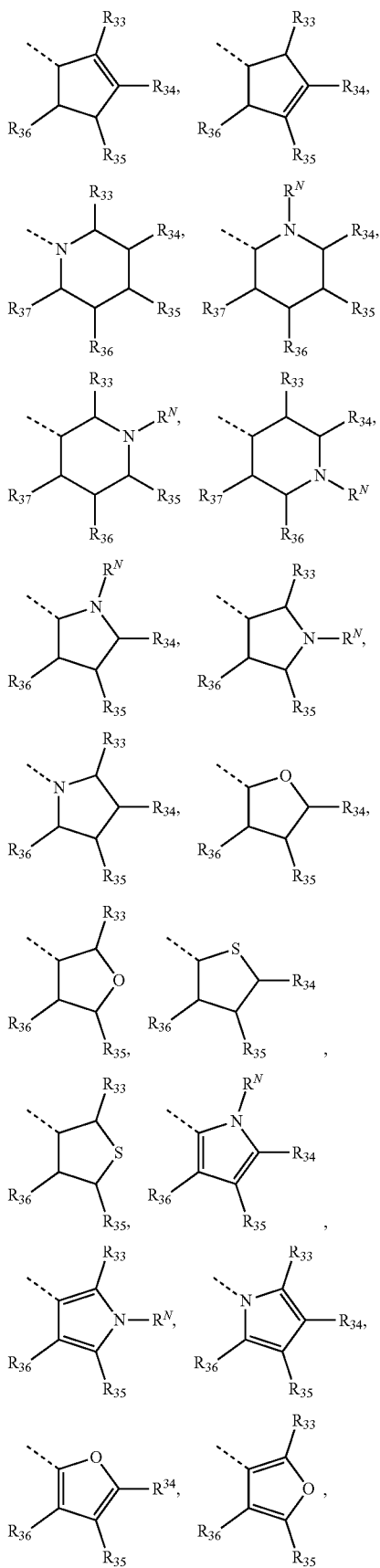
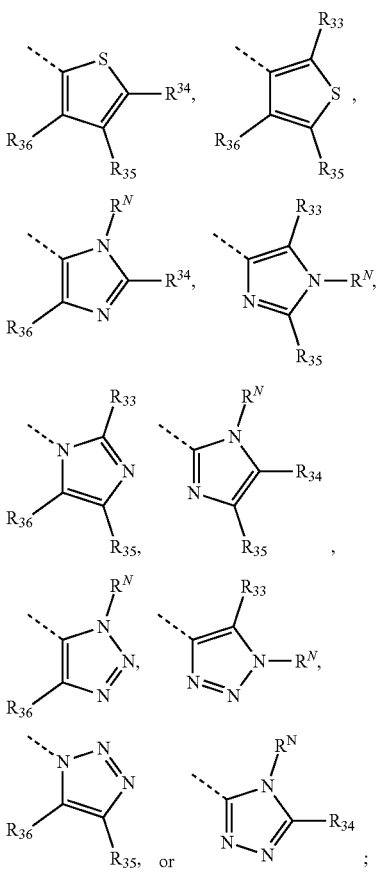
wherein in each of the substructures $R^C$ one of the substituents $R^1$, $R^2$, $R^3$, $R^4$, $R^5$, $R^{33}$, $R^{34}$, $R^{35}$, $R^{36}$, $R^{37}$ or $R^N$ is replaced by L, —O-L, —C(=O)NR$^{Me}$-L, or —NR$^{Me}$-L;
L represents: X5 or
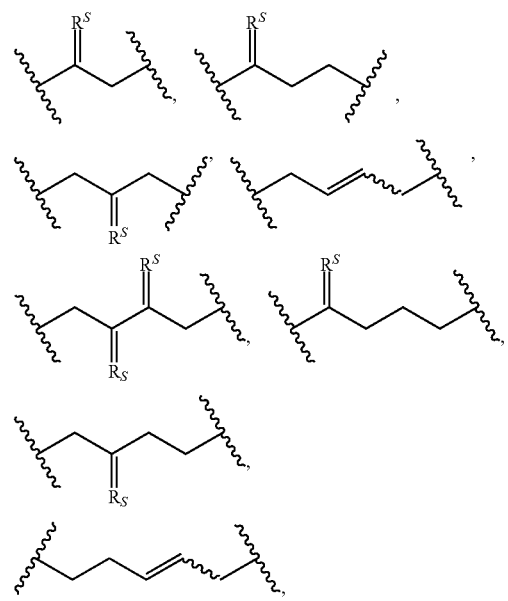

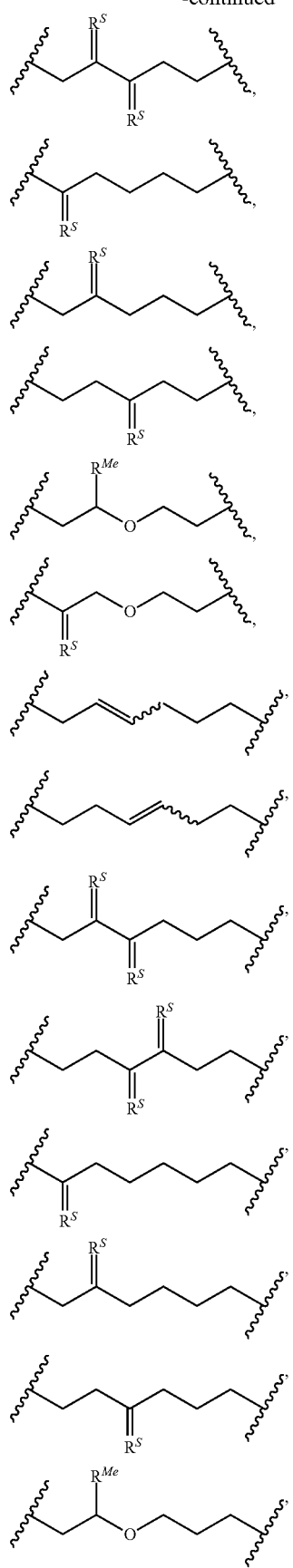
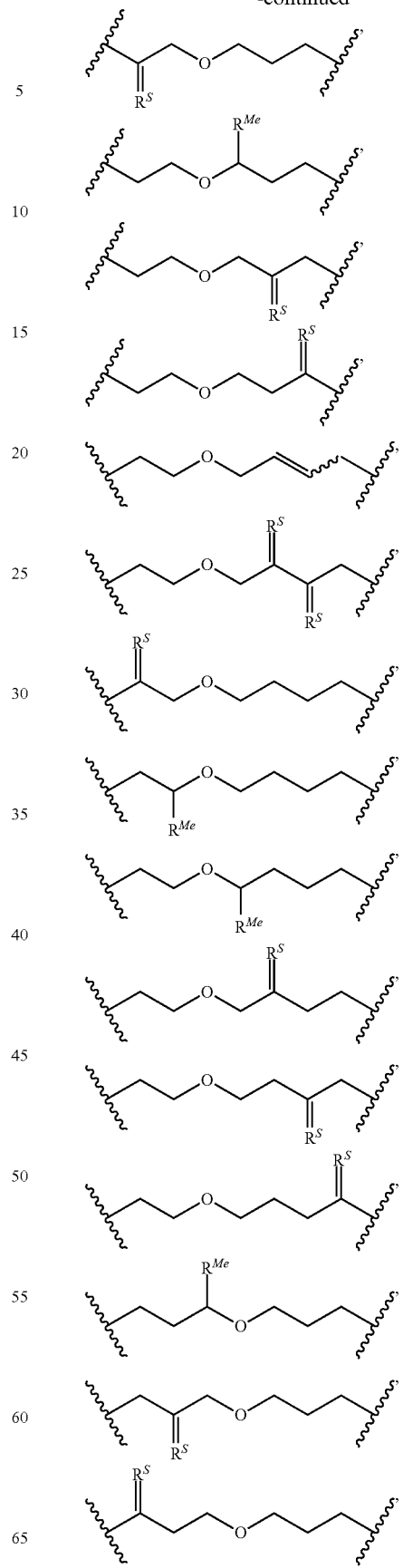

107
-continued
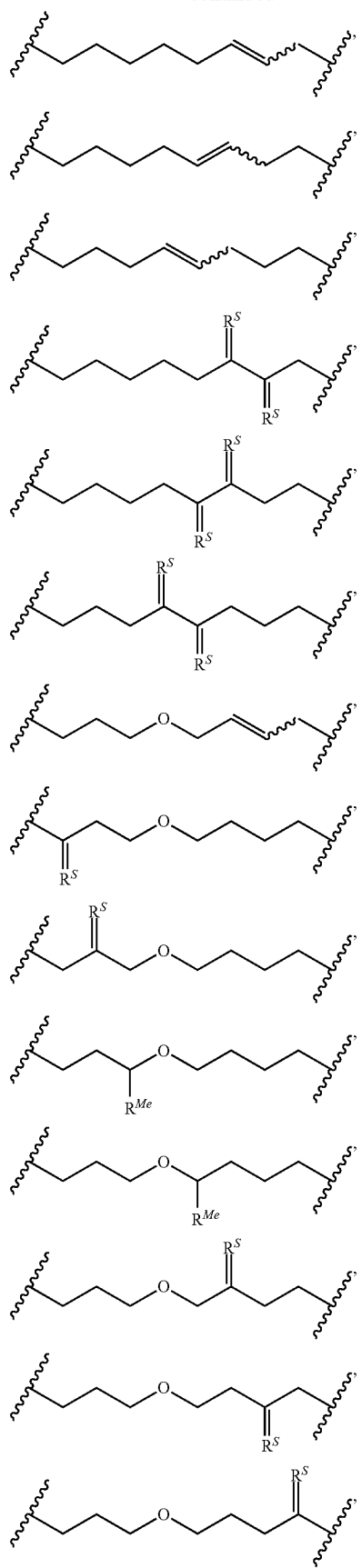
108
-continued
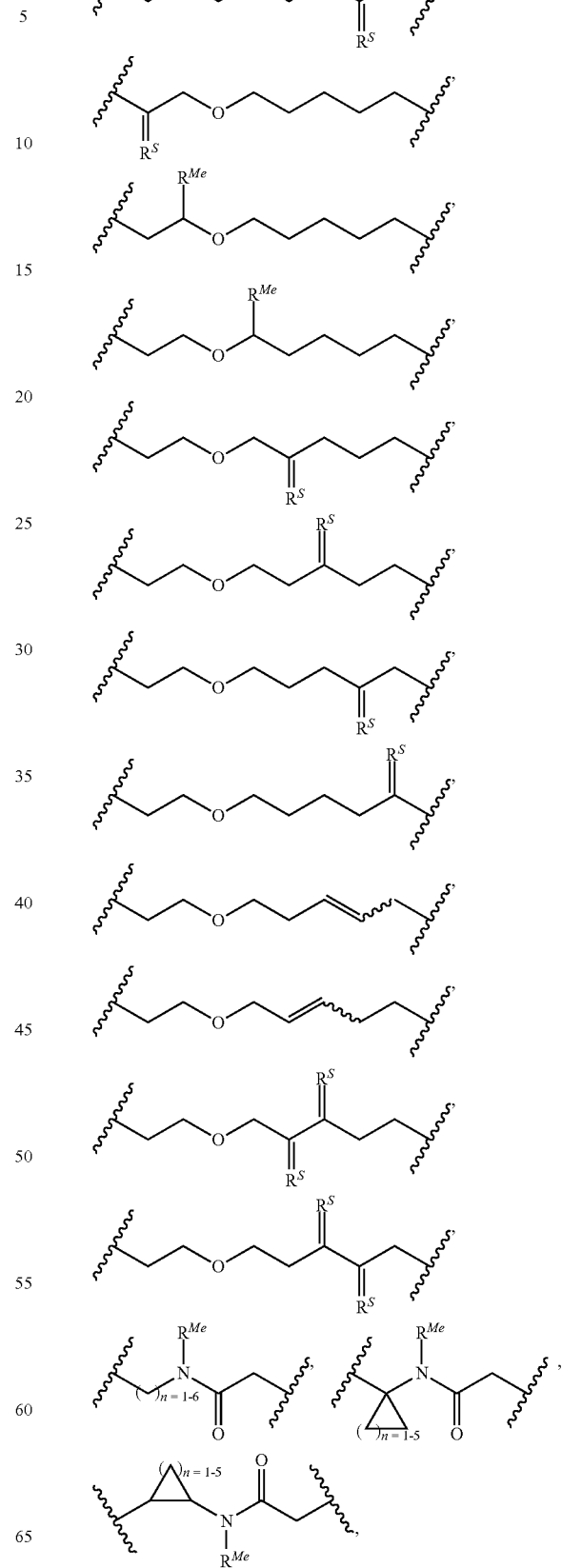

-continued
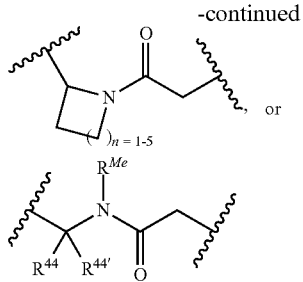
wherein L is connected to $R^C$ and $R^L$ as follows: $R^C$-L-$R^L$ or $R^L$-L-$R^C$;
$R^{Me}$ represents H or Me;
═══ $R^S$ represent independently of each other —H, -Me, —OH or ═O;
$R^A$ represents $R^{28}$, or:
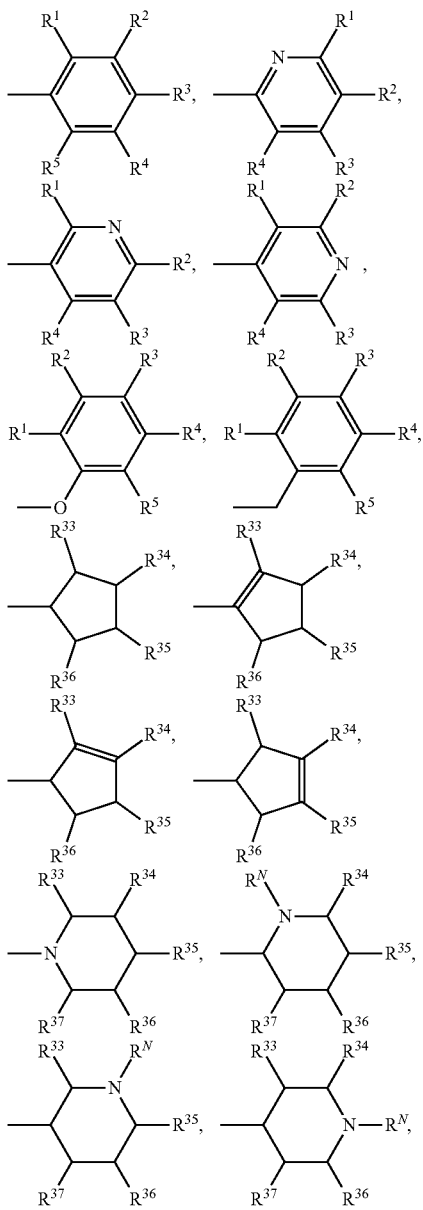
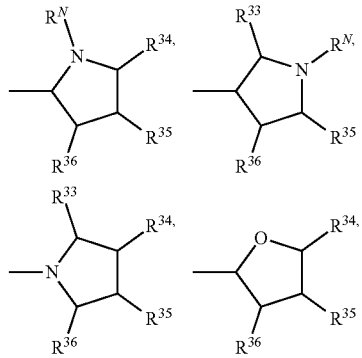
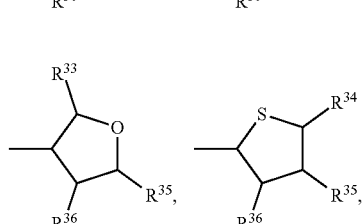
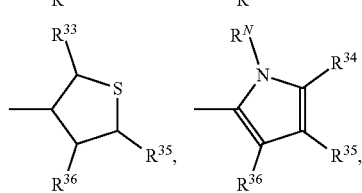
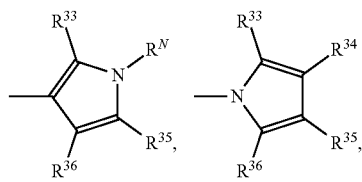
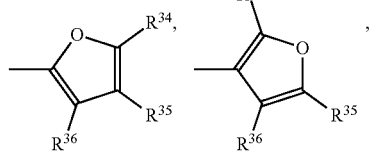
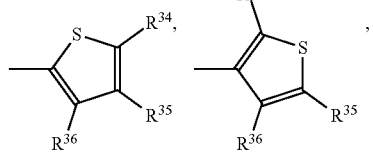
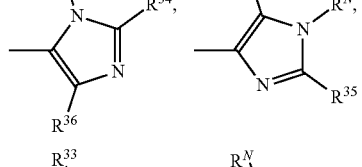
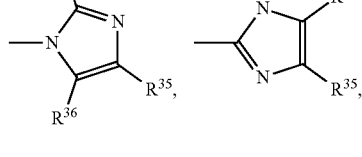

111
-continued
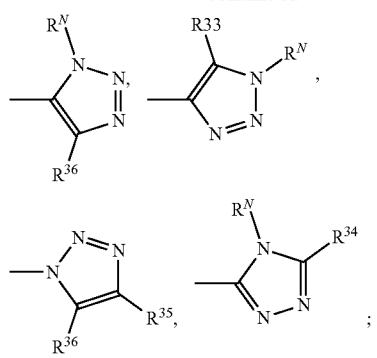
$R^B$ represents $R^{27}$, or:
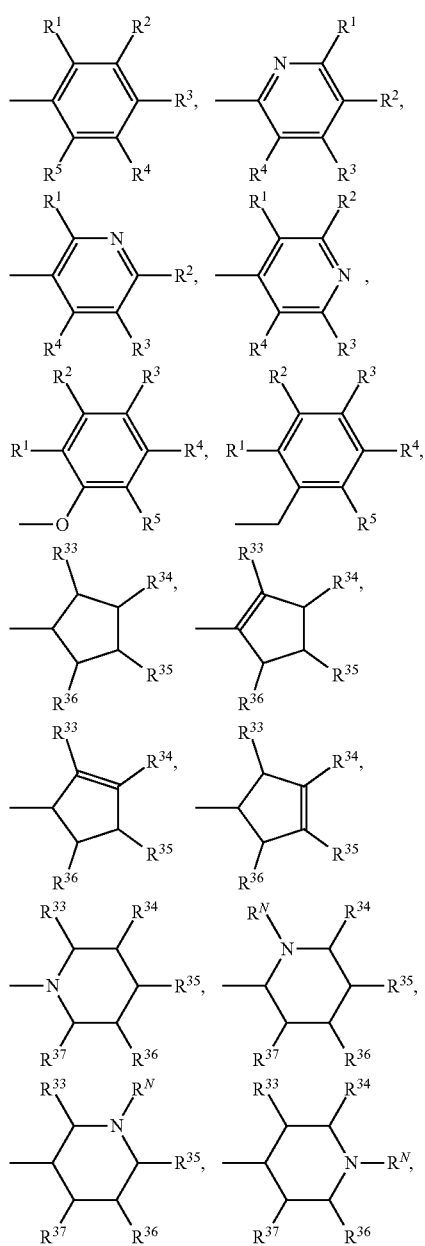
112
-continued
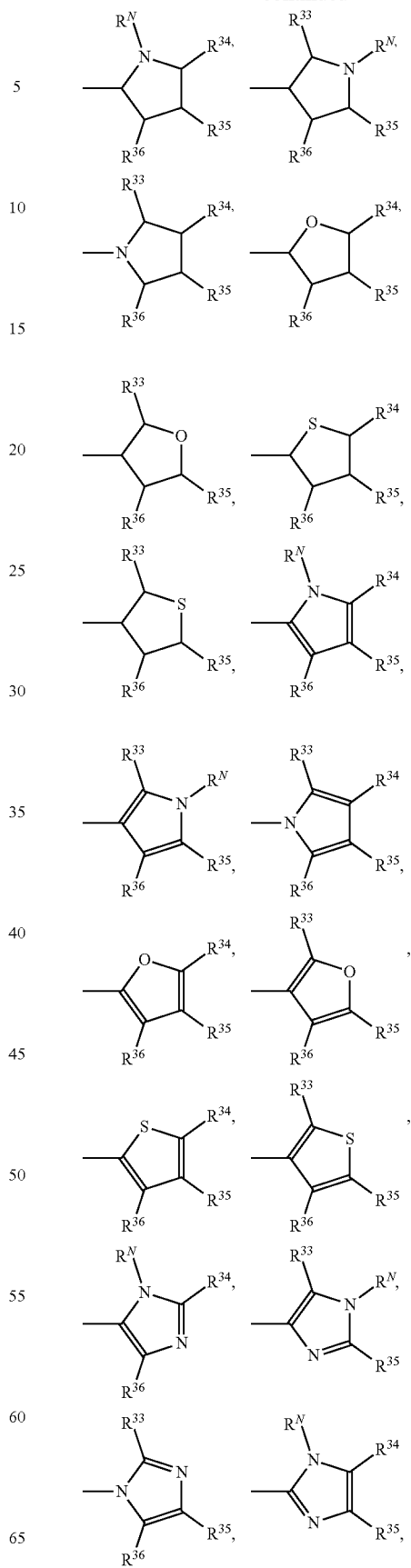

-continued

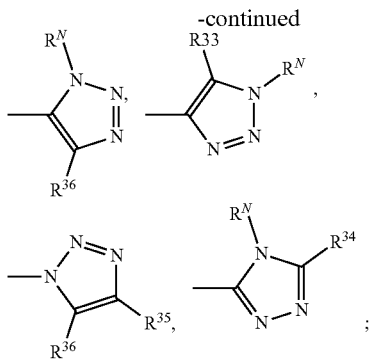

$R^1$-$R^{22}$, $R^{18'}$-$R^{22'}$, $R^{26}$-$R^{43}$, represent independently of each other —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OCH$_2$—COOH, —OPh, —OCH$_2$-Ph, —OCPh$_3$, —CH$_2$—OH, —C$_2$H$_4$—OH, —C$_3$H$_5$—OH, —CH(OH)—CH$_2$—OH, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_5$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —P(O)(OH)$_2$, —P(O)(OCH$_3$)$_2$, —P(O)(OC$_2$H$_5$)$_2$, —P(O)(OCH(CH$_3$)$_2$)$_2$, —C(OH)[P(O)(OH)$_2$]$_2$, —Si(CH$_3$)$_2$(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CH$_2$—CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —SO$_2$NH$_2$, —SO$_2$NHCH$_3$, —SO$_2$NHC$_2$H$_5$, —SO$_2$NHC$_3$H$_7$, —SO$_2$NH-cyclo-C$_3$H$_5$, —SO$_2$NHCH(CH$_3$)$_2$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N(cyclo-C$_3$H$_5$)$_2$, —SO$_2$N[CH(CH$_3$)$_2$]$_2$, —SO$_2$N[C(CH$_3$)$_3$]$_2$, —O—S(=O)CH$_3$, —O—S(=O)C$_2$H$_5$, —O—S(=O)C$_3$H$_7$, —O—S(=O)-cyclo-C$_3$H$_5$, —O—S(=O)CH(CH$_3$)$_2$, —O—S(=O)C(CH$_3$)$_3$, —S(=O)(=NH)CH$_3$, —S(=O)(=NH)C$_2$H$_5$, —S(=O)(=NH)C$_3$H$_7$, —S(=O)(=NH)-cyclo-C$_3$H$_5$, —S(=O)(=NH)CH(CH$_3$)$_2$, —S(=O)(=NH)C(CH$_3$)$_3$, —NH—SO$_2$—CH$_3$, —NH—SO$_2$—C$_2$H$_5$, —NH—SO$_2$—C$_3$H$_7$, —NH—SO$_2$-cyclo-C$_3$H$_5$, —NH—SO$_2$—CH(CH$_3$)$_2$, —NH—SO$_2$—C(CH$_3$)$_3$, —O—SO$_2$—CH$_3$, —O—SO$_2$—C$_2$H$_5$, —O—SO$_2$—C$_3$H$_7$, —O—SO$_2$-cyclo-C$_3$H$_5$, —O—SO$_2$—CH(CH$_3$)$_2$, —O—SO$_2$—C(CH$_3$)$_3$, —OCF$_3$, —CH$_2$—OCF$_3$, —C$_2$H$_4$—OCF$_3$, —C$_3$H$_6$—OCF$_3$, —OC$_2$F$_5$, —CH$_2$—OC$_2$F$_5$, —C$_2$H$_4$—OC$_2$F$_5$, —C$_3$H$_6$—OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CS—N(C$_3$H$_7$)$_2$, —NH—CO—NHC$_3$H$_7$, —NH—CO—N(C$_3$H$_7$)$_2$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—NH-cyclo-C$_3$H$_5$, —NH—CO—N(cyclo-C$_3$H$_5$)$_2$, —NH—CO—N[CH(CH$_3$)$_2$]$_2$, —NH—CS—N(C$_2$H$_5$)$_2$, —NH—CO—N[C(CH$_3$)$_3$]$_2$, —NH—CS—NH$_2$, —NH—CS—NHCH$_3$, —NH—CS—N(CH$_3$)$_2$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —O—CO—NH-cyclo-C$_3$H$_5$, —NH—C(=NH)—NH-cyclo-C$_3$H$_5$, —NH—C(=NH)—NH[CH(CH$_3$)$_2$], —O—CO—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —O—CO—NHC$_3$H$_7$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_5$H$_9$, -cyclo-C$_6$H$_{11}$, —CH$_2$-cyclo-C$_6$H$_{11}$, —CH$_2$—CH$_2$-cyclo-C$_6$H$_{11}$, -cyclo-C$_7$H$_{13}$, -cyclo-C$_8$H$_{15}$, -Ph, —CH$_2$-Ph, —CH$_2$—CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH═CH$_2$, —CH$_2$—CH═CH$_2$, —C(CH$_3$)═CH$_2$, —CH═CH—CH$_3$, —C$_2$H$_4$—CH═CH$_2$, —CH$_2$—CH═CH—CH$_3$, —CH═CH—C$_2$H$_5$, —CH$_2$—C(CH$_3$)═CH$_2$, —CH(CH$_3$)—CH═CH, —CH═C(CH$_3$)$_2$, —C(CH$_3$)═CH—CH$_3$, —CH═CH—CH═CH$_2$, —C$_3$H$_6$—CH═CH$_2$, —C$_2$H$_4$—CH═CH—CH$_3$, —CH$_2$—CH═CH—C$_2$H$_5$, —CH═CH—C$_3$H$_7$, —CH$_2$—CH═CH—CH═CH$_2$, —CH═CH—CH═CH—CH$_3$, —CH═CH—CH$_2$—CH═CH$_2$, —C(CH$_3$)═CH—CH═CH$_2$, —CH═C(CH$_3$)—CH═CH$_2$, —CH═CH—C(CH$_3$)═CH$_2$, —C$_2$H$_4$—C(CH$_3$)═CH$_2$, —CH$_2$—CH(CH$_3$)—CH═CH$_2$, —CH(CH$_3$)—CH$_2$—CH═CH$_2$, —CH$_2$—CH═C(CH$_3$)$_2$, —CH$_2$—C(CH$_3$)═CH—CH$_3$, —CH(CH$_3$)—CH═CH—CH$_3$, —CH═CH—CH(CH$_3$)$_2$, —CH═C(CH$_3$)—C$_2$H$_5$, —C(CH$_3$)═CH—C$_2$H$_5$, —C(CH$_3$)═C(CH$_3$)$_2$, —C(CH$_3$)$_2$—CH═CH$_2$, —C(CH$_3$)$_2$—CH═CH—CH$_3$, —C(CH$_3$)═CH—CH$_2$—CH$_3$, —CH═CH—C(CH$_3$)═CH$_2$, —C$_4$H$_8$—CH═CH$_2$, —C$_3$H$_6$—CH═CH—CH$_3$, —C$_2$H$_4$—CH═CH—C$_2$H$_5$, —CH$_2$—CH═CH—C$_3$H$_7$, —CH═CH—C$_4$H$_9$,

—C$_3$H$_6$—C(CH$_3$)═CH$_2$, —C$_2$H$_4$—CH(CH$_3$)—CH═CH$_2$,

—CH$_2$—CH(CH$_3$)—CH$_2$—CH═CH$_2$, —C$_2$H$_4$—CH═C(CH$_3$)$_2$,

—CH(CH$_3$)—C$_2$H$_4$—CH═CH$_2$, —C$_2$H$_4$—C(CH$_3$)═CH—CH$_3$, —CH$_2$—CH(CH$_3$)—CH═CH—CH$_3$, —CH(CH$_3$)—CH$_2$—CH═CH—CH$_3$, —CH$_2$—CH═CH—CH(CH$_3$)$_2$, —CH$_2$—CH═C(CH$_3$)—C$_2$H$_5$,

—CH$_2$—C(CH$_3$)═CH—C$_2$H$_5$, —CH(CH$_3$)—CH═CH—C$_2$H$_5$,

—CH═CH—CH$_2$—CH(CH$_3$)$_2$, —CH═CH—CH(CH$_3$)—C$_2$H$_5$, —CH═C(CH$_3$)—C$_3$H$_7$, —C(CH$_3$)═CH—C$_3$H$_7$, —CH$_2$—CH(CH$_3$)—C(CH$_3$)═CH$_2$, —C[C(CH$_3$)$_3$]═CH$_2$, —CH(CH$_3$)—CH$_2$—C(CH$_3$)═CH$_2$, —CH(CH$_3$)—CH(CH$_3$)—CH═CH$_2$, —CH═CH—C$_2$H$_4$—CH═CH$_2$, —CH$_2$—C(CH$_3$)$_2$—CH═CH$_2$, —C(CH$_3$)$_2$—CH$_2$—CH═CH$_2$, —CH$_2$—C(CH$_3$)═C(CH$_3$)$_2$, —CH(CH$_3$)—CH═C(CH$_3$)$_2$, —C(CH$_3$)$_2$—CH═CH—CH$_3$, —CH═CH—CH$_2$—CH═CH—CH$_3$, —CH(CH$_3$)—C(CH$_3$)═CH—CH$_3$, —CH═C(CH$_3$)—CH(CH$_3$)$_2$,

—C(CH$_3$)═CH—CH(CH$_3$)$_2$, —C(CH$_3$)═C(CH$_3$)—C$_2$H$_5$,

—CH═CH—C(CH$_3$)$_3$, —C(CH$_3$)$_2$—C(CH$_3$)═CH$_2$, —CH(C$_2$H$_5$)—C(CH$_3$)═CH$_2$, —C(CH$_3$)(C$_2$H$_5$)—CH═CH$_2$, —CH(CH$_3$)—C(C$_2$H$_5$)═CH$_2$, —CH$_2$—C(C$_3$H$_7$)═CH$_2$, —CH$_2$—C(C$_2$H$_5$)═CH—CH$_3$, —CH(C$_2$H$_5$)—CH═CH—CH$_3$, —C(C$_4$H$_9$)═CH$_2$, —C(C$_3$H$_7$)═CH—CH$_3$, —C(C$_2$H$_5$)═CH—C$_2$H$_5$, —C(C$_2$H$_5$)═C(CH$_3$)$_2$, —C[CH(CH$_3$)(C$_2$H$_5$)]═CH$_2$, —C[CH$_2$—CH(CH$_3$)$_2$]═CH$_2$, —C$_2$H$_4$—CH═CH—CH═CH$_2$, —CH$_2$—CH═CH—CH$_2$—CH═CH$_2$, —C$_3$H$_6$—C≡C—CH$_3$, —CH$_2$—CH═CH—CH═CH—CH$_3$, —CH═CH—CH(CH$_3$)—CH═CH$_2$, —CH$_2$—CH═C(CH$_3$)—CH═CH$_2$, —CH$_2$—CH═CH—C(CH$_3$)═CH$_2$, —CH(CH$_3$)—CH═CH—CH═CH$_2$, —CH(CH$_3$)—CH$_2$—C≡CH, —CH═CH—CH═CH—CH$_2$, —CH═CH—CH$_2$—C(CH$_3$)═CH$_2$, —CH(CH$_3$)—C≡C—CH$_3$, —CH═CH—CH(CH$_3$)—CH═CH$_2$, —CH═C(CH$_3$)—CH$_2$—CH═CH$_2$, —C$_2$H$_4$—CH(CH$_3$)—C≡CH, —C(CH$_3$)═CH—CH$_2$—CH═CH$_2$, —CH═CH—CH═C(CH$_3$)$_2$, —CH$_2$—CH(CH$_3$)—CH$_2$—C≡CH, —CH═CH—C(CH$_3$)═CH—CH$_3$, —CH═C(CH$_3$)—CH═CH—CH$_3$, —CH$_2$—CH(CH$_3$)—C≡CH, —C(CH$_3$)═CH—CH═CH—CH$_3$, —CH═C(CH$_3$)—C(CH$_3$)═CH$_2$, —C(CH$_3$)═CH—C(CH$_3$)═CH$_2$, —C(CH$_3$)═C(CH$_3$)—CH═CH$_2$, —CH═CH—CH═CH—CH═CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_8$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —CH$_2$—CH(C≡CH)$_2$, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C(C≡CH)$_2$—CH$_3$, —C≡C—CH(CH$_3$)—C≡CH, —CH(CH$_3$)—C≡C—C≡CH, —CH(C≡CH)—CH$_2$—C≡CH, —CH(C≡CH)—C≡C—CH$_3$,

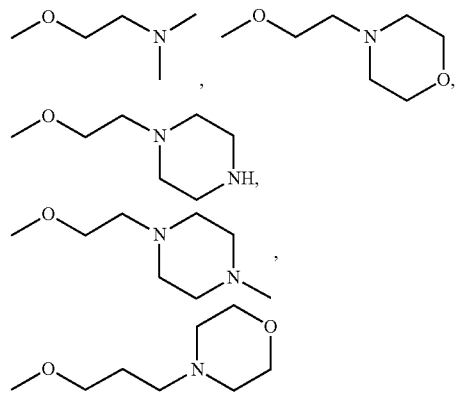

or

R$^{18}$ and R$^{18'}$ or R$^{19}$ and R$^{19'}$ or R$^{20}$ and R$^{20'}$ or R$^{21}$ and R$^{21'}$ or R$^{22}$ and R$^{22'}$ can form together

═O,

or ═CR$^{23'}$R$^{24'}$, wherein R$^{23'}$ and R$^{24'}$ represent independently of each other —H, —CH$_3$, —C$_2$H$_5$, —CF$_3$, —CH$_2$CF$_3$, —C$_2$F$_5$;

$R^{23}$-$R^{25}$ or $R^{45}$ represent independently of each other —H, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_5$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_5$—OPh, —CH$_2$—OCH$_2$-Ph, —C$_2$H$_4$—OCH$_2$-Ph, —C$_3$H$_6$—OCH$_2$-Ph, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_8$H$_{15}$, -Ph, —CH$_2$-Ph, —CH$_2$—CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)—CH=CH—CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —C$_2$H$_4$—CH=C(CH$_3$)$_2$, —CH(CH$_3$)—C$_2$H$_4$—CH=CH$_2$, —C$_2$H$_4$—C(CH$_3$)=CH—CH$_3$, —CH$_2$—CH(CH$_3$)—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH=CH—C$_2$H$_4$—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH=CH—CH$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —C$_3$H$_6$—C≡C—CH$_3$, —CH$_2$—CH=CH—CH=CH—CH$_3$, —CH=CH—CH=CH—C$_2$H$_5$, —CH$_2$—CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH$_2$—C≡CH, —CH(CH$_3$)—CH=CH—CH=CH$_2$, —CH=CH—CH$_2$—C(CH$_3$)=CH$_2$, —CH(CH$_3$)—C≡C—CH$_3$, —CH=CH—CH(CH$_3$)—CH=CH$_2$, —CH=C(CH$_3$)—CH$_2$—CH=CH$_2$, —C$_2$H$_4$—CH(CH$_3$)—C≡CH, —C(CH$_3$)=CH—CH$_2$—CH=CH$_2$, —CH=CH—CH=C(CH$_3$)$_2$, —CH$_2$—CH(CH$_3$)—CH$_2$—C≡CH, —CH=CH—C(CH$_3$)=CH—CH$_3$, —CH=C(CH$_3$)—CH=CH—CH$_3$, —CH$_2$—CH(CH$_3$)—C≡CH, —CH(CH$_3$)—C≡CH, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_9$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C—C≡CH, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —CH$_2$—CH(C≡CH)$_2$, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—C≡C—C$_2$H$_5$, —C(C≡CH)$_2$—CH$_3$, —C≡C—CH(CH$_3$)—C≡CH, —CH(CH$_3$)—C≡C—C≡CH, —CH(C≡CH)—CH$_2$—C≡CH, —CH(C≡CH)—C≡C—CH$_3$;

$R^{44}$ and $R^{44'}$ represent independently of each other $R^{45}$, —H, —CH$_3$, —CH(CH$_3$)—CH$_2$—CH$_3$, —CH$_2$—CH(CH$_3$)$_2$, —CH$_2$—CH$_2$—S—CH$_3$, —CH(CH$_3$)$_2$, —CH$_2$-Ph, —CH$_2$-Ph-ortho-OH, —CH$_2$-Ph-meta-OH, —CH$_2$-Ph-para-OH, —CH$_2$—CONH$_2$, —CH$_2$SH, —CH$_2$—CH$_2$—CONH$_2$, —CH$_2$—OH, —CH₂—CH(CH₃)(OH), —CH₂—CH₂—CH₂—NH—C(=NH)(—NH₂), —CH₂—CH₂—CH₂—CH₂—NH₂, —CH₂—CH₂—COOH,

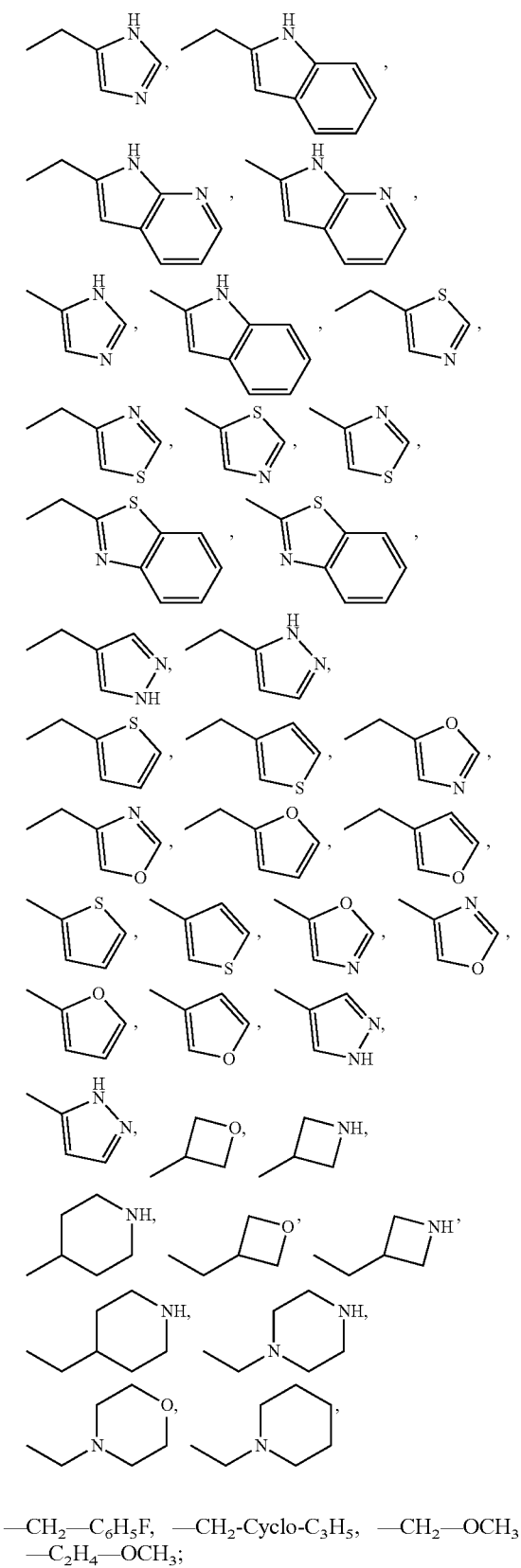

—CH₂—C₆H₅F, —CH₂-Cyclo-C₃H₅, —CH₂—OCH₃, —C₂H₄—OCH₃;

R⁴⁴ and R⁴⁴' can form together a cyclic ring selected from the group consisting of:

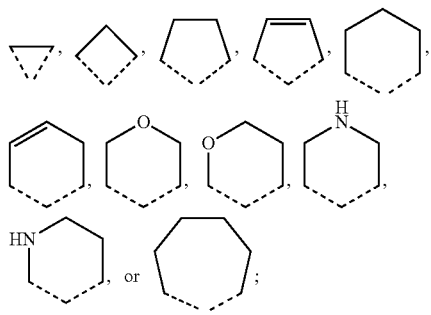

$R^N$ represents —H, —CH₂—OCH₃, —C₂H₄—OCH₃, —C₃H₆—OCH₃, —CH₂—OC₂H₅, —C₂H₄—OC₂H₅, —C₃H₇—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₅—O-cyclo-C₃H₅, —CH₂—OCH(CH₃)₂, —C₂H₄—OCH(CH₃)₂, —C₃H₆—OCH(CH₃)₂, —CH₂—OC(CH₃)₃,
—C₂H₄—OC(CH₃)₃, —C₃H₅—OC(CH₃)₃, —CH₂—OC₄H₉, —C₂H₄—OC₄H₉, —C₃H₆—OC₄H₉, —CH₂—OPh, —C₂H₄—OPh, —C₃H₅—OPh, —CH₂—OCH₂-Ph, —C₂H₄—OCH₂-Ph, —C₃H₅—OCH₂-Ph, —CHO, —COCH₃, —COC₂H₅, —COC₃H₇, —CO-cyclo-C₃H₅, —COCH(CH₃)₂, —COC(CH₃)₃, —COCN, —COOCH₃, —COOC₂H₅, —COOC₃H₇, —COO-cyclo-C₃H₅, —COOCH(CH₃)₂, —COOC(CH₃)₃, —CONH₂, —CONHCH₃, —CONHC₂H₅,
—CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —SO₂CH₃, —SO₂C₂H₅,
—SO₂C₃H₇, —SO₂-cyclo-C₃H₅, —SO₂CH(CH₃)₂, —SO₂C(CH₃)₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂—CH₂-Ph, —CH=CH-Ph, —CPh₃, —CH₃,
—C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂,
—C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅,
—C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂,
—CH₂—CH=CH—CH₃, —CH=CH—C₂H₅, —CH₂—C(CH₃)=CH₂, —CH(CH₃)—CH=CH, —CH=C $-(CH_3)_2$, $-C(CH_3)=CH-CH_3$, $-CH=CH-CH=CH_2$, $-C_3H_6-CH=CH_2$, $-C_2H_4-CH=CH-CH_3$, $-CH_2-CH=CH-C_2H_5$, $-CH=CH-C_3H_7$, $-CH_2-CH_2-CH=CH-CH_2-$, $-CH=CH-CH=CH-CH_3$, $-CH=CH-CH_2-CH=CH_2$, $-C(CH_3)=CH-CH=CH_2$, $-CH=C(CH_3)-CH=CH_2$, $-CH=CH-C(CH_3)=CH_2$, $-C_2H_4-C(CH_3)=CH_2$, $-CH_2-CH(CH_3)-CH=CH_2$, $-CH(CH_3)-CH_2-CH=CH_2$, $-CH_2-CH=C(CH_3)_2$, $-CH_2-C(CH_3)=CH-CH_3$, $-CH(CH_3)-CH=CH-CH_3$, $-CH=CH-CH(CH_3)_2$, $-CH=C(CH_3)-C_2H_5$, $-C(CH_3)=CH-C_2H_5$, $-C(CH_3)=C(CH_3)_2$, $-C(CH_3)_2-CH=CH_2$, $-CH(CH_3)-C(CH_3)=CH_2$, $-C(CH_3)_2-CH=CH-CH_2$, $-CH=C(CH_3)-CH=CH_2$, $-CH=CH-C(CH_3)=CH_2$, $-C_4H_8-CH=CH_2$, $-C_3H_6-CH=CH-CH_3$, $-C_2H_4-CH=CH-C_2H_5$, $-CH_2-CH=CH-C_3H_7$, $-CH=CH-C_4H_9$, $-C_3H_6-C(CH_3)=CH_2$, $-C_2H_4-CH(CH_3)-CH=CH_2$, $-CH_2-CH(CH_3)-CH_2-CH=CH_2$, $-C_2H_4-CH=C(CH_3)_2$, $-CH(CH_3)-C_2H_4-CH=CH_2$, $-C_2H_4-C(CH_3)=CH-CH_3$, $-CH_2-CH(CH_3)-CH=CH-CH_3$, $-CH(CH_3)-CH_2-CH=CH-CH_3$, $-CH_2-CH=CH-CH(CH_3)_2$, $-CH_2-CH=C(CH_3)-C_2H_5$, $-CH_2-C(CH_3)=CH-C_2H_5$, $=CH-C_2H_5$, $-CH(CH_3)-CH=CH-C_2H_5$, $-CH=CH-CH_2-CH(CH_3)_2$, $-CH=CH-CH(CH_3)-C_2H_5$, $-CH=C(CH_3)-C_3H_7$, $-C(CH_3)=CH-C_3H_7$, $-CH_2-CH(CH_3)-C(CH_3)=CH_2$, $-C[C(CH_3)_3]=CH_2$, $-CH(CH_3)-CH_2-C(CH_3)=CH_2$, $-CH(CH_3)-CH(CH_3)-CH=CH_2$, $-CH=CH-C_2H_4-CH=CH_2$, $-CH_2-C(CH_3)_2-CH=CH_2$, $-C(CH_3)_2-CH_2-CH=CH_2$, $-CH_2-C(CH_3)=C(CH_3)_2$, $-CH(CH_3)-CH=C(CH_3)_2$, $-C(CH_3)_2-CH=CH-CH_3$, $-CH=CH-CH_2-CH=CH-CH_3$, $-CH(CH_3)-C(CH_3)=CH-CH_3$, $-CH=C(CH_3)-CH(CH_3)_2$, $-C(CH_3)=CH-CH(CH_3)_2$, $-C(CH_3)=C(CH_3)-C_2H_5$, $-CH=CH-C(CH_3)_3$, $-C(CH_3)_2-C(CH_3)=CH_2$, $-CH(C_2H_5)-C(CH_3)=CH_2$, $-C(CH_3)(C_2H_5)-CH=CH_2$, $-CH(CH_3)-C(C_2H_5)=CH_2$, $-CH_2-C(C_3H_7)=CH_2$, $-CH_2-C(C_2H_5)=CH-CH_3$, $-CH(C_2H_5)-CH=CH-CH_3$, $-C(C_4H_9)=CH_2$, $-C(C_3H_7)=CH-CH_3$, $-C(C_2H_5)=CH-C_2H_5$, $-C(C_2H_5)=C(CH_3)_2$, $-C[CH(CH_3)(C_2H_5)]=CH_2$, $-C[CH_2-CH(CH_3)_2]=CH_2$, $-C_2H_4-CH=CH-CH=CH_2$, $-CH_2-CH=CH-CH_2-CH=CH_2$, $-C_3H_6-C≡C-CH_3$, $-CH_2-CH=CH-CH=CH-CH_3$, $-CH=CH-CH=CH-C_2H_5$, $-CH_2-CH=CH-C(CH_3)=CH_2$, $-CH_2-CH=C(CH_3)-CH=CH_2$, $-CH_2-C(CH_3)=CH-CH=CH_2$, $-CH(CH_3)-CH_2-C≡CH$, $-CH(CH_3)-CH=CH-CH=CH_2$, $-CH=CH-CH_2-C(CH_3)=CH_2$, $-CH(CH_3)-C≡C-CH_3$, $-CH=CH-CH(CH_3)-CH=CH_2$, $-CH=C(CH_3)-CH_2-CH=CH_2$, $-C(CH_3)=CH-CH_2-CH=CH_2$, $-CH=CH-CH=C(CH_3)_2$, $-CH_2-CH(CH_3)-CH_2-C≡CH$, $-CH=CH-C(CH_3)=CH-CH_3$, $-CH=C(CH_3)-CH=CH-CH_3$, $-CH_2-CH(CH_3)-C≡CH$, $-CH(CH_3)-C≡C-CH_3$, $-CH=C(CH_3)-CH(CH_3)_2$, $-C(CH_3)=CH-CH=CH-CH_3$, $-CH_2-CH(CH_3)-C≡CH$, $-C(CH_3)=CH-CH=CH-CH_3$, $-CH=C(CH_3)-C(CH_3)=CH_2$, $-C(CH_3)=C(CH_3)-CH=CH_2$, $-CH=CH-CH=CH-C_2H_5$, $-C≡CH$, $-C≡C-CH_3$, $-CH_2-C≡CH$, $-C_2H_4-C≡CH$, $-CH_2-C≡C-CH_3$, $-C≡C-C_2H_5$, $-C_3H_6-C≡CH$, $-C_2H_4-C≡C-CH_3$, $-CH_2-C≡C-C_2H_5$, $-C≡C-C_3H_7$, $-CH(CH_3)-C≡CH$, $-C_4H_8-C≡CH$, $-C_2H_4-C≡C-C_2H_5$, $-CH_2-C≡C-C_3H_7$, $-C≡C-C_4H_9$, $-C≡C-C(CH_3)_3$, $-CH(CH_3)-C_2H_4-C≡CH$, $-CH_2-CH(CH_3)-C≡C-CH_3$, $-CH(CH_3)-CH_2-C≡C-CH_3$, $-CH(CH_3)-C≡C-C_2H_5$, $-CH_2-C≡C-CH(CH_3)_2$, $-C≡C-CH(CH_3)-C_2H_5$, $-C≡C-CH_2-CH(CH_3)_2$, $-CH(C_2H_5)-C≡C-CH_3$, $-C(CH_3)_2-C≡C-CH_3$, $-CH(C_2H_5)-CH_2-C≡CH$, $-CH_2-CH(C_2H_5)-C≡CH$, $-C(CH_3)_2-CH_2-C≡CH$, $-CH_2-C(CH_3)_2-C≡CH$, $-CH(CH_3)-CH(CH_3)-C≡CH$, $-CH(C_3H_7)-C≡CH$, $-C(CH_3)(C_2H_5)-C≡CH$, $-CH_2-CH(C≡CH)_2$, $-C≡C-C≡CH$, $-CH_2-C≡C-C≡CH$, $-C≡C-C≡C-CH_3$, $-CH(C≡CH)_2$, $-C_2H_4-C≡C-C≡CH$, $-CH_2-C≡C-CH_2-C≡CH$, $-C≡C-C_2H_4-C≡CH$, $-CH_2-C≡C-C≡C-CH_3$, $-C≡C-CH_2-C≡C-CH_3$, $-C≡C-C≡C-C_2H_5$, $-C(C≡CH)_2-CH_3$, $-C≡C-CH(CH_3)-C≡CH$, $-CH(CH_3)-C≡C-C≡CH$, $-CH(C≡CH)-CH_2-C≡CH$, $-CH(C≡CH)-C≡C-CH_3$;

X2, X3, X4 and X5 represent independently of each other:

a bond, $-CH_2-$, $-C_2H_4-$, $-C_3H_6-$, $-C_4H_8-$, $-C_5H_{10}-$, $-C_1H_{12}-$, $-C_7H_{14}-$, $-C_8H_{16}-$, $-C_9H_{18}-$, $-C_{10}H_{20}-$, $-CH(CH_3)-$, $-C[(CH_3)_2]-$, $-CH_2-CH(CH_3)-$, $-CH(CH_3)-CH_2-$, $-CH(CH_3)-C_2H_4-$, $-CH_2-CH(CH_3)-CH_2-$, $-C_2H_4-CH(CH_3)-$, $-CH_2-C[(CH_3)_2]-$, $-C[(CH_3)_2]-CH_2-$, $-CH(CH_3)-CH(CH_3)-$, $-C[(C_2H_5)(CH_3)]-$, $-CH(C_3H_7)-$, $-CH_2CH_2O-$, $-(CH_2-CH_2-O)_m-CH_2-CH_2-$, $-C(CH_3)=CH-C(CH_3)=CH$, $-C_2H_4-CH=CH-CH=CH-$, $-CH_2-CH=CH-CH_2-CH=CH-$, $-C_3H_6-C≡C-CH_2-$, $-CH_2-CH=CH-CH=CH-CH_2-$, $-CH=CH-CH=CH-C_2H_4-$, $-CH_2-CH=C(CH_3)-CH=CH-$, $-CH_2-CH=C(CH_3)-CH=CH-$, $-CH_2-C(CH_3)=CH-CH=CH-$, $-CH(CH_3)-CH=CH-CH=CH-$, $-CH=CH-CH_2-C(CH_3)=CH-$, $-CH(CH_3)-C≡C-CH_2-$, $-CONH-$, $-NHCO-$, $-CH_2-CONH-$, $-CONH-CH_2-$, $-NHCO-CH_2-$, $-CH_2-NHCO-$;

wherein m is an integer from 1 to 10; or $X^4-R^A$ and $X^3-R^B$ can form together a cyclic ring selected from the group consisting of:

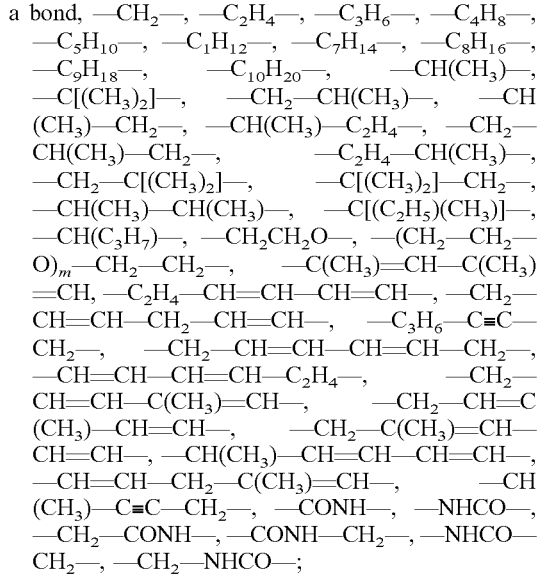

and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

2. The compound of claim 1, wherein the compound binds selectively to FKBP51, but not to FKBP52 and/or FKBP 12/12.6.

3. The compound of claim 1, wherein the compound inhibits the activity of FKBP51.
4. The compound of claim 1,
wherein L represents:
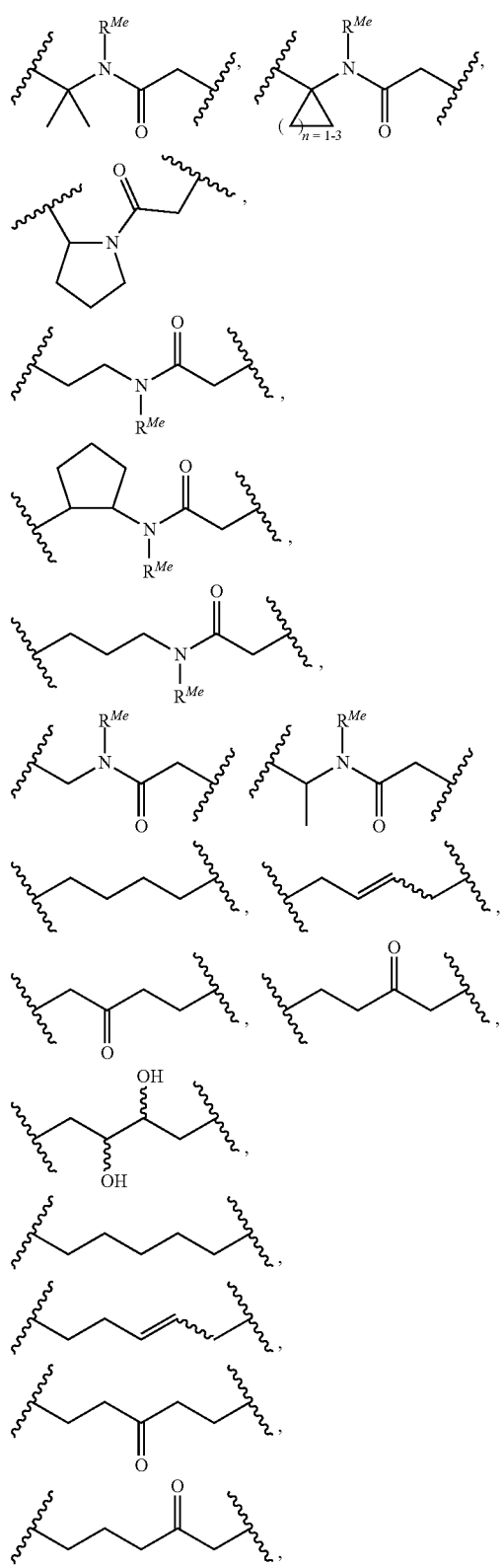
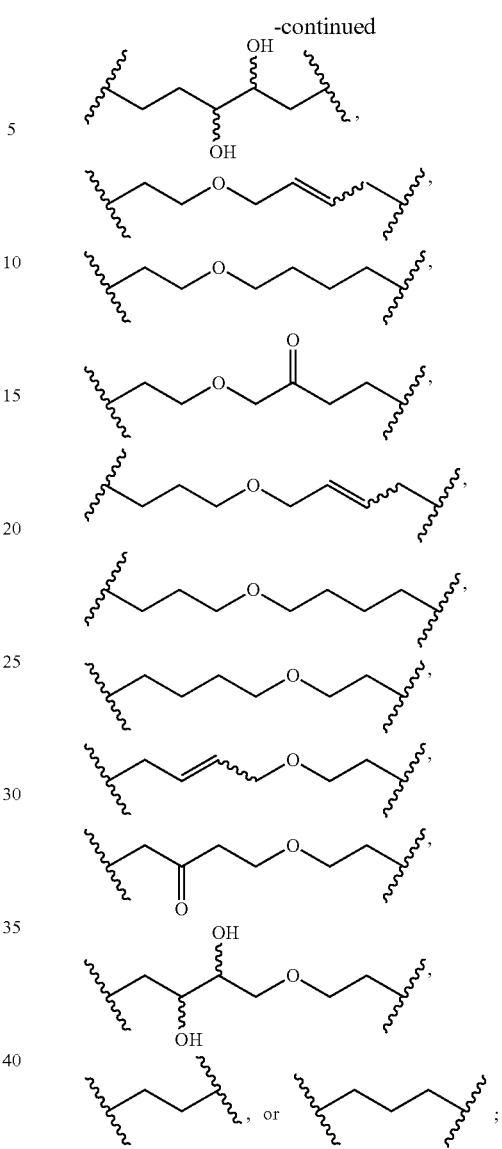
wherein L can be connected to $R^C$ and $R^L$ as follows: $R^C$-L-$R^L$ or $R^L$-L-$R^C$.
5. The compound of claim 1, wherein the core molecule is selected from:
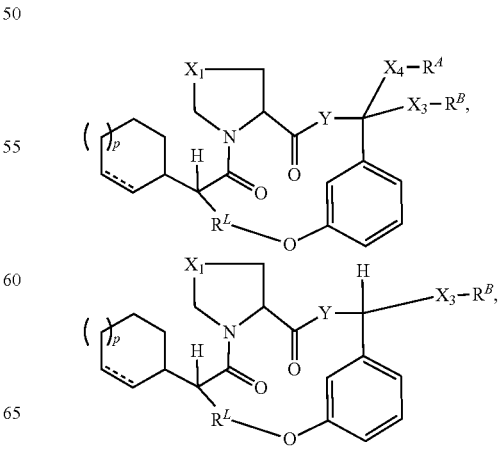

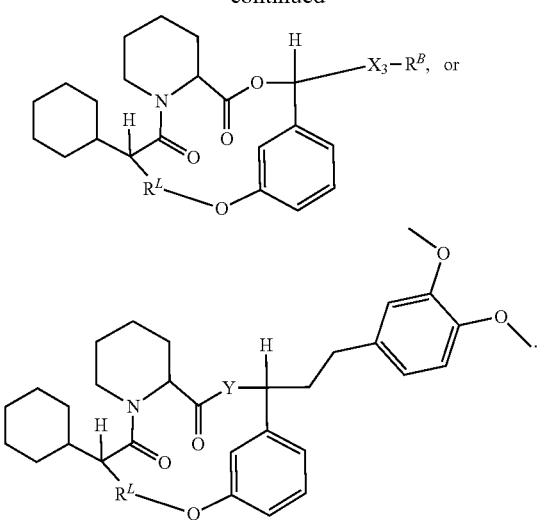

6. The compound of claim 1 for the use in the treatment or prophylaxis of a disease selected from psychiatric disorder such as depression and posttraumatic stress disorder, cancers such glioblastoma, prostate cancer and malignant carcinoma, metabolic disorders such as obesity and diabetes, pain disorders such as neuropathic pain or fibromyalgia, glucocorticoid hyposensitivity syndrome or asthma, and for neuroprotection, neuroregeneration, stimulating neurite growth, wound healing.

7. The compound for the use according to claim 6, wherein the psychiatric disorder is an affective disorder or an anxiety disorder;
wherein the affective disorder is selected from the group consisting of depression, bipolar disorder, mania, substance induced mood disorder and seasonal affective disorder (SAD); and
wherein the anxiety disorder is selected from the group consisting of generalized anxiety disorder, panic disorder, panic disorder with agoraphobia, phobias, obsessive-compulsive disorder, post-traumatic stress disorder, separation anxiety and childhood anxiety disorders.

8. A pharmaceutical composition comprising at least one compound according to claim 1 together with at least one pharmaceutically acceptable carrier, solvent or excipient.

9. The pharmaceutical composition according to claim 8, further comprising at least one active agent selected from the group consisting of an anti-depressant and other psychotropic drugs.

10. The pharmaceutical composition according to claim 9, wherein the anti-depressant is selected from amitriptyline, amioxide clomipramine, doxepine, duloxetine, imipramine trimipramine, mirtazapine, reboxetine, citaloprame, fluoxetine, moclobemide and sertraline.

* * * * *

UNITED STATES PATENT AND TRADEMARK OFFICE
CERTIFICATE OF CORRECTION

PATENT NO. : 11,834,463 B2  
APPLICATION NO. : 18/019369  
DATED : December 5, 2023  
INVENTOR(S) : Felix Hausch, Andreas Voll and Michael Bauder Page 1 of 1

It is certified that error appears in the above-identified patent and that said Letters Patent is hereby corrected as shown below:

In the Claims

Column 125, Claim 5:

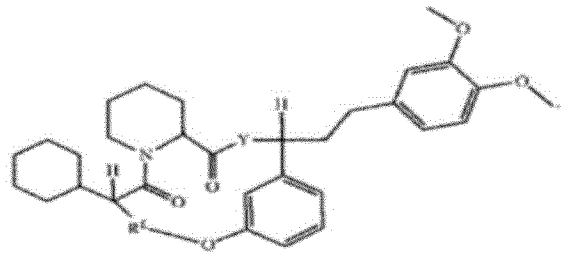

Should read:

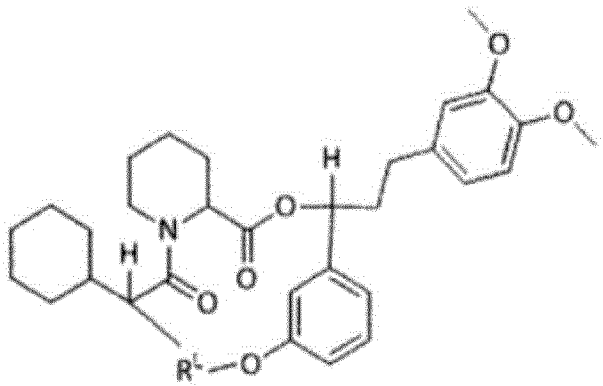

Signed and Sealed this  
Third Day of September, 2024

Katherine Kelly Vidal  
*Director of the United States Patent and Trademark Office*